United States Patent
Kuramoto et al.

(10) Patent No.: US 10,774,082 B2
(45) Date of Patent: *Sep. 15, 2020

(54) QUINAZOLINE COMPOUND

(71) Applicant: Astellas Pharma Inc., Tokyo (JP)

(72) Inventors: Kazuyuki Kuramoto, Tokyo (JP); Michinori Akaiwa, Tokyo (JP); Tomoaki Abe, Tokyo (JP); Takanobu Araki, Tokyo (JP); Susumu Yamaki, Tokyo (JP); Shigeki Kunikawa, Tokyo (JP); Tomoyoshi Imaizumi, Tokyo (JP); Takahiro Nigawara, Tokyo (JP); Keisuke Arakawa, Tokyo (JP); Itsuro Shimada, Tokyo (JP); Masashi Shimazaki, Tokyo (JP); Yoshiki Satake, Tokyo (JP); Kazushi Watanabe, Tokyo (JP); Takanori Koike, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/712,018

(22) Filed: Dec. 12, 2019

(65) Prior Publication Data
US 2020/0140437 A1 May 7, 2020

Related U.S. Application Data

(63) Continuation of application No. 16/432,077, filed on Jun. 5, 2019, now Pat. No. 10,556,906, which is a continuation of application No. PCT/JP2018/003323, filed on Feb. 1, 2018.

(30) Foreign Application Priority Data

Feb. 2, 2017 (JP) ................................ 2017-017266
Jul. 25, 2017 (JP) ................................ 2017-143607

(51) Int. Cl.
C07D 471/10 (2006.01)
A61K 31/517 (2006.01)
A61P 35/00 (2006.01)

(52) U.S. Cl.
CPC .......... *C07D 471/10* (2013.01); *A61K 31/517* (2013.01); *A61P 35/00* (2018.01)

(58) Field of Classification Search
CPC ...... C07D 471/10; A61K 31/517; A61P 35/00
USPC .......................... 544/284; 514/266.2, 266.23
See application file for complete search history.

(56) References Cited

FOREIGN PATENT DOCUMENTS

| JP | 2015-519308 A | 7/2015 |
|---|---|---|
| JP | 2016-532656 A | 10/2016 |
| WO | 2016/164675 A1 | 10/2016 |
| WO | 2017/087528 A1 | 5/2017 |

OTHER PUBLICATIONS

Patricelli, et al., Selective Inhibition of Oncogenic KRAS Output with Small Molecules Targeting the Inactive State, Cancer Discovery, 2016, vol. 6, pp. 316-329.
Written Opinion dated Apr. 10, 2018 issued in corresponding application PCT/JP2018/003323 (with English translation).
International Search Report dated Apr. 10, 2018 issued in corresponding application PCT/JP2018/003323 (with English translation).
Examination Report dated Sep. 30, 2019 issued in corresponding GCC patent application No. 2018-34702.

*Primary Examiner* — Deepak R Rao
(74) *Attorney, Agent, or Firm* — Oblon, McClelland, Maier & Neustat, L.L.P.

(57) ABSTRACT

[Problem]
Provided is a compound which is useful as an active ingredient of a pharmaceutical composition for treating lung cancer.
[Means for Solution]
The present inventors have studied a compound useful as an active ingredient of a pharmaceutical composition for treating lung cancer, and as a result, it was found that a quinazoline compound has an excellent G12C mutation KRAS inhibitory activity, and which can be used as a therapeutic agent for lung cancer, and thereby the present invention has been completed. The quinazoline compound of the present invention and a salt thereof may be used as the therapeutic agent for lung cancer.

14 Claims, No Drawings

QUINAZOLINE COMPOUND

CROSS REFERENCE TO RELATED APPLICATIONS

The present application is a continuation of U.S. application Ser. No. 16/432,077, filed on Jun. 5, 2019, which is a continuation of international application no. PCT/JP2018/003323, filed on Feb. 1, 2018, and claims the benefit of the filing date of Japanese application nos. 2017-017266, filed on Feb. 2, 2017, and 2017-143607, filed on Jul. 25, 2017, the text of each of which is incorporated by reference.

TECHNICAL FIELD

The present invention relates to a quinazoline compound which is useful as a pharmaceutical composition and a G12C mutation KRAS inhibitor, and is expected to be useful as an active ingredient of a pharmaceutical composition, for example, a pharmaceutical composition for treating lung cancer.

BACKGROUND ART

It has been reported that the number of deaths due to lung cancer is the largest as 19% of all cancer deaths, and 1.8 million new cases per year worldwide are newly affected (GLOBOCAN, 2012). In non-small cell lung cancer (NSCLC) which is set to occupy nearly 80% of lung cancer, (American Cancer Society. Cancer Facts and Figures, 2016), although surgical therapy has been considered until a certain stage, and after that stage, chemotherapy or radiotherapy is used as a main treatment without having surgical adaptation. Based on cell morphology, adenocarcinoma and squamous cell carcinoma are classified as the most common type of NSCLC. The clinical course of these tumors is similar, but adenocarcinoma is characterized by the peripheral localization of the lungs.

RAS protein is a small molecule guanosine triphosphate (GTP) binding protein of approximately 21 kDa consisting of 188 to 189 amino acids, and there are four main proteins (KRAS (KRAS4A and KRAS4B), NRAS, HRAS) generated from three genes such as KRAS gene, NRAS gene, and HRAS gene. RAS protein has two types of a GTP binding type which is an active form and a guanosine diphosphate (GDP) binding type which is an inactive form. The RAS protein is activated by exchanging GDP for GTP by ligand stimulation to cell membrane receptor such as EGFR. The active form RAS binds to about 20 kinds of effector proteins such as RAF, PI3K, and RALGDS, and activates a signal cascade on the downstream. On the other hand, active form RAS becomes inactive by converting GTP to GDP by endogenous GTP hydrolysis (GTPase) activity. This GTPase activity is enhanced by GAP (GTPase activating protein). From this, RAS plays an important "molecular switch" function in intracellular signaling pathway such as EGFR and plays an important role in progress of cell growth, proliferation, and blood vessel formation (Nature rev. cancer, 11, 761, 2011, Nature rev. drug discov., 13, 828, 2014, Nature rev. drug discov., 15, 771, 2016).

When amino acid substitution occurs due to mutation of RAS gene, it is considered that the proportion of the active form increases due to a decrease in endogenous GTPase activity or a decrease in affinity for GAP. It is considered that excessive signal transmission resulting from this causes carcinogenesis and cancer growth proliferation. In the lung cancer, the mutation of the RAS gene was observed in 32% of pulmonary adenocarcinoma. It has been reported that the breakdown of the mutation frequency is 96% of the KRAS gene, 3% of the NRAS gene, and 1% of the HRAS gene, and there are many point mutations of KRAS exon 2 (codon 12, codon 13). In particular, the G12C mutation in which glycine at codon 12 is substituted with cysteine is a frequent mutation in the KRAS gene and occupies the highest proportion as 44% of the KRAS gene mutation observed in pulmonary adenocarcinoma (Nature rev. drug discov., 13, 828, 2014).

In the creation of a KRAS inhibitor, it is ideal to selectively inhibit a function of KRAS mutant protein. On the other hand, since a resulting mutation site is a distal from an effector binding site, obtaining a compound having selectivity in an inhibitory activity of a mutant type and a wild type is generally considered to be difficult (Bioorg. Med. Chem. Lett., 22, 5766, 2012). In recent years, a compound which is irreversibly bonded to G12C mutation KRAS (Nature, 503, 548, 2013, Angew. Chem., Int. Ed. Engl., 53, 199, 2014, Cancer Discov., 6, 316, 2016) by forming a covalent bond with respect to a mutation cysteine has been reported along with the existence of an allosteric pocket in the vicinity of a region called switch II being shown (Nature, 503, 548, 2013) against the G12C mutation KRAS. A G12C mutation KRAS selective inhibitor inhibits conversion from the inactive form to the active form by covalently binding to the G12C mutation KRAS and induces cancer cell death by blocking the downstream signal. Accordingly, a compound with this mechanism of action has been reported to be useful for a treatment of KRAS G12C mutation positive lung cancer.

It has been reported that compounds represented by Formula (A) and Formula (B) have binding capacity for the G12C mutation KRAS (Patent Documents 1, 2, and 3), and Patent Document 2 discloses a compound of Example 1-59 (hereinafter, also referred to as Compound C).

[Chem. 1]

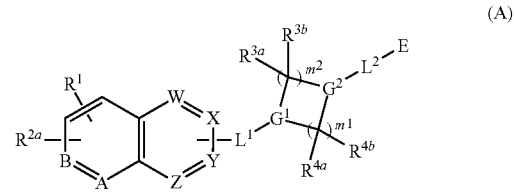

(A)

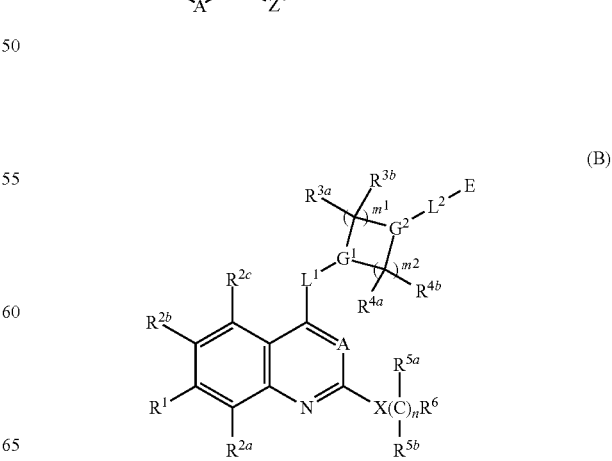

(B)

(The meanings of the symbols in the formulae refer to Patent Documents)

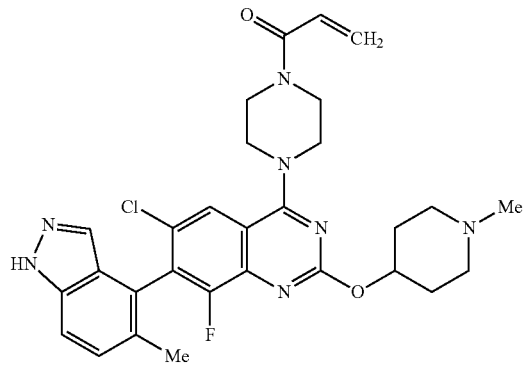

I-59

RELATED ART DOCUMENT

Patent Document

[Patent Document 1] Pamphlet of International Publication No. WO 2015/054572

[Patent Document 2] Pamphlet of International Publication No. WO 2016/164675

[Patent Document 3] Pamphlet of International Publication No. WO 2017/087528

DISCLOSURE OF INVENTION

Problems to be Solved by the Invention

There is provided a compound which is useful as a pharmaceutical composition such as a G12C mutation KRAS inhibitor, and is expected to be useful as an active ingredient of a pharmaceutical composition for treating lung cancer and KRAS G12C mutation positive lung cancer.

Means for Solving the Problems

The present inventors have earnestly studied compounds useful as an active ingredient of a pharmaceutical composition for treating lung cancer, and as a result, it was found that a quinazoline compound of Formula (I) has an excellent G12C mutation KRAS inhibitory activity, and thereby the present invention has been completed.

That is, the present invention relates to a compound of Formula (I) or a salt thereof, and a pharmaceutical composition containing the compound of Formula (I) or the salt thereof, and an excipient.

[Chem. 2]

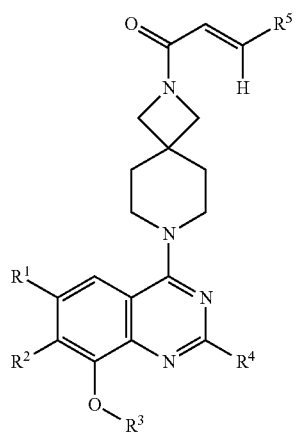

(I)

(in the formula,
$R^1$ is vinyl, (E)-1-propenyl or cyclopropyl,
$R^2$ is Formula (II) or (III),

[Chem. 3]

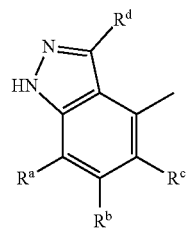

(II)

(III)

$R^3$ is $C_{3-4}$ alkyl, methyl or n-propyl each of which is substituted with two or more F's, ethyl or $C_{3-4}$ cycloalkyl each of which may be substituted with F, benzyl which may be substituted with $C_{1-3}$ alkyl, benzyl which may be substituted with —O—$C_{1-3}$ alkyl, or benzyl which may be substituted with —O—($C_{1-3}$ alkyl which is substituted with F),
$R^4$ is —O—$C_{3-5}$ alkyl which may be substituted, —O-cycloalkyl which may be substituted, or Formula (IV), (V), (VI), or (VII),

[Chem. 4]

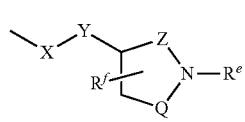

(IV)

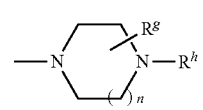

(V)

-continued

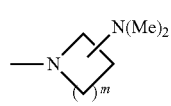
(VI)

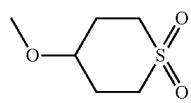
(VII)

$R^5$ is H or $CF_3$,
$R^a$ is H or F,
$R^b$ is H or F,
$R^c$ is H, methyl, vinyl, or Cl,
$R^d$ is H or Cl,
$R^e$ is $CO_2Me$, COMe, $CON(Me)_2$, $SO_2Me$, $C_{3-4}$ cycloalkyl, a nonaromatic heterocyclic group having 4 to 6 ring members which may be substituted, or $C_{1-3}$ alkyl which may be substituted with a group selected from the Group G,
the Group G is —O—$C_{1-3}$ alkyl, —O—($C_{1-3}$ alkyl which is substituted with F or $C_{3-4}$ cycloalkyl), $C_{3-4}$ cycloalkyl, —F, —CN, —$SO_2Me$, and aromatic heterocyclic group, a nonaromatic heterocyclic group having 4 to 6 ring members, —$N(C_{1-3}$ alkyl$)_2$, and —$C(Me)_2OH$,
$R^f$ is H, methyl, or F,
$R^g$ is H, methyl, or ethyl,
$R^h$ is $C_{1-3}$ alkyl which may be substituted with -OMe,
X is O, NH, S, or methylene,
Y is a bond or methylene,
Z is a bond, methylene, or ethylene,
Q is methylene or ethylene,
n is an integer of 1 or 2, and
m is an integer in a range of 1 to 3.)

Unless otherwise specified, in a case where symbols in certain chemical formulae in this specification are also used in other chemical formulae, the same symbols have the same meaning.

In addition, the present invention relates to a pharmaceutical composition for treating lung cancer, which contains a compound of Formula (I) or a salt thereof, and particularly, relates to a pharmaceutical composition for treating KRAS G12C mutation positive lung cancer. Note that, the pharmaceutical composition includes a therapeutic agent for lung cancer, particularly, KRAS G12C mutation positive lung cancer, which contains the compound of Formula (I) or the salt thereof.

In addition, the present invention relates to a compound of Formula (I) or a salt thereof which is a G12C mutation KRAS inhibitor; the compound of Formula (I) or the salt thereof for use as the G12C mutation KRAS inhibitor; the G12C mutation KRAS inhibitor containing the compound of Formula (I) or the salt thereof; use of the compound of Formula (I) or the salt thereof for the manufacture of a pharmaceutical composition for treating lung cancer, particularly, KRAS G12C mutation positive lung cancer; use of the compound of Formula (I) or the salt thereof for treating lung cancer, particularly, KRAS G12C mutation positive lung cancer; the compound of Formula (I) or the salt thereof for use in the treatment of lung cancer, particularly, KRAS G12C mutation positive lung cancer; and a method of treating lung cancer, particularly, KRAS G12C mutation positive lung cancer including administering an effective dose of the compound of Formula (I) or the salt thereof to a target. Note that, "target" is a human or other animals in need of treatment thereof, and as an embodiment, the target is a human in need of prevention or treatment thereof.

Effects of the Invention

The compound of Formula (I) or the salt thereof has G12C mutation KRAS inhibitory activity, and can be used as a therapeutic agent for lung cancer.

EMBODIMENTS FOR CARRYING OUT THE INVENTION

Hereinafter, the present invention will be described in detail.

In the present specification, a phrase "may be substituted with" means having no substituted group or 1 to 3 substituents.

"Substituted" means having 1 to 5 substituents, and "substituted with two or more F's" means having 2 to 5 F atoms.

"$C_{1-3}$ alkyl" is a linear or branched alkyl having 1 to 3 carbon atoms, and examples thereof include methyl, ethyl, n-propyl, and isopropyl. As an embodiment, $C_{1-3}$ alkyl is methyl, ethyl, or n-propyl, as an embodiment, it is methyl or ethyl, as an embodiment, it is methyl or n-propyl, as an embodiment, it is ethyl or n-propyl, as an embodiment, it is methyl, as an embodiment, it is ethyl, and as an embodiment, it is n-propyl.

"$C_{3-4}$ alkyl" means a linear or branched alkyl having 3 to 4 carbon atoms, and examples thereof include n-propyl, isopropyl, n-butyl, sec-butyl, isobutyl, and tert-butyl. As an embodiment, $C_{3-4}$ alkyl is n-propyl or isobutyl, and as an embodiment, it is isobutyl.

"$C_{3-5}$ alkyl" means a linear or branched alkyl having 3 to 5 carbon atoms, and examples thereof include n-propyl, isopropyl, n-butyl, sec-butyl, isobutyl, tert-butyl, and n-pentyl. As an embodiment, $C_{3-5}$ alkyl is n-propyl, n-butyl, or n-pentyl, as an embodiment, it is n-propyl or n-butyl, and as an embodiment, it is n-propyl.

"Cycloalkyl" means a saturated hydrocarbon ring group having 3 to 10 ring members which may have a crosslink, and examples thereof include cyclopropyl, cyclobutyl, cyclopentyl, cyclohexyl, cycloheptyl, cyclooctyl, and adamantyl. As an embodiment, Cycloalkyl is cyclopentyl, cyclohexyl, or cycloheptyl, and as an embodiment, it is cyclohexyl.

"$C_{3-4}$ cycloalkyl" means cycloalkyl having 3 to 4 ring members. As an embodiment. $C_{3-4}$ cycloalkyl is cyclopropyl or cyclobutyl, as an embodiment, it is cyclopropyl, and as an embodiment, it is cyclobutyl.

A "nonaromatic heterocyclic group having 4 to 6 ring members" means a monovalent group of a nonaromatic heterocyclic group having 4 to 6 ring members, which has 1 to 2 identical or different heteroatoms selected from the group consisting of N, O, and S, and examples thereof include azetidinyl, oxetanyl, pyrrolidinyl, piperidinyl, piperazinyl, morpholinyl, thiomorpholinyl, tetrahydropyranyl, tetrahydrofuryl, tetrahydrothienyl, and tetrahydrothiopyranyl. As an embodiment, the nonaromatic heterocyclic group having 4 to 6 ring members is oxetanyl, tetrahydropyranyl, piperidinyl, pyrrolidinyl, or morpholinyl, as an embodiment, it is oxetanyl or tetrahydropyranyl, as an embodiment, it is pyrrolidinyl, morpholinyl, or tetrahydropyranyl, as an embodiment, it is to oxetanyl, and as an embodiment, it is tetrahydropyranyl.

An "aromatic heterocyclic group" means a monovalent group of an aromatic heterocycle having 5 to 10 ring members having 1 to 4 identical or different heteroatoms selected from the group consisting of N, O and S. and examples thereof include pyridyl, pyrrolyl, pyrazinyl, pyrimidinyl, pyridazinyl, imidazolyl, pyrazolyl, thiazolyl, oxazolyl, thienyl, furyl, and 1,2,4-oxadiazolyl, as an embodiment, it is an aromatic heterocyclic group having 5 to 6 ring members having 1 to 2 N atoms, and as an embodiment, it is pyridyl.

"G12C mutation" indicates a mutation in the wild-type gene in which the residue corresponding to position 12 is converted from glycine into cysteine.

"G12C mutation KRAS" means KRAS having the above-described "G12C mutation" in the gene encoding wild-type KRAS.

"Lung cancer" is, for example, small cell lung cancer and non-small cell lung cancer, and as an embodiment, it is non-small cell lung cancer, as an embodiment, it is pulmonary adenocarcinoma, as an embodiment, it is KRAS G12C mutation positive lung cancer, as an embodiment, it is KRAS G12C mutation positive non-small cell lung cancer, and as an embodiment, it is KRAS G12C mutation positive pulmonary adenocarcinoma.

An embodiment of the compound of Formula (I) of the present invention or the salt thereof will be described below.

(1) A compound or a salt thereof in which $R^1$ is vinyl, (E)-1-propenyl, or cyclopropyl. As an embodiment, a compound or a salt thereof in which $R^1$ is vinyl or cyclopropyl. As an embodiment, a compound or a salt thereof in which $R^1$ is vinyl. As an embodiment, a compound or a salt thereof in which $R^1$ is cyclopropyl.

(2) A compound or a salt thereof in which $R^2$ is Formula (II) or Formula (III). As an embodiment, a compound or a salt thereof in which $R^2$ is Formula (II). As an embodiment, a compound or a salt thereof in which $R^2$ is Formula (III).

(3) A compound or a salt thereof in which $R^a$ is H or F in Formula (II). As an embodiment, a compound or a salt thereof in which $R^a$ is H in Formula (II). As an embodiment, a compound or a salt thereof in which $R^a$ is F in Formula (II).

(4) A compound or a salt thereof in which $R^b$ is H or F in Formula (II). As an embodiment, a compound or a salt thereof in which $R^b$ is H in Formula (II). As an embodiment, a compound or a salt thereof in which $R^b$ is F in Formula (II).

(5) A compound or a salt thereof in which $R^c$ is methyl, vinyl, or Cl in Formula (II). As an embodiment, a compound or a salt thereof in which $R^c$ is methyl or Cl in Formula (II). As an embodiment, a compound or a salt thereof in which $R^c$ is methyl or vinyl in Formula (II). As an embodiment, a compound or a salt thereof in which $R^c$ is methyl in Formula (II). As an embodiment, a compound or a salt thereof in which $R^c$ is vinyl in Formula (II). As an embodiment, a compound or a salt thereof in which $R^c$ is Cl in Formula (II).

(6) A compound or a salt thereof in which $R^d$ is H or Cl in Formula (II). As an embodiment, a compound or a salt thereof in which $R^d$ is H in Formula (II). As an embodiment, a compound or a salt thereof in which $R^d$ is Cl in Formula (II).

(7) A compound or a salt thereof in which $R^3$ is $C_{3-4}$ alkyl, methyl or n-propyl each of which is substituted with two or more F's, ethyl or $C_{3-4}$ cycloalkyl each of which may be substituted with F, benzyl which may be substituted with $C_{1-3}$ alkyl, benzyl which may be substituted with —O—$C_{1-3}$ alkyl, or benzyl which may be substituted with —O—($C_{1-3}$ alkyl which is substituted with F). As an embodiment, a compound or a salt thereof in which $R^3$ is $C_{3-4}$ alkyl, methyl or n-propyl each of which is substituted with two or more F's, or ethyl or $C_{3-4}$ cycloalkyl each of which may be substituted with F. As an embodiment, a compound or a salt thereof in which $R^3$ is $C_{3-4}$ alkyl, methyl or n-propyl each of which is substituted with two or more F's. As an embodiment, a compound or a salt thereof in which $R^3$ is ethyl, cyclopropyl, or cyclobutyl each of which may be substituted with F. As an embodiment, a compound or a salt thereof in which $R^3$ is ethyl which may be substituted with F. As an embodiment, a compound or a salt thereof in which $R^3$ is ethyl, difluoroethyl, or trifluoroethyl. As an embodiment, a compound or a salt thereof in which $R^3$ is ethyl or difluoroethyl. As an embodiment, a compound or a salt thereof in which $R^3$ is ethyl or trifluoroethyl. As an embodiment, a compound or a salt thereof in which $R^3$ is ethyl or 2,2,2-trifluoroethyl. As an embodiment, a compound or a salt thereof in which $R^3$ is difluoroethyl, or trifluoroethyl. As an embodiment, a compound or a salt thereof in which $R^3$ is ethyl. As an embodiment, a compound or a salt thereof in which $R^3$ is difluoroethyl. As an embodiment, a compound or a salt thereof in which $R^3$ is 2,2-difluoroethyl. As an embodiment, a compound or a salt thereof in which $R^3$ is trifluoroethyl. As an embodiment, a compound or a salt thereof in which $R^3$ is 2,2,2-trifluoroethyl. As an embodiment, a compound or a salt thereof in which $R^3$ is $C_{3-4}$ alkyl. As an embodiment, a compound or a salt thereof in which $R^3$ is isobutyl. As an embodiment, a compound or a salt thereof in which $R^3$ is methyl or n-propyl each of which is substituted with two or more F's. As an embodiment, a compound or a salt thereof in which $R^3$ is $C_{3-4}$ cycloalkyl which may be substituted with F. As an embodiment, a compound or a salt thereof in which $R^3$ is cyclobutyl which may be substituted with F. As an embodiment, a compound or a salt thereof in which $R^3$ is cyclobutyl. As an embodiment, a compound or a salt thereof in which $R^3$ is ethyl or cyclobutyl each of which may be substituted with F.

(8) A compound or a salt thereof in which $R^4$ is —O—$C_{3-5}$ alkyl which may be substituted, —O-cycloalkyl which may be substituted, or Formula (IV), (V), (VI), or (VII). As an embodiment, a compound or a salt thereof in which $R^4$ is —O—$C_{3-5}$ alkyl which may be substituted or is —O-cycloalkyl which may be substituted. As an embodiment, a compound or a salt thereof in which $R^4$ is Formula (IV). As an embodiment, a compound or a salt thereof in which $R^4$ is Formula (V). As an embodiment, a compound or a salt thereof in which $R^4$ is Formula (VI). As an embodiment, a compound or a salt thereof in which $R^4$ is Formula (VII).

(9) A compound or a salt thereof in which $R^e$ in Formula (IV) is a nonaromatic heterocyclic group having 4 to 6 ring members which may be substituted, or $C_{1-3}$ alkyl which may be substituted with a substituent selected from the Group G. As an embodiment, a compound or a salt thereof in which $R^e$ in Formula (IV) is oxetanyl, tetrahydropyranyl, or $C_{1-3}$ alkyl which may be substituted with a substituent selected from the group consisting of —O—$C_{1-3}$ alkyl and —C(Me)$_2$OH. As an embodiment, a compound or a salt thereof in which $R^e$ in Formula (IV) is oxetanyl, tetrahydropyranyl, or $C_{1-3}$ alkyl which may be substituted with a substituent selected from the group consisting of -OMe, -OEt, and —C(Me)$_2$OH. As an embodiment, a compound or a salt thereof in which $R^e$ in Formula (IV) is $C_{1-3}$ alkyl which may be substituted with -OMe. As an embodiment, a compound or a salt thereof in which $R^e$ in Formula (IV) is $C_{1-3}$ alkyl which may be substituted with -OEt. As an embodiment, a compound or a salt thereof in which $R^e$ in Formula (IV) is $C_{1-3}$ alkyl which may be substituted with —C(Me)$_2$OH. As an embodiment, a compound or a salt thereof in which $R^e$ in Formula (IV) is $C_{1-3}$ alkyl. As an embodiment, a compound or a salt thereof in which $R^e$ in Formula (IV) is methyl or ethyl. As an embodiment, a compound or a salt thereof in which $R^c$ in Formula (IV) is methyl. As an embodiment, a compound or a salt thereof in which $R^e$ in Formula (IV) is to ethyl. As an embodiment, a compound or a salt thereof in which $R^e$ in Formula (IV) is methoxyethyl. As an embodiment, a compound or a salt thereof in which $R^c$ in Formula (IV) is ethoxyethyl. As an embodiment, a compound or a salt thereof in which $R^c$ in Formula (IV) is methoxypropyl.

(10) A compound or a salt thereof in which $R^f$ in Formula (IV) is H, methyl, or F. As an embodiment, a compound or a salt thereof in which $R^f$ in Formula (IV) is H. As an embodiment, a compound or a salt thereof in which $R^f$ in Formula (IV) is methyl. As an embodiment, a compound or a salt thereof in which $R^1$ in Formula (IV) is F.

(11) A compound or a salt thereof in which X in Formula (IV) is O, NH, S. or methylene. As an embodiment, a compound or a salt thereof in which X in Formula (IV) is O. As an embodiment, a compound or a salt thereof in which X in Formula (IV) is NH. As an embodiment, a compound or a salt thereof in which X in Formula (IV) is S. As an embodiment, a compound or a salt thereof in which X in Formula (IV) is methylene.

(12) A compound or a salt thereof in which Y in Formula (IV) is a bond or methylene. As an embodiment, a compound or a salt thereof in which Y in Formula (IV) is a bond. As an embodiment, a compound or a salt thereof in which Y in Formula (IV) is methylene.

(13) A compound or a salt thereof in which Z in Formula (IV) is a bond, methylene, or ethylene. As an embodiment, a compound or a salt thereof in which Z in Formula (IV) is a bond. As an embodiment, a compound or a salt thereof in which Z in Formula (IV) is methylene. As an embodiment, a compound or a salt thereof in which Z in Formula (IV) is ethylene.

(14) A compound or a salt thereof in which Q in Formula (IV) is methylene or ethylene. As an embodiment, a compound or a salt thereof in which Q in Formula (IV) is methylene. As an embodiment, a compound or a salt thereof in which Q in Formula (IV) is ethylene.

(15) A compound or a salt thereof in which $R^5$ is H or $CF_3$. As an embodiment, a compound or a salt thereof in which $R^5$ is H. As an embodiment, a compound or a salt thereof in which $R^5$ is $CF_3$.

(16) A compound or a salt thereof which is a combination of arbitrary two or more which are not contradictory, among the embodiments described in the above (1) to (15).

Examples of the embodiments described in the above (16) include the following compounds or salts thereof.

(17) A compound or a salt thereof in which $R^1$ is vinyl, (E)-1-propenyl, or cyclopropyl, $R^2$ is Formula (II) or (III), $R^3$ is $C_{2-4}$ alkyl, methyl or n-propyl each of which is substituted with two or more F's, ethyl or $C_{3-4}$ cycloalkyl each of which may be substituted with F, benzyl which may be substituted with $C_{1-3}$ alkyl, benzyl which may be substituted with —O—$C_{1-3}$ alkyl, or benzyl which may be substituted with —O—($C_{1-3}$ alkyl substituted with F), $R^4$ is —O—$C_{3-5}$ alkyl which may be substituted. —O-cycloalkyl which may be substituted, or Formula (IV), (V), (VI), or (VII), $R^5$ is H or $CF_3$, $R^a$ is H or F. $R^b$ is H or F. $R^c$ is H, methyl, vinyl, or Cl, $R^d$ is H or Cl, $R^e$ is $CO_2Me$, COMe, $CON(Me)_2$, $SO_2Me$, or $C_{3-4}$ cycloalkyl, a nonaromatic heterocyclic group having 4 to 6 ring members which may be substituted, $C_{1-3}$ alkyl which may be substituted with a group selected from the Group G in which the Group G is —O—$C_{1-3}$ alkyl, —O—($C_{1-3}$ alkyl substituted with F or $C_{3-4}$ cycloalkyl), $C_{3-4}$ cycloalkyl, —F, —CN, —$SO_2Me$, an aromatic heterocyclic group, a nonaromatic heterocyclic group having 4 to 6 ring members, —N($C_{1-3}$ alkyl)$_2$, and —C(Me)$_2$OH, $R^f$ is H, methyl, or F, $R^g$ is H, methyl, or ethyl, $R^h$ is $C_{1-3}$ alkyl which may be substituted with -OMe, X is O, NH, S, or methylene, Y is a bond or methylene, Z is a bond, methylene, or ethylene, Q is methylene or ethylene, n is an integer of 1 or 2, and m is an integer in a range of 1 to 3.

(18) The compound or the salt thereof described in (17) in which $R^2$ is Formula (II).

(19) The compound or the salt thereof described in (18) in which $R^4$ is Formula (IV).

(20) The compound or the salt thereof described in (19) in which X is O.

(21) The compound or the salt thereof described in (20) in which $R^5$ is H.

(22) The compound or the salt thereof described in (21) in which $R^1$ is vinyl or cyclopropyl.

(23) The compound or the salt thereof described in (22) in which $R^a$ is H, $R^b$ is H or F, $R^c$ is methyl or Cl, and $R^d$ is H.

(24) The compound or the salt thereof described in (23) in which $R^3$ is $C_{3-4}$ alkyl, methyl or n-propyl each of which is substituted with two or more F's, or ethyl or $C_{3-4}$ cycloalkyl each of which may be substituted with F.

(25) The compound or the salt thereof described in (24) in which $R^e$ is a nonaromatic heterocyclic group having 4 to 6 ring members which may be substituted, or $C_{1-3}$ alkyl which may be substituted with a substituent selected from the Group G.

(26) The compound or the salt thereof described in (25) in which R is oxetanyl, tetrahydropyranyl, or $C_{1-3}$ alkyl which may be substituted with a substituent selected from the group consisting of -OMe, -OEt, and —C(Me)$_2$OH.

(27) The compound or the salt thereof described in (25) or (26) in which $R^1$ is H.

(28) The compound or the salt thereof described in (27) in which Y is a bond.

(29) The compound or the salt thereof described in (28) in which Z is ethylene.

(30) The compound or the salt thereof described in (29) in which Q is methylene.

As the combination of the embodiments described in the above (16), specific examples are as follows.

(31) A compound of Formula (I) or a salt thereof in which $R^1$ is vinyl or cyclopropyl, $R^2$ is Formula (II), $R^3$ is ethyl, cyclopropyl, or cyclobutyl each of which is substituted with F, $R^4$ is Formula (IV), $R^5$ is H, $R^a$ is H, $R^b$ is H or F, R is methyl or Cl, $R^d$ is H, $R^e$ is oxetanyl, tetrahydropyranyl, or $C_{1-3}$ alkyl which may be substituted with a substituent selected from the group consisting of -OMe, -OEt, and —C(Me)$_2$OH, $R^f$ is H, X is O, Y is a bond or methylene, Z is a bond, methylene, or ethylene, Q is methylene or ethylene.

(32) A compound of Formula (I) or a salt thereof in which $R^1$ is vinyl or cyclopropyl, $R^2$ is Formula (II), $R^3$ is ethyl, cyclopropyl, or cyclobutyl each of which may be substituted with F, $R^4$ is Formula (IV). $R^5$ is H. $R^a$ is H, $R^b$ is H or F, $R^c$ is methyl or Cl, $R^d$ is H, $R^e$ is $C_{1-3}$ alkyl which may be substituted with -OMe, $R^f$ is H, X is O, Y is a bond or methylene, Z is a bond, methylene, or ethylene, Q is methylene or ethylene.

(33) A compound of Formula (I) or a salt thereof in which $R^1$ is vinyl or cyclopropyl, $R^2$ is Formula (II), $R^4$ is Formula (IV), $R^5$ is H, $R^a$ is H, $R^b$ is H, $R^c$ is methyl, $R^d$ is H, $R^e$ is $C_{1-3}$ alkyl which may be substituted with -OMe, $R^f$ is H, X is O, Y is a bond, Z is ethylene, Q is methylene.

As an example of specific compounds included in the present invention, the following compounds can be exemplified as an embodiment. 1-(7-{8-(2,2-difluoroethoxy)-7-(5-methyl-1H-indazol-4-yl)-2-[(1-methylpiperidin-4-yl)oxy]-6-vinylquinazolin-4-yl}-2,7-diazaspiro[3.5]non-2-yl)prop-2-en-1-one, 1-(7-{6-cyclopropyl-8-ethoxy-7-(5-methyl-1H-indazol-4-yl)-2-[(1-methylpiperidin-4-yl)oxy]quinazolin-4-yl}-2,7-diazaspiro[3.5]non-2-yl)prop-2-en-1-one, 1-(7-{6-cyclopropyl-8-(2,2-difluoroethoxy)-7-(5-methyl-1H-indazol-4-yl)-2-[(1-methylpiperidin-4-yl)oxy]quinazolin-4-yl}-2,7-diazaspiro[3.5]non-2-yl)prop-2-en-1-one, 1-{7-[6-cyclopropyl-8-(2,2-difluoroethoxy)-7-(5-methyl-1H-indazol-4-yl)-2-{[(2S)-1-methylpyrrolidin-2-yl]methoxy}quinazolin-4-yl]-2,7-diazaspiro[3.5]non-2-yl}prop-2-en-1-one, and 1-(7-{8-ethoxy-7-(5-methyl-1H-indazol-4-yl)-2-[(1-methylpiperidin-4-yl)oxy]-6-vinylquinazolin-4-yl}-2,7-diazaspiro[3.5]non-2-yl)prop-2-en-1-one, and a salt thereof.

As an example of specific compounds included in the present invention, the following compounds can be exemplified as another embodiment.

1-(7-{8-(2,2-difluoroethoxy)-7-(5-methyl-1H-indazol-4-yl)-2-[(1-methylpiperidin-4-yl)oxy]-6-vinylquinazolin-4-yl}-2,7-diazaspiro[3.5]non-2-yl)prop-2-en-1-one, 1-(7-{6-cyclopropyl-8-ethoxy-7-(5-methyl-1H-indazol-4-yl)-2-[(1-methylpiperidin-4-yl)oxy]quinazolin-4-yl}-2,7-diazaspiro[3.5]non-2-yl)prop-2-en-1-one, 1-(7-{6-cyclopropyl-8-(2,2-difluoroethoxy)-7-(5-methyl-1H-indazol-4-yl)-2-[(1-methylpiperidin-4-yl)oxy]quinazolin-4-yl}-2,7-diazaspiro[3.5]non-2-yl)prop-2-en-1-one, 1-{7-[6-cyclopropyl-8-(2,2-difluoroethoxy)-7-(5-methyl-1H-indazol-4-yl)-2-{[(2S)-1-methylpyrrolidin-2-yl]methoxy}quinazolin-4-yl]-2,7-diazaspiro[3.5]non-2-yl}prop-2-en-1-one, 1-(7-{8-ethoxy-7-(5-methyl-1H-indazol-4-yl)-2-[(1-methylpiperidin-4-yl)oxy]-6-vinylquinazolin-4-yl}-2,7-diazaspiro[3.5]non-2-yl)prop-2-en-1-one, (+)-1-(7-{8-ethoxy-7-(5-methyl-1H-indazol-4-yl)-2-[(1-methylpiperidin-4-yl)oxy]-6-vinylquinazolin-4-yl)}-2,7-diazaspiro[3.5]non-2-yl)prop-2-en-1-one, 1-{7-[6-cyclopropyl-2-{[1-(2-methoxyethyl)piperidin-4-yl]oxy}-7-(5-methyl-1H-indazol-4-yl)-8-(2,2,2-trifluoroethoxy)quinazolin-4-yl]-2,7-diazaspiro[3.5]non-2-yl}prop-2-en-1-one, 1-{7-[6-cyclopropyl-2-({[1-(3-methoxy propyl)piperidin-4-yl]oxy}-7-(5-methyl-1H-indazol-4-yl)-8-(2,2,2-trifluoroethoxy)quinazolin-4-yl]-2,7-diazaspiro[3.5]non-2-yl}prop-2-en-1-one, and a salt thereof.

Further, as an example of specific compounds included in the present invention, the following compounds can be exemplified as another embodiment.

(+)-1-(7-{8-ethoxy-7-(5-methyl-1H-indazol-4-yl)-2-[(1-methylpiperidin-4-yl)oxy]-6-vinylquinazolin-4-yl}-2,7-diazaspiro[3.5]non-2-yl)prop-2-en-1-one, (+)-1-{7-[6-cyclopropyl-2-{[1-(2-methoxyethyl)piperidin-4-yl]oxy}-7-(5-methyl-1H-indazol-4-yl)-8-(2,2,2-trifluoroethoxy)quinazolin-4-yl]-2,7-diazaspiro[3.5]non-2-yl}prop-2-en-1-one, (+)-1-(7-[2-{[1-(2-methoxyethyl)piperidin-4-yl]oxy}-7-(5-methyl-1H-indazol-4-yl)-8-(2,2,2-trifluoroethoxy)-6-vinylquinazolin-4-yl]-2,7-diazaspiro[3.5]non-2-yl prop-2-en-1-one, (+)-1-{7-[2-{[1-(2-ethoxyethyl)piperidin-4-yl]oxy}-7-(5-methyl-1H-indazol-4-yl)-8-(2,2,2-trifluoroethoxy)-6-vinylquinazolin-4-yl]-2,7-diazaspiro[3.5]non-2-yl}prop-2-en-1-one, (+)-1-{7-[6-cyclopropyl-2-{[1-(3-methoxypropyl)piperidin-4-yl]oxy}-7-(5-methyl-1H-indazol-4-yl)-8-(2,2,2-trifluoroethoxy)quinazolin-4-yl]-2,7-diazaspiro[3.5]non-2-yl}prop-2-en-1-one, (+)-1-{7-[7-(5-methyl-1H-indazol-4-yl)-2-{[1-(tetrahydro-2H-pyran-4-yl)piperidin-4-yl]oxy}-8-(2,2,2-trifluoroethoxy)-6-vinylquinazolin-4-yl]-2,7-diazaspiro[3.5]non-2-yl}prop-2-en-1-one, and (+)-1-{7-[2-{[1-(2-hydroxy-2-methylpropyl)piperidin-4-yl]oxy}-7-(5-methyl-1H-indazol-4-yl)-8-(2,2,2-trifluoroethoxy)-6-vinylquinazolin-4-yl]-2,7-diazaspiro[3.5]non-2-yl}prop-2-en-1-one, and a salt thereof.

A tautomer or a geometric isomer may be present in the compound of Formula (I) depending on the type of the substituent. In the present specification, the compound of Formula (I) is described in only one embodiment of the isomer; however, the present invention includes other isomers, separated isomers, or a mixture thereof.

In addition, the compound of Formula (I) may have asymmetric carbon atom and axis chirality, and based thereon, an optical isomer may exist. The present invention also includes separated forms of optical isomers of the compound of Formula (I), or a mixture thereof.

The present invention further includes a pharmaceutically acceptable prodrug of the compounds of Formula (I). A pharmacologically acceptable prodrug is a compound having a group that can be converted into an amino group, a hydroxyl group, a carboxyl group or the like by solvolysis or under physiological conditions. Examples of a group forming a prodrug include groups disclosed in Prog. Med., 5, 2157-2161 (1985) and "Development of pharmaceuticals" (Hirokawa Shoten, 1990) Volume 7, Molecular Design 163-198.

In addition, the salt of the compound of Formula (I) is a pharmaceutically acceptable salt of the compound of Formula (I), and depending on the kind of the substituent, it may form an acid addition salt or a salt with a base. Specifically, examples thereof include an acid addition salt of an inorganic acid such as a hydrochloric acid, a hydrobromic acid, a hydroiodic acid, a sulfuric acid, a nitric acid, and a phosphoric acid, and an organic acid such as a formic acid, an acetic acid, a propionic acid, an oxalic acid, a malonic acid, a succinic acid, a fumaric acid, a maleic acid, a lactic acid, a malic acid, a mandelic acid, a tartaric acid, a dibenzoyltartaric acid, a ditoluoyltartaric acid, a citric acid, a methanesulfonic acid, an ethanesulfonic acid, a benzenesulfonic acid, a p-toluenesulfonic acid, an aspartic acid, and a glutamic acid, a salt with inorganic metal such as sodium, potassium, magnesium, calcium, and aluminum, a salt with an organic base such as methylamine, ethylamine, and ethanolamine, various amino acids such as acetyl leucine, lysine, and ornithine, a salt with amino acid derivative, and an ammonium salt.

Furthermore, the present invention also includes various hydrates and solvates of the compound of Formula (I) and salts thereof, and substances of crystalline polymorphism. In addition, the invention also includes compounds labeled with various radioactive or nonradioactive isotopes.

(Preparing Method)

The compound of Formula (I) and a salt thereof can be prepared by applying various known synthetic methods by using features based on the basic structure thereof or the type of substituent. Depending on the type of the functional group, it may be effective to substitute a functional group with an appropriate protecting group (a group which can be easily converted into the functional group) at a stage from a starting material to the intermediate. As such a protecting group, for example, a protecting group disclosed in "Greene's Protective Groups in Organic Synthesis (5 Edition, 2014)" written by Wuts (P. G. M. Wuts) and Greene (T. W. Greene) can be exemplified, and it may be appropriately selected and used according to these reaction conditions. In such a method, a desired compound can be obtained by introducing the protecting group and performing the reaction, and then removing the protecting group as necessary.

In addition, similar to the above-described protecting group, the prodrug of the compound of Formula (I) can be prepared by introducing a specific group at the stage from the starting material to the intermediate or further performing the reaction by using the obtained compound of Formula (I). The reaction can be performed by applying methods known to those skilled in the art such as ordinary esterification, amidation, dehydration, and the like.

Hereinafter, a typical preparing method of the compound of Formula (I) will be described. Each preparing method can also be performed with reference to the references attached to the explanation. The preparing method of the present invention is not limited to the examples described below.

In the present specification, the following abbreviations may be used.

TEA: triethylamine, DIPEA: N,N-diisopropylethylamine, NMO: N-methylmorpholine, DABCO: 1,4-diazabicyclo[2.2.2]octane, THF: tetrahydrofuran, DMF: N,N-dimethylformamide, DMSO: dimethyl sulfoxide

[Chem. 5]

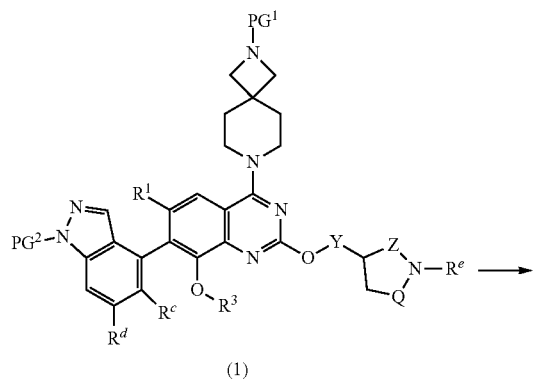

(1)

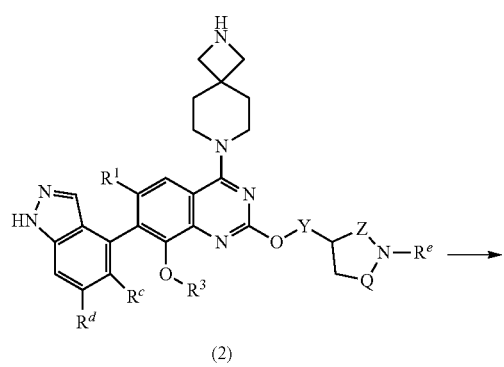

(2)

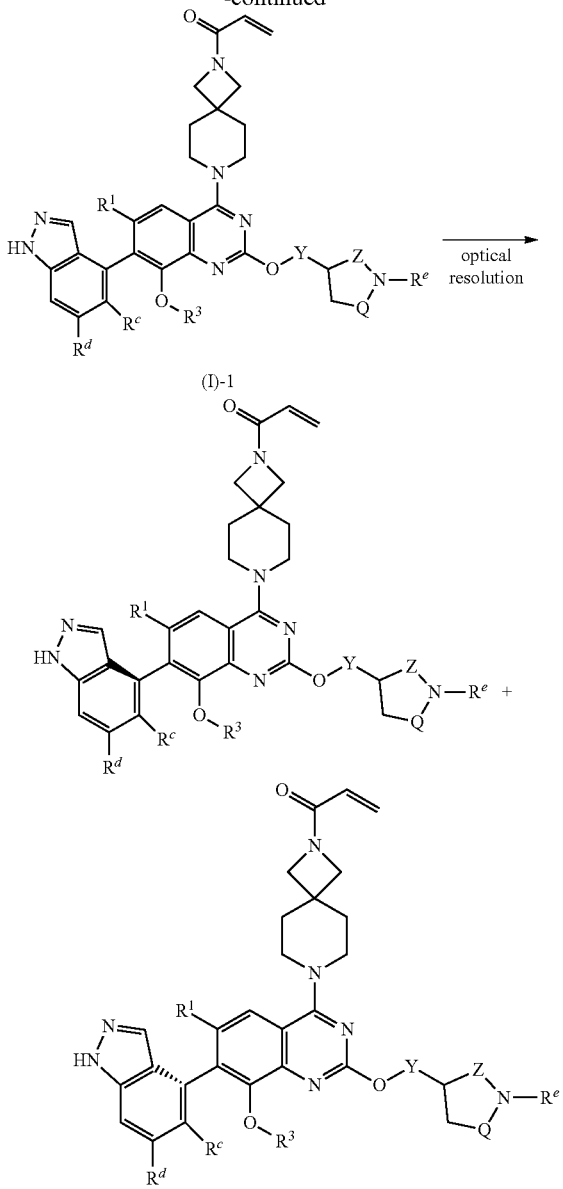

(in the formula, PG$^1$ represents a protecting group, and PG$^2$ represents a protecting group or a hydrogen atom.)

A compound of Formula (I)-1 representing the compound of Formula (I) can be obtained by subjecting the compound (1) to a deprotection reaction so as to obtain a compound (2), and then subjecting to an acylation reaction. Here, examples of the protecting group include a tert-butoxycarbonyl group, a benzyl group, a benzyloxycarbonyl group, a (trimethylsilyl)ethoxymethyl group, a trifluoroacetyl group, an allyl group, and a tetrahydro-2H-pyran-2-yl group.

The deprotection reaction performed with reference to "Protective Groups in Organic Synthesis" written by Greene and Wuts, 5th Edition, published by John Wiley & Sons Inc, 2014.

In the acylation reaction, an equivalent amount of the compound (2) obtained in the preceding step and an acylation reagent, or an excess amount of one thereof is used, the mixture is reacted in a solvent inert to the reaction, under the presence of a base, and stirred the mixture under cooling to heating, at a preferably temperature of −20° C. to 80° C., usually for 0.1 hours to 1 day. The solvent to be used here is not particularly limited, and examples thereof include halogenated hydrocarbons such as dichloromethane, 1,2-dichloroethane, and chloroform, aromatic hydrocarbons such as benzene, toluene, and xylene, ethers such as diethyl ether, THF, 1,4-dioxane, and 1,2-dimethoxyethane, DMF, DMSO, ethyl acetate, acetonitrile, water, and a mixture thereof. In addition, examples of the base used here include an inorganic base such as sodium carbonate, potassium carbonate, and sodium hydrogen carbonate, or an organic base such as TEA, DIPEA, and NMO. Further, examples of the acylation reagent include an acyl halide and an acid anhydride. Examples of the acyl halide include such as acryloyl chloride and 3-chloropropanoyl chloride. In addition, a method of reacting the mixture obtained by using an equivalent amount of the compound (2) and a carboxylic acid, or an excess amount of one thereof under the presence of a condensing agent can be used. The condensing agent is not particularly limited, and examples thereof include 1-(3-dimethylaminopropyl)-3-ethylcarbodiimide, dicyclohexylcarbodiimide, 1,1'-carbonyldiimidazole, diphenylphosphate azide, and phosphorus oxychloride.

Note that, the present reaction may be performed after once isolating the compound (2) which is an amine compound obtained by deprotection reaction.

It may also be necessary to remove excessively reacted acylation reagent under the presence of the inorganic base such as an aqueous sodium carbonate solution.

In addition, in order to obtain the compound of Formula (I)-1, it may be necessary to subject a compound obtained by acylation reaction with 3-chloropropanoyl chloride or the like to elimination reaction under the presence of a base in a solvent inert to the reaction. The solvent used here is not particularly limited, and examples thereof include alcohols such as isopropyl alcohol, water, and a mixture thereof. In addition, examples of the base include an inorganic base such as sodium hydroxide.

Further, the compound of Formula (I)-1 may have axial chirality, and can be obtained as a mixture of atropisomers, but the respective atropisomers can be isolated by performing ordinary resolution operation, for example, optical resolution using supercritical fluid chiral column chromatography.

REFERENCE

J. Med. Chem. 43, 2591-2600, 2000

(Starting Material Synthesis 1)

[Chem. 6]

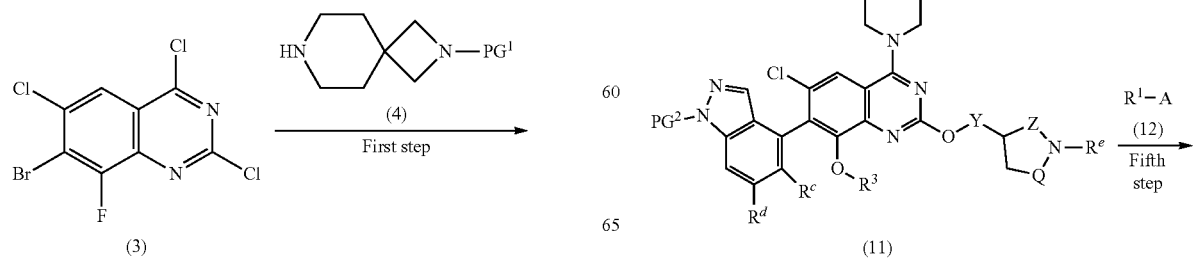

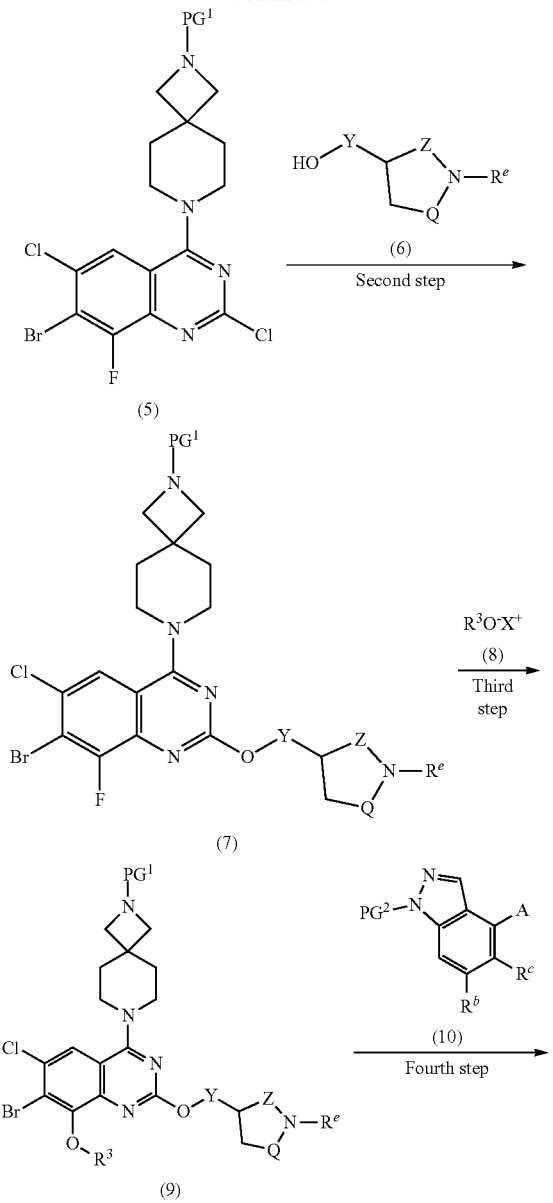

-continued

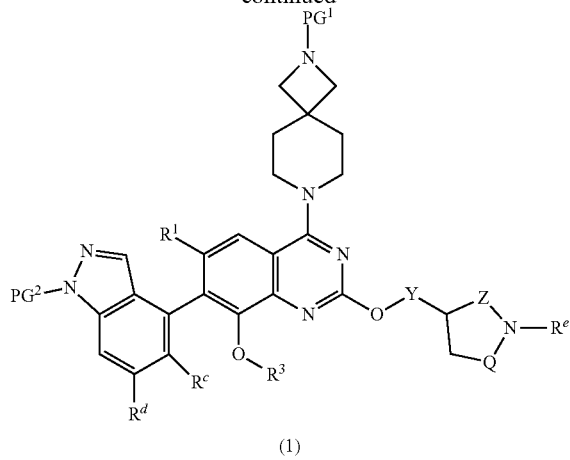

(1)

(In the formula, A represents a boronic acid, boronate ester, or a trifluoroborate salt. In addition, X$^+$ represents a metal cation, such as Na$^+$, K$^+$, and Cs$^+$.)

The present preparing method is a first method of preparing a starting compound (1).

(First Step)

This step is a method of preparing the compound (5) by an ipso-substitution reaction between the compound (3) and the compound (4).

In the present reaction, an equivalent amount of the compound (3) and compound (4), or an excess amount of one thereof is used, and the mixture thereof is stirred in a solvent inert to the reaction, or under the absence of solvent, under cooling to heating reflux, preferably temperature of 0° C. to 80° C., usually for 0.1 hours to 5 days. The solvent to be used here is not particularly limited, and examples thereof include halogenated hydrocarbons such as dichloromethane, 1,2-dichloroethane, and chloroform, aromatic hydrocarbons such as benzene, toluene, and xylene, ethers such as diethyl ether, THF, 1,4-dioxane, and 1,2-dimethoxyethane, DMF, DMSO, ethyl acetate, acetonitrile, and a mixture thereof. It may be advantageous to perform the reaction in the presence of an organic base such as TEA, DIPEA, NMO, and DABCO, and an inorganic base such as potassium carbonate, sodium carbonate, and cesium carbonate in order to smoothly progress the reaction.

(Second Step)

This step is a method of preparing the compound (7) by an ipso-substitution reaction between the compound (5) and the compound (6).

The reaction conditions are similar to the first step of Starting material synthesis 1.

(Third Step)

This step is a method of preparing the compound (9) by an ipso-substitution reaction between the compound (7) and the compound (8).

The reaction conditions are similar to the first step of Starting material synthesis 1.

The compound (8) used in the present reaction may be prepared by stirring the corresponding alcohol with base in a solvent inert to the reaction under cooling to room temperature usually for 0.1 hours to 1 hour. The solvent to be used herein is not particularly limited, and examples thereof include ethers such as diethyl ether, THF, 1,4-dioxane, and 1,2-dimethoxyethane, DMF, DMSO, and a mixture thereof. Further, examples of the base used here include an inorganic base such as sodium hydride and cesium carbonate, or an organic base such as potassium tert-butoxide.

(Fourth Step)

This step is a method of preparing the compound (11) by Suzuki coupling reaction between the compound (9) and the compound (10).

In the present reaction, an equivalent amount of the compound (9) and compound (10), or an excess amount of one thereof is used, and the mixture thereof is stirred in a solvent inert to the reaction under the presence of a base and a palladium catalyst under room temperature to heating reflux, usually for 0.1 hours to 5 days. The solvent to be used here is not particularly limited, and examples thereof include halogenated hydrocarbons such as dichloromethane, 1,2-dichloroethane, and chloroform, aromatic hydrocarbons such as benzene, toluene, and xylene, ethers such as diethyl ether, THF, 1,4-dioxane, and 1,2-dimethoxyethane, alcohols such as methanol, ethanol, isopropyl alcohol, and butanol, DMF, DMSO, acetonitrile, 1,3-dimethylimidazolidin-2-one, water, and a mixture thereof. Examples of the base include an inorganic base such as tripotassium phosphate, sodium carbonate, potassium carbonate, and sodium hydroxide. Examples of a palladium catalyst include tetrakis(triphenylphosphine)palladium, bis(triphenylphosphine)palladium(II) dichloride, [1,1'-bis(diphenylphosphino)ferrocene]palladium(II) dichloride dichloromethane adduct, and (1E, 4E)-1,5-diphenylpenta-1,4-dien-3-one/palladium (3:2). It may be advantageous to perform the reaction in the presence of a ligand such as dicyclohexyl(2',6'-dimethoxybiphenyl-2-yl) phosphine in order to smoothly progress the reaction. It may be advantageous to heat the mixture by microwave irradiation in order to smoothly progress the reaction.

REFERENCE

J. Am. Chem. Soc. 127, 4685-4696, 2005

(Fifth Step)

This step is a method of preparing the compound (1) by Suzuki coupling reaction between the compound (11) and the compound (12).

The reaction conditions are similar to the fourth step of Starting material synthesis 1.

(Starting Material Synthesis 2)

[Chem. 7]

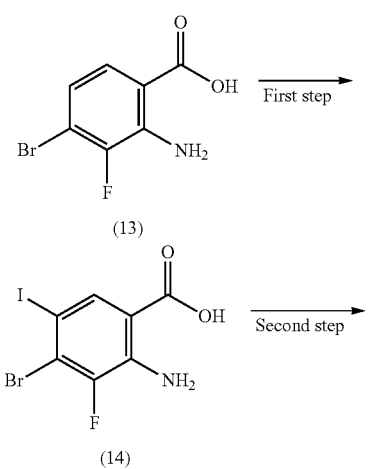

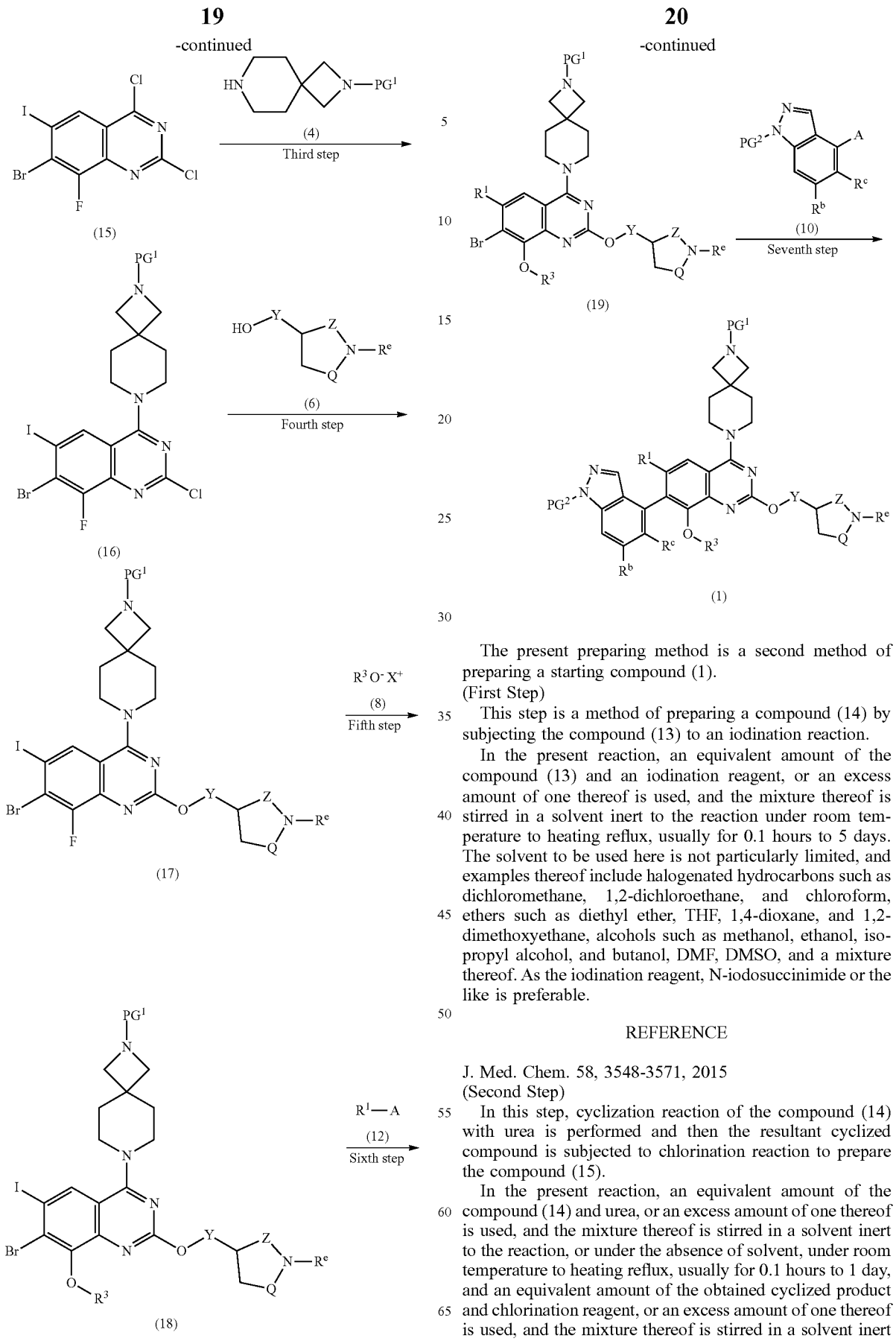

The present preparing method is a second method of preparing a starting compound (1).

(First Step)

This step is a method of preparing a compound (14) by subjecting the compound (13) to an iodination reaction.

In the present reaction, an equivalent amount of the compound (13) and an iodination reagent, or an excess amount of one thereof is used, and the mixture thereof is stirred in a solvent inert to the reaction under room temperature to heating reflux, usually for 0.1 hours to 5 days. The solvent to be used here is not particularly limited, and examples thereof include halogenated hydrocarbons such as dichloromethane, 1,2-dichloroethane, and chloroform, ethers such as diethyl ether, THF, 1,4-dioxane, and 1,2-dimethoxyethane, alcohols such as methanol, ethanol, isopropyl alcohol, and butanol, DMF, DMSO, and a mixture thereof. As the iodination reagent, N-iodosuccinimide or the like is preferable.

REFERENCE

J. Med. Chem. 58, 3548-3571, 2015

(Second Step)

In this step, cyclization reaction of the compound (14) with urea is performed and then the resultant cyclized compound is subjected to chlorination reaction to prepare the compound (15).

In the present reaction, an equivalent amount of the compound (14) and urea, or an excess amount of one thereof is used, and the mixture thereof is stirred in a solvent inert to the reaction, or under the absence of solvent, under room temperature to heating reflux, usually for 0.1 hours to 1 day, and an equivalent amount of the obtained cyclized product and chlorination reagent, or an excess amount of one thereof is used, and the mixture thereof is stirred in a solvent inert to the reaction, or under the absence of solvent, under room temperature to heating reflux, usually for 0.1 hours to 1 day. The solvent to be used here are not particularly limited, and examples thereof include halogenated hydrocarbons such as dichloromethane, 1,2-dichloroethane, and chloroform, aromatic hydrocarbons such as benzene, toluene, and xylene, ethers such as diethyl ether, THF, 1,4-dioxane, and 1,2-dimethoxyethane, DMF, DMSO, and a mixture thereof. As the chlorination reagent, phosphorus oxychloride, thionyl chloride and the like are preferable. It may be advantageous to perform the reaction in the presence of the organic base such as DIPEA in order to smoothly progress the reaction.

The cyclized product as an intermediate in this step can be obtained by subjecting the compound (14) to a condensation reaction with aqueous ammonia in a solvent inert to the reaction under the presence of condensing agent, and then by reacting the obtained amide product with 1,1'-carbonyldiimidazole in a solvent inert to the reaction under the presence of base. The solvent to be used here is not particularly limited, and examples thereof include halogenated hydrocarbons such as dichloromethane, 1,2-dichloroethane, and chloroform, aromatic hydrocarbons such as benzene, toluene, and xylene, ethers such as diethyl ether, THF, 1,4-dioxane, and 1,2-dimethoxyethane, DMF, DMSO, and a mixture thereof. In addition, as the condensing agent, 1H-benzotriazol-1-ol, 1-(3-dimethyl aminopropyl)-3-ethyl-carbodiimide, and the like are preferable. Further, examples of the base include an inorganic base such as potassium carbonate, sodium carbonate, and cesium carbonate, and an organic base such as TEA, DIPEA, and NMO.

Note that, it may be advantageous to perform the following reaction after isolating the intermediate amide and cyclized products respectively in order to smoothly progress the reaction.

REFERENCE

J. Med. Chem. 58, 3548-3571, 2015
(Third Step)
This step is a method of preparing the compound (16) by an ipso-substitution reaction between the compound (15) and the compound (4).
The reaction conditions are similar to the first step of Starting material synthesis 1.
(Fourth Step)
This step is a method of preparing the compound (17) by an ipso-substitution reaction between the compound (16) and the compound (6).
The reaction conditions are similar to the second step of Starting material synthesis 1.
(Fifth Step)
This step is a method of preparing the compound (18) by an ipso-substitution reaction between the compound (17) and the compound (8).
The reaction conditions are similar to the third step of Starting material synthesis 1.
(Sixth Step)
This step is a method of preparing the compound (19) by Suzuki coupling reaction between the compound (18) and the compound (12).
The reaction conditions are similar to the fifth step of Starting material synthesis 1.
(Seventh Step)
This step is a method of preparing the compound (1) by Suzuki coupling reaction between the compound (19) and the compound (10).
The reaction conditions are similar to the fourth step of Starting material synthesis 1.

(Starting Material Synthesis 3)

[Chem. 8]

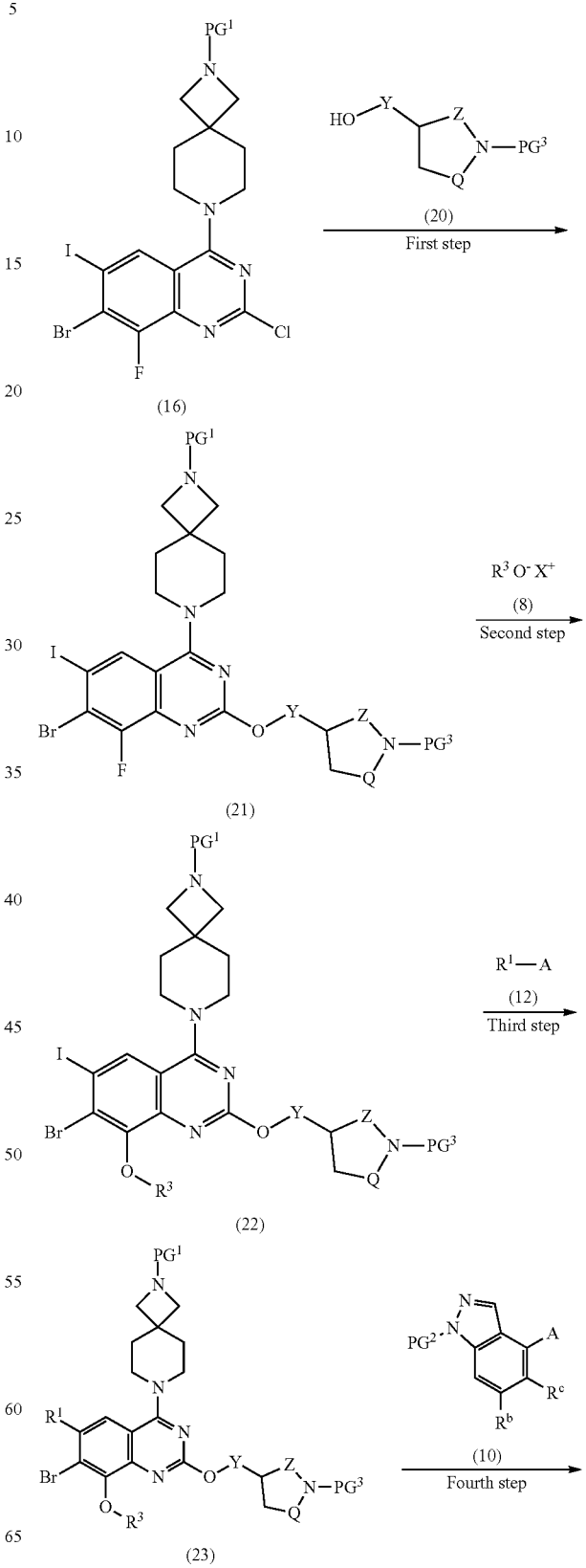

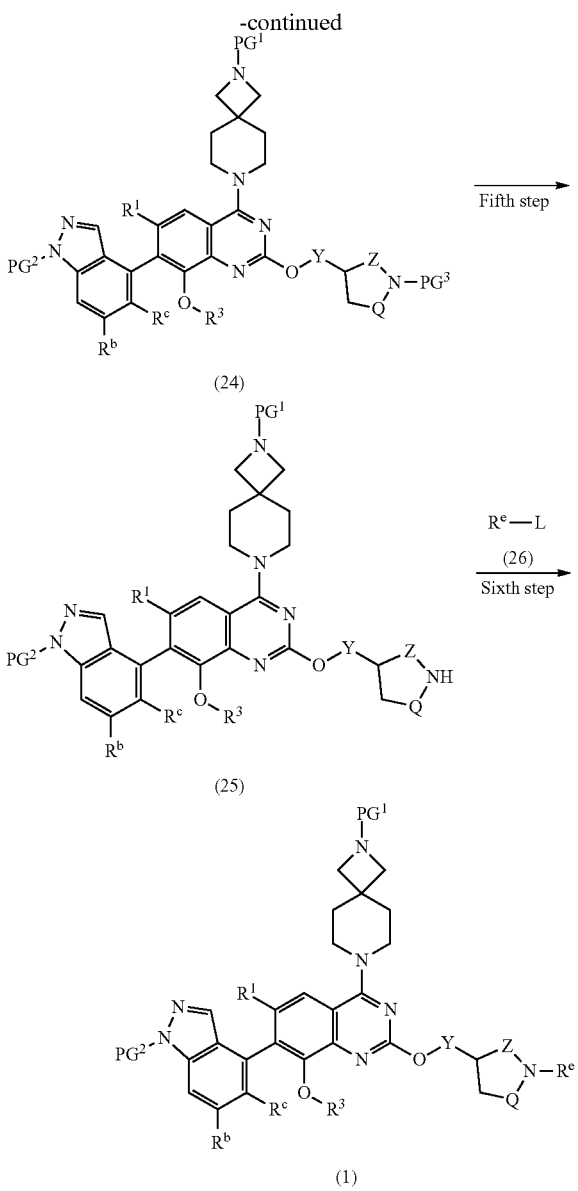

(in the formula. PG³ represents a protecting group, and L represents a leaving group.)

The present preparing method is a third method of preparing a starting compound (1).

(First Step)

This step is a method of preparing the compound (21) by an ipso-substitution reaction between the compound (16) and the compound (20).

The reaction conditions are similar to the second step of Starting material synthesis 1.

(Second Step)

This step is a method of preparing the compound (22) by an ipso-substitution reaction between the compound (21) and the compound (8).

The reaction conditions are similar to the third step of Starting material synthesis 1.

(Third Step)

This step is a method of preparing the compound (23) by Suzuki coupling reaction between the compound (22) and the compound (12).

The reaction conditions are similar to the fifth step of Starting material synthesis 1.

(Fourth Step)

This step is a method of preparing the compound (24) by Suzuki coupling reaction between the compound (23) and the compound (10).

The reaction conditions are similar to the fourth step of Starting material synthesis 1.

(Fifth Step)

This step is a method of preparing a compound (25) by subjecting the protecting group represented by PG³ of the compound (24) to a selective deprotection reaction. Here, examples of PG³ include a 2-(trimethylsilyl)ethoxycarbonyl group, a tert-butoxycarbonyl group, a benzyl group, a benzyloxycarbonyl group, a (trimethylsilyl)ethoxymethyl group, a trifluoroacetyl group, and an allyl group. The deprotection reaction performed with reference to "Protective Groups in Organic Synthesis" written by Greene and Wuts, 5th Edition, published by John Wiley & Sons Inc, 2014.

(Sixth Step)

This step is a method of preparing the compound (1) by a reaction between the compound (25) and the compound (26). Here, examples of the leaving group include halogen, methanesulfonyloxy, and a p-toluenesulfonyloxy group. It is possible to obtain a desired compound (1) by reacting an epoxide compound such as 2,2-dimethyloxirane instead of the compound (26).

In the present reaction, an equivalent amount of the compound (25) and compound (26), or an excess amount of one thereof is used, and the mixture thereof is stirred in a solvent inert to the reaction, or under the absence of solvent, under cooling to heating to reflux, preferably temperature of 0° C. to 120° C., usually for 0.1 hours to 5 days. The solvent to be used here is not particularly limited, and examples thereof include halogenated hydrocarbons such as dichloromethane, 1,2-dichloroethane, and chloroform, aromatic hydrocarbons such as benzene, toluene, and xylene, ethers such as diethyl ether, THF, 1,4-dioxane, and 1,2-dimethoxyethane, alcohols such as methanol, ethanol, isopropyl alcohol, and butanol, DMF, DMSO, ethyl acetate, acetonitrile, water, and a mixture thereof. It may be advantageous to perform the reaction in the presence of the organic base such as TEA, DIPEA, or NMO, or the inorganic base such as potassium carbonate, sodium carbonate, cesium carbonate, or potassium hydroxide in order to smoothly progress the reaction. It may be advantageous to heat the mixture by microwave irradiation in order to smoothly progress the reaction.

The compound of Formula (I) is isolated and purified as a free compound, a salt thereof, a hydrate, a solvate or a substance of crystalline polymorphism. The salt of the compound of Formula (I) can also be prepared by subjecting it to a conventional salt formation reaction.

The isolation and purification are carried out by applying ordinary chemical operations such as extraction, fractional crystallization, various fractionation chromatography and the like.

Various kinds of isomers can be prepared by selecting an appropriate starting compound or can be separated utilizing a difference in physicochemical properties between isomers. For example, the optical isomer can be obtained by a general optical resolution method of the racemic compound (for example, fractional crystallization leading to a diastereomeric salt with an optically active base or an acid, chromatography using a chiral column or the like), and can also be prepared from a suitably optical active starting compound.

The pharmacological activity of the compound of Formula (I) was confirmed by the following test.

TEST EXAMPLE 1

Evaluation of KRAS G12C/SOS/c-Raf Complex Formation Inhibitory Action

Human Recombinant KRAS G12C, SOS, and c-Raf protein were used, and with respect to the complex formation of these proteins, an inhibitory action of the test compound was examined through a time-resolved fluorescence resonance energy transfer (TR-FRET) method.

Biotinylated AviTag-KRAS G12C (amino acid region 1-185, GDP) (2.5 µL; 400 nM) dissolved in assay buffer (50 mM HEPES, 150 mM NaCl, 5 mM $MgCl_2$, 0.05% Tween 20, pH 7.4) and test compound were added in a volume of 2.5 µL from 4,000 nM to 4 nM were added to 384 well plate (Corning Inc). Son of Sevenless (SOS) (amino acid region 564-1049, 2.5 µL; 1.3 µM) and c-Raf (amino acid region 51-131) GST containing GTP (Sigma-Aldrich Co. LLC) (2.5 µL; 130 nM and 4 µM of each) were added to the above mixture, and the resultant was left to stand for one hour at room temperature. Thereafter, a mixed solution (10 µL) of LANCE Ulight-anti-GST (120 nM, PerkinElmer. Co., Ltd) and LANCE Eu-W1024 labeled Streptoavidin (100 ng/mL, PerkinElmer. Co., Ltd) was added, and a fluorescence intensity on the condition of wavelength of 620 nm and 665 nm was measured by using EnVision 2103 Multilabel Reader (PerkinElmer Co., Ltd.) under the condition of excitation wavelength of 337 nm. After a value at the fluorescence intensity in reference wavelength of 620 nm was standardized, when a signal value in a solvent treatment was set as 0% inhibition, and a signal value without addition of GTP was set as 1000/% inhibition, 50% inhibitory concentration ($IC_{50}$) was calculated through Sigmoid-Emax model non-linear regression analysis. The results of several test compounds of Formula (I) are indicated in Table 1. In Tables, Ex represents Example numbers described later. In addition, in Tables, Compound C represents a test compound of Example I-59 disclosed in Pamphlet of International Publication No. WO 2016/164675, and the structures of Reference Example 1 and Reference Example 2 are indicated in Table 168 described below (the same shall apply hereinafter).

TABLE 1

| Ex | $IC_{50}$ (nM) |
|---|---|
| 1 | 34 |
| 2 | 37 |
| 3 | 29 |
| 4 | 35 |
| 5 | 31 |
| 6 | 37 |
| 7 | 33 |
| 8 | 32 |
| 9 | 55 |
| 10 | 34 |
| 11 | 38 |
| 12 | 23 |
| 13 | 37 |
| 14 | 50 |
| 15 | 52 |
| 16 | 45 |
| 17 | 34 |
| 18 | 46 |
| 19 | 48 |
| 20 | 32 |
| 21 | 65 |
| 22 | 39 |
| 23 | 39 |
| 24 | 21 |
| 25 | 48 |
| 26 | 41 |
| 27 | 40 |
| 28 | 38 |
| 29 | 49 |
| 30 | 45 |
| 31 | 45 |
| 32 | 39 |
| 33 | 44 |
| 34 | 36 |
| 35 | 17 |
| 36 | 21 |
| 37 | 17 |
| 38 | 15 |
| 39 | 14 |
| 40 | 15 |
| 41 | 42 |
| 42 | 44 |
| 43 | 50 |
| 44 | 41 |
| 45 | 38 |
| 46 | 48 |
| 47 | 43 |
| 48 | 54 |
| 49 | 41 |
| 50 | 50 |
| 51 | 59 |
| 52 | 56 |
| 53 | 37 |
| 54 | 60 |
| 55 | 83 |
| 56 | 63 |
| 57 | 52 |
| 58 | 57 |
| 59 | 63 |
| 60 | 98 |
| 61 | 56 |
| 62 | 37 |
| 63 | 53 |
| 64 | 32 |
| 65 | 46 |
| 66 | 47 |
| 67 | 43 |
| 68 | 45 |
| 69 | 50 |
| 70 | 79 |
| 71 | 40 |
| 72 | 41 |
| 73 | 44 |
| 74 | 50 |
| 75 | 51 |
| 76 | 43 |
| 77 | 56 |
| 78 | 47 |
| 79 | 57 |
| 80 | 166 |
| 81 | 41 |
| 82 | 43 |
| 83 | 108 |
| 84 | 43 |
| 85 | 56 |
| 86 | 72 |
| 87 | 39 |
| 88 | 148 |
| 89 | 53 |
| 90 | 55 |
| 91 | 42 |
| Reference example 1 | 37 |
| Reference example 2 | 35 |
| Compound C | 68 |

TEST EXAMPLE 2

Evaluation of ERK Phosphorylation Inhibitory Action with Respect to Human KRAS G12C Mutation Positive Non-Small Cell Lung Cancer Strain NCI-H1373

The ERK phosphorylation inhibitory action by the test compound was evaluated by measuring phosphorylation of 202th threonine (Thr 202) and 204th tyrosine (Tyr 204) of ERK on the downstream of the KRAS signal by Cell ELISA.

NCI-H1373 cells (ATCC, CRL-5866) were seeded in 384 well plates (Greiner bio-one) at 36 µL/well each so as to be $2\times10^4$ cell per well. Cell culture was performed under the conditions of temperature of 37° C. in the presence of 5% $CO_2$ by using RPMI 1640 medium (Sigma-Aldrich Co. LLC) containing 10% fetal bovine serum (GE Life Sciences).

The next day, the test compounds (six points in a range of final concentration 1,000 nM to 0.3 nM), final concentration 1 µM of Trametinib (GlaxoSmithKline Inc.; MEK inhibitor) as a positive control, and DMSO which is a solvent of the test compound as a negative control were diluted 100-fold with fresh medium, 4 µL each was added to each well, and then cultured for 2 hours. Immediately after culturing, 30 µL of 30% glyoxal solution (Wako: 40% glyoxal diluted with Phosphate Buffered Saline (PBS; Wako)) was added to each well, and the cells were left to stand at room temperature for one hour to be fixed. Thereafter, the supernatant was removed by centrifuging the plate (110×g for 7 seconds, unless otherwise stated below under the same conditions), and 20 µL of PBS containing 0.1% Triton X-100 (Amersham Biosciences Corp.) was added to each well. After being left to stand at room temperature for 10 minutes, the supernatant was removed by centrifugation, and the same operation was repeated. Next, 20 µL of PBS containing 0.5% SDS (Invitrogen) was added to each well, and the mixture was left to stand at room temperature for 30 minutes, and then centrifuged to remove the supernatant. Subsequently, 20 µL of a blocking solution (ODYSSEY Blocking Buffer; LI-COR Biosciences) was added to each well, and left to stand at room temperature for one hour. The supernatant was removed by centrifugation, and 10 µL of a blocking solution prepared by diluting ERK (Thr 202/Tyr 204) of a phosphorylation antibody (Cell Signaling Technology, Inc.) as a primary antibody to be ½, 500 amount with respect to a stock solution was added to each well and was left to stand at 4° C. for overnight.

The next day, a reaction liquid is removed by centrifuging the plate, 20 µL of 0.05% Tween-20-containing PBS (Thermo Scientific; 20×PBS Tween-20 diluted 20-fold with ion exchanged water) was added to each well, and each well was washed by removing the supernatant by centrifugation. Washing was performed three times in total. After washing, 10 µL of a blocking solution prepared by diluting IRDye 800CW Goat anti-Rabbit IgG (LI-COR Biosciences) as a secondary antibody to be 1/1,000 amount with respect to a stock solution was added to each well and was left to stand at room temperature for one hour. The reaction liquid was removed by centrifuging the plate, and each well was washed three times with 0.05% Tween-20-containing PBS in the same manner as after primary antibody reaction. The centrifugation after the third wash was 171×g for 17 seconds. After removal of the cleaning solution, the plate was left to air dry at room temperature for three hours or more and the fluorescent signal at 800 nm was measured by Aerius (LI-COR Biosciences).

When a signal value at the time of adding DMSO was set as 0% inhibition, and a signal value at the time of adding 1 µM of Trametinib was set as 100% inhibition, a value of 50% inhibition ($IC_{50}$) was calculated through Sigmoid-Emax model nonlinear regression analysis. The results of several test compounds of Formula (I) are indicated in Table 2.

TABLE 2

| Ex | $IC_{50}$ (nM) |
| --- | --- |
| 1 | 6.4 |
| 2 | 4.4 |
| 3 | 3.3 |
| 4 | 2.9 |
| 5 | 4.7 |
| 6 | 3.5 |
| 7 | 8.8 |
| 8 | 2.6 |
| 9 | 3.8 |
| 10 | 5.7 |
| 11 | 10 |
| 12 | 6.7 |
| 13 | 11 |
| 14 | 6.1 |
| 15 | 11 |
| 16 | 9.1 |
| 17 | 4.9 |
| 18 | 5.9 |
| 19 | 4.5 |
| 20 | 6.5 |
| 21 | 14 |
| 22 | 4.6 |
| 23 | 4.9 |
| 24 | 3.7 |
| 25 | 2.5 |
| 26 | 3.3 |
| 27 | 3.3 |
| 28 | 3.5 |
| 29 | 4.2 |
| 30 | 3.1 |
| 31 | 6.3 |
| 32 | 5.7 |
| 33 | 4.6 |
| 34 | 5.8 |
| 35 | 2.5 |
| 36 | 3.0 |
| 37 | 2.5 |
| 38 | 3.4 |
| 39 | 3.0 |
| 40 | 3.1 |
| 41 | 6.2 |
| 42 | 4.4 |
| 43 | 5.0 |
| 44 | 5.1 |
| 45 | 5.2 |
| 46 | 5.5 |
| 47 | 5.6 |
| 48 | 5.9 |
| 49 | 2.9 |
| 50 | 6.4 |
| 51 | 8.9 |
| 52 | 6.7 |
| 53 | 6.8 |
| 54 | 7.2 |
| 55 | 7.4 |
| 56 | 7.7 |
| 57 | 8.2 |
| 58 | 8.4 |
| 59 | 8.4 |
| 60 | 8.8 |
| 61 | 8.8 |
| 62 | 8.8 |
| 63 | 6.6 |
| 64 | 9.1 |
| 65 | 9.3 |
| 66 | 9.7 |
| 67 | 11 |
| 68 | 12 |
| 69 | 12 |
| 70 | 18 |
| 71 | 14 |

TABLE 2-continued

| Ex | IC$_{50}$ (nM) |
|---|---|
| 72 | 14 |
| 73 | 15 |
| 74 | 15 |
| 75 | 15 |
| 76 | 15 |
| 77 | 16 |
| 78 | 16 |
| 79 | 16 |
| 80 | 16 |
| 81 | 16 |
| 82 | 16 |
| 83 | 16 |
| 84 | 17 |
| 85 | 17 |
| 86 | 12 |
| 87 | 18 |
| 88 | 19 |
| 89 | 19 |
| 90 | 22 |
| 91 | 22 |
| Reference example 1 | 22 |
| Reference example 2 | 17 |
| Compound C | 210 |

TEST EXAMPLE 3

Evaluation of Anchorage-Independent Cell Proliferation Inhibitory Action with Respect to Human KRAS G12C Mutation Positive Non-Small Cell Lung Cancer Strain NCI-H1373

An anchorage-independent cell proliferation inhibitory action by the test compound was evaluated by a spheroid three-dimensional culture.

NCI-H1373 cells were seeded in cell low adsorption U bottom 384 well plates (Prime Surface: Sumitomo Bakelite Co., Ltd.) at 36 µL/well each so as to be $5 \times 10^2$ cell per well. The cell culture was performed under the same conditions as Test example 2.

The next day, the test compounds (six points in a range of final concentration 1,000 nM to 0.3 nM) and DMSO which is a solvent of the test compound as a negative control were diluted 100-fold with fresh medium, 4 µL each was added to each well. After culturing at 37° C. in the presence of 5% CO$_2$ for six days, 20 µL of CellTiter Glo or to CellTiter Glo 2.0 (Promega Corporation) was added to each well. After stirring for one hour at room temperature using a plate mixer (FINEPCR), an emission signal was measured with ARVO X3 (PerkinElmer Co., Ltd.).

When a signal value in a DMSO treatment was set as 0% inhibition, and a signal value in cell-free medium only was set as 100% inhibition, a value of 50% inhibition (IC$_{50}$) was calculated through Sigmoid-Emax model nonlinear regression analysis. The results of several test compounds of Formula (I) are indicated in Table 3.

TABLE 3

| Ex | IC$_{50}$ (nM) |
|---|---|
| 1 | 12 |
| 2 | 6.2 |
| 3 | 4.7 |
| 4 | 3.4 |
| 5 | 8.1 |
| 6 | 12 |
| 7 | 11 |
| 8 | 3.5 |
| 9 | 5.5 |
| 10 | 10 |
| 11 | 12 |
| 12 | 11 |
| 13 | 13 |
| 14 | 8.8 |
| 15 | 14 |
| 16 | 10 |
| 17 | 12 |
| 18 | 7.3 |
| 19 | 15 |
| 20 | 11 |
| 21 | 27 |
| 22 | 15 |
| 23 | 5.9 |
| 24 | 6.1 |
| 25 | 5.2 |
| 26 | 8.6 |
| 27 | 6.5 |
| 28 | 5.8 |
| 29 | 10 |
| 30 | 5.4 |
| 31 | 8.3 |
| 32 | 7.1 |
| 33 | 8.7 |
| 34 | 7.5 |
| 35 | 2.5 |
| 36 | 3.2 |
| 37 | 8.8 |
| 38 | 2.5 |
| 39 | 4.3 |
| 40 | 5.1 |
| 41 | 14 |
| 42 | 13 |
| 43 | 6.0 |
| 44 | 7.6 |
| 45 | 7.3 |
| 46 | 8.1 |
| 47 | 17 |
| 48 | 15 |
| 49 | 4.6 |
| 50 | 16 |
| 51 | 24 |
| 52 | 16 |
| 53 | 9.8 |
| 54 | 6.8 |
| 55 | 43 |
| 56 | 21 |
| 57 | 39 |
| 58 | 17 |
| 59 | 26 |
| 60 | 35 |
| 61 | 17 |
| 62 | 14 |
| 63 | 14 |
| 64 | 15 |
| 65 | 27 |
| 66 | 39 |
| 67 | 18 |
| 68 | 16 |
| 69 | 17 |
| 70 | 71 |
| 71 | 10 |
| 72 | 24 |
| 73 | 28 |
| 74 | 21 |
| 75 | 43 |
| 76 | 25 |
| 77 | 32 |
| 78 | 24 |
| 79 | 43 |
| 80 | 75 |
| 81 | 26 |
| 82 | 62 |
| 83 | 51 |
| 84 | 33 |
| 85 | 27 |
| 86 | 37 |
| 87 | 35 |

TABLE 3-continued

| Ex | IC$_{50}$ (nM) |
|---|---|
| 88 | 90 |
| 89 | 40 |
| 90 | 53 |
| 91 | 39 |
| Reference example 1 | 32 |
| Reference example 2 | 22 |
| Compound C | 320 |

TEST EXAMPLE 4

Evaluation of Intratumoral pERK Inhibitory Action

The phosphorylation amount of ERK in tumor sample after administration of test compound was examined by using pERK measurement kit (Advanced ERK phospho-T202/Y204 kit, Cisbio co., Ltd) through a TR-FRET method.

2.0 to 5.0×10$^6$ NCI-H1373 cells were prepared by using a solution in which an equivalent amount of Matrigel (Becton. Dickinson and Company) was added to PBS, were injected subcutaneously in a volume of 100 μL and planted to male nude mice of 4-5 weeks old (CAnN.Cg-Foxn 1 nu/CrlCrlj (nu/nu), Charles River Laboratories Japan, Inc.), and then the male nude mice were used for the test 15 to 26 days later. The test was conducted with three mice in a solvent group and three mice in a test compound administration group, and the test compounds were prepared by using a solvent such that the dosage thereof is as indicated in Table 4. The test compound was administered subcutaneously or orally. For subcutaneous administration, physiological saline supplemented with equimolar hydrochloric acid was used as a solvent. For oral administration, 6% 2-hydroxypropyl-β-cyclodextrin (Sigma-Aldrich Co. LLC) was used as a solvent. Six hours after the administration, a tumor was excised from a cervical dislocated mouse under isoflurane anesthesia, and a part thereof was put into a 2 mL Eppendorf tube and frozen using liquid nitrogen. The tumor sample was stored in a deep freezer at −80° C. until it was subjected to the pERK measurement test.

500 μL of lysis buffer 1 (Phospholysis buffer [Cisbio Co., Ltd], Complete EDTA free [Roche Diagnostics K.K.], Phosphatase inhibitor cocktail 2 [Sigma-Aldrich Co. LLC]) and one bead (5 mm YTZ ball [Nikkato Corp.]) was added to the tumor sample, and crushed (frequency 25/s for 3 minutes) by using Tissue Lyser II (QIAGEN GmbH). The whole amount was transferred to a new tube and centrifuged (20,400×g for 10 minutes, 4° C.) by using a micro amount high speed cooling centrifuge so as to obtain a tumor lysate which is a supernatant. Protein quantification of tumor lysate was performed by using a protein quantification kit (Pierce 660 nm Protein Assay Kit [Thermo Fisher Scientific Inc.]), and each sample was diluted by using lysis buffer 2 (Phosphorysis buffer [Cisbio Co., Ltd], Blocking Agent [attached to pERK measurement kit]) such that the amount thereof is to be a final concentration of 0.5 μg/μL.

Each of p-ERK1/2 Cryptate antibody and p-ERK1/2 d2 antibody (attached to pERK measurement kit) was diluted 20-fold with each detection buffer (attached to pERK measurement kit), and thereby a mixed solution of these two types of antibodies was prepared. A mixed solution of antibody was added to a 384 well plate at a volume of 4 μL/well. Further, tumor lysate diluted to 0.5 μg/μL was added at a volume of 16 μL/well. After standing at room temperature in a wet box for about 17 hours, the fluorescence intensity at 620 nm and 665 nm was measured under the condition of excitation wavelength of 337 nm by using EnVision 2103 Multilabel Reader (PerkinElmer Co., Ltd.). After normalizing the value with the fluorescence intensity at the reference wavelength of 620 nm, the count of the vehicle administration group was set as 0% inhibition, the count without addition of lysate was set as 100% inhibition, and an inhibition value of the test compound administration sample was calculated % by inhibition rate. The results of several test compounds of Formula (I) are indicated in Table 4.

TABLE 4

| Ex | Route of administration | Dosage (mg/kg) | pERK inhibition (%) |
|---|---|---|---|
| 2 | Subcutaneous administration | 1 | 54 |
| 3 | Subcutaneous administration | 1 | 57 |
| 4 | Subcutaneous administration | 1 | 58 |
| 5 | Subcutaneous administration | 3 | 72 |
| 7 | Subcutaneous administration | 3 | 59 |
| 15 | Subcutaneous administration | 3 | 53 |
| 16 | Subcutaneous administration | 3 | 51 |
| 24 | Oral administration | 40 | 72 |
| 25 | Oral administration | 10 | 66 |
| 26 | Oral administration | 10 | 50 |
| 28 | Oral administration | 10 | 46 |
| 29 | Oral administration | 10 | 62 |
| 30 | Oral administration | 10 | 56 |
| 31 | Oral administration | 10 | 51 |
| 32 | Oral administration | 10 | 55 |
| 33 | Oral administration | 10 | 71 |
| 34 | Oral administration | 10 | 54 |
| 35 | Oral administration | 10 | 68 |
| 36 | Oral administration | 10 | 46 |
| 37 | Oral administration | 10 | 63 |
| 38 | Oral administration | 10 | 66 |
| 39 | Oral administration | 10 | 43 |
| 40 | Oral administration | 10 | 58 |
| 50 | Oral administration | 10 | 63 |
| 52 | Oral administration | 10 | 68 |
| 56 | Oral administration | 10 | 53 |
| 65 | Oral administration | 10 | 68 |
| Compound C | Subcutaneous administration | 30 | 54 |

TEST EXAMPLE 5

Evaluation of Antitumor Effect in Human KRAS G12C Mutation Positive Non-Small Cell Lung Cancer Strain NCI-H1373 Tumor-Bearing Mouse A cell suspension prepared per 3.0×10$^7$/mL by suspending NCI-H1373 cells in PBS, an equivalent amount of Matrigel (Becton, Dickinson and Company) was added thereto, and the cell suspension was subcutaneously planted in a volume of 100 μL to male nude mice of 4-5 weeks old (CAnN.Cg-Foxnlnu/CrlCrlj (nu/nu), Charles River Laboratories Japan, Inc.). Approximately 2 weeks after planting, groups were divided so that tumor volume and body weight between the groups were almost equivalent to each other, and administration of the test compound was started from the next day. The test was conducted with five mice in a solvent group and five mice in a test compound administration group, and an aqueous solution of 6% 2-hydroxypropyl-β-cyclodextrin (Sigma-Aldrich Co. LLC) was orally administered to the solvent group and an aqueous solution of 6% 2-hydroxypropyl-β-cyclodextrin which the test compound (10 or 40 mg/kg) was mixed was orally administered to the test compound administration group. The administration was performed once a day for 13 or 14 days, and tumor diameter and volume were measured twice a week. For calculation of tumor volume, the following formula was used.

[tumor volume (mm$^3$)]=[major diameter (mm) of tumor]×[minor diameter (mm) of tumor]$^2$×0.5

The tumor growth inhibition rate (%) by the test compound was calculated by setting the tumor volume of the test compound administration group on the day before the administration started as 100% inhibition, and the tumor volume of the solvent group on the last day of administration as 0% inhibition. In addition, in a case where the tumor volume of the test compound administration group was lower than the tumor volume on the day before the administration started, the tumor regression rate (%) of the test compound was calculated by setting the tumor volume on the day before the administration started as 0% regression, and the tumor volume 0 as 100% regression. The results of several test compounds of Formula (I) are indicated in Table 5.

TABLE 5

| Ex | Dosage (mg/kg) | Antitumor effect |
|---|---|---|
| 24 | 40 | 48% regression |
| 35 | 10 | 72% regression |
| 36 | 10 | 43% regression |
| 37 | 10 | 58% regression |
| 38 | 10 | 58% regression |
| 39 | 10 | 96% inhibition |
| 40 | 10 | 15% regression |

As a result of the above tests, G12C mutation KRAS inhibitory action was confirmed in several compounds of Formula (I). Accordingly, the compound of Formula (I) can be used for treatment of lung cancer, KRAS G12C mutation positive lung cancer, and the like.

A pharmaceutical composition containing the compound of Formula (I) or one or more kinds of salts as active ingredients can be prepared by using an excipient commonly used in this field, that is, an excipient for pharmaceuticals and a carrier for pharmaceuticals through the commonly used methods.

The administration may be any of oral administration with tablets, pills, capsules, granules, powders, solutions, and the like, and parenteral administration with injections such as intra-articular, intravenous, intramuscular, and the like, suppositories, eye drops, ophthalmic ointments, transdermal solutions, ointments, transdermal patches, transmucosal solutions, transmucosal patches, and inhalant.

As a solid composition for the oral administration, tablets, powders, granules and the like are used. In such a solid composition, one or more active ingredients are mixed with at least one kind of inert excipient. The composition may contain an inert additive such as a lubricant, a disintegrant, a stabilizer, and a solubilizing agent according to the conventional method. The tablets or pills may be coated with a sugar coating or a film of gastric or enteric substance, if necessary.

A liquid composition for the oral administration includes a pharmaceutically acceptable emulsion, a solution, a suspension, a syrup, an elixir, and the like, and further includes commonly used inert diluent such as purified water or ethanol. The liquid composition may include a solubilizing agent, a wetting agent, an adjuvant such as a suspending agent, a sweetening agent, a flavoring agent, an aromatic, and a preservative, in addition to the inert diluent.

An injection for parenteral administration includes a sterile aqueous or nonaqueous solution, a suspension, or an emulsion. Examples of an aqueous solvent include distilled water for injection or physiological saline. Examples of a nonaqueous solvent include alcohols such as ethanol. Such a composition may further include an isotonizing agent, a preservative, a wetting agent, an emulsifying agent, a dispersing agent, a stabilizing agent, or a solubilizing agent. These compositions are sterilized, for example, by filtration through a bacteria-retaining filter, blending of a sterilizing agent, or irradiation. In addition, these compositions are used to prepare a sterile solid composition, and can be used by being dissolved or suspended in sterile water or a sterile injectable solvent before use.

A transmucosal agent such as an inhalation agent and a transnasal agent are in a state of solid, liquid, or semisolid, and can be prepared according to conventionally known methods. For example, in addition to the well-known excipient, a pH adjuster, a preservative, a surfactant, a lubricant, a stabilizer, and a thickener may be appropriately added. For administration, a device for suitable inhalation or insufflation can be used. For example, using a known device such as a metered administration inhalation device or a nebulizer, the compound may be administered alone or as a powder of the formulated mixture, or as a solution or a suspension in combination with a pharmaceutically acceptable carrier. A dry powder inhaler or the like may be used for single or multiple administrations, and dry powder or powder containing capsules can be used. Alternatively, a suitable ejection agent, for example, a form of pressurized aerosol spray using suitable gases such as chlorofluoroalkane or carbon dioxide may be employed.

In a case of the common oral administration, a suitable dosage per day is approximately in a range of 0.001 to 100 mg/kg per body weight, is preferably in a range of 0.1 to 30 mg/kg, and further preferably in a range of 0.1 to 10 mg/kg, and the administration is performed once or two to four divided dosages. In a case of intravenous administration, a suitable dosage per day is approximately in a range of 0.0001 to 10 mg/kg per body weight, and the administration is performed once a day to several times a day. Further, as the transmucosal agent, approximately 0.001 to 100 mg/kg per body weight is administered once to several times a day. The dosage is appropriately decided according to individual cases in consideration of symptoms, age, sex, and the like.

Depending on an administration route, a dosage form, an administration site, the types of excipients and additives, the pharmaceutical composition of the present invention contains one or more kinds of the compounds of Formula (I) or salts thereof having active ingredients in a range of 0.01% to 100% by weight, and as an embodiment, active ingredients in a range of 0.01% to 50% by weight.

The compound of Formula (I) can be used in combination with various therapeutic or prophylactic agents for diseases in which the compound of Formula (I) is considered to exhibit efficacy. The combination may be administered simultaneously, or separately in succession, or at a desired time interval. Co-administered preparation may be a compounding agent or separately formulated.

EXAMPLES

Hereinafter, the preparation method of the compound of Formula (I) will be described in more detail based on the Example. It is to be noted that the present invention is not limited to the compounds described in the following Examples. In addition, the preparing method of the starting compound is described in Preparation Examples respectively. Further, the preparing method of the compound of Formula (I) is not limited to only the preparing methods of the specific examples described below, and the compound of Formula (I) may be prepared by combining these preparing methods, or may be prepared by methods obvious to those skilled in the art.

In the present specification, there are cases where naming software such as ACD/Name (registered trademark, Advanced Chemistry Development, Inc.) is used for naming compounds.

Also, for convenience, the concentration mol/L is represented as M. For example, 1 M sodium hydroxide aqueous solution means 1 mol/L sodium hydroxide aqueous solution.

PREPARATION EXAMPLE 1

A mixture of 2-amino-4-bromo-3-fluorobenzoic acid (4.0 g), N-iodosuccinimide (4.0 g), and N,N-dimethylformamide (hereinafter, abbreviated as DMF) (40 mL) was stirred at 50° C. for 2 hours under an argon flow. N-iodosuccinimide (1.5 g) was added to the reaction mixture at 50° C., and the mixture was stirred at the same temperature for 1.5 hours. N-iodosuccinimide (1.5 g) was added to the reaction mixture at 50° C., and the mixture was stirred at the same temperature overnight. The reaction mixture was cooled to room temperature, then water was added and the mixture was stirred at room temperature for 5 hours. The precipitated solid was collected by filtration and air-dried at room temperature. The obtained solid was suspended in water and stirred at room temperature for 1 hour. The solid was collected by filtration, washed with water and dried at 50° C. under reduced pressure to obtain 2-amino-4-bromo-3-fluoro-5-iodobenzoic acid (5.6 g) as a solid.

PREPARATION EXAMPLE 2

A mixture of 2-amino-4-bromo-3-fluoro-5-iodobenzoic acid (5.6 g) and urea (4.7 g) was stirred at 200° C. for 3 hours. The reaction mixture was cooled to room temperature, then water was added and the mixture was stirred at room temperature for 15 minutes. The solid was collected by filtration, washed with water, and dried at 50° C. under reduced pressure. The obtained solid was ground into powder, then was mixed with phosphorus oxychloride (80 mL), cooled in ice bath, and N,N-diisopropylethylamine (hereinafter, abbreviated as DIPEA) (8.0 mL) was added dropwise to the mixture in a nitrogen flow. The reaction mixture was stirred at 150° C. for 2.5 hours. The reaction mixture was cooled to room temperature, then concentrated under reduced pressure, and ethyl acetate was added to the obtained residue. The reaction mixture was poured into ice water, then an insoluble material was separated by filtration, and the filtrate was extracted with ethyl acetate. An organic layer was washed with a saturated aqueous sodium chloride solution, and then dried by anhydrous magnesium sulfate so as to concentrate a solution under reduced pressure. The obtained residue was purified by silica gel column chromatography (hexane/ethyl acetate) so as to obtain 7-bromo-2,4-dichloro-8-fluoro-6-iodoquinazoline (3.6 g) as a solid.

PREPARATION EXAMPLE 3

A mixture of 7-bromo-2,4-dichloro-8-fluoro-6-iodoquinazoline (3.6 g) and 1,4-dioxane (35 mL) was cooled in ice bath, then DIPEA (8.0 mL) and tert-butyl 2,7-diazaspiro[3.5]nonane-2-carboxylate (2.0 g) were added to the mixture in a nitrogen flow, and the mixture was stirred at room temperature for 1.5 hours. Water was added to the reaction mixture and extracted with chloroform. An organic layer was dried by anhydrous magnesium sulfate, and then a solution was concentrated under reduced pressure. The obtained residue was purified by silica gel column chromatography (chloroform/ethyl acetate) so as to obtain tert-butyl 7-(7-bromo-2-chloro-8-fluoro-6-iodoquinazolin-4-yl)-2,7-diazaspiro[3.5]nonane-2-carboxylate (4.6 g) as a solid.

PREPARATION EXAMPLE 4

1-methylpiperidin-4-ol (3.5 mL), cesium carbonate (9.6 g), and 1,4-diazabicyclo[2.2.2]octane (hereinafter, abbreviated as DABCO) (220 mg) were added to a mixture of tert-butyl 7-(7-bromo-2-chloro-8-fluoro-6-iodoquinazolin-4-yl)-2,7-diazaspiro[3.5]nonane-2-carboxylate (6.0 g), DMF (60 mL) and tetrahydrofuran (hereinafter, abbreviated as THF) (60 mL) under the argon atmosphere, and then stirred at room temperature for 14 hours. Water was added to the reaction mixture and extracted with ethyl acetate. An organic layer was washed with a saturated aqueous sodium chloride solution, and then dried by anhydrous sodium sulfate. After concentrating the solution under reduced pressure, the obtained residue was purified by silica gel column chromatography (chloroform/methanol/28% ammonia water) so as to obtain tert-butyl 7-{7-bromo-8-fluoro-6-iodo-2-[(1-methylpiperidin-4-yl)oxy]quinazolin-4-yl}-2,7-diazaspiro[3.5]nonane-2-carboxylate (6.3 g).

PREPARATION EXAMPLE 5

A mixture of 2,2-difluoroethanol (0.37 mL) and DMF (20 mL) were cooled in ice bath, sodium hydride (55%, liquid paraffin dispersion, 250 mg) was added to the mixture, stirred at the same temperature for 5 minutes under the argon atmosphere, and then stirred at room temperature for 20 minutes (mixture A). A mixture of tert-butyl 7-{7-bromo-8-fluoro-6-iodo-2-[(1-methylpiperidin-4-yl)oxy]quinazolin-4-yl}-2,7-diazaspiro[3.5]nonane-2-carboxylate (2.0 g) and THF (40 mL) were cooled in ice bath, the mixture A was added dropwise to the mixture, stirred at the same temperature for 1 hour under the argon atmosphere, and then stirred at room temperature for 2 hours. Under the argon atmosphere, a mixture of 2,2-difluoroethanol (92 μL) and DMF (5 mL) were cooled in ice bath, sodium hydride (55%, liquid paraffin dispersion, 63 mg) was added to the mixture, stirred at the same temperature for 5 minutes, and then stirred at room temperature for 20 minutes (mixture B). The reaction mixture was cooled in ice bath, then the mixture B was added, and the mixture was stirred at room temperature for 3 hours. Water and a saturated aqueous sodium chloride solution were added to the reaction mixture and extracted with ethyl acetate. An organic layer was washed with a saturated aqueous sodium chloride solution, and then dried by anhydrous magnesium sulfate. After concentrating the solution under reduced pressure, the obtained residue was purified by silica gel column chromatography (amino silica gel, hexane/ethyl acetate) so as to obtain tert-butyl 7-{7-bromo-8-(2,2-difluoroethoxy)-6-iodo-2-[(1-methylpiperidin-4-yl)oxy]quinazolin-4-yl}-2,7-diazaspiro[3.5]nonane-2-carboxylate (2.0 g).

PREPARATION EXAMPLE 6

Potassium carbonate (1.1 g) and [1,1'-bis(diphenylphosphino)ferrocene]palladium(II) dichloride dichloromethane adduct (hereinafter, abbreviated as PdCl$_2$(dppf).CH$_2$Cl$_2$) (210 mg) were added to a mixture of tert-butyl 7-{7-bromo-8-(2,2-difluoroethoxy)-6-iodo-2-[(1-methylpiperidin-4-yl)oxy]quinazolin-4-yl}-2,7-diazaspiro[3.5]nonane-2-carboxylate (2.0 g), 4,4,5,5-tetramethyl-2-vinyl-1,3,2-dioxaborolane (0.88 mL), 1,4-dioxane (40 mL), and water (4.0 mL), and the mixture was stirred at 80° C. for 1 hour. After the reaction mixture was cooled to room temperature, and ethyl acetate and a saturated aqueous sodium chloride solution were added to the reaction mixture. An insoluble material was separated by filtration, then a filtrate was extracted with ethyl acetate, and an organic layer was dried with anhydrous magnesium sulfate. After concentrating the solution under reduced pressure, the obtained residue was purified by silica gel column chromatography (amino silica gel, hexane/ethyl acetate). The obtained purified product was purified by silica gel column chromatography (chloroform-methanol/28% ammonia water). Ethyl acetate and hexane were added to the obtained purified product, the solvent was evaporated under reduced pressure so as to obtain tert-butyl 7-{7-bromo-8-(2,2-difluoroethoxy)-2-[(1-methylpiperidin-4-yl)oxy]-6-vinylquinazolin-4-yl}-2,7-diazaspiro[3.5]nonane-2-carboxylate (1.4 g).

PREPARATION EXAMPLE 7

A mixture of tert-butyl 7-{7-bromo-8-(2,2-difluoroethoxy)-2-[(1-methylpiperidin-4-yl)oxy]-6-vinylquinazolin-4-yl}-2,7-diazaspiro[3.5]nonane-2-carboxylate (1.4 g), (5-methyl-1H-indazol-4-yl)boronic acid (760 mg), 1,4-dioxane (17 mL), and water (1.7 mL) was bubbled under argon, then tripotassium phosphate (2.3 g), dicyclohexyl(2',6'-dimethoxybiphenyl-2-yl)phosphine (hereinafter, abbreviated as SPhos) (270 mg), and (1E,4E)-1,5-diphenylpenta-1,4-dien-3-one/palladium (3:2) (hereinafter, abbreviated as Pd$_2$(dba)$_3$) (400 mg) were added to the mixture, and the mixture was stirred at 120° C. for 1 hour under microwave irradiation. Ethyl acetate was added to the reaction mixture, and the mixture was washed with a saturated aqueous sodium chloride solution. An organic layer was dried by anhydrous magnesium sulfate, and then a solution was concentrated under reduced pressure. The obtained residue was purified by silica gel column chromatography (amino silica gel, hexane/ethyl acetate). The obtained purified product was purified by silica gel column chromatography (chloroform/methanol/28% ammonia water) so as to obtain tert-butyl 7-{8-(2,2-difluoroethoxy)-7-(5-methyl-1H-indazol-4-yl)-2-[(1-methylpiperidin-4-yl)oxy]-6-vinylquinazolin-4-yl}-2,7-diazaspiro[3.5]nonane-2-carboxylate (290 mg).

PREPARATION EXAMPLE 8

Sodium ethoxide (390 mg) was added to a mixture of tert-butyl 7-{7-bromo-8-fluoro-6-iodo-2-[(1-methylpiperidin-4-yl}oxy]quinazolin-4-yl)-2,7-diazaspiro[3.5]nonane-2-carboxylate (3.3 g) and THF (65 mL), and the mixture was stirred at 40° C. overnight. Sodium ethoxide (390 mg) was added to the reaction mixture, and the mixture was stirred at 40° C. overnight. A saturated aqueous ammonium chloride solution was added to the reaction mixture, and the mixture was extracted with ethyl acetate. An organic layer was washed with a saturated aqueous sodium chloride solution, and then dried by anhydrous magnesium sulfate. After concentrating the solution under reduced pressure, the obtained residue was purified by silica gel column chromatography (amino silica gel, hexane/ethyl acetate) so as to obtain tert-butyl 7-{7-bromo-8-ethoxy-6-iodo-2-[(1-methylpiperidin-4-yl)oxy]quinazolin-4-yl}-2,7-diazaspiro[3.5]nonane-2-carboxylate (1.3 g) as a solid.

PREPARATION EXAMPLE 9

A mixture of tert-butyl 7-{7-bromo-8-ethoxy-6-iodo-2-[(1-methylpiperidin-4-yl)oxy]quinazolin-4-yl}-2,7-diazaspiro[3.5]nonane-2-carboxylate (1.3 g), 1,4-dioxane (25 mL), water (5.0 mL), cyclopropylboronic acid (160 mg), tripotassium phosphate (1.4 g), PdCl$_2$(dppf)-CH$_2$Cl$_2$ (150 mg) was stirred at 100° C. overnight under the argon atmosphere. The reaction mixture was cooled to room temperature, then water was added, and the mixture was extracted with ethyl acetate. An organic layer was washed with a saturated aqueous sodium chloride solution, and then dried by anhydrous sodium sulfate. After concentrating the solution under reduced pressure, the obtained residue was purified by silica gel column chromatography (amino silica gel, hexane/ethyl acetate) so as to obtain tert-butyl 7-{7-bromo-6-cyclopropyl-8-ethoxy-2-[(1-methylpiperidin-4-yl)oxy]quinazolin-4-yl}-2,7-diazaspiro[3.5]nonane-2-carboxylate (800 mg).

PREPARATION EXAMPLE 10

Under the argon atmosphere, tert-butyl 7-{7-bromo-6-cyclopropyl-8-ethoxy-2-[(1-methylpiperidin-4-yl)oxy]quinazolin-4-yl)}-2,7-diazaspiro[3.5]nonane-2-carboxylate (420 mg), (5-methyl-1H-indazol-4-yl)boronic acid (230 mg). Pd$_2$(dba)$_3$ (61 mg), SPhos (55 mg), tripotassium phosphate (500 mg), 1,4-dioxane (10 mL), and water (1.0 mL) were mixed, and the mixture was stirred at 120° C. for 2 hours under microwave irradiation. A saturated aqueous ammonium chloride solution was added to the reaction mixture, and the mixture was extracted with ethyl acetate. An organic layer was washed with a saturated aqueous sodium chloride solution, and then dried by anhydrous magnesium sulfate. After concentrating the solution under reduced pressure, the obtained residue was purified by silica gel column chromatography (amino silica gel, hexane/ethyl acetate) so as to obtain tert-butyl 7-{6-cyclopropyl-8-ethoxy-7-(5-methyl-H-indazol-4-yl)-2-[(1-methylpiperidin-4-yl)oxy]quinazolin-4-yl}-2,7-diazaspiro[3.5]nonane-2-carboxylate (180 mg).

PREPARATION EXAMPLE 11

A mixture of tert-butyl 7-(7-bromo-2-chloro-8-fluoro-6-iodoquinazolin-4-yl)-2,7-diazaspiro[3.5]nonane-2-carboxylate (5.0 g), benzyl 4-hydroxypiperidine-1-carboxylate (3.7 mL), DMF (75 mL), cesium carbonate (8.0 g), and DABCO (140 mg) was stirred at room temperature for 16 hours under the argon atmosphere. Water was added to the reaction mixture and extracted with ethyl acetate. An organic layer was washed with water and a saturated aqueous sodium chloride solution, and then dried by anhydrous sodium sulfate. After concentrating the solution under reduced pressure, the obtained residue was purified by silica gel column chromatography (hexane/ethyl acetate) so as to obtain tert-butyl 7-[2-({1-[(benzyloxy)carbonyl]piperidin-4-yl}oxy)-7-bromo-8-fluoro-6-iodoquinazolin-4-yl]-2,7-diazaspiro[3.5]nonane-2-carboxylate (4.1 g).

PREPARATION EXAMPLE 12

A mixture of 2,2-difluoroethanol (0.42 mL) and DMF (30 mL) was cooled in ice bath, sodium hydride (55%, liquid paraffin dispersion, 290 mg) was added to the mixture, and stirred at room temperature for 5 minutes under the argon atmosphere. The reaction mixture was cooled in ice bath, and then a mixture of tert-butyl 7-[2-({1-[(benzyloxy)carbonyl]piperidin-4-yl}oxy)-7-bromo-8-fluoro-6-iodoquinazolin-4-yl]-2,7-diazaspiro[3.5]nonane-2-carboxylate (2.7 g) and DMF (15 mL) was added thereto. The reaction mixture was stirred at the same temperature for 10 minutes, and then stirred at room temperature for 4 hours. Water was added to the reaction mixture and extracted with ethyl acetate. An organic layer was washed with a saturated aqueous sodium chloride solution, and then dried by anhydrous sodium sulfate. After concentrating the solution under reduced pressure, the obtained residue was purified by silica gel column chromatography (amino silica gel, hexane/ethyl acetate) so as to obtain tert-butyl 7-[2-(({1-[(benzyloxy)carbonyl]piperidin-4-yl}oxy)-7-bromo-8-(2,2-difluoroethoxy)-6-iodoquinazolin-4-yl]-2,7-diazaspiro[3.5]nonane-2-carboxylate (2.7 g) as a solid.

PREPARATION EXAMPLE 13

Cyclopropylboronic acid (290 mg), tripotassium phosphate (2.3 g), and PdCl$_2$(dppf)-CH$_2$Cl$_2$ (250 mg) were added to a mixture of tert-butyl 7-[2-({1-[(benzyloxy)carbonyl]piperidin-4-yl}oxy)-7-bromo-8-(2,2-difluoroethoxy)-6-iodoquinazolin-4-yl]-2,7-diazaspiro[3.5]nonane-2-carboxylate (2.6 g), 1,4-dioxane (52 mL), and water (10 mL), and the mixture was stirred at 90° C. for 14 hours under the argon atmosphere. A cyclopropylboronic acid (100 mg) was added to the reaction mixture, and the mixture was stirred at 90° C. for 8 hours. After the reaction mixture was cooled to room temperature, a saturated aqueous sodium chloride solution was added to the reaction mixture, and the mixture was extracted with ethyl acetate. An organic layer was dried by anhydrous magnesium sulfate, and then a solution was concentrated under reduced pressure. The obtained residue was purified by silica gel column chromatography (hexane/ethyl acetate) so as to obtain tert-butyl 7-[2-({1-[(benzyloxy)carbonyl]piperidin-4-yl}oxy)-7-bromo-6-cyclopropyl-8-(2,2-difluoroethoxy)quinazolin-4-yl]-2,7-diazaspiro[3.5]nonane-2-carboxylate (1.4 g) as a solid.

PREPARATION EXAMPLE 14

A mixture of tert-butyl 7-[2-({1-[(benzyloxy)carbonyl]piperidin-4-yl}oxy)-7-bromo-6-cyclopropyl-8-(2,2-difluoroethoxy)quinazolin-4-yl]-2,7-diazaspiro[3.5]nonane-2-carboxylate (1.4 g), 5-methyl-1-(tetrahydro-2H-pyran-2-yl)-4-(4,4,5,5-tetramethyl-1,3,2-dioxaborolan-2-yl)-1H-indazole (700 mg), tripotassium phosphate (1.2 g), SPhos (140 mg), Pd$_2$(dba)$_3$ (160 mg), 1,4-dioxane (30 mL), and water (3.0 mL) was divided into equal amounts, and under the argon atmosphere, the mixture was stirred at 120° C. for 1 hour under microwave irradiation. The reaction mixture was mixed, and the mixture was concentrated under reduced pressure. The obtained residue was purified by silica gel column chromatography (amino silica gel, hexane/ethyl acetate) so as to obtain tert-butyl 7-{2-({1-[(benzyloxy)carbonyl]piperidin-4-yl}oxy)-6-cyclopropyl-8-(2,2-difluoroethoxy)-7-[5-methyl-1-(tetrahydro-2H-pyran-2-yl)-1H-indazol-4-yl]quinazolin-4-yl}-2,7-diazaspiro[3.5]nonane-2-carboxylate (820 mg) as a solid.

PREPARATION EXAMPLE 15

Formaldehyde (37% aqueous solution, 0.40 mL) and 10% palladium carbon (wetted with ca. 50% water, 180 mg) were added to a mixture of tert-butyl 7-{2-({1-[(benzyloxy)carbonyl]piperidin-4-yl}oxy)-6-cyclopropyl-8-(2,2-difluoroethoxy)-7-[5-methyl-1-(tetrahydro-2H-pyran-2-yl)-1H-indazol-4-yl]quinazolin-4-yl}-2,7-diazaspiro[3.5]nonane-2-carboxylate (820 mg) and methanol (16 mL), and the mixture was stirred at room temperature under hydrogen atmosphere for 8 hours. The reaction mixture was filtered through celite and the filtrate was concentrated under reduced pressure. The obtained residue was purified by silica gel column chromatography (amino silica gel, hexane/ethyl acetate) so as to obtain tert-butyl 7-{6-cyclopropyl-8-(2,2-difluoroethoxy)-2-[(1-methylpiperidin-4-yl)oxy]-7-[5-methyl-1-(tetrahydro-2H-pyran-2-yl)-1H-indazol-4-yl]quinazolin-4-yl}-2,7-diazaspiro[3.5]nonane-2-carboxylate (530 mg) as a solid.

PREPARATION EXAMPLE 16

A mixture of tert-butyl 7-(7-bromo-2-chloro-8-fluoro-6-iodoquinazolin-4-yl)-2,7-diazaspiro[3.5]nonane-2-carboxylate (3.0 g), [(2S)-1-methylpyrrolidin-2-yl]methanol (2.4 mL), acetonitrile (30 mL), and potassium carbonate (2.1 g) was stirred at 80° C. for 18 hours under the argon atmosphere. [(2S)-1-methylpyrrolidin-2-yl]methanol (0.60 mL) was added to the reaction mixture, and the mixture was stirred at 80° C. for 5 hours. The reaction mixture was cooled to room temperature, then water was added, and the mixture was extracted with ethyl acetate. An organic layer was washed with a saturated aqueous sodium chloride solution, and then dried by anhydrous sodium sulfate. After concentrating the solution under reduced pressure, the obtained residue was purified by silica gel column chromatography (amino silica gel, hexane/ethyl acetate) so as to obtain tert-butyl 7-(7-bromo-8-fluoro-6-iodo-2-{[(2S)-1-methylpyrrolidin-2-yl]methoxy}quinazolin-4-yl)-2,7-diazaspiro[3.5]nonane-2-carboxylate (2.8 g).

PREPARATION EXAMPLE 17

A mixture of 2,2-difluoroethanol (600 mg) and DMF (30 mL) were cooled in ice bath, sodium hydride (55%, liquid paraffin dispersion, 310 mg) was added to the mixture, and stirred at room temperature for 5 minutes under the argon atmosphere (mixture C). After the mixture of tert-butyl 7-(7-bromo-8-fluoro-6-iodo-2-{[(2S)-1-methylpyrrolidin-2-yl]methoxy}quinazolin-4-yl)-2,7-diazaspiro[3.5]nonane-2-carboxylate (2.8 g), and THF (30 mL) was cooled in ice bath, the mixture C was added to the mixture, the mixture was stirred at the same temperature for 10 minutes, and then stirred at room temperature for 3 hours. Water was added to the reaction mixture and extracted with ethyl acetate. An organic layer was washed with a saturated aqueous sodium chloride solution, and then dried by anhydrous sodium sulfate. After concentrating the solution under reduced pressure, the obtained residue was purified by silica gel column chromatography (amino silica gel, hexane/ethyl acetate) so as to obtain tert-butyl 7-[7-bromo-8-(2,2-difluoroethoxy)-6-iodo-2-{[(2S)-1-methylpyrrolidin-2-yl]methoxy}quin- azolin-4-yl]-2,7-diazaspiro[3.5]nonane-2-carboxylate (2.3 g).

PREPARATION EXAMPLE 18

A mixture of tert-butyl 7-[7-bromo-8-(2,2-difluoroethoxy)-6-iodo-2-{[(2S)-1-methylpyrrolidin-2-yl]methoxy}quinazolin-4-yl]-2,7-diazaspiro[3.5]nonane-2-carboxylate (2.2 g), 1,4-dioxane (45 mL), water (4.5 mL), cyclopropylboronic acid (280 mg), tripotassium phosphate (2.3 g), and PdCl$_2$(dppf).CH$_2$Cl$_2$ (240 mg) was stirred at 95° C. for 8 hours under the argon atmosphere, and then stirred at 100° C. for 16 hours. The reaction mixture was cooled to room temperature, then water was added, and the mixture was extracted with ethyl acetate. An organic layer was washed with a saturated aqueous sodium chloride solution, and then dried by anhydrous sodium sulfate. After concentrating the solution under reduced pressure, the obtained residue was purified by silica gel column chromatography (amino silica gel, hexane/ethyl acetate) so as to obtain tert-butyl 7-[7-bromo-6-cyclopropyl-8-(2,2-difluoroethoxy)-2-{[(2S)-1-methylpyrrolidin-2-yl]methoxy}quinazolin-4-yl]-2,7-diazaspiro[3.5]nonane-2-carboxylate (980 mg).

PREPARATION EXAMPLE 19

Under the argon atmosphere, tert-butyl 7-[7-bromo-6-cyclopropyl-8-(2,2-difluoroethoxy)-2-{[(2S)-1-methylpyrrolidin-2-yl]methoxy}quinazolin-4-yl]-2,7-diazaspiro[3.5]nonane-2-carboxylate (980 mg), (5-methyl-1H-indazol-4-yl)boronic acid (520 mg), Pd$_2$(dba)$_3$ (140 mg). SPhos (120 mg), tripotassium phosphate (1.1 g), 1,4-dioxane (15 mL), and water (1.2 mL) were mixed, and the mixture was stirred at 120° C. for 2 hours under microwave irradiation. Water was added to the reaction mixture and extracted with ethyl acetate. An organic layer was washed with a saturated aqueous sodium chloride solution, and then dried by anhydrous sodium sulfate. After concentrating the solution under reduced pressure, the obtained residue was purified by silica gel column chromatography (amino silica gel, hexane/ethyl acetate) so as to obtain tert-butyl 7-[6-cyclopropyl-8-(2,2-difluoroethoxy)-7-(5-methyl-1H-indazol-4-yl)-2-{[(2S)-1-methylpyrrolidin-2-yl]methoxy}quinazolin-4-yl]-2,7-diazaspiro[3.5]nonane-2-carboxylate (470 mg).

PREPARATION EXAMPLE 20

A mixture of 7-bromo-2,4,6-trichloro-8-fluoroquinazoline (30 g) and 1,4-dioxane (300 mL) was cooled in ice bath, then DIPEA (85 mL) and tert-butyl 2,7-diazaspiro[3.5]nonane-2-carboxylate (21 g) were added to the mixture in a nitrogen flow, and the mixture was stirred at room temperature for overnight. Water was added to the reaction mixture, and the mixture was stirred at room temperature for 1 hour. The precipitated solid was collected by filtration, washed with water, and then washed with hexane/ethyl acetate (4:1). The obtained solid was dried at 50° C. under reduced pressure so as to obtain tert-butyl 7-(7-bromo-2,6-dichloro-8-fluoroquinazolin-4-yl)-2,7-diazaspiro[3.5]nonane-2-carboxylate (47 g) as a solid.

PREPARATION EXAMPLE 21

A mixture of tert-butyl 7-(7-bromo-2,6-dichloro-8-fluoroquinazolin-4-yl)-2,7-diazaspiro[3.5]nonane-2-carboxylate (5.0 g), 1-methylpiperidin-4-ol (2.8 mL), DMF (50 mL), and cesium carbonate (11 g), and DABCO (160 mg) was stirred at room temperature for 3 days. Water was added to the reaction mixture and extracted with ethyl acetate. An organic layer was washed with a saturated aqueous sodium chloride solution, and then dried by anhydrous magnesium sulfate. After concentrating the solution under reduced pressure, the obtained residue was purified by silica gel column chromatography (amino silica gel, hexane-ethyl acetate) so as to obtain tert-butyl 7-{7-bromo-6-chloro-8-fluoro-2-[(1-methylpiperidin-4-yl)oxy]quinazolin-4-yl}-2,7-diazaspiro[3.5]nonane-2-carboxylate (4.9 g) as a solid.

PREPARATION EXAMPLE 22

Sodium ethoxide (830 mg) was added to a mixture of tert-butyl 7-{7-bromo-6-chloro-8-fluoro-2-[(1-methylpiperidin-4-yl)oxy]quinazolin-4-yl}-2,7-diazaspiro[3.5] nonane-2-carboxylate (4.9 g) and THF (100 mL), and the mixture was stirred at room temperature for 1 day. Sodium ethoxide (830 mg) was added to the reaction mixture, and the mixture was stirred at room temperature for 1 day. Water was added to the reaction mixture and extracted with ethyl acetate. An organic layer was washed with water and a saturated aqueous sodium chloride solution, and then dried by anhydrous magnesium sulfate. After concentrating the solution under reduced pressure, the obtained residue was purified by silica gel column chromatography (amino silica gel, hexane/ethyl acetate) so as to obtain tert-butyl 7-{7-bromo-6-chloro-8-ethoxy-2-[(1-methylpiperidin-4-yl)oxy]quinazolin-4-yl}-2,7-diazaspiro[3.5]nonane-2-carboxylate (3.8 g) as a solid.

PREPARATION EXAMPLE 23

A mixture of tert-butyl 7-{7-bromo-6-chloro-8-ethoxy-2-[(1-methylpiperidin-4-yl)oxy]quinazolin-4-yl}-2,7-diazaspiro[3.5]nonane-2-carboxylate (3.8 g), (5-methyl-1H-indazol-4-yl)boronic acid (1.6 g), Pd$_2$(dba)$_3$ (1.1 g), SPhos (1.0 g), 1,4-dioxane (60 mL), tripotassium phosphate (6.5 g), and water (15 mL) was stirred at 115° C. for 3 hours under the argon atmosphere. The reaction mixture was cooled to room temperature, then water was added, and the mixture was extracted with ethyl acetate. An organic layer was washed with a saturated aqueous sodium chloride solution, and then dried by anhydrous magnesium sulfate. After concentrating the solution under reduced pressure, the obtained residue was purified by silica gel column chromatography (chloroform/methanol). The obtained purified product was purified by silica gel column chromatography (amino silica gel, hexane/ethyl acetate). The obtained purified product was purified by silica gel column chromatography (chloroform/methanol) so as to obtain tert-butyl 7-{6-chloro-8-ethoxy-7-(5-methyl-1H-indazol-4-yl)-2-[(1-methylpiperidin-4-yl)oxy]quinazolin-4-yl}-2,7-diazaspiro[3.5]nonane-2-carboxylate (1.0 g) as a solid.

PREPARATION EXAMPLE 24

A mixture of tert-butyl 7-(6-chloro-8-ethoxy-7-(5-methyl-1H-indazol-4-yl)-2-[(1-methylpiperidin-4-yl)oxy]quinazolin-4-yl)-2,7-diazaspiro[3.5]nonane-2-carboxylate (1.0 g), 1,4-dioxane (12 mL), 4,4,5,5-tetramethyl-2-vinyl-1,3,2-dioxaborolane (1.3 mL), Pd$_2$(dba)$_3$ (140 mg), SPhos (180 mg), tripotassium phosphate (1.6 g), and water (3.0 mL) was stirred at 150° C. for 1.5 hours under microwave irradiation, 4,4,5,5-tetramethyl-2-vinyl-1,3,2-dioxaborolane (0.25 mL), Pd$_2$(dba)$_3$ (140 mg), and SPhos (180 mg) were added to the reaction mixture, and the mixture was stirred at 150° C. for 30 minutes under microwave irradiation, and further stirred at the same temperature for 30 minutes. Water was added to the reaction mixture and extracted with ethyl acetate. An organic layer was washed with a saturated aqueous sodium chloride solution, and then dried by anhydrous magnesium sulfate. After concentrating the solution under reduced pressure, the obtained residue was purified by silica gel column chromatography (chloroform/methanol). The obtained purified product was purified by silica gel column chromatography (amino silica gel, hexane/ethyl acetate) so as to obtain tert-butyl 7-{8-ethoxy-7-(5-methyl-1H-indazol-4-yl)-2-[(1-methylpiperidin-4-yl)oxy]-6-vinylquinazolin-4-yl}-2,7-diazaspiro[3.5]nonane-2-carboxylate (360 mg).

PREPARATION EXAMPLE 24-2

A mixture of tert-butyl 7-{7-bromo-8-ethoxy-2-[(1-methylpiperidin-4-yl)oxy]-6-vinylquinazolin-4-yl}-2,7-diazaspiro[3.5]nonane-2-carboxylate (5.7 g), (5-methyl-1H-indazol-4-yl)boronic acid (2.4 g), Pd$_2$(dba)$_3$ (850 mg), SPhos (760 mg), 1,4-dioxane (60 mL), tripotassium phosphate (10 g), and water (12 mL) was stirred at 120° C. for 4 hours under the argon atmosphere. After the reaction mixture was cooled to room temperature, ethyl acetate and a saturated aqueous sodium chloride solution were added to the reaction mixture, and an insoluble material was separated by filtration. The filtrate was extracted with ethyl acetate. An organic layer was dried by anhydrous magnesium sulfate. After concentrating the solution under reduced pressure, the obtained residue was purified by silica gel column chromatography (chloroform/methanol/28% ammonia water). Acetonitrile was added to the obtained purified product, and then the mixture was stirred at room temperature for 6 hours. The precipitated solid was collected by filtration so as to obtain tert-butyl 7-{8-ethoxy-7-(5-methyl-1H-indazol-4-yl)-2-[(1-methylpiperidin-4-yl)oxy]-6-vinylquinazolin-4-yl}-2,7-diazaspiro[3.5]nonane-2-carboxylate (2.2 g) as a solid.

PREPARATION EXAMPLE 28

A trifluoroacetic acid (hereinafter, abbreviated as TFA) (5.0 mL) was added to a mixture of tert-butyl 7-{8-(cyclobutyloxy)-6-cyclopropyl-2-[(1-methylpiperidin-4-yl)oxy]-7-[5-methyl-1-(tetrahydro-2H-pyran-2-yl)-1H-indazol-4-yl]quinazolin-4-yl}-2,7-diazaspiro[3.5]nonane-2-carboxylate (540 mg) and dichloromethane (10 mL), and the mixture was stirred at room temperature for 4 hours. Toluene was added to the reaction mixture, and the mixture was concentrated under reduced pressure. The obtained residue was purified by silica gel column chromatography (chloroform/methanol/28% ammonia water) so as to obtain 8-(cyclobutyloxy)-6-cyclopropyl-4-(2,7-diazaspiro[3.5]non-7-yl)-7-(5-methyl-1H-indazol-4-yl)-2-[(1-methylpiperidin-4-yl)oxy]quinazoline (310 mg) as a solid.

PREPARATION EXAMPLE 33

TFA (1.0 mL) was added to a mixture of tert-butyl 7-{8-ethoxy-2-[(1-ethylpiperidine-4-yl)oxy]-7-(5-methyl-1H-indazol-4-yl)-6-vinylquinazolin-4-yl}-2,7-diazaspiro[3.5]nonane-2-carboxylate (560 mg) and dichloromethane (1.0 mL), and the mixture was stirred at room temperature for 1 hour. After concentrating the reaction mixture under reduced pressure, the obtained residue was purified by silica gel column chromatography (octadecylsilyl (hereinafter, abbreviated as ODS) silica gel, water/acetonitrile/TFA). A saturated aqueous sodium hydrogen carbonate solution and water were added to the obtained purified product, a mixture was extracted with chloroform/methanol (4:1), and an organic layer was dried with anhydrous magnesium sulfate. The solvent was evaporated under reduced pressure so as to obtain 4-(2,7-diazaspiro[3.5]non-7-yl)-8-ethoxy-2-[(1-ethylpiperidin-4-yl)oxy]-7-(5-methyl-1H-indazol-4-yl)-6-vinylquinazoline (370 mg).

PREPARATION EXAMPLE 34

After a mixture of 3-bromo-5-fluoro-2,4-dimethylaniline (1.1 g), 12M hydrochloric acid (6.0 mL), and water (4.0 mL) was cooled in ice bath, a mixture of sodium nitrite (380 mg) and water (4.0 mL) was added dropwise to the mixture, and the mixture was stirred at the same temperature for 30 minutes. 12M hydrochloric acid (2.0 mL) was added to the reaction mixture, and the mixture was stirred at the same temperature for 1 hour. Sodium tetrafluoroborate (720 mg) was added to the reaction mixture, and the mixture was stirred at the same temperature for 1 hour. The precipitated solid was collected by filtration, washed with cold water, and then air-dried so as to obtain a solid (solid A). A mixture of potassium acetate (670 mg), 1,4,7,10,13,16-hexaoxacyclooctadecane (47 mg), and chloroform (44 mL) were added to a solid A, and the mixture was stirred at room temperature for 5 hours. After an insoluble material was separated by filtration, a filtrate was washed with a saturated aqueous sodium chloride solution, and dried by anhydrous magnesium sulfate. After concentrating the solution under reduced pressure, the obtained residue was purified by silica gel column chromatography (hexane/ethyl acetate) so as to obtain 4-bromo-6-fluoro-5-methyl-1H-indazole (240 mg) as a solid.

PREPARATION EXAMPLE 35

3,4-dihydro-2H-pyran (0.24 mL) and p-toluenesulfonic acid monohydrate (40 mg) were added to a mixture of 4-bromo-6-fluoro-5-methyl-1H-indazole (240 mg) and dichloromethane (10 mL), and the mixture was stirred at room temperature for 2 hours. After the reaction mixture was cooled in ice bath, a saturated aqueous sodium hydrogen carbonate solution was added to the reaction mixture, and the reaction mixture was extracted with chloroform. An organic layer was dried by anhydrous magnesium sulfate, and then a solution was concentrated under reduced pressure. The obtained residue was purified by silica gel column chromatography (hexane/ethyl acetate) so obtain 4-bromo-6-fluoro-5-methyl-1-(tetrahydro-2H-pyran-2-yl)-1H-indazole (350 mg) as an oil.

PREPARATION EXAMPLE 36

Potassium acetate (310 mg) and PdCl$_2$(dppf).CH$_2$Cl$_2$ (68 mg) were added to a mixture of 4-bromo-6-fluoro-5-methyl-1-(tetrahydro-2H-pyran-2-yl)-1H-indazole (330 mg), 4,4,4',4',5,5,5',5'-octamethyl-2,2'-bi-1,3,2-dioxaborolane (320 mg), and 1,4-dioxane (7.0 mL), and the mixture was stirred at 100° C. for 3 hours under the argon atmosphere. The reaction mixture was cooled to room temperature, then ethyl acetate was added, and an insoluble material was separated by filtration. After concentrating the filtrate under reduced pressure, the obtained residue was purified by silica gel column chromatography (hexane/ethyl acetate) so as to obtain 6-fluoro-5-methyl-1-(tetrahydro-2H-pyran-2-yl)-4-(4,4,5,5-tetramethyl-1,3,2-dioxaborolan-2-yl)-1H-indazole (220 mg) as an oil.

PREPARATION EXAMPLE 39

A mixture of tert-butyl 7-{7-bromo-6-chloro-2-[(1-ethylpiperidin-4-yl)oxy]-8-fluoroquinazolin-4-yl}-2,7-diazaspiro[3.5]nonane-2-carboxylate (2.5 g), 2,2,2-trifluoroethanol (0.59 mL), cesium carbonate (2.7 g), and DMF (25 mL) was stirred at room temperature under the argon atmosphere for 3 days. Water was added to the reaction mixture, the mixture was stirred at room temperature for 10 minutes, and then the precipitated solid was collected by filtration. The obtained solid was dissolved in dichloromethane, dried by anhydrous magnesium sulfate, and then a solution was concentrated under reduced pressure. The obtained residue was purified by silica gel column chromatography (amino silica gel, hexane/ethyl acetate) so as to obtain tert-butyl 7-{7-bromo- 6-chloro-2-[(1-ethylpiperidin-4-yl)oxy]-8-(2,2,2-trifluoroethoxy)quinazolin-4-yl}-2,7-diazaspiro[3.5]nonane-2-carboxylate (2.4 g).

PREPARATION EXAMPLE 94

Potassium carbonate (5.5 g) and PdCl$_2$(dppf)·CH$_2$Cl$_2$ (1.1 g) were added to a mixture of tert-butyl 7-{7-bromo-8-ethoxy-6-iodo-2-[(1-methylpiperidin-4-yl)oxy]quinazolin-4-yl}-2,7-diazaspiro[3.5]nonane-2-carboxylate (9.5 g), 4,4,5,5-tetramethyl-2-vinyl-1,3,2-dioxaborolane (4.5 mL), 1,4-dioxane (100 mL), and water (10 mL), and the mixture was stirred at 80° C. for 1 hour under the argon atmosphere. After the reaction mixture was cooled to room temperature, ethyl acetate, a saturated aqueous sodium chloride solution, and celite were added to the reaction mixture, and the reaction mixture was stirred at room temperature for 10 minutes. An insoluble material was separated by filtration, then a filtrate was extracted with ethyl acetate, and an organic layer was dried with anhydrous magnesium sulfate. After concentrating the solution under reduced pressure, the obtained residue was purified by silica gel column chromatography (amino silica gel, hexane/ethyl acetate) so as to obtain tert-butyl 7-{7-bromo-8-ethoxy-2-[(1-methylpiperidin-4-yl)oxy]-6-vinylquinazolin-4-yl}-2,7-diazaspiro[3.5]nonane-2-carboxylate (6.8 g) as a solid.

PREPARATION EXAMPLE 95

A mixture of tert-butyl 7-(7-bromo-2-chloro-8-fluoro-6-iodoquinazolin-4-yl)-2,7-diazaspiro[3.5]nonane-2-carboxylate (8.1 g), 1-(2-methoxyethyl)piperidin-4-ol (5.3 g), cesium carbonate (13 g), DABCO (220 mg), DMF (65 mL), and THF (65 mL) was stirred at room temperature for 3 days under the argon atmosphere. Water was added to the reaction mixture and extracted with ethyl acetate. An organic layer was washed with a saturated aqueous sodium chloride solution, and then dried by anhydrous magnesium sulfate. After concentrating the solution under reduced pressure, the obtained residue was purified by silica gel column chromatography (amino silica gel, hexane/ethyl acetate) so as to obtain tert-butyl 7-(7-bromo-8-fluoro-6-iodo-2-{[1-(2-methoxyethyl)piperidin-4-yl]oxy}quinazolin-4-yl)-2,7-diazaspiro[3.5]nonane-2-carboxylate (7.9 g).

PREPARATION EXAMPLE 96

A mixture of tert-butyl 7-(7-bromo-8-fluoro-6-iodo-2-{[1-(2-methoxyethyl)piperidin-4-yl]oxy}quinazolin-4-yl)-2,7-diazaspiro[3.5]nonane-2-carboxylate (3.8 g), 2,2,2-trifluoroethanol (0.75 mL), cesium carbonate (3.4 g), and DMF (40 mL) was stirred at room temperature for 20 hours under the argon atmosphere. 2,2,2-trifluoroethanol (0.40 mL) and cesium carbonate (1.7 g) were added to the reaction mixture, and the mixture was stirred at room temperature for 24 hours under the argon atmosphere. Water was added to the reaction mixture, and the mixture was stirred at room temperature for 10 minutes. The precipitated solid was collected by filtration, then chloroform/methanol (9:1) was added thereto, and the obtained solution was dried with anhydrous magnesium sulfate. After concentrating the solution under reduced pressure, the obtained residue was purified by silica gel column chromatography (amino silica gel, hexane/ethyl acetate) so as to obtain tert-butyl 7-[7-bromo-6-iodo-2-{[1-(2-methoxyethyl)piperidin-4-yl]oxy}-8-(2,2,2-trifluoroethoxy)quinazolin-4-yl]-2,7-diazaspiro[3.5]nonane-2-carboxylate (3.1 g) as a solid.

PREPARATION EXAMPLE 99

Potassium carbonate (1.5 g) and PdCl$_2$(dppf)·CH$_2$Cl$_2$ (30 mg) were added to a mixture of tert-butyl 7-[7-bromo-6-iodo-2-({[1-(2-methoxyethyl)piperidin-4-yl]oxy}-8-(2,2,2-trifluoroethoxy)quinazolin-4-yl]-2,7-diazaspiro[3.5]nonane-2-carboxylate (3.0 g), potassium vinyltrifluoroborate (640 mg), 1,4-dioxane (30 mL), and water (3.0 mL), and the mixture was stirred at 50° C. for 2 hours under a nitrogen atmosphere. PdCl$_2$(dppf)·CH$_2$Cl$_2$ (150 mg) was added to the reaction mixture, and the mixture was stirred at 60° C. for 4 hours under a nitrogen atmosphere. The reaction mixture was cooled to room temperature, then ethyl acetate and water were added thereto. An insoluble material was separated by filtration, and a filtrate was extracted with ethyl acetate. An organic layer was dried by anhydrous magnesium sulfate, and then a solution was concentrated under reduced pressure. The obtained residue was purified by silica gel column chromatography (amino silica gel, hexane/ethyl acetate) so as to obtain tert-butyl 7-[7-bromo-2-{[1-(2-methoxyethyl)piperidin-4-yl]oxy}-8-(2,2,2-trifluoroethoxy)-6-vinylquinazolin-4-yl]-2,7-diazaspiro[3.5]nonane-2-carboxylate (2.2 g).

PREPARATION EXAMPLE 100

(5-methyl-1H-indazol-4-yl)boronic acid (490 mg), Pd$_2$(dba)$_3$ (130 mg), and SPhos (120 mg) were added to a mixture of tert-butyl 7-[7-bromo-2-{[1-(2-methoxyethyl)piperidin-4-yl]oxy}-8-(2,2,2-trifluoroethoxy)-6-vinylquinazolin-4-yl]-2,7-diazaspiro[3.5]nonane-2-carboxylate (1.0 g), tripotassium phosphate (900 mg), 1,4-dioxane (10 mL), and water (2.0 mL), and the mixture was stirred at 130° C. for 4 hours under the argon atmosphere. The reaction mixture was cooled to room temperature, then ethyl acetate and water were added thereto. An insoluble material was separated by filtration, and a filtrate was extracted with ethyl acetate. An organic layer was dried by anhydrous magnesium sulfate, and then a solution was concentrated under reduced pressure. The obtained residue was purified by silica gel column chromatography (chloroform/methanol/28% ammonia water). The obtained purified product was purified by silica gel column chromatography (amino silica gel, hexane/ethyl acetate). Acetonitrile was added to the obtained solid, and then the mixture was stirred at room temperature. The precipitated solid was collected by filtration so as to obtain tert-butyl 7-[2-{[1-(2-methoxyethyl)piperidin-4-yl]oxy}-7-(5-methyl-1H-indazol-4-yl)-8-(2,2,2-trifluoroethoxy)-6-vinylquinazolin-4-yl]-2,7-diazaspiro[3.5]nonane-2-carboxylate (630 mg) as a solid.

PREPARATION EXAMPLE 101

A mixture of tert-butyl 7-(7-bromo-2-chloro-8-fluoro-6-iodoquinazolin-4-yl)-2,7-diazaspiro[3.5]nonane-2-carboxylate (9.5 g), 1-(3-methoxypropyl)piperidin-4-ol (6.8 g), cesium carbonate (15 g), DABCO (260 mg), DMF (76 mL), and THF (76 mL) was stirred at room temperature for overnight under the argon atmosphere. Water was added to the reaction mixture and extracted with ethyl acetate. An organic layer was washed with a saturated aqueous sodium chloride solution, and then dried by anhydrous magnesium sulfate. After concentrating the solution under reduced pressure, diisopropyl ether was added to the obtained solid, and the mixture was stirred at room temperature. The solid was collected by filtration, and dried at 50° C. under reduced pressure so as to obtain tert-butyl 7-(7-bromo-8-fluoro-6- iodo-2-{[1-(3-methoxypropyl)piperidin-4-yl]oxy}quinazolin-4-yl)-2,7-diazaspiro[3.5]nonane-2-carboxylate (9.1 g) as a solid.

PREPARATION EXAMPLE 102

A mixture of tert-butyl 7-(7-bromo-8-fluoro-6-iodo-2-{[1-(3-methoxypropyl)piperidin-4-yl]oxy}quinazolin-4-yl)-2,7-diazaspiro[3.5]nonane-2-carboxylate (5.0 g), 2,2,2-trifluoroethanol (1.4 mL), cesium carbonate (6.5 g), and DMF (50 mL) was stirred at room temperature for 5 hours. The reaction mixture was stirred at 50° C. for 1.5 hours. The reaction mixture was cooled to room temperature, then water was added, and the mixture was extracted with ethyl acetate. An organic layer was washed with water and a saturated aqueous sodium chloride solution, and then dried by anhydrous magnesium sulfate. After concentrating the solution under reduced pressure, the obtained residue was purified by silica gel column chromatography (amino silica gel, hexane/ethyl acetate) so as to obtain tert-butyl 7-[7-bromo-6-iodo-2-{[1-(3-methoxypropyl)piperidin-4-yl]oxy}-8-(2,2,2-trifluoroethoxy)quinazolin-4-yl]-2,7-diazaspiro[3.5]nonane-2-carboxylate (5.5 g).

PREPARATION EXAMPLE 105

A mixture of tert-butyl 7-[7-bromo-6-iodo-2-{[1-(3-methoxypropyl)piperidin-4-yl]oxy}-8-(2,2,2-trifluoroethoxy)quinazolin-4-yl]-2,7-diazaspiro[3.5]nonane-2-carboxylate (2.7 g), cyclopropylboronic acid (560 mg), tripotassium phosphate (2.5 g), PdCl$_2$(dppf).CH$_2$Cl$_2$ (270 mg), 1,4-dioxane (20 mL), acetonitrile (20 mL), and water (8.6 mL) was stirred at 100° C. for 4 hours under the argon atmosphere. After the reaction mixture was cooled to room temperature, a saturated aqueous sodium chloride solution was added to the reaction mixture, and the mixture was extracted with ethyl acetate. An organic layer was dried by anhydrous magnesium sulfate, and then a solution was concentrated under reduced pressure. The obtained residue was purified by silica gel column chromatography (amino silica gel, hexane/ethyl acetate) so as to obtain tert-butyl 7-[7-bromo-6-cyclopropyl-2-({[1-(3-methoxypropyl)piperidin-4-yl]oxy}-8-(2,2,2-trifluoroethoxy)quinazolin-4-yl]-2,7-diazaspiro[3.5]nonane-2-carboxylate (1.9 g).

PREPARATION EXAMPLE 106

Under the argon atmosphere, tert-butyl 7-[7-bromo-6-cyclopropyl-2-{[1-(3-methoxypropyl)piperidin-4-yl]oxy}-8-(2,2,2-trifluoroethoxy)quinazolin-4-yl]-2,7-diazaspiro[3.5]nonane-2-carboxylate (1.9 g), (5-methyl-1H-indazol-4-yl)boronic acid (710 mg). Pd$_2$(dba)$_3$ (230 mg), SPhos (210 mg), tripotassium phosphate (2.2 g), 1,4-dioxane (15 mL), and water (2.8 mL) were mixed, and the mixture was stirred at 120° C. for 70 minutes under microwave irradiation. After concentrating the reaction mixture under reduced pressure, the obtained residue was purified by silica gel column chromatography (amino silica gel, hexane/ethyl acetate). Acetonitrile was added to the obtained purified product, and then the mixture was stirred at room temperature for 30 minutes. The precipitated solid was collected by filtration so as to obtain tert-butyl 7-[6-cyclopropyl-2-{[1-(3-methoxypropyl)piperidin-4-yl]oxy}-7-(5-methyl-1H-indazol-4-yl)-8-(2,2,2-trifluoroethoxy)quinazolin-4-yl]-2,7-diazaspiro[3.5]nonane-2-carboxylate (630 mg) as a solid.

PREPARATION EXAMPLE 111

A mixture of tert-butyl 7-(7-bromo-2-chloro-8-fluoro-6-iodoquinazolin-4-yl)-2,7-diazaspiro[3.5]nonane-2-carboxylate (4.5 g), 1-(tetrahydro-2H-pyran-4-yl)piperidin-4-ol (4.1 g), cesium carbonate (7.2 g). DABCO (120 mg), DMF (45 mL), and THF (45 mL) was stirred at room temperature for 16 hours. Water was added to the reaction mixture and extracted with ethyl acetate. An organic layer was washed with a saturated aqueous sodium chloride solution, and then dried by anhydrous magnesium sulfate. After concentrating the solution under reduced pressure, the obtained residue was purified by silica gel column chromatography (hexane/ethyl acetate, and then chloroform/methanol/28% ammonia water). The obtained purified product was purified by silica gel column chromatography (amino silica gel, hexane/ethyl acetate) so as to obtain tert-butyl 7-(7-bromo-8-fluoro-6-iodo-2-{[1-(tetrahydro-2H-pyran-4-yl)piperidin-4-yl]oxy}quinazolin-4-yl)-2,7-diazaspiro[3.5]nonane-2-carboxylate (5.2 g) as a solid.

PREPARATION EXAMPLE 112

A mixture of tert-butyl 7-(7-bromo-8-fluoro-6-iodo-2-{[1-(tetrahydro-2H-pyran-4-yl)piperidin-4-yl]oxy}quinazolin-4-yl)-2,7-diazaspiro[3.5]nonane-2-carboxylate (5.2 g), 2,2,2-trifluoroethanol (1.5 mL), cesium carbonate (6.7 g), and DMF (50 mL) was stirred at 50° C. for overnight. The reaction mixture was cooled to room temperature, then water was added, and the mixture was extracted with ethyl acetate. An organic layer was washed with water and a saturated aqueous sodium chloride solution, and then dried by anhydrous magnesium sulfate. After concentrating the solution under reduced pressure, the obtained residue was purified by silica gel column chromatography (amino silica gel, hexane/ethyl acetate). Diisopropyl ether was added to the obtained solid, and the mixture was stirred at room temperature for 1 hour. The solid was collected by filtration so as to obtain tert-butyl 7-[7-bromo-6-iodo-2-{[1-(tetrahydro-2H-pyran-4-yl)piperidin-4-yl]oxy}-8-(2,2,2-trifluoroethoxy)quinazolin-4-yl]-2,7-diazaspiro[3.5]nonane-2-carboxylate (4.1 g) as a solid.

PREPARATION EXAMPLE 113

Potassium carbonate (740 mg) and PdCl$_2$(dppf).CH$_2$Cl$_2$ (15 mg) were added to a mixture of tert-butyl 7-[7-bromo-6-iodo-2-{[1-(tetrahydro-2H-pyran-4-yl)piperidin-4-yl]oxy}-8-(2,2,2-trifluoroethoxy)quinazolin-4-yl]-27-diazaspiro[3.5]nonane-2-carboxylate (1.5 g), potassium vinyltrifluoroborate (290 mg), 1,4-dioxane (15 mL), and water (1.5 mL), and the mixture was stirred at 40° C. for 18 hours under the argon atmosphere. After the reaction mixture was cooled to room temperature, ethyl acetate, water and a saturated aqueous sodium chloride solution were added to the reaction mixture. An insoluble material was separated by filtration, and a filtrate was extracted with ethyl acetate. An organic layer was washed with water and a saturated aqueous sodium chloride solution, and then dried by anhydrous magnesium sulfate. After concentrating the solution under reduced pressure, the obtained residue was purified by silica gel column chromatography (amino silica gel, hexane/ethyl acetate). Diisopropyl ether was added to the obtained solid, and the mixture was stirred at room temperature for 1 hour. The solid was collected by filtration so as to obtain tert-butyl 7-[7-bromo-2-{[1-(tetrahydro-2H-pyran-4-yl)piperidin-4-yl]oxy}-8-(2,2,2-trifluoroethoxy)-6-vinylquinazolin-4-yl]-2,7-diazaspiro[3.5]nonane-2-carboxylate (940 mg) as a solid.

PREPARATION EXAMPLE 114

Pd$_2$(dba)$_3$ (120 mg), and SPhos (110 mg) were added to a mixture of tert-butyl 7-[7-bromo-2-{[1-(tetrahydro-2H- pyran-4-yl)piperidin-4-yl]oxy}-8-(2,2,2-trifluoroethoxy)-6-vinylquinazolin-4-yl]-2,7-diazaspiro[3.5]nonane-2-carboxylate (940 mg). (5-methyl-1H-indazol-4-yl)boronic acid (330 mg), tripotassium phosphate (1.3 g), 1,4-dioxane (10 mL), and water (2.0 mL), and the mixture was stirred at 120° C. for 4 hours under the argon atmosphere. After the reaction mixture was cooled to room temperature, ethyl acetate, water, and a saturated aqueous sodium chloride solution were added to the reaction mixture. An insoluble material was separated by filtration, and a filtrate was extracted with ethyl acetate. An organic layer was dried by anhydrous magnesium sulfate, and then a solution was concentrated under reduced pressure. The obtained residue was purified by silica gel column chromatography (amino silica gel, hexane/ethyl acetate). Acetonitrile was added to the obtained solid, and then the mixture was stirred at room temperature for 5 hours. The precipitated solid was collected by filtration so as to obtain tert-butyl 7-[7-(5-methyl-1H-indazol-4-yl)-2-{([1-(tetrahydro-2H-pyran-4-yl)piperidin-4-yl]oxy}-8-(2,2,2-trifluoroethoxy)-6-vinylquinazolin-4-yl]-2,7-diazaspiro[3.5]nonane-2-carboxylate (610 mg) as a solid.

PREPARATION EXAMPLE 115

2-(trimethylsilyl)ethyl 4-hydroxypiperidine-1-carboxylate (1.0 g), cesium carbonate (2.7 g), and DABCO (31 mg) were added to a mixture of tert-butyl 7-(7-bromo-2-chloro-8-fluoro-6-iodoquinazolin-4-yl)-2,7-diazaspiro[3.5]nonane-2-carboxylate (1.7 g), DMF (5.0 mL), and THF (5.0 mL), and the mixture was stirred at room temperature for 16 hours under the argon atmosphere. 2,2,2-trifluoroethanol (0.60 mL) and cesium carbonate (1.8 g) were added to the reaction mixture, and the mixture was stirred at room temperature for 3 days. Water was added to the reaction mixture, and the mixture was stirred at room temperature for 2 hours. The precipitated solid was collected by filtration so as to obtain tert-butyl 7-{7-bromo-6-iodo-8-(2,2,2-trifluoroethoxy)-2-{[1-([2-(trimethylsilyl)ethoxy]carbonyl}piperidin-4-yl)oxy]quinazolin-4-yl}-2,7-diazaspiro[3.5]nonane-2-carboxylate (2.7 g) as a solid.

PREPARATION EXAMPLE 118

Tetrabutylammonium fluoride (1M THF solution, 3.6 mL) was added dropwise to a mixture of tert-butyl 7-{7-[5-methyl-1-(tetrahydro-2H-pyran-2-yl)-1H-indazol-4-yl]-8-(2,2,2-trifluoroethoxy)-2-[(1-{[2-(trimethylsilyl)ethoxy]carbonyl}piperidin-4-yl)oxy]-6-vinylquinazolin-4-yl}-2,7-diazaspiro[3.5]nonane-2-carboxylate (1.7 g) and THF (25 mL), and the mixture was stirred at 50° C. for 5 hours. The reaction mixture was cooled to room temperature, and then was concentrated under reduced pressure. Ethyl acetate was added to the obtained residue, and the mixture was washed with water and a saturated aqueous sodium chloride solution. An organic layer was dried by anhydrous magnesium sulfate, and then a solution was concentrated under reduced pressure so as to obtain tert-butyl 7-{7-[5-methyl-1-(tetrahydro-2H-pyran-2-yl)-1H-indazol-4-yl]-2-(piperidin-4-yloxy)-8-(2,2,2-trifluoroethoxy)-6-vinylquinazolin-4-yl}-2,7-diazaspiro[3.5]nonane-2-carboxylate (1.3 g).

PREPARATION EXAMPLE 119 tert-butyl 7-{7-[5-methyl-1-(tetrahydro-2H-pyran-2-yl)-1H-indazol-4-yl]-2-(piperidin-4-yloxy)-8-(2,2,2-trifluoroethoxy)-6-vinylquinazolin-4-yl}-2,7-diazaspiro[3.5]nonane-2-carboxylate (500 mg), 2,2-dimethyloxirane (68 µL), triethylamine (0.18 mL), and ethanol (4.0 mL) were mixed, and the mixture was stirred at 80° C. for 30 minutes under microwave irradiation. The reaction mixture was stirred at 100° C. for 30 minutes under microwave irradiation. 2,2-dimethyloxirane (28 µL) was added to the reaction mixture, and the mixture was stirred at 100° C. for 1 hour under microwave irradiation. The reaction mixture was stirred at 120° C. for 1 hour under microwave irradiation. Water was added to the reaction mixture and extracted with ethyl acetate. An organic layer was washed with a saturated aqueous sodium chloride solution, and then dried by anhydrous magnesium sulfate. After concentrating the solution under reduced pressure, the obtained residue was purified by silica gel column chromatography (chloroform/methanol). The obtained purified product was purified by silica gel column chromatography (amino silica gel, hexane/ethyl acetate) so as to obtain tert-butyl 7-[2-{[1-(2-hydroxy-2-methylpropyl)piperidin-4-yl]oxy}-7-[5-methyl-1-(tetrahydro-2H-pyran-2-yl)-1H-indazol-4-yl]-8-(2,2,2-trifluoroethoxy)-6-vinylquinazolin-4-yl]-2,7-diazaspiro[3.5]nonane-2-carboxylate (450 mg).

PREPARATION EXAMPLE 132

A mixture of 2,2,6,6-tetramethylpiperidine (4.3 mL) and THF (50 mL) was cooled to −70° C., then n-butyllithium (1.6M hexane solution, 16 mL) was added dropwise to the mixture under the argon atmosphere, and the mixture was stirred at the same temperature for 10 minutes. A mixture of 1-bromo-4,5-difluoro-2-methylbenzene (5.0 g) and THF (25 mL) was added dropwise to the reaction mixture, and the mixture was stirred at the same temperature for 2 hours. After DMF (2.0 mL) was added to the reaction mixture, the temperature of the reaction mixture was raised to −20° C. 1M hydrochloric acid was added dropwise to the reaction mixture, and the reaction mixture was extracted with diethyl ether. An organic layer was washed with 1M hydrochloric acid and a saturated aqueous sodium chloride solution, and then dried by anhydrous magnesium sulfate. A solvent was evaporated under reduced pressure so as to obtain 2-bromo-5,6-difluoro-3-methylbenzaldehyde (5.2 g) as a solid.

PREPARATION EXAMPLE 133

O-methylhydroxylamine hydrochloride (2.2 g) was added to a mixture of 2-bromo-5,6-difluoro-3-methylbenzaldehyde (5.2 g), potassium carbonate (3.9 g), and 1,2-dimethoxyethane (25 mL), and the mixture was stirred at room temperature for 3 days. An insoluble material was separated by filtration and a filtrate was concentrated under reduced pressure. The obtained residue was purified by silica gel column chromatography (hexane/ethyl acetate). Hydrazine monohydrate (20 mL) was added to a mixture of the obtained oil (4.2 g) and 1,2-dimethoxyethane (20 mL), and the mixture was stirred at 100° C. for 20 hours. After the reaction mixture was cooled to room temperature, ethyl acetate was added to the reaction mixture, and the mixture was washed with a saturated aqueous sodium chloride solution. An organic layer was dried by anhydrous magnesium sulfate, and then a solvent was evaporated under reduced pressure so as to obtain 4-bromo-7-fluoro-5-methyl-1H-indazole (3.6 g) as a solid.

PREPARATION EXAMPLE 136

Potassium carbonate (3.0 g) and $PdCl_2(dppf)\cdot CH_2Cl_2$ (580 mg) were added to a mixture of 5-bromo-4-chloro-1-

(tetrahydro-2H-pyran-2-yl)-1H-indazole (2.3 g), trivinylboroxine/pyridine (1:1) (1.4 g), 1,4-dioxane (22 mL), and water (4.5 mL), and the mixture was stirred at 70° C. for 15 hours under a nitrogen atmosphere. The reaction mixture was cooled to room temperature, then ethyl acetate and water were added, and an insoluble material was separated by filtration. After extracting the filtrate with ethyl acetate, an organic layer was washed with a saturated aqueous sodium chloride solution, and then dried by anhydrous magnesium sulfate. After concentrating the solution under reduced pressure, the obtained residue was purified by silica gel column chromatography (hexane/ethyl acetate) so as to obtain 4-chloro-1-(tetrahydro-2H-pyran-2-yl)-5-vinyl-1H-indazole (1.6 g) as a solid.

PREPARATION EXAMPLE 137

Potassium acetate (720 mg), palladium acetate (26 mg), and dicyclohexyl(2',4',6'-triisopropylbiphenyl-2-yl)phosphine (120 mg) were added to a mixture of 4-chloro-1-(tetrahydro-2H-pyran-2-yl)-5-vinyl-1H-indazole (630 mg), 4,4,4',4',5,5,5',5'-octamethyl-2,2'-bi-1,3,2-dioxaborolane (1.0 g), and 1,4-dioxane (6.0 mL), and the mixture was stirred at 100° C. for 15 hours under a nitrogen atmosphere. The reaction mixture was cooled to room temperature, then ethyl acetate was added, and an insoluble material was separated by filtration. After concentrating the filtrate under reduced pressure, the obtained residue was purified by silica gel column chromatography (hexane/ethyl acetate) so as to obtain 1-(tetrahydro-2H-pyran-2-yl)-4-(4,4,5,5-tetramethyl-1,3,2-dioxaborolan-2-yl)-5-vinyl-1H-indazole (390 mg) as an oil.

PREPARATION EXAMPLE 138

4,4,4',4',5,5,5',5'-octamethyl-2,2'-bi-1,3,2-dioxaborolane (720 mg), potassium acetate (700 mg), and PdCl$_2$(dppf).CH$_2$Cl$_2$ (190 mg) were added to a mixture of 7-bromo-6-methyl-1H-indazole (500 mg) and 1,4-dioxane (8.0 mL), and the mixture was stirred at 100° C. for 18 hours under the argon atmosphere. The reaction mixture was cooled to room temperature, then ethyl acetate and water were added, and an insoluble material was separated by filtration. After extracting the filtrate with ethyl acetate, an organic layer was washed with a saturated aqueous sodium chloride solution, and then dried by anhydrous sodium sulfate. After concentrating the solution under reduced pressure, the obtained residue was purified by silica gel column chromatography (hexane/ethyl acetate) so as to obtain 6-methyl-7-(4,4,5,5-tetramethyl-1,3,2-dioxaborolan-2-yl)-1H-indazole (350 mg) as a solid.

PREPARATION EXAMPLE 139

1-({[2-(trimethylsilyl)ethoxy]carbonyl}oxy)pyrrolidine-2,5-dione (4.0 g) was added to a mixture of methyl piperidin-4-ylacetate hydrochloride (3.0 g), triethylamine (5.4 mL), and DMF (15 mL), and the mixture was stirred at room temperature for 30 minutes. Water was added to the reaction mixture and extracted with ethyl acetate/hexane (10:1). An organic layer was washed with 1M aqueous sodium hydroxide solution, 1M hydrochloric acid, and a saturated aqueous sodium chloride solution, and then dried by anhydrous magnesium sulfate. The solvent was evaporated under reduced pressure so as to obtain 2-(trimethylsilyl)ethyl 4-(2-methoxy-2-oxoethyl)piperidine-1-carboxylate (4.7 g) as an oil.

PREPARATION EXAMPLE 140

1M aqueous sodium hydroxide solution (31 mL) was added to 2-(trimethylsilyl)ethyl 4-(2-methoxy-2-oxoethyl)piperidine-1-carboxylate (4.7 g) and methanol (23 mL), and the mixture was stirred at room temperature for 3 hours. After the reaction mixture was concentrated under reduced pressure, 1M hydrochloric acid (31 mL) was added to the reaction mixture, and then extracted with chloroform. An organic layer was dried by anhydrous magnesium sulfate. The solvent was evaporated under reduced pressure so as to obtain (1-{[2-(trimethylsilyl)ethoxy]carbonyl}piperidin-4-yl)acetic acid (4.2 g) as a solid.

PREPARATION EXAMPLE 141

1,3-difluoropropan-2-yl p-toluenesulfonate (13 g) was added to a mixture of piperidin-4-ol (5.0 g), potassium iodide (1.6 g), potassium carbonate (13 g), and DMF (40 mL), and the mixture was stirred at 70° C. for 16 hours. The reaction mixture was cooled to room temperature, and an insoluble material was separated by filtration. After concentrating the filtrate under reduced pressure, the obtained residue was purified by silica gel column chromatography (amino silica gel, hexane/ethyl acetate) so as to obtain 1-(1,3-difluoropropan-2-yl)piperidin-4-ol (5.0 g) as an oil.

PREPARATION EXAMPLE 142

A mixture of 2-amino-4-bromo-3-fluoro-5-iodobenzoic acid (1.0 g), 1H-benzotriazole-1-ol (450 mg), 1-(3-dimethylaminopropyl)-3-ethylcarbodiimide hydrochloride (640 mg), and DMF (5.0 mL) was stirred at room temperature for 30 minutes. 28% ammonia water (0.28 mL) was added to the reaction mixture, and the mixture was stirred at room temperature for 1.5 hours. A saturated aqueous sodium hydrogen carbonate solution was added to the reaction mixture, and the mixture was stirred at room temperature. The precipitated solid was collected by filtration, and washed with water, and the obtained solid was dried at 50° C. under reduced pressure so as to obtain 2-amino-4-bromo-3-fluoro-5-iodobenzamide (1.0 g) as a solid.

PREPARATION EXAMPLE 143

1,1'-carbonyldiimidazole (920 mg) was added to a mixture of 2-amino-4-bromo-3-fluoro-5-iodobenzamide (1.0 g), potassium carbonate (1.0 g), and DMF (5.0 mL), and the mixture was stirred at room temperature for 30 minutes. 1,1'-carbonyldiimidazole (1.4 g) was added to the reaction mixture, and the mixture was stirred at room temperature for 30 minutes. Water and 1M hydrochloric acid were added to the reaction mixture, and the mixture was stirred at room temperature for 2 hours. The precipitated solid was collected by filtration, washed with water, and dried at 50° C. under reduced pressure so as to obtain 7-bromo-8-fluoro-6-iodoquinazoline-2,4(1H,3H)-dione (1.0 g) as a solid.

PREPARATION EXAMPLE 144

2-bromoethyl cyclopropylmethyl ether (170 mg) was added to a mixture of tert-butyl 7-{7-[5-methyl-1-(tetrahydro-2H-pyran-2-yl)-1H-indazol-4-yl]-2-(piperidin-4-yloxy)-8-(2,2,2-trifluoroethoxy)-6-vinylquinazolin-4-yl}-2,7-diazaspiro[3.5]nonane-2-carboxylate (500 mg), DIPEA (0.33 mL), and DMF (5.0 mL), and the mixture was stirred at 70° C. for 16 hours. The reaction mixture was cooled to room temperature, then water was added, and the mixture was extracted with ethyl acetate. An organic layer was washed with water and a saturated aqueous sodium chloride solution, and then dried by anhydrous magnesium sulfate. After concentrating the solution under reduced pressure, the obtained residue was purified by silica gel column chromatography (amino silica gel, hexane/ethyl acetate) so as to obtain tert-butyl 7-[2-({1-[2-(cyclopropylmethoxy)ethyl]piperidin-4-yl}oxy)-7-[5-methyl-1-(tetrahydro-2H-pyran-2-yl)-1H-indazol-4-yl]-8-(2,2,2-trifluoroethoxy)-6-vinylquinazolin-4-yl]-2,7-diazaspiro[3.5]nonane-2-carboxylate (470 mg).

PREPARATION EXAMPLE 155

Sodium triacetoxyborohydride (180 mg) was added to a mixture of tert-butyl 7-[7-(5-methyl-1H-indazol-4-yl)-2-(piperidin-4-yloxy)-8-(2,2,2-trifluoroethoxy)-6-vinylquinazolin-4-yl]-2,7-diazaspiro[3.5]nonane-2-carboxylate (310 mg), tetrahydro-2H-pyran-4-carbaldehyde (100 mg), acetic acid (0.12 mL), and dichloromethane (3.0 mL), and the mixture was stirred at room temperature for 18 hours. A saturated aqueous sodium hydrogen carbonate solution and water were added to the reaction mixture, and the mixture was extracted with chloroform. An organic layer was purified by silica gel column chromatography (chloroform/methanol/28% ammonia water) so as to obtain tert-butyl 7-[7-(5-methyl-1H-indazol-4-yl)-2-{[1-(tetrahydro-2H-pyran-4-ylmethyl)piperidin-4-yl]oxy}-8-(2,2,2-trifluoroethoxy)-6-vinylquinazolin-4-yl]-2,7-diazaspiro[3.5]nonane-2-carboxylate (300 mg) as an oil.

PREPARATION EXAMPLE 175

A mixture of tert-butyl 7-{7-bromo-8-fluoro-6-iodo-2[(1-methylpiperidin-4-yl)sulfanyl]quinazolin-4-yl}-2,7-diazaspiro[3.5]nonane-2-carboxylate (180 mg), 2,2,2-trifluoroethanol (92 µL), cesium carbonate (420 mg), and DMF (5.0 mL) was stirred at room temperature for overnight. Water was added to the reaction mixture, and extracted with chloroform, and an organic layer was dried with anhydrous magnesium sulfate. After concentrating the solution under reduced pressure, the obtained residue was purified by silica gel column chromatography (amino silica gel, hexane/ethyl acetate). Potassium carbonate (60 mg) and PdCl$_2$(dppf).CH$_2$Cl$_2$ (10 mg) were added to a mixture of the obtained purified product (100 mg), 4,4,5,5-tetramethyl-2-vinyl-1,3,2-dioxaborolane (50 µL), 1,4-dioxane (5.0 mL), and water (0.50 mL), and the mixture was stirred at 60° C. for 2 hours. After the reaction mixture was cooled to room temperature, a saturated aqueous sodium chloride solution was added to the reaction mixture, and the mixture was extracted with chloroform. An organic layer was dried by anhydrous magnesium sulfate. After concentrating the solution under reduced pressure, the obtained residue was purified by silica gel column chromatography (amino silica gel, hexane/ethyl acetate) so as to obtain tert-butyl 7-{7-bromo-2-[(1-methyl-piperidin-4-yl)sulfanyl]-8-(2,2,2-trifluoroethoxy)-6-vinylquinazolin-4-yl}-2,7-diazaspiro[3.5]nonane-2-carboxylate (73 mg).

PREPARATION EXAMPLE 181

Cesium carbonate (1.0 g) and sodium chloro(difluoro)acetate (490 mg) were added to a mixture of tert-butyl 7-{7-bromo-8-hydroxy-6-iodo-2-[(1-{[2-(trimethylsilyl)ethoxy]carbonyl}piperidin-4-yl)oxy]quinazolin-4-yl}-2,7-diazaspiro[3.5]nonane-2-carboxylate (1.1 g), DMF (10 mL), and water (1.0 mL), and the mixture was stirred at 100° C. for 2 hours. After the reaction mixture was cooled to room temperature, ethyl acetate was added to the reaction mixture, and the mixture was washed with water and a saturated aqueous sodium chloride solution. An organic layer was dried by anhydrous magnesium sulfate, and then a solution was concentrated under reduced pressure. The obtained residue was purified by silica gel column chromatography (hexane/ethyl acetate) so as to obtain tert-butyl 7-{7-bromo-8-(difluoromethoxy)-6-iodo-2-[(1-{[2-(trimethylsilyl)ethoxy]carbonyl}piperidin-4-yl)oxy]quinazolin-4-yl}-2,7-diazaspiro[3.5]nonane-2-carboxylate (1.0 g).

PREPARATION EXAMPLE 227

A mixture of tert-butyl 7-(7-bromo-2-chloro-8-fluoro-6-iodoquinazolin-4-yl)-2,7-diazaspiro[3.5]nonane-2-carboxylate (2.0 g), 1-methylpiperidine-4-amine (750 mg), DIPEA (1.7 mL), and 1-methylpyrrolidin-2-one (20 mL) was stirred at 100° C. for overnight. The reaction mixture was cooled to room temperature, then water was added, and the mixture was extracted with ethyl acetate. An organic layer was washed with water and a saturated aqueous sodium chloride solution, and then dried by anhydrous sodium sulfate. After concentrating the solution under reduced pressure, the obtained residue was purified by silica gel column chromatography (amino silica gel, hexane/ethyl acetate) so as to obtain tert-butyl 7-{7-bromo-8-fluoro-6-iodo-2-[(1-methyl-piperidin-4-yl)amino]quinazolin-4-yl}-2,7-diazaspiro[3.5]nonane-2-carboxylate (730 mg).

PREPARATION EXAMPLE 235

A mixture of tert-butyl 7-[7-(5-methyl-1H-indazol-4-yl)-2-(piperidin-4-yloxy)-8-(2,2,2-trifluoroethoxy)-6-vinylquinazolin-4-yl]-2,7-diazaspiro[3.5]nonane-2-carboxylate (300 mg), triethylamine (0.18 mL), and dichloromethane (6.0 mL) was cooled in ice bath, and then dimethylcarbamoyl chloride (39 µL) was added dropwise to the mixture, and the mixture was stirred at room temperature for 2 hours. The reaction mixture was purified by silica gel column chromatography (chloroform/methanol) so as to obtain tert-butyl 7-[2-{[1-(dimethylcarbamoyl)piperidin-4-yl]oxy}-7-(5-methyl-1H-indazol-4-yl)-8-(2,2,2-trifluoroethoxy)-6-vinylquinazolin-4-yl]-2,7-diazaspiro[3.5]nonane-2-carboxylate (290 mg).

PREPARATION EXAMPLE 253

N-chlorosuccinimide (32 mg) was added to a mixture of tert-butyl 7-[2-{[1-(2-methoxyethyl)piperidin-4-yl]oxy}-7-(5-methyl-H-indazol-4-yl)-8-(2,2,2-trifluoroethoxy)-6-vinylquinazolin-4-yl]-2,7-diazaspiro[3.5]nonane-2-carboxylate (150 mg), 1M aqueous sodium hydroxide solution (1.6 mL), and ethanol (3.0 mL), and the mixture was stirred at room temperature for 30 minutes. N-chlorosuccinimide (16 mg) was added to the reaction mixture, and the mixture was stirred at room temperature for 15 minutes. A sodium sulfite aqueous solution was added to the reaction mixture and extracted with ethyl acetate. An organic layer was washed with a saturated aqueous sodium hydrogen carbonate solution, and a saturated aqueous sodium chloride solution, and then dried by anhydrous magnesium sulfate. After concentrating the solution under reduced pressure, the obtained residue was purified by silica gel column chromatography (amino silica gel, hexane/ethyl acetate) so as to obtain tert-butyl 7-[7-(3-chloro-5-methyl-1H-indazol-4-yl)-2-{[1-(2-methoxyethyl)piperidin-4-yl]oxy}-8-(2,2,2-trifluoroethoxy)-6-vinylquinazolin-4-yl]-2,7-diazaspiro[3.5]nonane-2-carboxylate (130 mg) as a solid.

PREPARATION EXAMPLE 283

Thionyl chloride (2.0 mL) was added to a mixture of (1-{[2-(trimethylsilyl)ethoxy]carbonyl}piperidin-4-yl)acetic acid (1.9 g) and toluene (20 mL), and the mixture was stirred at 60° C. for 1 hour. The reaction mixture was cooled to room temperature, and then was concentrated under reduced pressure. The obtained residue was azeotroped with toluene. 2-amino-4-bromo-3-fluoro-5-iodobenzamide (2.0 g) and pyridine (2.0 mL) were added to a mixture of the obtained residue and dichloromethane (20 mL), and then the mixture was stirred at room temperature for overnight. After concentrating the reaction mixture under reduced pressure, 1,4-dioxane (30 mL) and 1M aqueous sodium hydroxide solution (30 mL) were added to the obtained residue, and the mixture was stirred at room temperature for 2 hours. 1 M hydrochloric acid (30 mL) was added to the reaction mixture, and then the precipitated solid was collected by filtration. The obtained solid was purified by silica gel column chromatography (chloroform/methanol) so as to obtain 2-(trimethylsilyl)ethyl 4-[(7-bromo-8-fluoro-6-iodo-4-oxo-3,4-dihydroquinazolin-2-yl)methyl]piperidine-1-carboxylate (3.5 g) as a solid.

PREPARATION EXAMPLE 284

(1H-benzotriazol-1-yloxy)[tri(pyrrolidin-1-yl)]phosphonium hexafluorophosphate (4.4 g) was added to a mixture of 2-(trimethylsilyl)ethyl 4-[(7-bromo-8-fluoro-6-iodo-4-oxo-3,4-dihydroquinazolin-2-yl)methyl]piperidine-1-carboxylate (3.5 g), tert-butyl 2,7-diazaspiro[3.5]nonane-2-carboxylate (1.9 g), 1,8-diazabicyclo[5.4.0]-7-undecene (1.7 mL), and acetonitrile (50 mL), and the mixture was stirred at room temperature for 30 minutes. Water was added to the reaction mixture and extracted with ethyl acetate. An organic layer was washed with 1M hydrochloric acid, a saturated aqueous sodium hydrogen carbonate solution, and a saturated aqueous sodium chloride solution, and then dried by anhydrous magnesium sulfate. After concentrating the solution under reduced pressure, the obtained residue was purified by silica gel column chromatography (hexane/ethyl acetate) so as to obtain tert-butyl 7-{7-bromo-8-fluoro-6-iodo-2-[(1-{[2-(trimethylsilyl)ethoxy]carbonyl}piperidin-4-yl)methyl]quinazolin-4-yl}-2,7-diazaspiro[3.5]nonane-2-carboxylate (3.7 g).

The compounds indicated in Tables 6 to 118 below were prepared in the same manner as the preparation methods in the Preparation Examples described above. The preparing method, structure, and physicochemical data of the compounds in the respective Preparation Examples are indicated in Tables 6 to 118

EXAMPLE 1

A mixture of tert-butyl 7-{8-(2,2-difluoroethoxy)-7-(5-methyl-1H-indazol-4-yl)-2-[(1-methylpiperidin-4-yl)oxy]-6-vinylquinazolin-4-yl}-2,7-diazaspiro[3.5]nonane-2-carboxylate (290 mg), and dichloromethane (6.0 mL) was cooled in ice bath, then TFA (3.0 mL) was added to the mixture, and the mixture was stirred at room temperature for 1 hour. After concentrating the reaction mixture under reduced pressure, the reaction mixture was azeotroped with toluene, and then was azeotroped with THF. After a mixture of the obtained residue and THF (6.0 mL) was cooled in ice bath, a saturated aqueous sodium hydrogen carbonate solution (3.0 mL) and acryloyl chloride (35 µL) were added to the mixture, and the mixture was stirred at the same temperature for 30 minutes. A saturated aqueous sodium hydrogen carbonate solution and a saturated aqueous sodium chloride solution were added to the reaction mixture, and was extracted with chloroform/isopropyl alcohol (hereinafter, abbreviated as IPA) (4:1). An organic layer was dried by anhydrous magnesium sulfate, and then a solution was concentrated under reduced pressure. The obtained residue was purified by silica gel column chromatography (chloroform/methanol/28% ammonia water). Acetonitrile was added to the obtained purified product, and then the mixture was stirred at room temperature. The precipitated solid was collected by filtration so as to obtain 1-(7-{8-(2,2-difluoroethoxy)-7-(5-methyl-1H-indazol-4-yl)-2-[(1-methylpiperidin-4-yl)oxy]-6-vinylquinazolin-4-yl}-2,7-diazaspiro[3.5]non-2-yl)prop-2-en-1-one (77 mg).

EXAMPLE 2

A mixture of tert-butyl 7-{6-cyclopropyl-8-ethoxy-7-(5-methyl-1H-indazol-4-yl)-2-[(1-methylpiperidin-4-yl)oxy]quinazolin-4-yl}-2,7-diazaspiro[3.5]nonane-2-carboxylate (180 mg) and dichloromethane (3.0 mL) was cooled in ice bath, then TFA (3.0 mL) was added to the mixture, and the mixture was stirred at the same temperature for 1 hour. After concentrating the reaction mixture under reduced pressure, the reaction mixture was azeotroped with toluene. After a mixture of the obtained residue and THF (5.0 mL) was cooled in ice bath, 1M sodium hydrogen carbonate solution (5.0 mL) and acryloyl chloride (24 µL) were added to the mixture, and the mixture was stirred at the same temperature for 3 hours. After concentrating the reaction mixture, the obtained residue was purified by silica gel column chromatography (ODS silica gel, water/acetonitrile). Hexane and ethyl acetate were added to the obtained purified product and sonicated. The precipitated solid was collected by filtration so as to obtain 1-(7-{6-cyclopropyl-8-ethoxy-7-(5-methyl-1H-indazol-4-yl)-2-[(1-methylpiperidin-4-yl)oxy]quinazolin-4-yl}-2,7-diazaspiro[3.5]non-2-yl)prop-2-en-1-one (62 mg) as a solid.

EXAMPLE 3

TFA (5.0 mL) was added to a mixture of tert-butyl 7-{6-cyclopropyl-8-(2,2-difluoroethoxy)-2-[(1-methylpiperidin-4-yl)oxy]-7-[5-methyl-1-(tetrahydro-2H-pyran-2-yl)-1H-indazol-4-yl]quinazolin-4-yl}-2,7-diazaspiro[3.5]nonane-2-carboxylate (530 mg), and dichloromethane (10 mL), and the mixture was stirred at room temperature for 4 hours. After concentrating the reaction mixture under reduced pressure, the reaction mixture was azeotroped with toluene. After a mixture of the obtained residue and THF (10 mL) was cooled in ice bath, a saturated aqueous sodium hydrogen carbonate solution (4.0 mL) and acryloyl chloride (55 µL) were added to the mixture, and the mixture was stirred at the same temperature for 30 minutes. The reaction mixture was extracted with chloroform/IPA (4:1). An organic layer was dried by anhydrous magnesium sulfate, and then a solution was concentrated under reduced pressure. The obtained residue was purified by silica gel column chromatography (ODS silica gel, water/methanol). The obtained purified product was purified by silica gel column chromatography (chloroform/methanol/28% ammonia water). Hexane was added to the obtained purified product and sonicated. The precipitated solid was collected by filtration so as to obtain 1-(7-{6-cyclopropyl-8-(2,2-difluoroethoxy)-7-(5-methyl-1H-indazol-4-yl)-2-[(1-methylpiperidin-4-yl)oxy]quinazolin-4-yl}-2,7-diazaspiro[3.5]non-2-yl)prop-2-en-1-one (120 mg) as a solid.

EXAMPLE 4

TFA (2.5 mL) was added to a mixture of tert-butyl 7-[6-cyclopropyl-8-(2,2-difluoroethoxy)-7-(5-methyl-1H-indazol-4-yl 1)-2-{[(2S)-1-methylpyrrolidin-2-yl]methoxy}quinazolin-4-yl]-2,7-diazaspiro[3.5]nonane-2-carboxylate (470 mg), and dichloromethane (9.0 mL), and the mixture was stirred at room temperature for 1 hour. After concentrating the reaction mixture under reduced pressure, the reaction mixture was azeotroped with THF. After a mixture of the obtained residue and THF (9.0 mL) was cooled in ice bath, a saturated aqueous sodium hydrogen carbonate solution (4.0 mL) and THF (2.0 mL) solution of acryloyl chloride (63 µL) were added to the mixture, and the mixture was stirred at the same temperature for 1 hour. Water was added to the reaction mixture, and the reaction mixture was extracted with chloroform/IPA (4:1). An organic layer was dried by anhydrous sodium sulfate, and then a solution was concentrated under reduced pressure. The obtained residue was purified by silica gel column chromatography (ODS silica gel, water/acetonitrile) so as to obtain 1-{7-[6-cyclopropyl-8-(2,2-difluoroethoxy)-7-(5-methyl-1H-indazol-4-yl)-2-{[(2S)-1-methylpyrrolidin-2-yl]methoxy}quinazolin-4-yl]-2,7-diazaspiro[3.5]non-2-yl}prop-2-en-1-one (88 mg) as a solid.

EXAMPLE 5

TFA (1.0 mL) was added to a mixture of tert-butyl 7-{8-ethoxy-7-(5-methyl-1H-indazol-4-yl)-2-[(1-methylpiperidin-4-yl)oxy]-6-vinylquinazolin-4-yl}-2,7-diazaspiro[3.5]nonane-2-carboxylate (360 mg), and dichloromethane (6.0 mL), and the mixture was stirred at room temperature for 1 hour. After concentrating the reaction mixture under reduced pressure, the reaction mixture was azeotroped with chloroform. After THF (3.0 mL), water (3.0 mL), and sodium hydrogen carbonate (740 mg) were added to the obtained residue, and cooled in ice bath, THF (1.0 mL) solution of acryloyl chloride (54 µL) was added to the mixture. The reaction mixture was stirred at room temperature for 1 hour. A saturated aqueous sodium hydrogen carbonate solution was added to the reaction mixture, and the mixture was stirred for 10 minutes. Water was added to the reaction mixture and extracted with chloroform. An organic layer was dried by anhydrous magnesium sulfate, and then a solution was concentrated under reduced pressure. The obtained residue was purified by silica gel column chromatography (chloroform/methanol). Hexane was added to the obtained purified product and sonicated. The precipitated solid was collected by filtration so as to obtain 1-(7-{8-ethoxy-7-(5-methyl-1H-indazol-4-yl)-2-[(1-methylpiperidin-4-yl)oxy]-6-vinylquinazolin-4-yl}-2,7-diazaspiro[3.5]non-2-yl)prop-2-en-1-one (85 mg) as a solid.

EXAMPLE 5-2

A mixture of tert-butyl 7-{8-ethoxy-7-(5-methyl-1H-indazol-4-yl)-2-[(1-methylpiperidin-4-yl)oxy]-6-vinylquinazolin-4-yl}-2,7-diazaspiro[3.5]nonane-2-carboxylate (1.3 g), and 1M hydrochloric acid (13 mL) was stirred at room temperature for 18 hours. After the reaction mixture was cooled in ice bath, dichloromethane (6.5 mL), 3-chloropropanoyl chloride (0.41 mL), sodium hydrogen carbonate (1.6 g) were added to the reaction mixture, and the mixture was stirred at the same temperature for 30 minutes. IPA (13 mL) and 4M aqueous sodium hydroxide solution (4.9 mL) were added to the reaction mixture at the same temperature, and the mixture was stirred at room temperature for 4 hours. After the reaction mixture was cooled in ice bath, 1M hydrochloric acid (6.4 mL), 5% aqueous sodium hydrogen carbonate solution (26 mL), and chloroform (39 mL) were added to the reaction mixture, and the mixture was stirred at room temperature for 10 minutes. The reaction mixture was filtered through celite and the filtrate was extracted with chloroform. An organic layer was dried by anhydrous magnesium sulfate, and then a solution was concentrated under reduced pressure. The obtained residue was purified by silica gel column chromatography (chloroform/methanol/28% ammonia water). Acetonitrile was added to the obtained purified product, and then the precipitated solid was collected by filtration. The obtained solid was dried at 50° C. under reduced pressure so as to obtain 1-(7-{8-ethoxy-7-(5-methyl-1H-indazol-4-yl)-2-[(1-methylpiperidin-4-yl)oxy]-6-vinylquinazolin-4-yl}-2,7-diazaspiro[3.5]non-2-yl)prop-2-en-1-one (980 mg) as a solid.

EXAMPLE 6

After a mixture of DIPEA (0.22 mL) and THF (3.0 mL) was cooled in ice bath, acryloyl chloride (0.10 mL) was added to the mixture. THF (6.0 mL) solution of 8-(cyclobutyloxy)-6-cyclopropyl-4-(2,7-diazaspiro[3.5]non-7-yl)-7-(5-methyl-1H-indazol-4-yl)-2-[(1-methylpiperidin-4-yl)oxy]quinazoline (310 mg) was added dropwise to the mixture, and the mixture was stirred at the same temperature for 30 minutes. 1M aqueous sodium hydroxide solution (3.0 mL) was added dropwise to the reaction mixture at the same temperature, and the mixture was stirred at room temperature for 1 hour. Water and a saturated aqueous sodium chloride solution were added to the reaction mixture, and the mixture was extracted with chloroform/IPA (4:1). An organic layer was washed with a saturated aqueous sodium chloride solution, and then dried by anhydrous magnesium sulfate. After concentrating the solution under reduced pressure, the obtained residue was purified by silica gel column chromatography (ODS silica gel, water/methanol). Hexane and ethyl acetate were added to the obtained purified product and triturated. The precipitated solid was collected by filtration so as to obtain 1-(7-{8-(cyclobutyloxy)-6-cyclopropyl-7-(5-methyl-1H-indazol-4-yl)-2-[(1-methylpiperidin-4-yl)oxy]quinazolin-4-yl}-2,7-diazaspiro[3.5]non-2-yl)prop-2-en-1-one (120 mg) as a solid.

EXAMPLE 7

A mixture of 4-(2,7-diazaspiro[3.5]non-7-yl)-8-ethoxy-2-[(1-ethylpiperidin-4-yl)oxy]-7-(5-methyl-1H-indazol-4-yl)-6-vinylquinazoline (150 mg), sodium hydrogen carbonate (320 mg), THF (1.5 mL), and water (1.5 mL) were cooled in ice bath, and a THF (0.50 mL) solution of acryloyl chloride (21 µL) was added to the mixture, and the mixture was stirred at the same temperature for 30 minutes. After concentrating the reaction mixture, the obtained residue was purified by silica gel column chromatography (ODS silica gel, water/acetonitrile). Acetonitrile was added to the obtained purified product, and a solvent was evaporated under reduced pressure. The precipitated solid was collected by filtration so as to obtain 1-(7-{8-ethoxy-2-[(1-ethylpiperidin-4-yl)oxy]-7-(5-methyl-1H-indazol-4-yl)-6-vinylquinazolin-4-yl}-2,7-diazaspiro[3.5]non-2-yl)prop-2-en-1-one (90 mg) as a solid.

EXAMPLE 24

1-(7-{8-ethoxy-7-(5-methyl-1H-indazol-4-yl)-2-[(1-methylpiperidin-4-yl)oxy]-6-vinylquinazolin-4-yl}-2,7-diazaspiro[3.5]non-2-yl)prop-2-en-1-one (1.5 g) was fractionated by supercritical fluid chromatography (chiral column, carbon dioxide/ethanol/triethylamine). Hexane and ethyl acetate were added to the obtained fractionated product and triturated. The precipitated solid was collected by filtration so as to obtain (+)-1-(7-{8-ethoxy-7-(5-methyl-1H-indazol-4-yl)-2-[(1-methylpiperidin-4-yl)oxy]-6-vinylquinazolin-4-yl}-2,7-diazaspiro[3.5]non-2-yl)prop-2-en-1-one (670 mg) as a solid.

A solid (3.0 g) obtained by performing the above-described method a plurality of times was purified by silica gel column chromatography (ODS silica gel, water/methanol). Acetonitrile was added to the obtained purified product, and then the mixture was stirred at room temperature. The precipitated solid was collected by filtration, and the obtained solid was dried at 40° C. under reduced pressure so as to obtain (+)-1-(7-{8-ethoxy-7-(5-methyl-1H-indazol-4-yl)-2-[(1-methylpiperidin-4-yl)oxy]-6-vinylquinazolin-4-yl}-2,7-diazaspiro[3.5]non-2-yl)prop-2-en-1-one (2.0 g) as a crystal.

EXAMPLE 25

A mixture of tert-butyl 7-[6-cyclopropyl-2-{([1-(2-methoxyethyl)piperidin-4-yl]oxy}-7-(5-methyl-1H-indazol-4-yl)-8-(2,2,2-trifluoroethoxy)quinazolin-4-yl]-2,7-diazaspiro[3.5]nonane-2-carboxylate (800 mg) and dichloromethane (4.0 mL) was cooled in ice bath, TFA (1.2 mL) was added to the mixture, and the mixture was stirred at room temperature for 6 hours. Chloroform/IPA (4:1) and 2M potassium carbonate aqueous solution (11 mL) were added to the reaction mixture. A water layer was extracted with chloroform/IPA (4:1), and an organic layer was dried by anhydrous magnesium sulfate, and then a solution was concentrated under reduced pressure (residue A). After a mixture of DIPEA (0.45 mL) and THF (16 mL) was cooled in an ice-methanol bath, acryloyl chloride (0.20 mL) was added to the mixture. To this mixture, a THF (12 mL) solution of residue A was added dropwise, and the mixture was stirred at the same temperature for 20 minutes. 1M aqueous sodium hydroxide solution (5.0 mL) was added dropwise to the reaction mixture at the same temperature, and the mixture was stirred at room temperature for 4 hours. A saturated aqueous sodium hydrogen carbonate solution was added to the reaction mixture, and the mixture was extracted with ethyl acetate. An organic layer was dried by anhydrous magnesium sulfate, and then a solution was concentrated under reduced pressure. The obtained residue was purified by silica gel column chromatography (chloroform/methanol/28% ammonia water). Acetonitrile was added to the obtained purified product and sonicated. The precipitated solid was collected by filtration so as to obtain 1-{7-[6-cyclopropyl-2-{[1-(2-methoxyethyl)piperidin-4-yl]oxy}-7-(5-methyl-1H-indazol-4-yl)-8-(2,2,2-trifluoroethoxy)quinazolin-4-yl]-2,7-diazaspiro[3.5]non-2-yl}prop-2-en-1-one (410 mg) as a solid.

EXAMPLE 26

A mixture of tert-butyl 7-[2-{[1-(2-methoxyethyl)piperidin-4-yl]oxy}-7-(5-methyl-1H-indazol-4-yl)-8-(2,2,2-trifluoroethoxy)-6-vinylquinazolin-4-yl]-2,7-diazaspiro[3.5]nonane-2-carboxylate (470 mg), and 1M hydrochloric acid (4.1 mL) was stirred at 50° C. for 1 hour. After the reaction mixture was cooled in ice bath, dichloromethane (2.3 mL), 3-chloropropanoyl chloride (0.13 mL), sodium hydrogen carbonate (520 mg) were added to the reaction mixture, and the mixture was stirred at the same temperature for 1 hour. IPA (4.7 mL) and 4M aqueous sodium hydroxide solution (2.3 mL) were added to the reaction mixture at the same temperature, and the mixture was stirred at room temperature for 2 hours. Water was added to the reaction mixture and extracted with ethyl acetate. An organic layer was washed with a saturated aqueous sodium chloride solution, and then dried by anhydrous magnesium sulfate. After concentrating the solution under reduced pressure, the obtained residue was purified by silica gel column chromatography (chloroform/methanol/28% ammonia water). Acetonitrile was added to the obtained purified product, and then the mixture was stirred at room temperature for 5 minutes. The precipitated solid was collected by filtration, and dried at 30° C. under reduced pressure so as to obtain 1-{7-[2-{[1-(2-methoxyethyl)piperidin-4-yl]oxy}-7-(5-methyl-H-indazol-4-yl)-8-(2,2,2-trifluoroethoxy)-6-vinylquinazolin-4-yl]-2,7-diazaspiro[3.5]non-2-yl}prop-2-en-1-one (320 mg) as a solid.

EXAMPLE 28

A mixture of tert-butyl 7-[6-cyclopropyl-2-{[1-(3-methoxypropyl)piperidin-4-yl]oxy}-7-(5-methyl-1H-indazol-4-yl)-8-(2,2,2-trifluoroethoxy)quinazolin-4-yl]-2,7-diazaspiro[3.5]nonane-2-carboxylate (630 mg) and 1M hydrochloric acid (5.5 mL) was stirred at 50° C. for 1 hour under the argon atmosphere. After the reaction mixture was cooled in ice bath, dichloromethane (3.2 mL), 3-chloropropanoyl chloride (0.17 mL), sodium hydrogen carbonate (670 mg) were added to the reaction mixture, and the mixture was stirred at the same temperature for 30 minutes. IPA (9.3 mL) and 4M aqueous sodium hydroxide solution (3.0 mL) were added to the reaction mixture at the same temperature, and the mixture was stirred at room temperature for 3 hours. After the reaction mixture was cooled in ice bath, then 1M hydrochloric acid (10 mL), a saturated aqueous sodium hydrogen carbonate solution, and ethyl acetate were added to the reaction mixture, and the reaction mixture was stirred at room temperature for 5 minutes. The reaction mixture was extracted with ethyl acetate, and then an organic layer was washed with a saturated aqueous sodium chloride solution. An organic layer was dried by anhydrous magnesium sulfate, and then a solution was concentrated under reduced pressure. The obtained residue was purified by silica gel column chromatography (chloroform/methanol). Acetonitrile was added to the obtained purified product, and then the mixture was stirred at room temperature for 1 hour. The precipitated solid was collected by filtration so as to obtain 1-{7-[6-cyclopropyl-2-{[1-(3-methoxypropyl)piperidin-4-yl]oxy}-7-(5-methyl-1H-indazol-4-yl)-8-(2,2,2-trifluoroethoxy)quinazolin-4-yl]-2,7-diazaspiro[3.5]non-2-yl}prop-2-en-1-one (230 mg) as a solid.

EXAMPLE 30

A mixture of tert-butyl 7-[7-(5-methyl-1H-indazol-4-yl)-2-{[1-(tetrahydro-2H-pyran-4-yl)piperidin-4-yl]oxy}-8-(2,2,2-trifluoroethoxy)-6-vinylquinazolin-4-yl]-2,7-diazaspiro[3.5]nonane-2-carboxylate (610 mg), and 1M hydrochloric acid (5.2 mL) was stirred at 50° C. for 30 minutes. After the reaction mixture was cooled in ice bath, dichloromethane (3.0 mL), 3-chloropropanoyl chloride (0.17 mL), sodium hydrogen carbonate (650 mg) were added to the reaction mixture, and the mixture was stirred at the same temperature for 1 hour. IPA (6.0 mL) and 4M aqueous sodium hydroxide solution (3.0 mL) were added to the reaction mixture at the same temperature, and the mixture was stirred at room temperature for 4 hours. After the reaction mixture was cooled in ice bath, then 1M hydrochloric acid (7.0 mL), a saturated aqueous sodium hydrogen carbonate solution, and ethyl acetate were added to the reaction mixture, and the reaction mixture was stirred at room temperature for 5 minutes. The reaction mixture was extracted with ethyl acetate, and an organic layer was dried with anhydrous magnesium sulfate. After concentrating the solution under reduced pressure, the obtained residue was purified by silica gel column chromatography (chloroform/methanol/28% ammonia water). Acetonitrile was added to the obtained purified product, and the precipitated solid was collected by filtration so as to obtain 1-{7-[7-(5-methyl-1H-indazol-4-yl)-2-{[1-(tetrahydro-2H-pyran-4-yl)piperidin-4-yl]oxy}-8-(2,2,2-trifluoroethoxy)-6-vinylquinazolin-4-yl]-2,7-diazaspiro[3.5]non-2-yl}prop-2-en-1-one (420 mg) as a solid.

EXAMPLE 31

A mixture of 1-(4-{[4-(2,7-diazaspiro[3.5]non-7-yl)-7-(5-methyl-1H-indazol-4-yl)-8-(2,2,2-trifluoroethoxy)-6-vinylquinazolin-2-yl]oxy}piperidin-1-yl)-2-methylpropan-2-ol (290 mg), 1M hydrochloric acid (3.0 mL), and dichloromethane (1.5 mL) was cooled in ice bath, and then 3-chloropropanoyl chloride (90 μL) was added thereto. Sodium hydrogen carbonate (430 mg) was added to the reaction mixture, and the mixture was stirred at the same temperature for 15 minutes. IPA (3.0 mL) and 4M aqueous sodium hydroxide solution (1.6 mL) were added to the reaction mixture at the same temperature, and the mixture was stirred at room temperature for 1 hour. Water was added to the reaction mixture and extracted with ethyl acetate. An organic layer was washed with a saturated aqueous sodium chloride solution, and then dried by anhydrous magnesium sulfate. After concentrating the solution under reduced pressure, the obtained residue was purified by silica gel column chromatography (chloroform/methanol/28% ammonia water). Hexane and ethyl acetate were added to the obtained purified product and triturated. The precipitated solid was collected by filtration so as to obtain 1-{7-[2-{{[11-(2-hydroxy-2-methylpropyl)piperidin-4-yl]oxy}-7-(5-methyl-1H-indazol-4-yl)-8-(2,2,2-trifluoroethoxy)-6-vinylquinazolin-4-yl]-2,7-diazaspiro[3.5]non-2-yl}prop-2-en-1-one (110 mg) as a solid.

EXAMPLE 36

1-{7-[2-{[1-(2-methoxyethyl)piperidin-4-yl]oxy}-7-(5-methyl-1H-indazol-4-yl)-8-(2,2,2-trifluoroethoxy)-6-vinylquinazolin-4-yl]-2,7-diazaspiro[3.5]non-2-yl}prop-2-en-1-one (2.0 g) was fractionated by supercritical fluid chromatography (chiral column, carbon dioxide/methanol/triethylamine, carbon dioxide/ethanol/triethylamine). The obtained fractionated material was purified by silica gel column chromatography (chloroform/methanol/28% ammonia water) so as to obtain (+)-1-{7-[2-{[1-(2-methoxyethyl)piperidin-4-yl]oxy}-7-(5-methyl-1H-indazol-4-yl)-8-(2,2,2-trifluoroethoxy)-6-vinylquinazolin-4-yl]-2,7-diazaspiro[3.5]non-2-yl}prop-2-en-1-one (810 mg).

EXAMPLE 38

1-{7-[6-cyclopropyl-2-{[1-(3-methoxypropyl)piperidin-4-yl]oxy}-7-(5-methyl-1H-indazol-4-yl)-8-(2,2,2-trifluoroethoxy)quinazolin-4-yl]-2,7-diazaspiro[3.5]non-2-yl}prop-2-en-1-one (2.2 g) was fractionated by supercritical fluid chromatography (chiral column, carbon dioxide/ethanol/triethylamine). The obtained fractionated material was purified by silica gel column chromatography (chloroform/methanol) so as to obtain (+)-1-{7-[6-cyclopropyl-2-{[1-(3-methoxypropyl)piperidin-4-yl]oxy}-7-(5-methyl-1H-indazol-4-yl)-8-(2,2,2-trifluoroethoxy)quinazolin-4-yl]-2,7-diazaspiro[3.5]non-2-yl}prop-2-en-1-one (1.1 g).

EXAMPLE 39

1-{7-[7-(5-methyl-1H-indazol-4-yl)-2-{[1-(tetrahydro-2H-pyran-4-yl)piperidin-4-yl]oxy}-8-(2,2,2-trifluoroethoxy)-6-vinylquinazolin-4-yl]-2,7-diazaspiro[3.5]non-2-yl}prop-2-en-1-one (2.0 g) was fractionated by high performance liquid chromatography (chiral column, hexane/ethanol/triethylamine). The obtained fractionated material was purified by silica gel column chromatography (chloroform/methanol) so as to obtain (+)-1-{7-[7-(5-methyl-1H-indazol-4-yl)-2-{[1-(tetrahydro-2H-pyran-4-yl)piperidin-4-yl]oxy}-8-(2,2,2-trifluoroethoxy)-6-vinylquinazolin-4-yl]-2,7-diazaspiro[3.5]non-2-yl}prop-2-en-1-one (930 mg).

EXAMPLE 41

A mixture of tert-butyl 7-[2-({1-[2-(cyclopropylmethoxy)ethyl]piperidin-4-yl}oxy)-7-[5-methyl-1-(tetrahydro-2H-pyran-2-yl)-1H-indazol-4-yl]-8-(2,2,2-trifluoroethoxy)-6-vinylquinazolin-4-yl]-2,7-diazaspiro[3.5]nonane-2-carboxylate (470 mg), 1M hydrochloric acid (4.0 mL), and THF (2.0 mL) was stirred at room temperature for 6 days. After the reaction mixture was cooled in ice bath, dichloromethane (3.0 mL), 3-chloropropanoyl chloride (0.12 mL), sodium hydrogen carbonate (450 mg) were added to the reaction mixture, and the mixture was stirred at the same temperature for 30 minutes. IPA (5.0 mL) and 4M aqueous sodium hydroxide solution (2.0 mL) were added to the reaction mixture at the same temperature, and the mixture was stirred at room temperature for 2 hours. Water was added to the reaction mixture and extracted with ethyl acetate. An organic layer was washed with a saturated aqueous sodium chloride solution, and then dried by anhydrous magnesium sulfate. After concentrating the solution under reduced pressure, the obtained residue was purified by silica gel column chromatography (chloroform/methanol/28% ammonia water). Acetonitrile was added to the obtained purified product, and then the precipitated solid was collected by filtration. The obtained solid was dried at 50° C. under reduced pressure so as to obtain 1-{7-[2-({1-[2-(cyclopropylmethoxy)ethyl]piperidin-4-yl}oxy)-7-(5-methyl-1H-indazol-4-yl)-8-(2,2,2-trifluoroethoxy)-6-vinylquinazolin-4-yl]-2,7-diazaspiro[3.5]non-2-yl}prop-2-en-1-one (82 mg) as a solid.

EXAMPLE 51

Tripotassium phosphate (120 mg), Pd$_2$(dba)$_3$ (30 mg), and SPhos (30 mg) were added to a mixture of tert-butyl 7-{7-bromo-2-[(1-methylpiperidin-4-yl)sulfanyl]-8-(2,2,2-trifluoroethoxy)-6-vinylquinazolin-4-yl}-2,7-diazaspiro[3.5]nonane-2-carboxylate (73 mg), (5-methyl-1H-indazol-4-yl)boronic acid (28 mg), 1,4-dioxane (5.0 mL), water (1.0 mL), and the mixture was stirred at 120° C. for 4 hours. The reaction mixture was cooled to room temperature, and an insoluble material was separated by filtration. After concentrating the filtrate under reduced pressure, the obtained residue was purified by silica gel column chromatography (amino silica gel, hexane/ethyl acetate). A mixture of the obtained purified product (40 mg) and 1M hydrochloric acid (2.0 mL) was stirred at 60° C. for 1 hour. After the reaction mixture was cooled in ice bath, dichloromethane (0.80 mL), 3-chloropropanoyl chloride (12 μL), sodium hydrogen carbonate (180 mg) were added to the reaction mixture, and the mixture was stirred at the same temperature for 30 minutes. IPA (2.4 mL) and 4M aqueous sodium hydroxide solution (0.80 mL) were added to the reaction mixture at the same temperature, and the mixture was stirred at room temperature for 4 hours. After the reaction mixture was cooled in ice bath, then 1M hydrochloric acid (1.7 mL) and saturated aqueous sodium hydrogen carbonate solution were added to the reaction mixture, and the reaction mixture was extracted with ethyl acetate. An organic layer was dried by anhydrous magnesium sulfate, and then a solution was concentrated under reduced pressure. The obtained residue was purified by silica gel column chromatography (chloroform/methanol/ 28% ammonia water) so as to obtain 1-{(7-[7-(5-methyl-1H-indazol-4-yl)-2-[(1-methylpiperidin-4-yl)sulfanyl]-8-(2, 2,2-trifluoroethoxy)-6-vinylquinazolin-4-yl]-2,7-diazaspiro [3.5]non-2-yl}prop-2-en-1-one (10 mg).

EXAMPLE 82

A mixture of 6-cyclopropyl-4-(2,7-diazaspiro[3.5]non-7-yl)-8-(2,2-difluoroethoxy)-2-{[1-(2-methoxyethyl)piperidin-4-yl]oxy}-7-(5-methyl-1H-indazol-4-yl)quinazoline (100 mg), (2E)-4,4,4-trifluorobut-2-enoic acid (33 mg), O-(7-azabenzotriazole-1-yl)-N,N,N',N'-tetramethyluronium hexafluorophosphate (89 mg), DIPEA (80 μL), and DMF (2.0 mL) was stirred at room temperature for overnight. A saturated aqueous sodium hydrogen carbonate solution was added to the reaction mixture, and the mixture was extracted with ethyl acetate. An organic layer was washed with water and a saturated aqueous sodium chloride solution, and then dried by anhydrous magnesium sulfate. After concentrating the solution under reduced pressure, the obtained residue was purified by silica gel column chromatography (amino silica gel, chloroform/methanol) so as to obtain (2E)-1-{7-[6-cyclopropyl-8-(2,2-difluoroethoxy)-2-{[1-(2-methoxyethyl)piperidin-4-yl]oxy}-7-(5-methyl-H-indazol-4-yl)quinazolin-4-yl]-2,7-diazaspiro[3.5]non-2-yl}-4,4,4-trifluorobut-2-en-1-one (25 mg) as a solid.

The compounds indicated in Tables 119 to 160 below were prepared in the same manner as the preparation methods of Examples described above. In addition, structures of compounds in the respective Examples are indicated in Tables 119 to 160 described below, and preparing methods and physicochemical data of compounds in the respective Examples are indicated in Tables 161 to 167.

In Tables described below, the following abbreviations may be used.
PEx: the number of Preparation Examples, Ex: the number of Examples, PSyn: the number of Preparation Examples prepared using the similar method, Syn: the number of Examples prepared using the similar method (for example, E1 represents Example 1), Str: chemical structural formula (Me: methyl, Et: ethyl, Boc: tert-butoxycarbonyl, THP: tetrahydro-2H-pyran-2-yl, Cbz: benzyloxycarbonyl, and Teoc: 2-(trimethylsilyl)ethoxycarbonyl. Note that, a compound denoted by "*" in a chemical structural formula indicates that the compound is an isomer having a stereochemistry of the notation structure. In addition, a compound denoted by "#" represents a single optical isomer based on axial chirality.), Dat: physicochemical data, ESI+: m/z value in mass spectrometry (ionization method ESI, unless otherwise [M+H]$^+$), ESI−: m/z value in mass spectrometry (ionization method ESI, unless otherwise [M−H]$^−$), CI+: m/z value in mass spectrometry (ionization method CI, unless otherwise [M+H]$^+$), NMR: a δ value (ppm) of a signal in $^1$H-NMR in DMSO-d6, s: singlet (spectrum), d: doublet (spectrum), t: triplet (spectrum), m: multiplet (spectrum), [α]$_D^{20}$: specific rotation at 20° C., c: concentration at the measurement of specific rotation (g/100 mL).

TABLE 6

| PEx | PSyn | Str | Dat |
|---|---|---|---|
| 1 | 1 | (structure) | ESI−; 359.8 |
| 2 | 2 | (structure) | CI+; 422.9 |
| 3 | 3 | (structure) | ESI+; 611.2, 613.2 |
| 4 | 4 | (structure) | ESI+; 692.3 |

TABLE 7
| PEx | PSyn | Str | Dat |
|---|---|---|---|
| 5 | 5 | 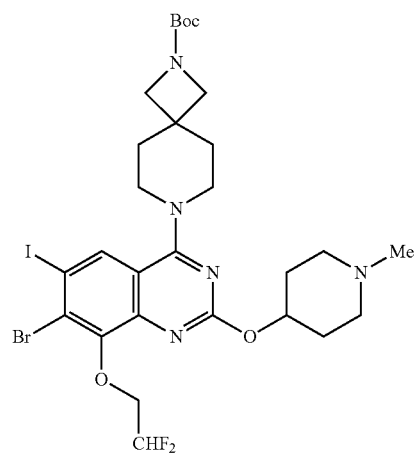 [SMILES: CN1CCC(Oc2nc(N3CCC4(CC3)CN(C(=O)OC(C)(C)C)C4)c3cc(I)c(Br)c(OCC(F)F)c3n2)CC1] | ESI+; 754.3 |
| 6 | 6 | 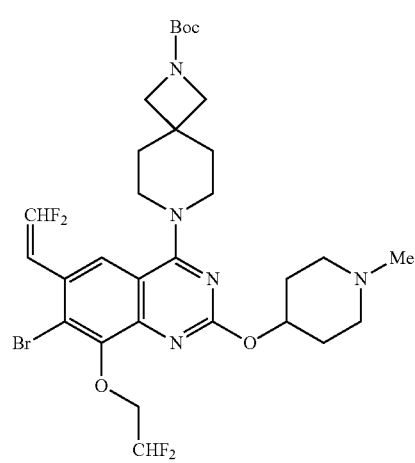 | ESI+; 654.4 |
TABLE 8
| PEx | PSyn | Str | Dat |
|---|---|---|---|
| 7 | 7 | 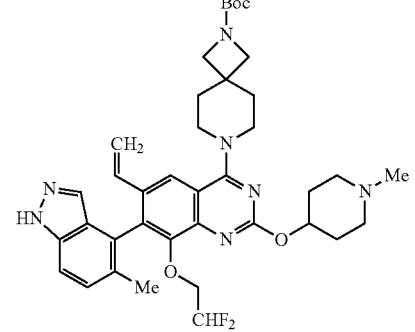 [SMILES: C=Cc1cc2c(N3CCC4(CC3)CN(C(=O)OC(C)(C)C)C4)nc(OC3CCN(C)CC3)nc2c(OCC(F)F)c1-c1c(C)ccc2[nH]ncc12] | ESI+; 704.6 |
TABLE 8-continued
| PEx | PSyn | Str | Dat |
|---|---|---|---|
| 8 | 8 | 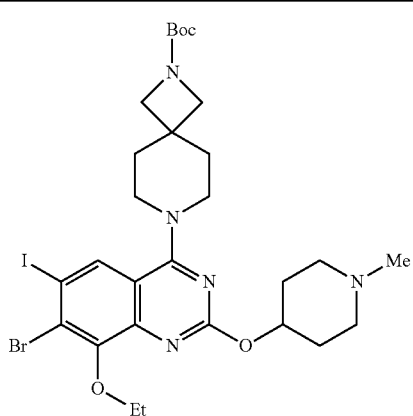 | ESI+; 718.3 |
TABLE 9
| PEx | PSyn | Str | Dat |
|---|---|---|---|
| 9 | 9 | 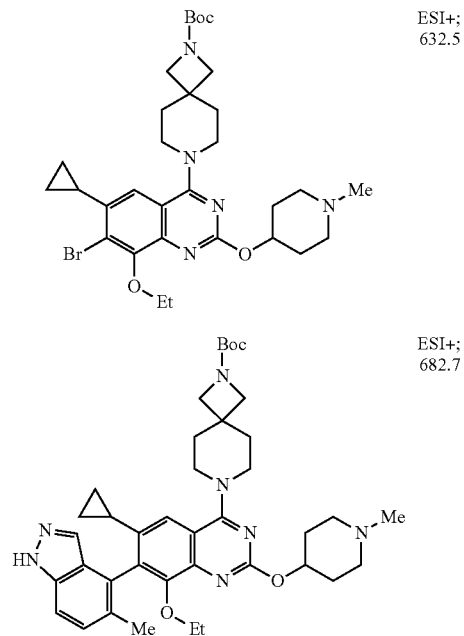 | ESI+; 632.5 |
| 10 | 10 | | ESI+; 682.7 |
| 11 | 11 | 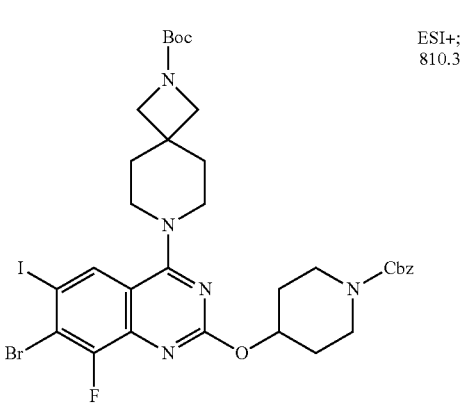 | ESI+; 810.3 |

TABLE 10
| PEx | PSyn | Str | Dat |
|---|---|---|---|
| 12 | 12 | 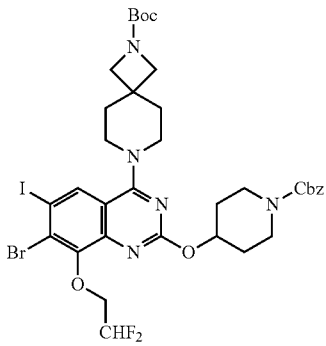 [SMILES: CC(C)(C)OC(=O)N1CC2(CCN(c3nc(OC4CCN(C(=O)OCc5ccccc5)CC4)nc4c(OCC(F)F)c(Br)c(I)cc34)CC2)C1] | ESI+; 874.4 |
TABLE 10-continued
| PEx | PSyn | Str | Dat |
|---|---|---|---|
| 13 | 13 | 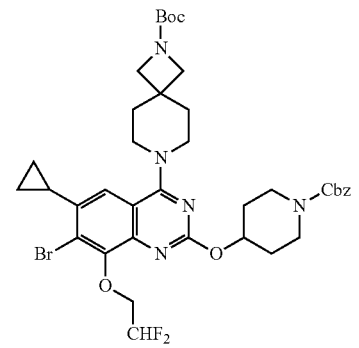 [SMILES: CC(C)(C)OC(=O)N1CC2(CCN(c3nc(OC4CCN(C(=O)OCc5ccccc5)CC4)nc4c(OCC(F)F)c(Br)c(C5CC5)cc34)CC2)C1] | ESI+; 788.5 |
TABLE 11
| PEx | PSyn | Str | Dat |
|---|---|---|---|
| 14 | 14 | 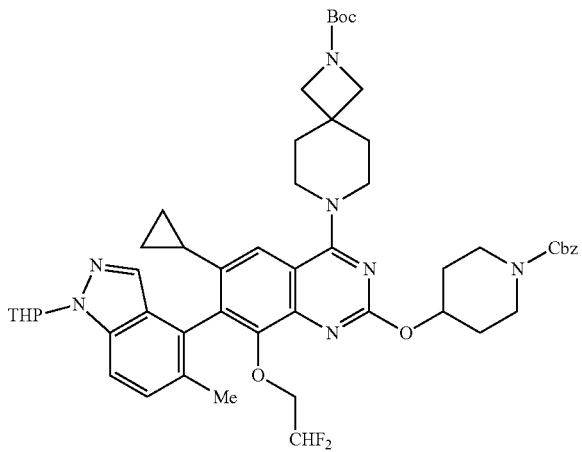 | ESI+; 922.8 |
| 15 | 15 | 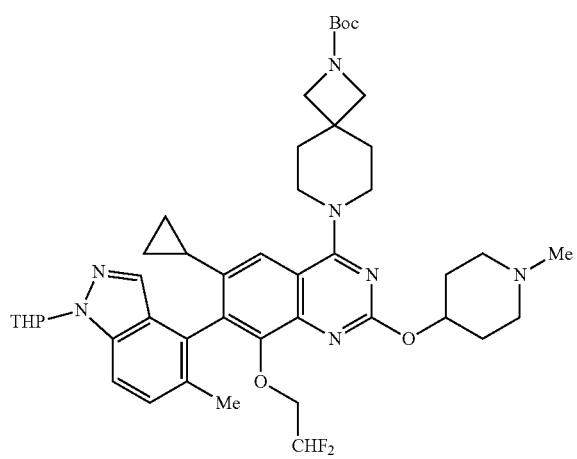 | ESI+; 802.7 |

TABLE 12
| PEx | PSyn | Str | Dat |
|---|---|---|---|
| 16 | 16 | 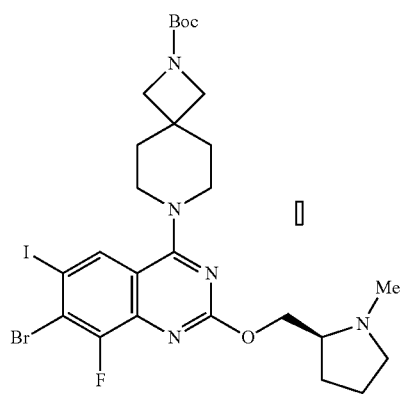 [SMILES: CN1CCC[C@H]1COc1nc(N2CCC3(CC2)CN(C(=O)OC(C)(C)C)C3)c2cc(I)c(Br)c(F)c2n1] | ESI+; 690.3 |
| 17 | 17 | 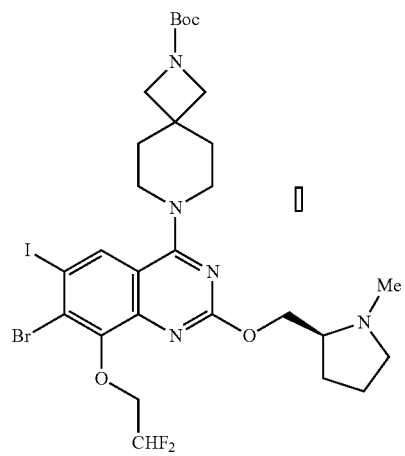 [SMILES: CN1CCC[C@H]1COc1nc(N2CCC3(CC2)CN(C(=O)OC(C)(C)C)C3)c2cc(I)c(Br)c(OCC(F)F)c2n1] | ESI+; 754.4 |
TABLE 13
| PEx | PSyn | Str | Dat |
|---|---|---|---|
| 18 | 18 | 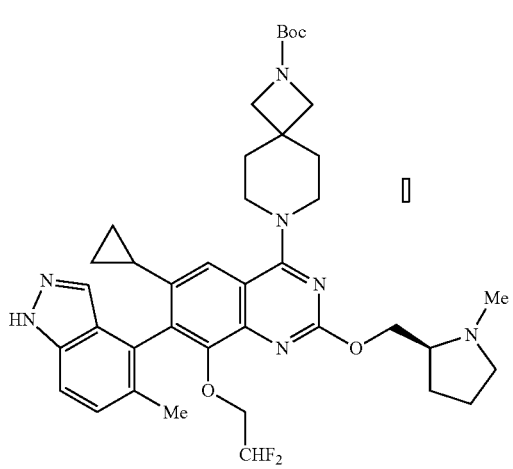 [SMILES: Cc1ccc2[nH]ncc2c1-c1c(C2CC2)cc2c(N3CCC4(CC3)CN(C(=O)OC(C)(C)C)C4)nc(OC[C@@H]3CCCN3C)nc2c1OCC(F)F] | ESI+; 668.5 |
| 19 | 19 | | ESI+; 718.6 |

TABLE 14

| PEx | PSyn | Str | Dat |
|---|---|---|---|
| 20 | 20 | (structure) | ESI+; 521.2 |
| 21 | 21 | (structure) | ESI+; 598.2, 600.2 |
| 22 | 22 | (structure) | ESI+; 624.1, 626.1 |

TABLE 15

| PEx | PSyn | Str | Dat |
|---|---|---|---|
| 23 | 23 | (structure) | ESI+; 676.3 |

TABLE 15-continued
| PEx | PSyn | Str | Dat |
|---|---|---|---|
| 24 | 24<br>24-2 | 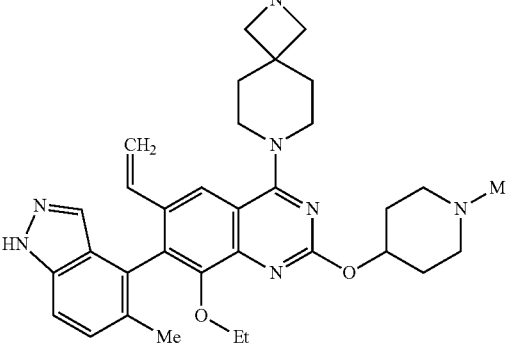 | ESI+;<br>668.3 |
| 25 | 5 | 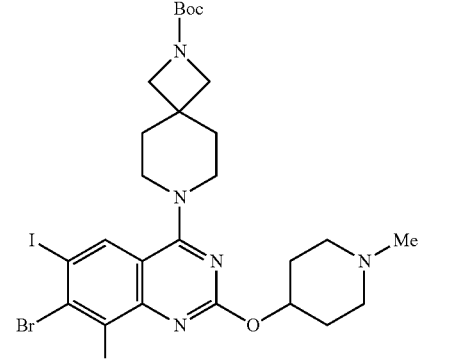 | ESI+;<br>744.3 |
TABLE 16
| PEx | PSyn | Str | Dat |
|---|---|---|---|
| 26 | 9 | 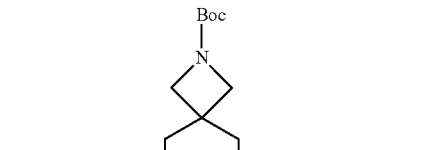 | ESI+;<br>658.5 |

TABLE 16-continued
| PEx | PSyn | Str | Dat |
|---|---|---|---|
| 27 | 7 | | ESI+; 792.7 |
TABLE 17
| PEx | PSyn | Str | Dat |
|---|---|---|---|
| 28 | 28 | | ESI+; 608.6 |
| 29 | 4 | | ESI+; 612.4, 614.4 |
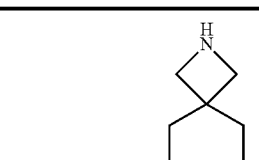

TABLE 17-continued
| PEx | PSyn | Str | Dat |
|---|---|---|---|
| 30 | 8 | 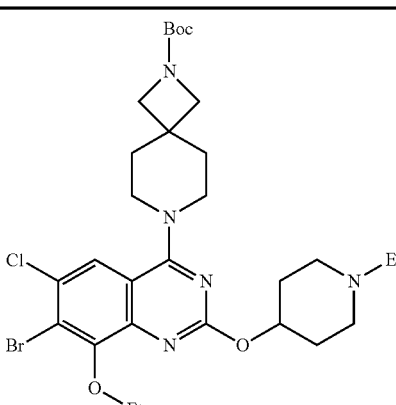 | ESI+; 638.4, 640.4 |
TABLE 18
| PEx | PSyn | Str | Dat |
|---|---|---|---|
| 31 | 23 | 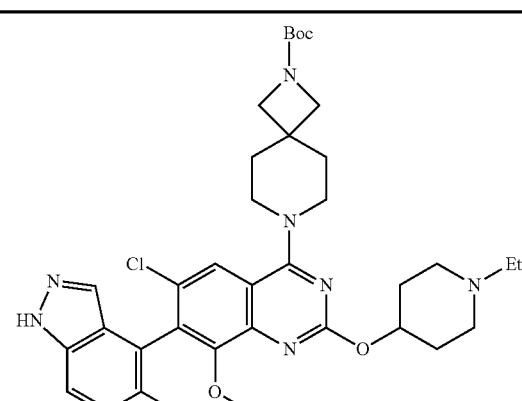 | ESI+; 690.7 |
| 32 | 24 | 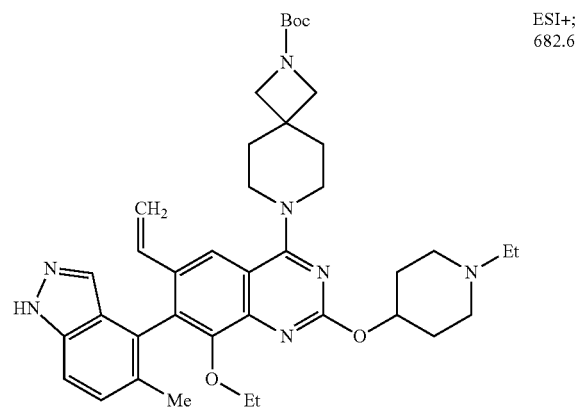 | ESI+; 682.6 |

TABLE 18-continued
| PEx | PSyn | Str | Dat |
|---|---|---|---|
| 33 | 33 | 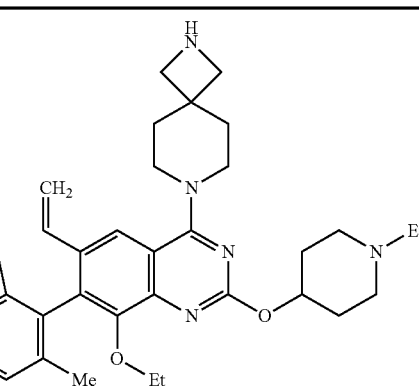 | ESI+; 582.6 |
TABLE 19
| PEx | PSyn | Str | Dat |
|---|---|---|---|
| 34 | 34 | 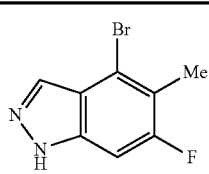 | ESI+; 231.0 |
| 35 | 35 | 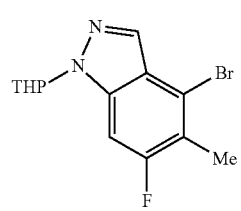 | ESI+; 313.1 |
| 36 | 36 | 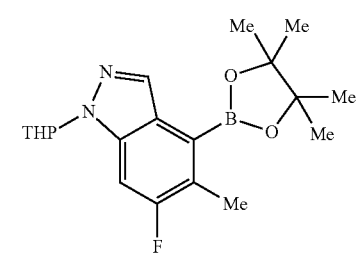 | ESI+; 361.3 |

TABLE 19-continued
| PEx | PSyn | Str | Dat |
|---|---|---|---|
| 37 | 7 | 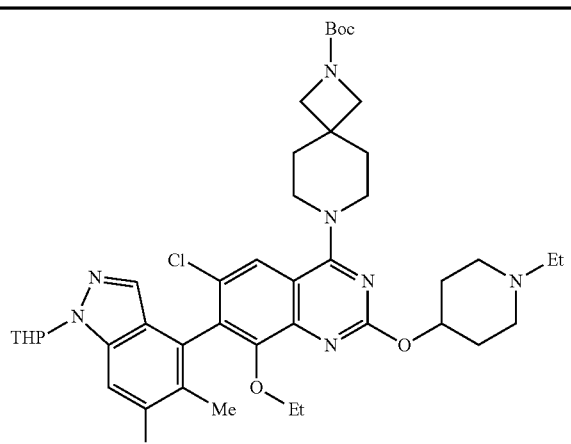 | ESI+; 792.7 |
TABLE 20
| PEx | PSyn | Str | Dat |
|---|---|---|---|
| 38 | 24 | 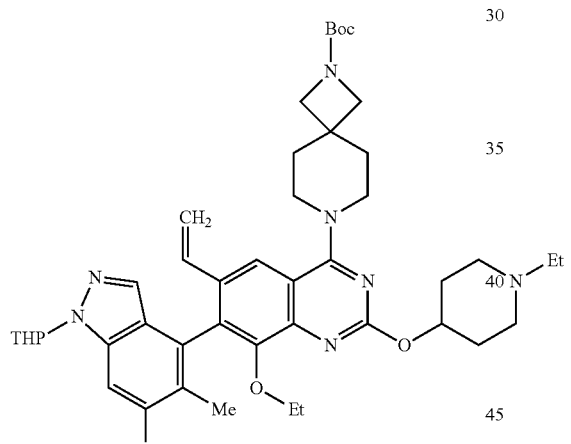 | ESI+; 784.7 |
| 39 | 39 | 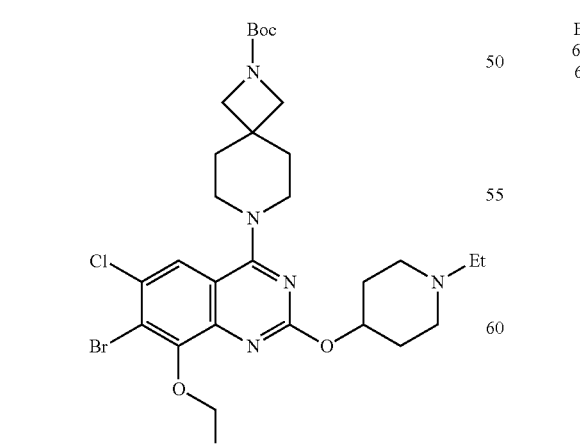 | ESI+; 692.5, 694.4 |

TABLE 21
| PEx | PSyn | Str | Dat |
|---|---|---|---|
| 40 | 7 | 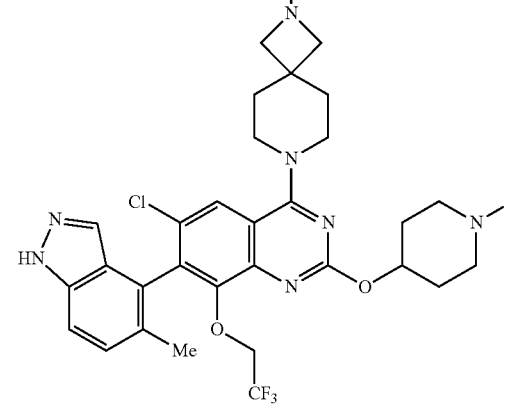 | ESI+; 744.6, 746.5 |
| 41 | 24 | | ESI+; 736.6 |
TABLE 22
| PEx | PSyn | Str | Dat |
|---|---|---|---|
| 42 | 5 | 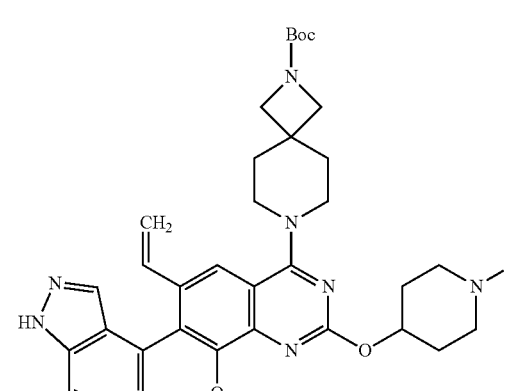 | ESI+; 676.4 |

TABLE 22-continued
| PEx | PSyn | Str | Dat |
|---|---|---|---|
| 43 | 23 | 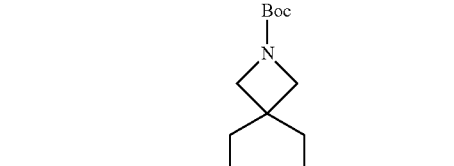 | ESI+; 726.6 |
TABLE 23
| PEx | PSyn | Str | Dat |
|---|---|---|---|
| 44 | 24 | | ESI+; 718.7 |
| 45 | 5 | | ESI+; 700.2, 702.2 |

TABLE 24
| PEx | PSyn | Str | Dat |
|---|---|---|---|
| 46 | 7 | 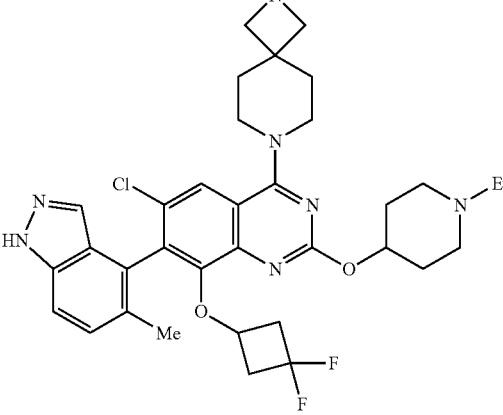 | ESI+; 752.6, 754.5 |
| 47 | 24 | 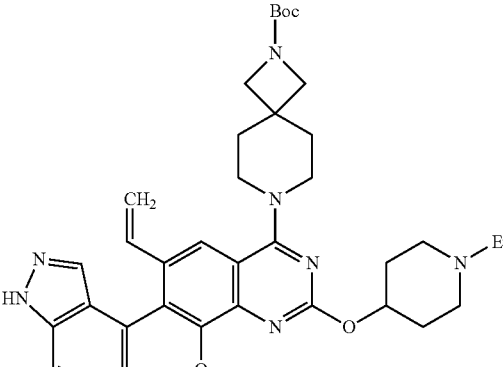 | ESI+; 744.6 |
TABLE 25
| PEx | PSyn | Str | Dat |
|---|---|---|---|
| 48 | 4 | 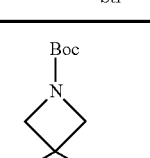 | ESI+; 628.2 |

TABLE 25-continued

| PEx | PSyn | Str | Dat |
|---|---|---|---|
| 49 | 8 | (structure) | ESI+; 652.2, 654.2 |
| 50 | 7 | (structure) | ESI+; 704.4 |

TABLE 26

| PEx | PSyn | Str | Dat |
|---|---|---|---|
| 51 | 24 | (structure) | ESI+; 696.3 |

TABLE 26-continued
| PEx | PSyn | Str | Dat |
|---|---|---|---|
| 52 | 4 | 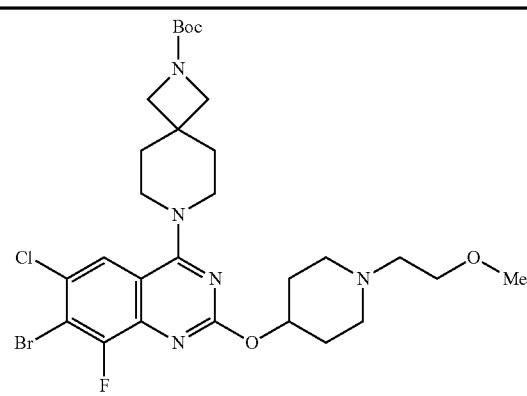 | ESI+; 644.1 |
| 53 | 8 | 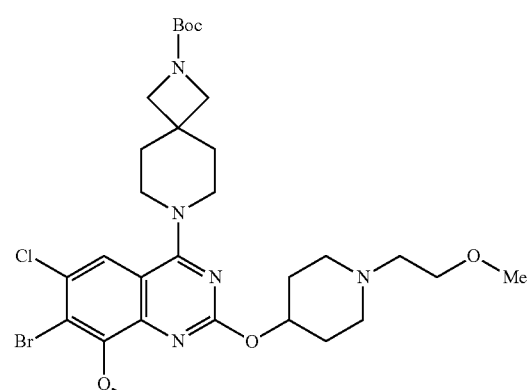 [SMILES: COCCN1CCC(Oc2nc(N3CCC4(CC3)CN(C(=O)OC(C)(C)C)C4)c3cc(Cl)c(Br)c(F)c3n2)CC1] | ESI+; 668.2, 670.2 |
TABLE 27
| PEx | PSyn | Str | Dat |
|---|---|---|---|
| 54 | 7 | 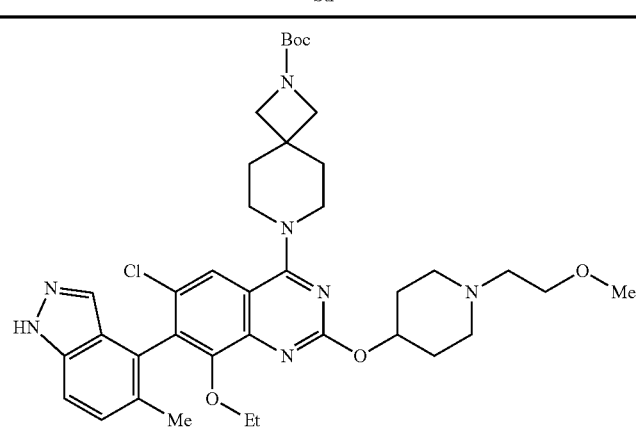 | ESI+; 720.5 |

TABLE 27-continued
| PEx | PSyn | Str | Dat |
|---|---|---|---|
| 55 | 24 | 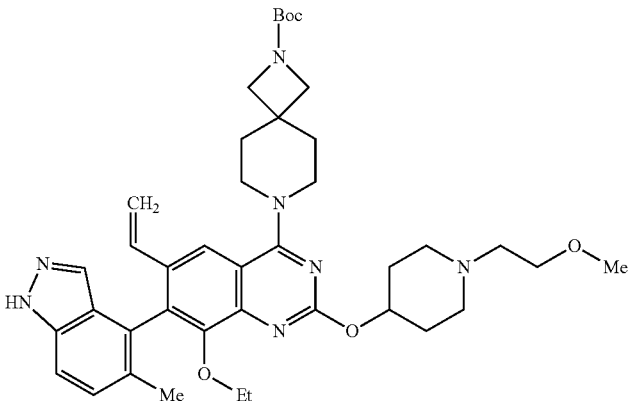 [SMILES: C=Cc1cc2c(N3CCC4(CC3)CN(C(=O)OC(C)(C)C)C4)nc(OC3CCN(CCOC)CC3)nc2c(OCC)c1-c1c(C)ccc2[nH]ncc12] | ESI+; 712.6 |
| 56 | 16 | 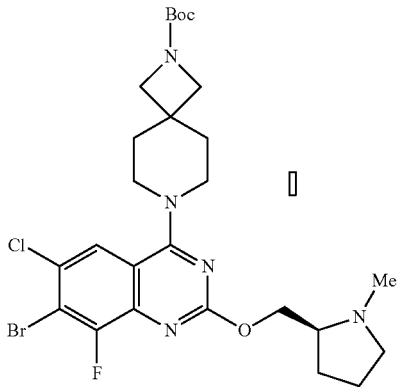 [SMILES: CN1CCC[C@H]1COc1nc(N2CCC3(CC2)CN(C(=O)OC(C)(C)C)C3)c2cc(Cl)c(Br)c(F)c2n1] | ESI+; 598.3, 600.3 |
TABLE 28
| PEx | PSyn | Str | Dat |
|---|---|---|---|
| 57 | 5 | 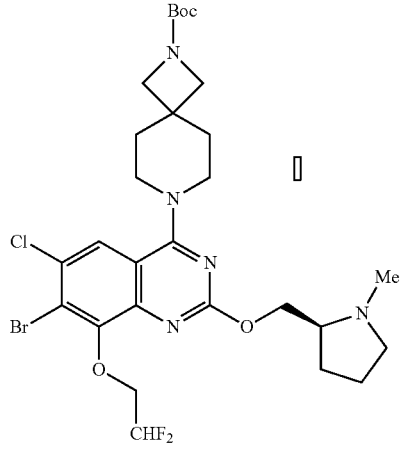 [SMILES: CN1CCC[C@H]1COc1nc(N2CCC3(CC2)CN(C(=O)OC(C)(C)C)C3)c2cc(Cl)c(Br)c(OCC(F)F)c2n1] | ESI+; 660.4, 662.4 |

TABLE 28-continued
| PEx | PSyn | Str | Dat |
|---|---|---|---|
| 58 | 7 | 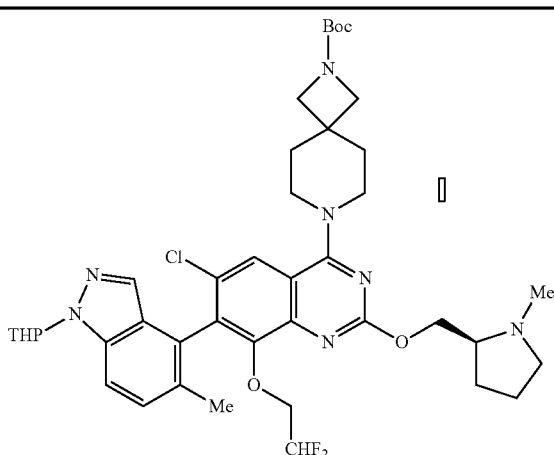 | ESI+; 796.6 |
TABLE 29
| PEx | PSyn | Str | Dat |
|---|---|---|---|
| 59 | 24 | 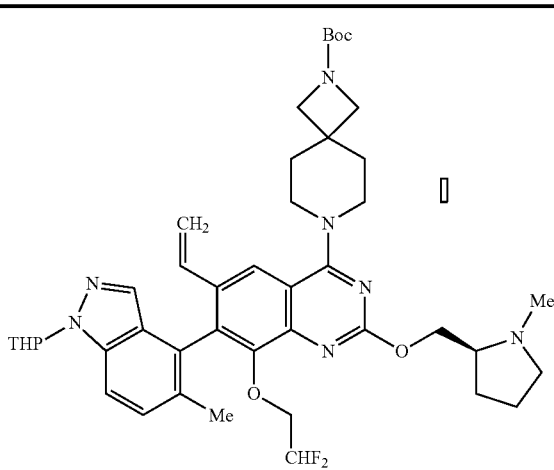 | ESI+; 788.8 |
| 60 | 5 | 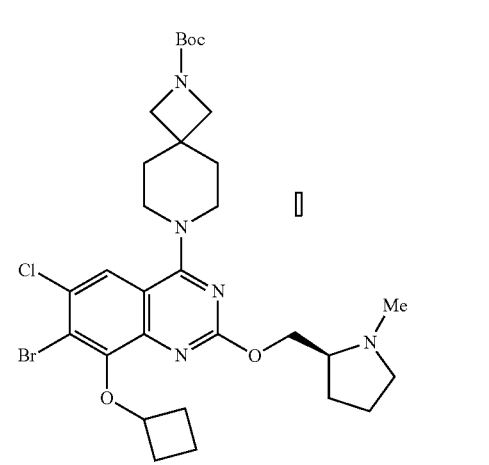 [SMILES: CN1CCC[C@H]1COc1nc(N2CCC3(CC2)CN(C(=O)OC(C)(C)C)C3)c2cc(Cl)c(Br)c(OC3CCC3)c2n1] | ESI+; 650.5, 652.5 |

TABLE 30
| PEx | PSyn | Str | Dat |
|---|---|---|---|
| 61 | 7 | 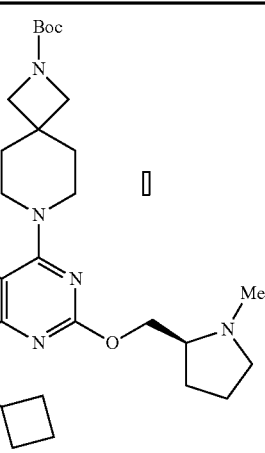 | ESI+; 702.4 |
| 62 | 24 | 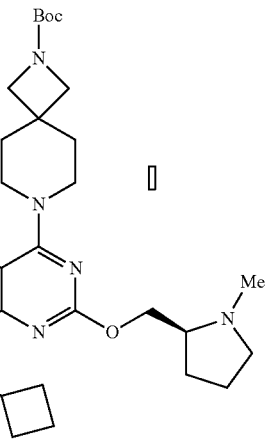 | ESI+; 694.6 |
| 63 | 8 | 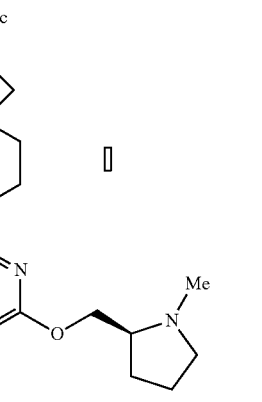 | ESI+; 624.4, 626.4 |

TABLE 31
| PEx | PSyn | Str | Dat |
|---|---|---|---|
| 64 | 23 | 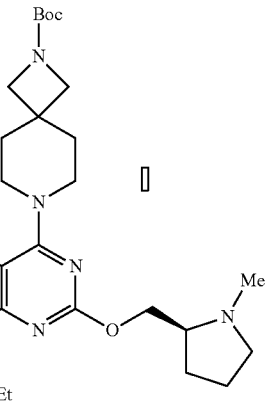 | ESI+; 676.6, 678.6 |
| 65 | 24 | 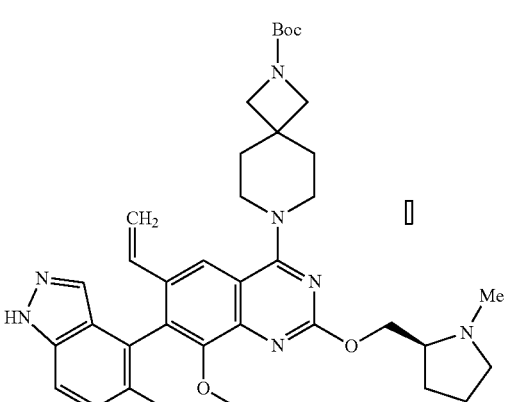 | ESI+; 668.5 |
| 66 | 6 | 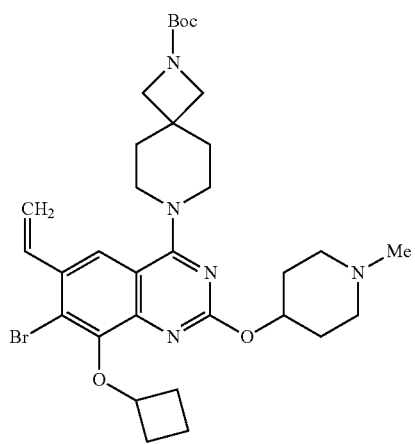 [SMILES: C=Cc1cc2c(N3CCC4(CC3)CN(C(=O)OC(C)(C)C)C4)nc(OC3CCN(C)CC3)nc2c(OC2CCC2)c1Br] | ESI+; 644.4 |

TABLE 32
| PEx | PSyn | Str | Dat |
|---|---|---|---|
| 67 | 7 | 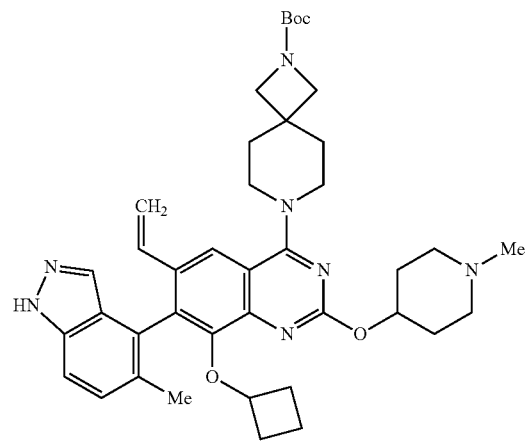 [SMILES: C=Cc1cc2c(N3CCC4(CC3)CN(C(=O)OC(C)(C)C)C4)nc(OC3CCN(C)CC3)nc2c(OC2CCC2)c1-c1c(C)ccc2[nH]ncc12] | ESI+; 694.6 |
| 68 | 4 | 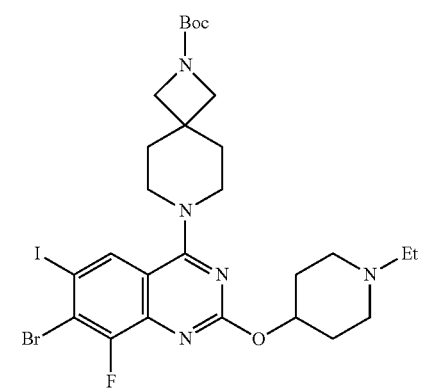 [SMILES: CCN1CCC(Oc2nc(N3CCC4(CC3)CN(C(=O)OC(C)(C)C)C4)c3cc(I)c(Br)c(F)c3n2)CC1] | ESI+; 706.3 |
| 69 | 8 | 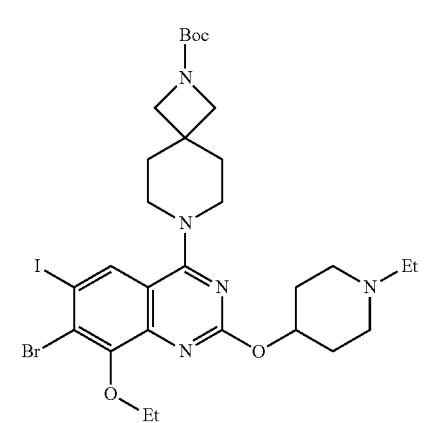 [SMILES: CCOc1c(Br)c(I)cc2c(N3CCC4(CC3)CN(C(=O)OC(C)(C)C)C4)nc(OC3CCN(CC)CC3)nc12] | ESI+; 732.3 |

TABLE 33
| PEx | PSyn | Str | Dat |
|---|---|---|---|
| 70 | 9 | 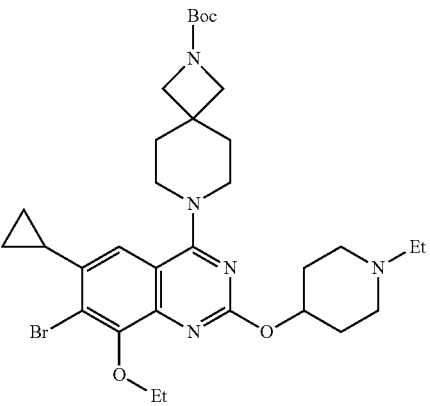 [SMILES: CCOc1c(Br)c(C2CC2)cc2c(N3CCC4(CC3)CN(C(=O)OC(C)(C)C)C4)nc(OC3CCN(CC)CC3)nc12] | ESI+; 646.5 |
| 71 | 7 | 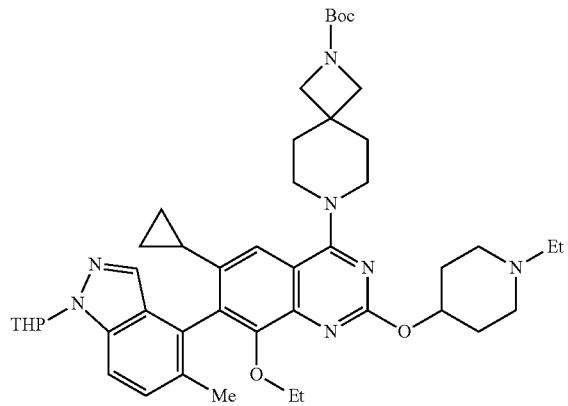 | ESI+; 780.6 |
| 72 | 5 | 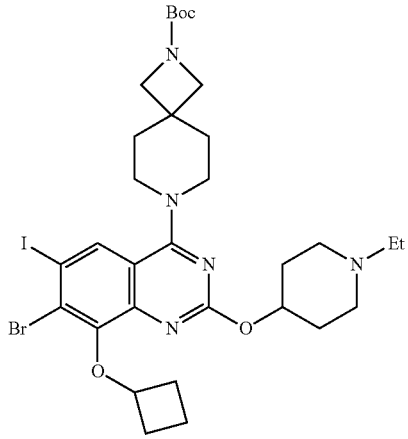 [SMILES: CCN1CCC(Oc2nc(N3CCC4(CC3)CN(C(=O)OC(C)(C)C)C4)c3cc(I)c(Br)c(OC4CCC4)c3n2)CC1] | ESI+; 758.4 |

TABLE 34

| PEx | PSyn | Str | Dat |
|---|---|---|---|
| 73 | 9 | | ESI+; 670.5 |
| 74 | 7 | | ESI+; 806.8 |

TABLE 35

| PEx | PSyn | Str | Dat |
|---|---|---|---|
| 75 | 6 | | ESI+; 658.4 |

TABLE 35-continued
| PEx | PSyn | Str | Dat |
|---|---|---|---|
| 76 | 7 | 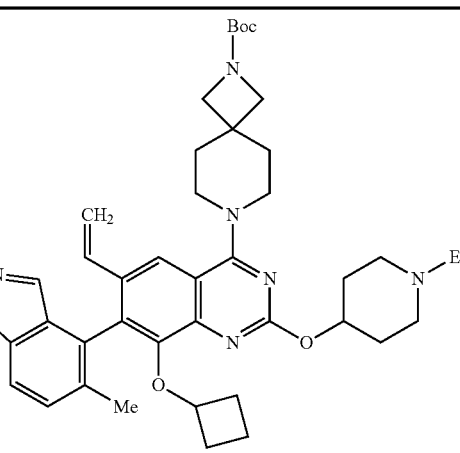 | ESI+; 792.7 |
| 77 | 35 | 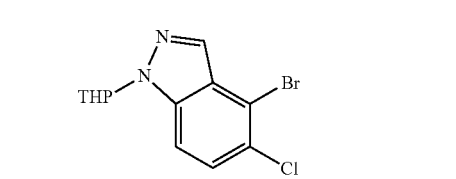 | ESI+; 317.1 |
TABLE 36
| PEx | PSyn | Str | Dat |
|---|---|---|---|
| 78 | 36 | 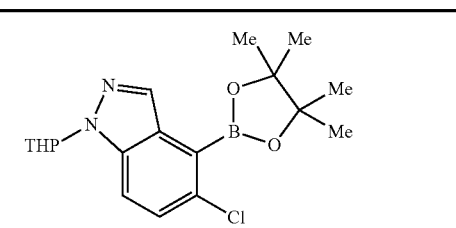 | ESI+; 363.3 |
| 79 | 6 | 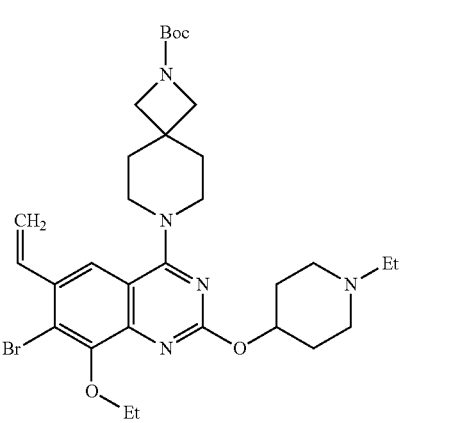 [SMILES: C=Cc1cc2c(N3CCC4(CC3)CN(C(=O)OC(C)(C)C)C4)nc(OC3CCN(CC)CC3)nc2c(OCC)c1Br] | ESI+; 632.5 |

TABLE 36-continued

| PEx | PSyn | Str | Dat |
|---|---|---|---|
| 80 | 7 | | ESI+; 786.6 |

TABLE 37

| PEx | PSyn | Str | Dat |
|---|---|---|---|
| 81 | 5 | | ESI+; 768.3 |
| 82 | 9 | | ESI+; 680.5 |

TABLE 38

| PEx | PSyn | Str | Dat |
|---|---|---|---|
| 83 | 7 | | ESI+; 816.6 |
| 84 | 28 | | ESI+; 632.5 |
| 85 | 8 | | ESI+; 718.3 |

TABLE 39
| PEx | PSyn | Str | Dat |
|---|---|---|---|
| 86 | 9 | 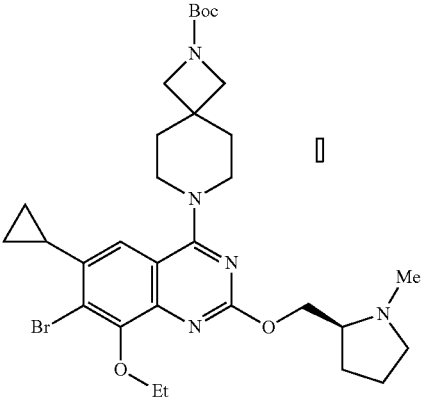 [SMILES: CCOc1c(Br)c(C2CC2)cc2c(N3CCC4(CC3)CN(C(=O)OC(C)(C)C)C4)nc(OC[C@@H]3CCCN3C)nc12] | ESI+; 632.5 |
| 87 | 7 | 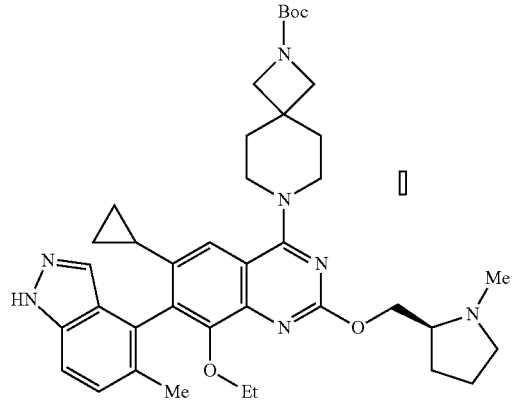 [SMILES: CCOc1c(-c2c(C)ccc3[nH]ncc23)c(C2CC2)cc2c(N3CCC4(CC3)CN(C(=O)OC(C)(C)C)C4)nc(OC[C@@H]3CCCN3C)nc12] | ESI+; 682.6 |
| 88 | 8 | 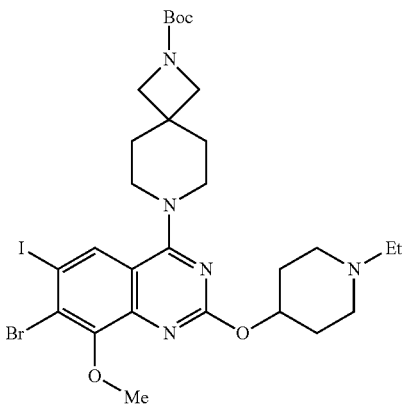 | ESI+; 716.3 |

TABLE 40

| PEx | PSyn | Str | Dat |
|---|---|---|---|
| 89 | 6 | | ESI+; 618.4 |
| 90 | 7 | | ESI+; 772.6 |
| 91 | 8 | | ESI+; 612.2 |

TABLE 41
| PEx | PSyn | Str | Dat |
|---|---|---|---|
| 92 | 7 | 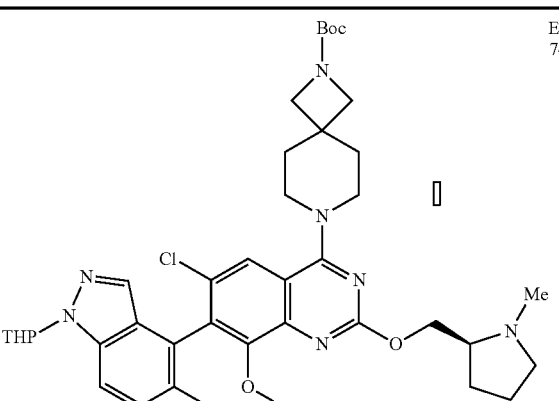 | ESI+; 746.4 |
| 93 | 24 | 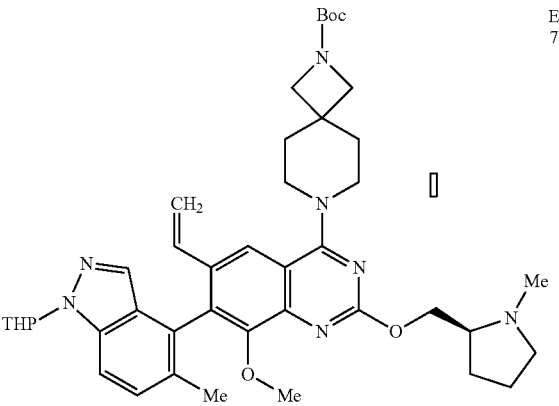 | ESI+; 738.4 |
TABLE 42
| PEx | PSyn | Str | Dat |
|---|---|---|---|
| 94 | 94 | 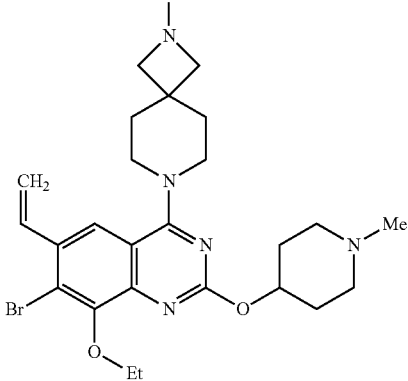 | ESI+; 618.3 |
| 95 | 95 | 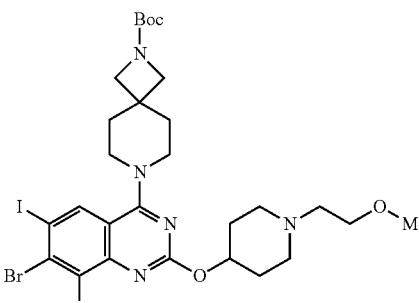 | ESI+; 734.3 |

TABLE 42-continued
| PEx | PSyn | Str | Dat |
|---|---|---|---|
| 96 | 96 | 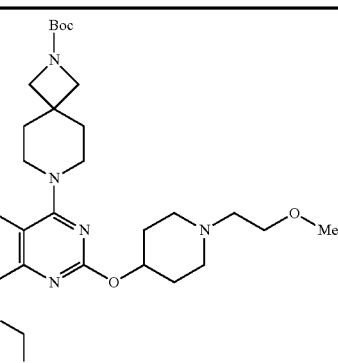 | ESI+; 814.2 |
TABLE 43
| PEx | PSyn | Str | Dat |
|---|---|---|---|
| 97 | 9 | 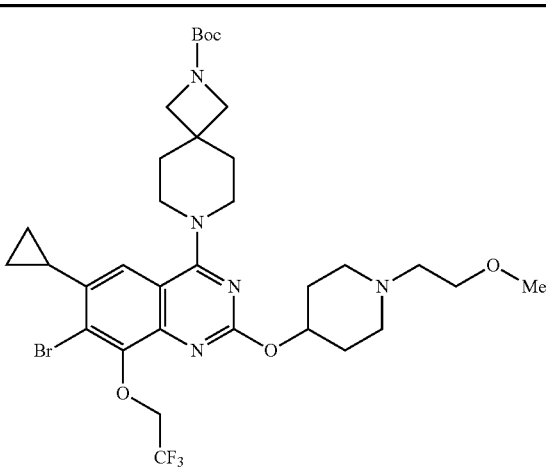 | ESI+; 730.4 |
| 98 | 7 | 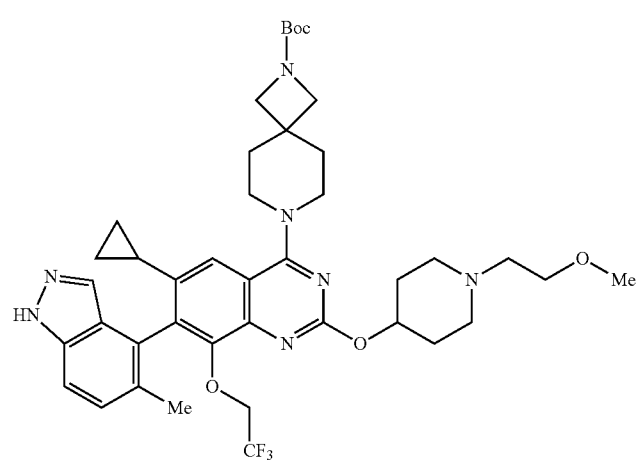 [SMILES: COCCN1CCC(Oc2nc(N3CCC4(CC3)CN(C(=O)OC(C)(C)C)C4)c3cc(C4CC4)c(-c4c(C)ccc5[nH]ncc45)c(OCC(F)(F)F)c3n2)CC1] | ESI+; 780.6 |

TABLE 44
| PEx | PSyn | Str | Dat |
|---|---|---|---|
| 99 | 99 | 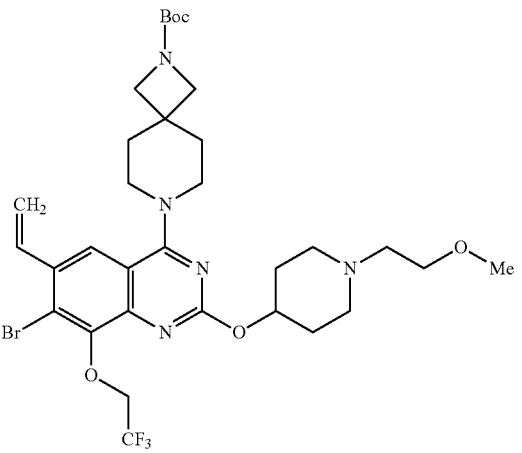 [SMILES: C=Cc1cc2c(N3CCC4(CC3)CN(C(=O)OC(C)(C)C)C4)nc(OC3CCN(CCOC)CC3)nc2c(OCC(F)(F)F)c1Br] | ESI+; 716.4 |
| 100 | 100 | 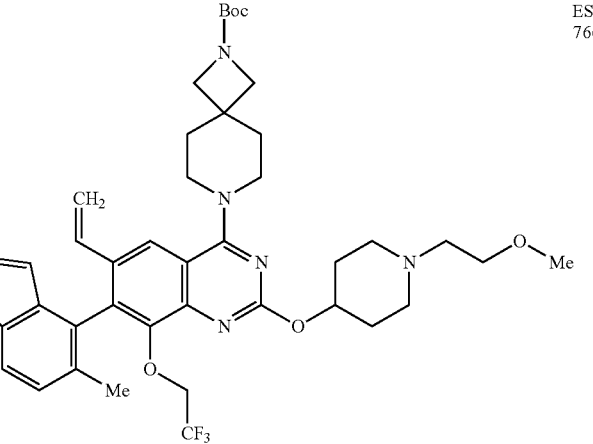 | ESI+; 766.5 |
TABLE 45
| PEx | PSyn | Str | Dat |
|---|---|---|---|
| 101 | 101 | 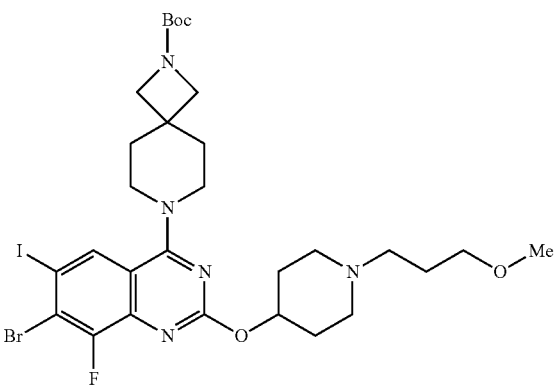 [SMILES: COCCCN1CCC(Oc2nc(N3CCC4(CC3)CN(C(=O)OC(C)(C)C)C4)c3cc(I)c(Br)c(F)c3n2)CC1] | ESI+; 748.3 |

TABLE 45-continued
| PEx | PSyn | Str | Dat |
|---|---|---|---|
| 102 | 102 | 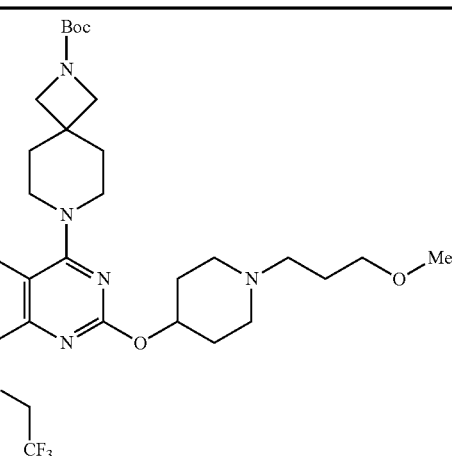 | ESI+; 830.2 |
| 103 | 6 | 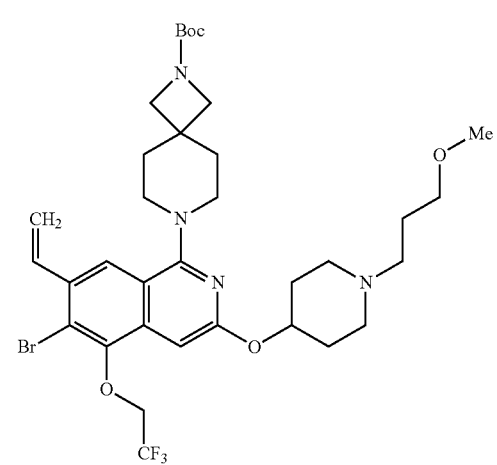 | ESI+; 730.4 |
TABLE 46
| PEx | PSyn | Str | Dat |
|---|---|---|---|
| 104 | 23 | 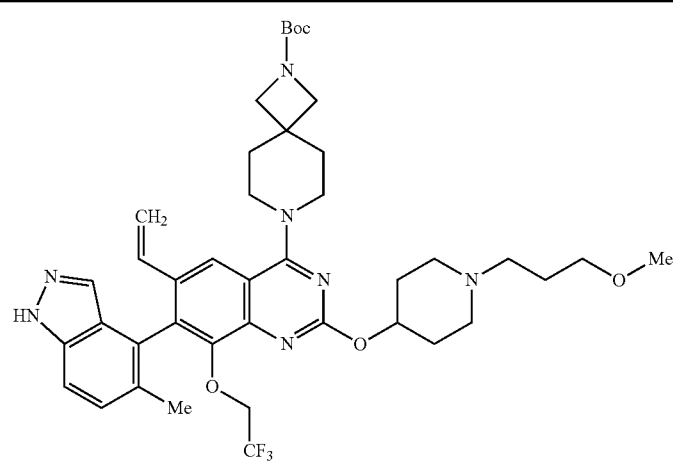 | ESI+; 780.6 |

TABLE 46-continued
| PEx | PSyn | Str | Dat |
|---|---|---|---|
| 105 | 105 | 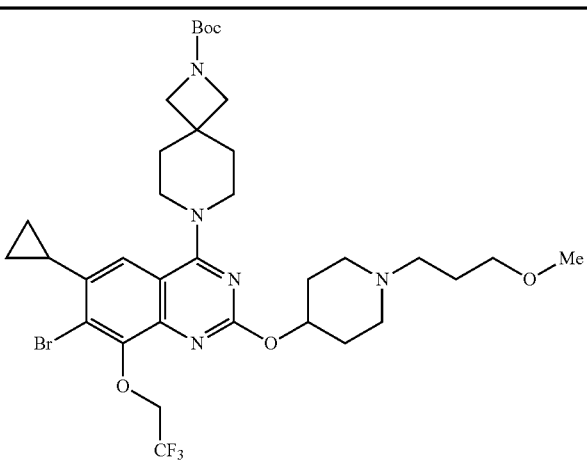 | ESI+; 744.3 |
TABLE 47
| PEx | PSyn | Str | Dat |
|---|---|---|---|
| 106 | 106 | 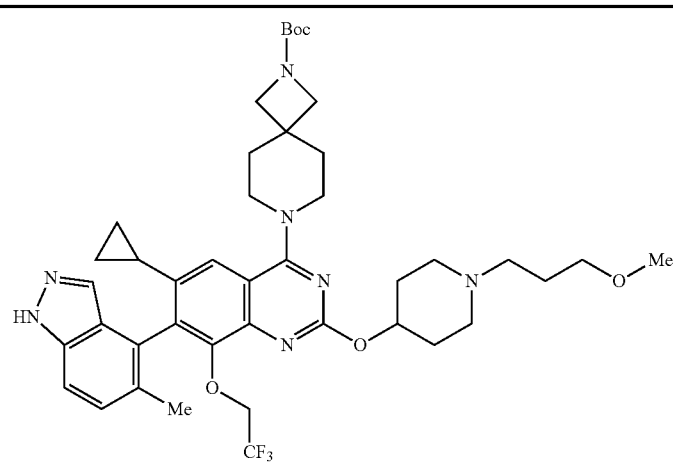 | ESI+; 794.5 |
| 107 | 4 | 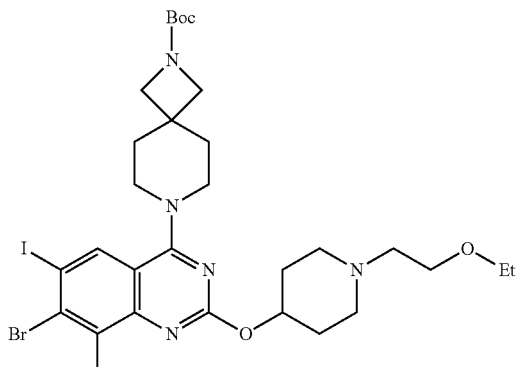 | ESI+; 750.3 |

TABLE 47-continued
| PEx | PSyn | Str | Dat |
|---|---|---|---|
| 108 | 39 |  | ESI+; 830.3 |
TABLE 48
| PEx | PSyn | Str | Dat |
|---|---|---|---|
| 109 | 6 | | ESI+; 728.4, 730.3 |
| 110 | 23 | | ESI+; 780.6 |

TABLE 48-continued
| PEx | PSyn | Str | Dat |
|---|---|---|---|
| 111 | 111 | | ESI+; 760.3, 762.4 |
TABLE 49
| PEx | PSyn | Str | Dat |
|---|---|---|---|
| 112 | 112 | | ESI+; 840.3 |
TABLE 49-continued
| PEx | PSyn | Str | Dat |
|---|---|---|---|
| 113 | 113 | | ESI+; 740.6 |
TABLE 50
| PEx | PSyn | Str | Dat |
|---|---|---|---|
| 114 | 114 | | ESI+; 792.6 |
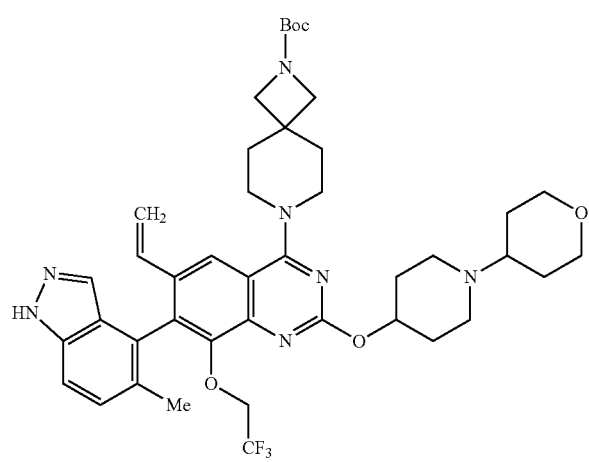 [SMILES: C=Cc1cc2c(N3CCC4(CC3)CN(C(=O)OC(C)(C)C)C4)nc(OC3CCN(C4CCOCC4)CC3)nc2c(OCC(F)(F)F)c1-c1c(C)ccc2[nH]ncc12]

TABLE 50-continued
| PEx | PSyn | Str | Dat |
|---|---|---|---|
| 115 | 115 | 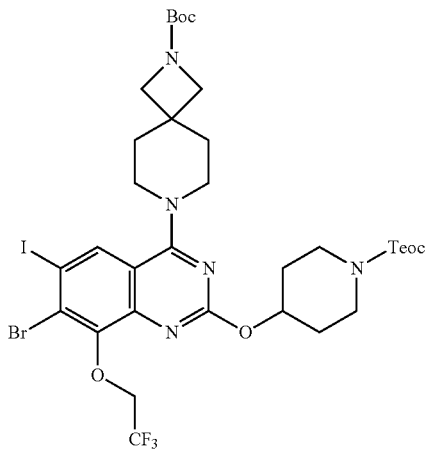 | ESI+; 900.4, 902.4 |
TABLE 51
| PEx | PSyn | Str | Dat |
|---|---|---|---|
| 116 | 6 | 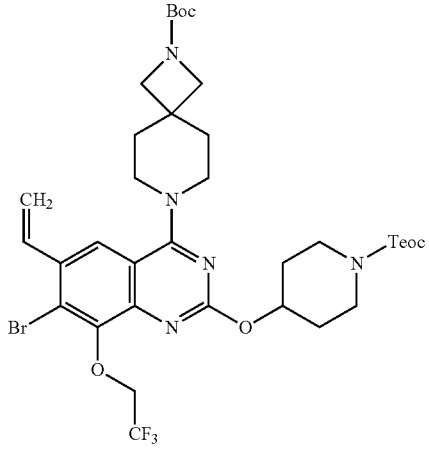 | ESI+; 800.5, 802.5 |
| 117 | 23 | 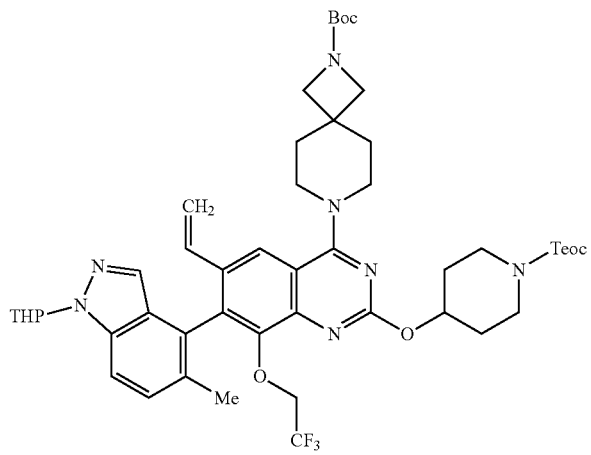 | ESI+; 936.6 |

133
TABLE 52
| PEx | PSyn | Str | Dat |
|---|---|---|---|
| 118 | 118 | 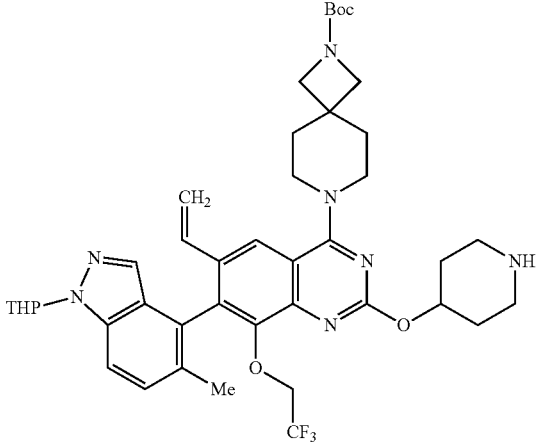 | ESI+; 792.5 |
| 119 | 119 | 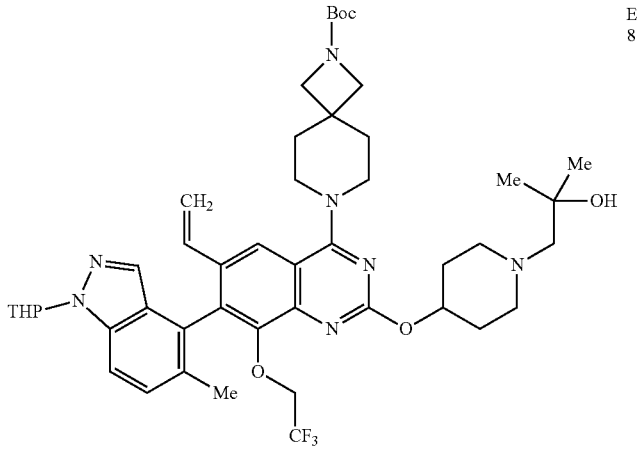 | ESI+; 864.6 |
TABLE 53
| PEx | PSyn | Str | Dat |
|---|---|---|---|
| 120 | 28 | 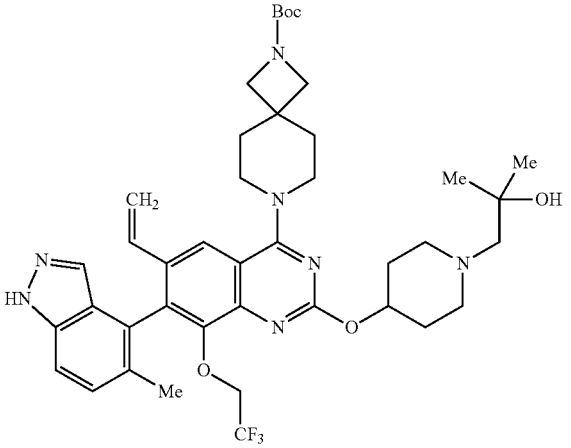 [SMILES: C=Cc1cc2c(N3CCC4(CC3)CN(C(=O)OC(C)(C)C)C4)nc(OC3CCN(CC(C)(C)O)CC3)nc2c(OCC(F)(F)F)c1-c1c(C)ccc2[nH]ncc12] | ESI+; 680.5 |

TABLE 53-continued

| PEx | PSyn | Str | Dat |
|---|---|---|---|
| 121 | 39 | | ESI+; 798.3 |

TABLE 54

| PEx | PSyn | Str | Dat |
|---|---|---|---|
| 112 | 9 | | ESI+; 712.5 |
| 123 | 23 | | ESI+; 762.6 |

TABLE 54-continued
| PEx | PSyn | Str | Dat |
|---|---|---|---|
| 124 | 4 | 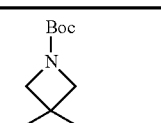 | ESI+; 732.2 |
TABLE 55
| PEx | PSyn | Str | Dat | | PEx | PSyn | Str | Dat |
|---|---|---|---|---|---|---|---|---|
| 125 | 39 | 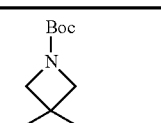 | ESI+; 812.3, 814.3 | | 126 | 6 | 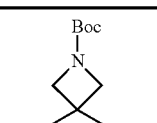 | ESI+; 712.4, 714.4 |
TABLE 56
| PEx | PSyn | Str | Dat |
|---|---|---|---|
| 127 | 23 | 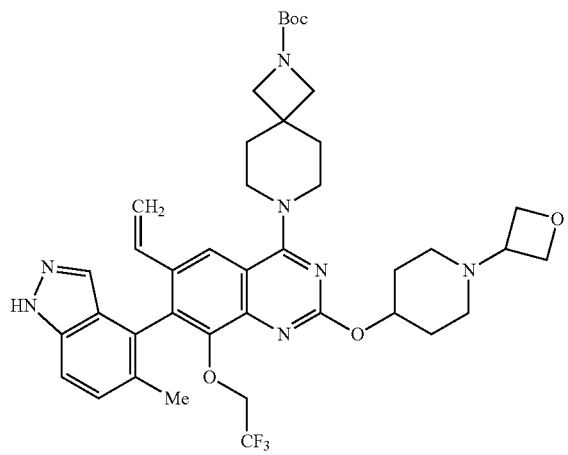 [SMILES: C=Cc1cc2c(N3CCC4(CC3)CN(C(=O)OC(C)(C)C)C4)nc(OC3CCN(C4COC4)CC3)nc2c(OCC(F)(F)F)c1-c1c(C)ccc2[nH]ncc12] | ESI+; 764.5 |

TABLE 56-continued
| PEx | PSyn | Str | Dat |
|---|---|---|---|
| 128 | 8 | 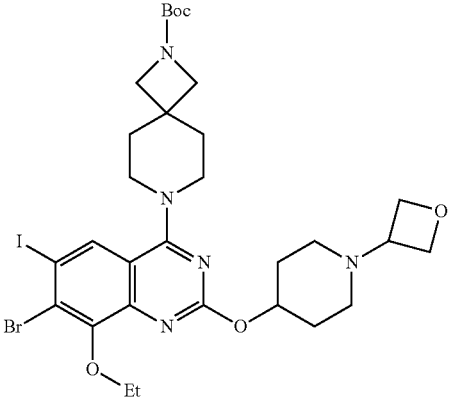 [SMILES: CCOc1c(Br)c(I)cc2c(N3CCC4(CC3)CN(C(=O)OC(C)(C)C)C4)nc(OC3CCN(C4COC4)CC3)nc12] | ESI+; 760.2 |
| 129 | 9 | 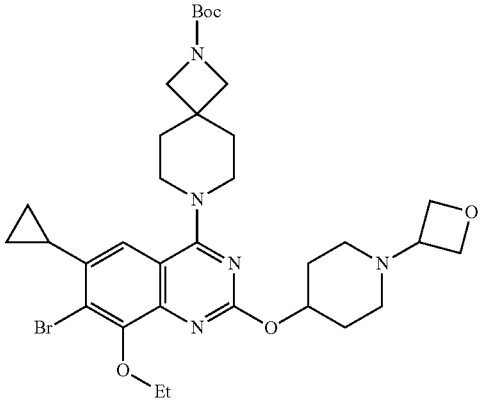 [SMILES: CCOc1c(Br)c(C2CC2)cc2c(N3CCC4(CC3)CN(C(=O)OC(C)(C)C)C4)nc(OC3CCN(C4COC4)CC3)nc12] | ESI+; 672.5, 674.4 |
TABLE 57
| PEx | PSyn | Str | Dat |
|---|---|---|---|
| 130 | 7 | 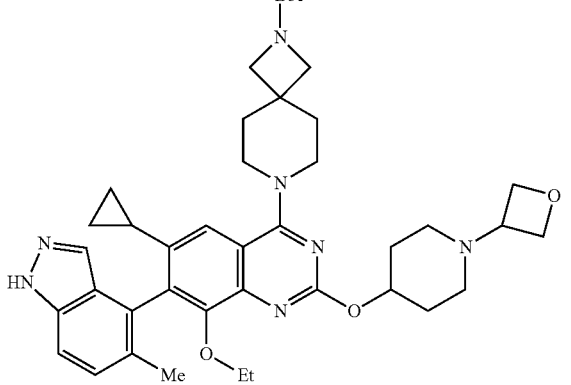 | ESI+; 724.7 |

TABLE 57-continued
| PEx | PSyn | Str | Dat |
|---|---|---|---|
| 131 | 33 | 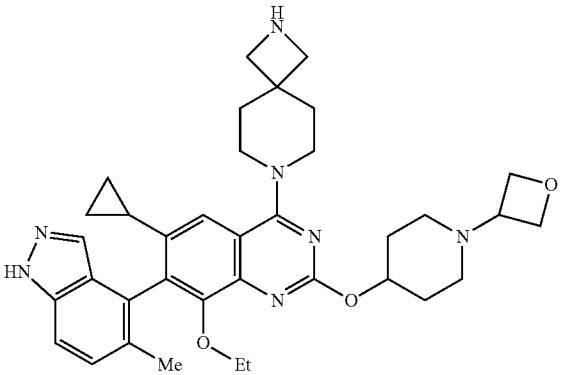 [SMILES: CCOc1c(-c2c(C)ccc3[nH]ncc23)c(C2CC2)cc2c(N3CCC4(CC3)CNC4)nc(OC3CCN(C4COC4)CC3)nc12] | ESI+; 624.5 |
TABLE 58
| PEx | PSyn | Str | Dat |
|---|---|---|---|
| 132 | 132 | 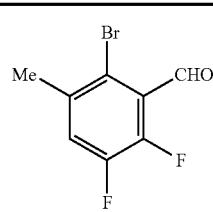 | CI+; 235.0 |
| 133 | 133 | 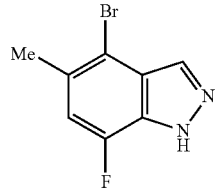 [SMILES: Cc1cc(F)c2[nH]ncc2c1Br] | ESI+; 228.9 |
| 134 | 35 | 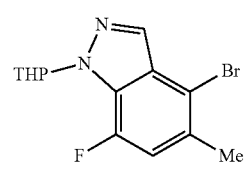 | ESI+; 313.0 |
| 135 | 36 | 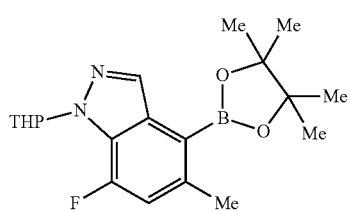 | ESI+; [M + Na]+ 383.3 |
| 136 | 136 | 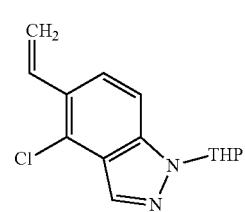 | ESI+; 263.2 |
TABLE 59
| PEx | PSyn | Str | Dat |
|---|---|---|---|
| 137 | 137 | 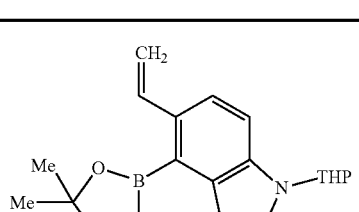 | ESI+; 355.3 |
| 138 | 138 | 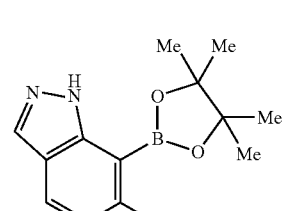 | ESI+; 259.2 |
| 139 | 139 | 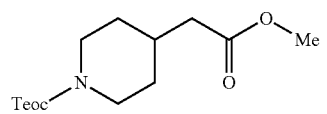 | ESI+; [M + Na]+ 324.2 |
| 140 | 140 | 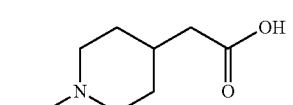 | ESI+; [M + Na]+ 310.1 |

TABLE 60
| PEx | PSyn | Str | Dat |
|---|---|---|---|
| 141 | 141 | 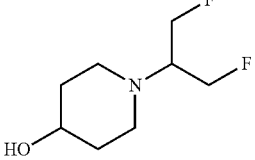 | ESI+; 180.1 |
| 142 | 142 | 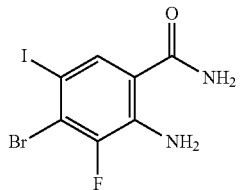 [SMILES: NC(=O)c1cc(I)c(Br)c(F)c1N] | ESI+; 359.0 |
| 143 | 143 | 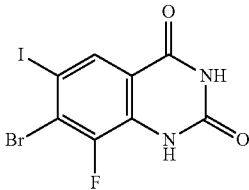 [SMILES: O=c1[nH]c(=O)c2cc(I)c(Br)c(F)c2[nH]1] | ESI+; 385.0, 386.9 |
| 144 | 144 | 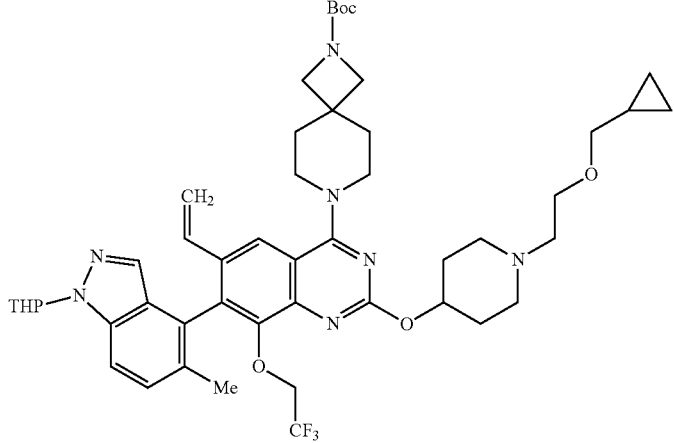 | ESI+; 890.7 |

TABLE 61

| PEx | PSyn | Str | Dat |
|-----|------|-----|-----|
| 145 | 4 | (structure) | ESI+; 705.3 |
| 146 | 39 | (structure) | ESI+; 785.2 |

TABLE 62

| PEx | PSyn | Str | Dat |
|-----|------|-----|-----|
| 147 | 6 | (structure) | ESI+; 683.4 |
| 148 | 7 | (structure) | ESI+; 735.5 |

TABLE 62-continued
| PEx | PSyn | Str | Dat |
|---|---|---|---|
| 149 | 4 | 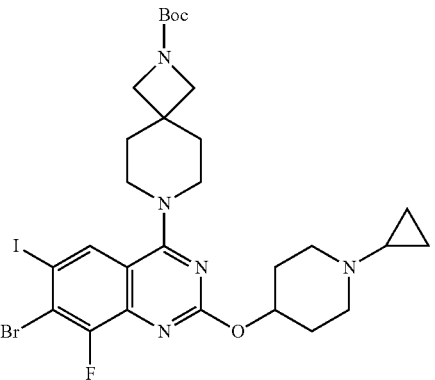 [SMILES: CC(C)(C)OC(=O)N1CC2(CCN(c3nc(OC4CCN(C5CC5)CC4)nc4c(F)c(Br)c(I)cc34)CC2)C1] | ESI+; 718.1 |
20
TABLE 63
| PEx | PSyn | Str | Dat |
|---|---|---|---|
| 150 | 8 | 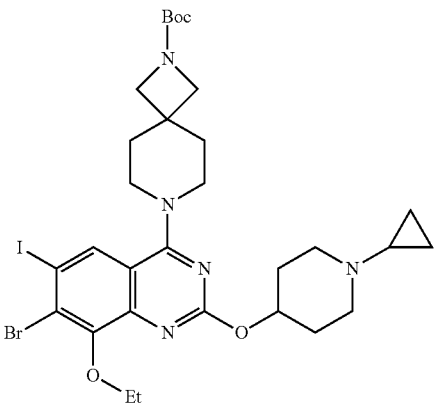 [SMILES: CCOc1c(Br)c(I)cc2c(N3CCC4(CC3)CN(C(=O)OC(C)(C)C)C4)nc(OC3CCN(C4CC4)CC3)nc12] | ESI+; 744.1 |
| 151 | 9 | 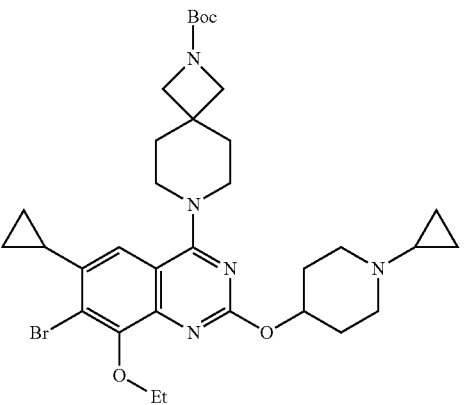 [SMILES: CCOc1c(Br)c(C2CC2)cc2c(N3CCC4(CC3)CN(C(=O)OC(C)(C)C)C4)nc(OC3CCN(C4CC4)CC3)nc12] | ESI+; 658.3 |

TABLE 63-continued
| PEx | PSyn | Str | Dat |
|---|---|---|---|
| 152 | 7 | 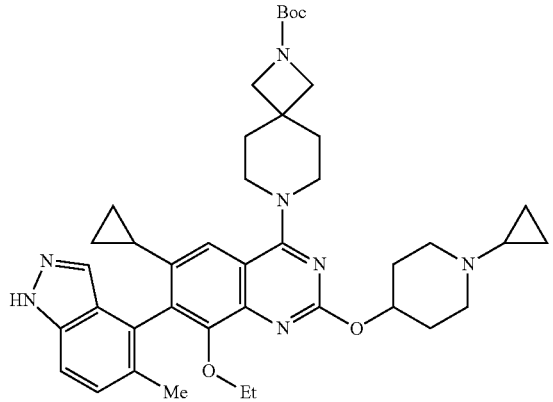 [SMILES: CCOc1c(-c2c(C)ccc3[nH]ncc23)c(C2CC2)cc2c(N3CCC4(CC3)CN(C(=O)OC(C)(C)C)C4)nc(OC3CCN(C4CC4)CC3)nc12] | ESI+; 708.4 |
TABLE 64
| PEx | PSyn | Str | Dat |
|---|---|---|---|
| 153 | 23 | 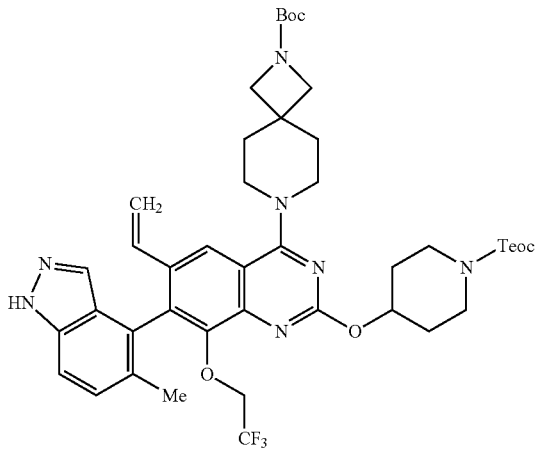 | ESI+; 852.6 |
| 154 | 118 | 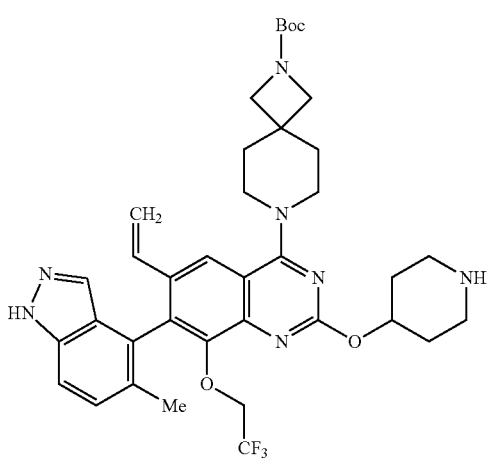 [SMILES: C=Cc1cc2c(N3CCC4(CC3)CN(C(=O)OC(C)(C)C)C4)nc(OC3CCNCC3)nc2c(OCC(F)(F)F)c1-c1c(C)ccc2[nH]ncc12] | ESI+; 708.5 |

TABLE 65
| PEx | PSyn | Str | Dat |
|---|---|---|---|
| 155 | 155 | 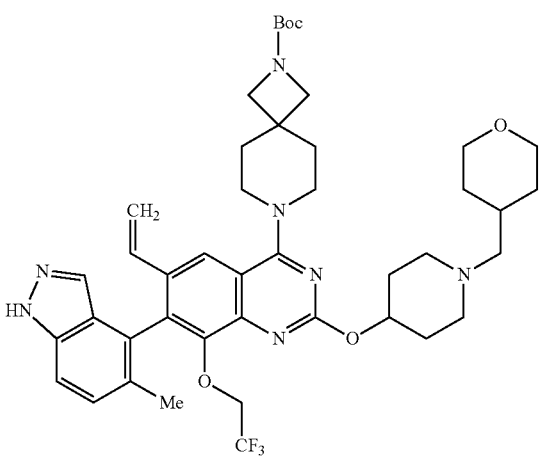 [SMILES: C=Cc1cc2c(N3CCC4(CC3)CN(C(=O)OC(C)(C)C)C4)nc(OC3CCN(CC4CCOCC4)CC3)nc2c(OCC(F)(F)F)c1-c1c(C)ccc2[nH]ncc12] | ESI+; 806.6 |
| 156 | 4 | 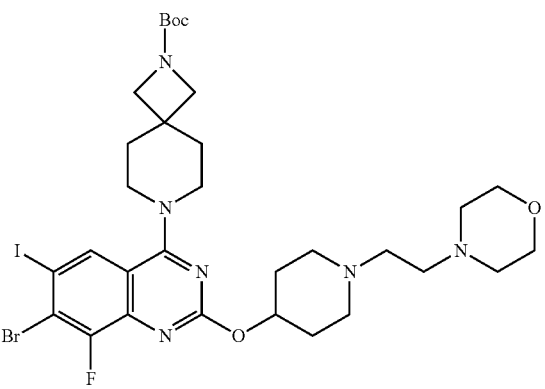 [SMILES: CC(C)(C)OC(=O)N1CC2(CCN(c3nc(OC4CCN(CCN5CCOCC5)CC4)nc4c(F)c(Br)c(I)cc34)CC2)C1] | ESI+; 791.3 |
| 157 | 39 | 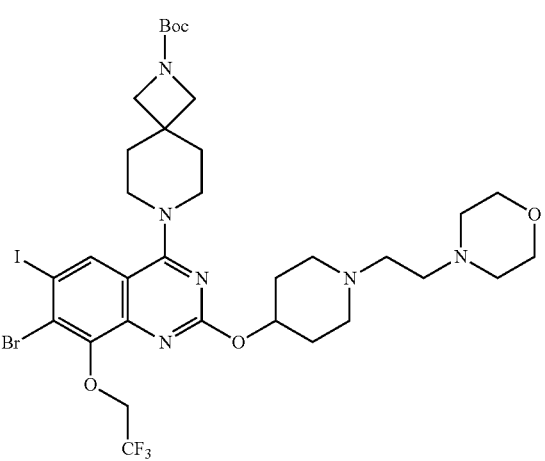 [SMILES: CC(C)(C)OC(=O)N1CC2(CCN(c3nc(OC4CCN(CCN5CCOCC5)CC4)nc4c(OCC(F)(F)F)c(Br)c(I)cc34)CC2)C1] | ESI+; 871.2 |

TABLE 66

| PEx | PSyn | Str | Dat |
|---|---|---|---|
| 158 | 9 | (structure) | ESI+; 785.5 |
| 159 | 23 | (structure) | ESI+; 835.6 |

TABLE 67

| PEx | PSyn | Str | Dat |
|---|---|---|---|
| 160 | 155 | (structure) | ESI+; 762.4 |

TABLE 67-continued
| PEx | PSyn | Str | Dat |
|---|---|---|---|
| 161 | 4 | 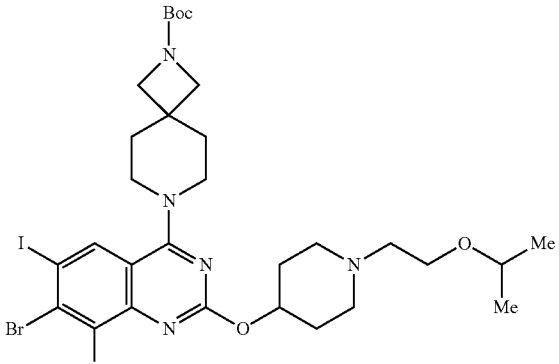 | ESI+; 762.4 |
| 162 | 39 | 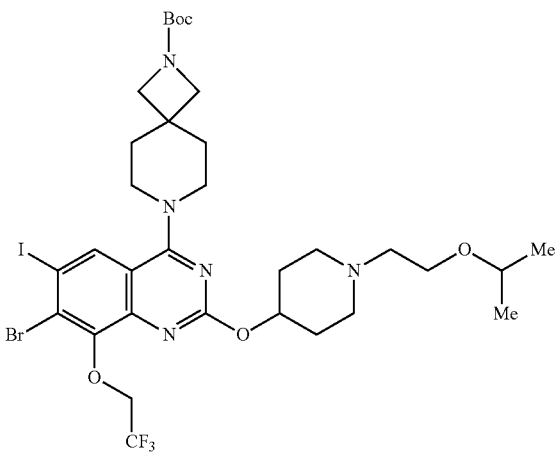 [SMILES: CC(C)OCCN1CCC(Oc2nc(N3CCC4(CC3)CN(C(=O)OC(C)(C)C)C4)c3cc(I)c(Br)c(OCC(F)(F)F)c3n2)CC1] | ESI+; 844.3 |
TABLE 68
| PEx | PSyn | Str | Dat |
|---|---|---|---|
| 163 | 6 | 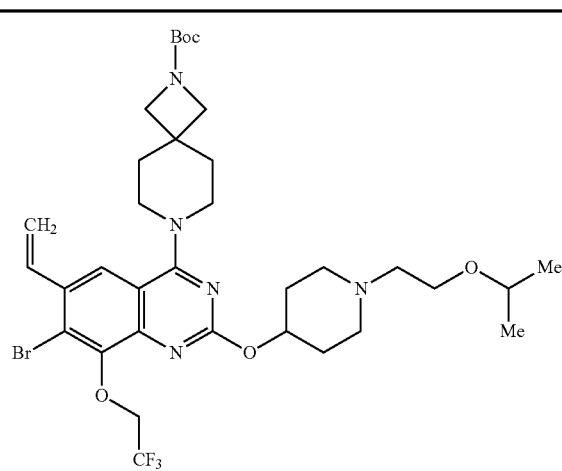 | ESI+; 744.4 |

TABLE 68-continued
| PEx | PSyn | Str | Dat |
|---|---|---|---|
| 164 | 23 | 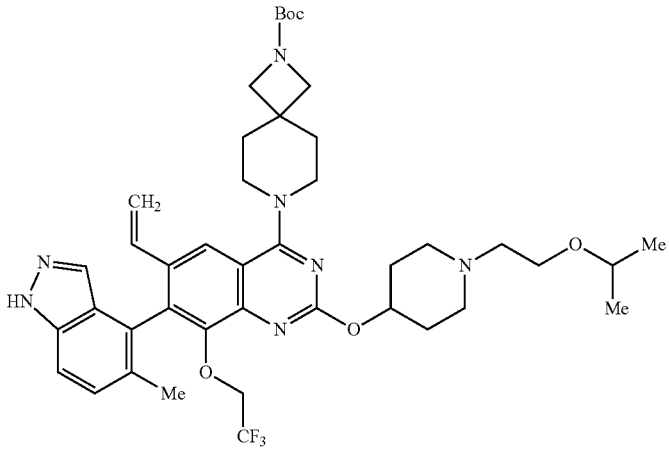 [SMILES: C=Cc1cc2c(N3CCC4(CC3)CN(C(=O)OC(C)(C)C)C4)nc(OC3CCN(CCOC(C)C)CC3)nc2c(OCC(F)(F)F)c1-c1c(C)ccc2[nH]ncc12] | ESI+; 794.6 |
| 165 | 4 | 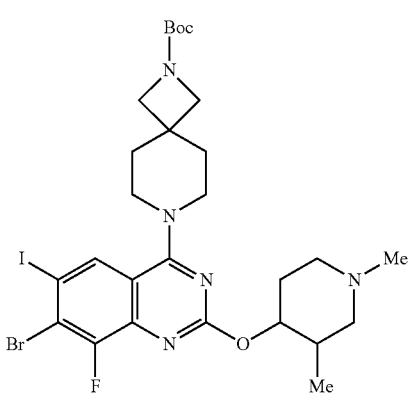 [SMILES: CC1CN(C)CCC1Oc1nc(N2CCC3(CC2)CN(C(=O)OC(C)(C)C)C3)c2cc(I)c(Br)c(F)c2n1] | ESI+; 706.2 |
TABLE 69
| PEx | PSyn | Str | Dat |
|---|---|---|---|
| 166 | 39 | 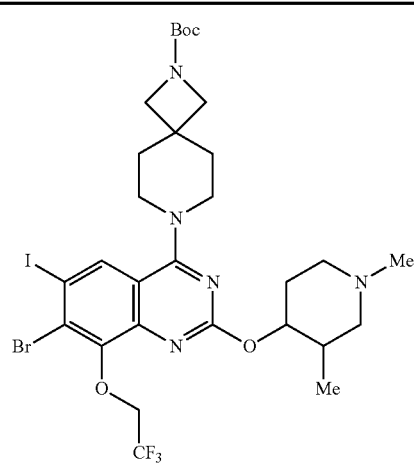 | ESI+; 786.2 |

TABLE 69-continued
| PEx | PSyn | Str | Dat |
|---|---|---|---|
| 167 | 6 | 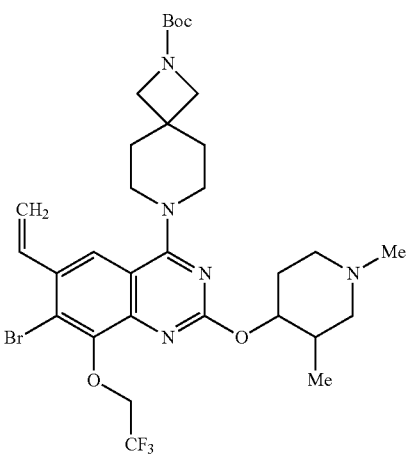 [SMILES: C=Cc1cc2c(N3CCC4(CC3)CN(C(=O)OC(C)(C)C)C4)nc(OC3CCN(C)CC3C)nc2c(OCC(F)(F)F)c1Br] | ESI+; 686.4 |
| 168 | 23 | 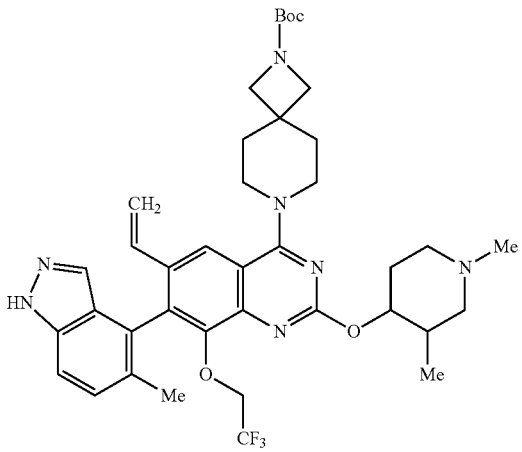 | ESI+; 736.5 |
TABLE 70
| PEx | PSyn | Str | Dat |
|---|---|---|---|
| 169 | 23 | 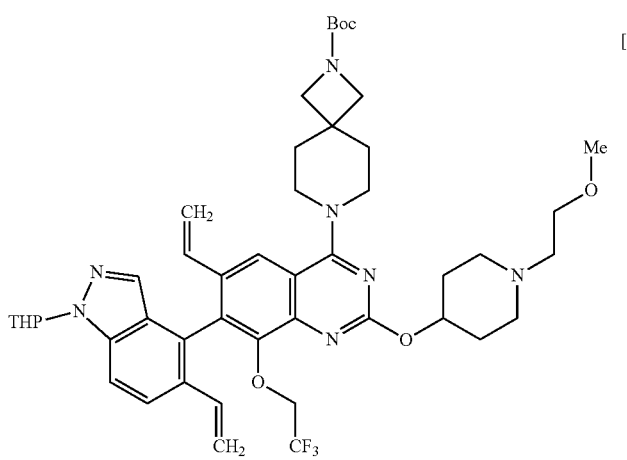 | ESI+; [M + Na]+ 884.8 |

TABLE 70-continued
| PEx | PSyn | Str | Dat |
|---|---|---|---|
| 170 | 4 | 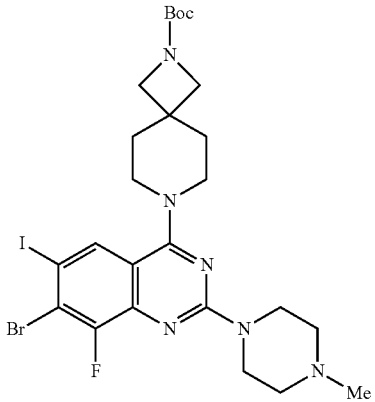 [SMILES: CN1CCN(c2nc(N3CCC4(CC3)CN(C(=O)OC(C)(C)C)C4)c3cc(I)c(Br)c(F)c3n2)CC1] | ESI+; 677.2 |
| 171 | 39 | 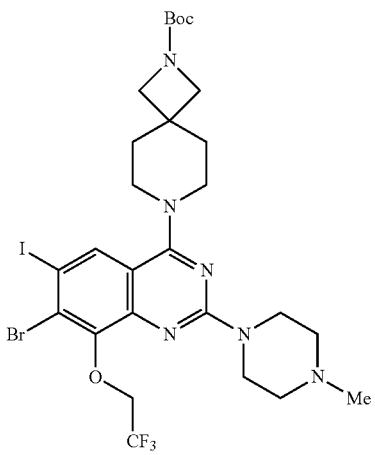 [SMILES: CN1CCN(c2nc(N3CCC4(CC3)CN(C(=O)OC(C)(C)C)C4)c3cc(I)c(Br)c(OCC(F)(F)F)c3n2)CC1] | ESI+; 757.2 |
TABLE 71
| PEx | PSyn | Str | Dat |
|---|---|---|---|
| 172 | 6 | 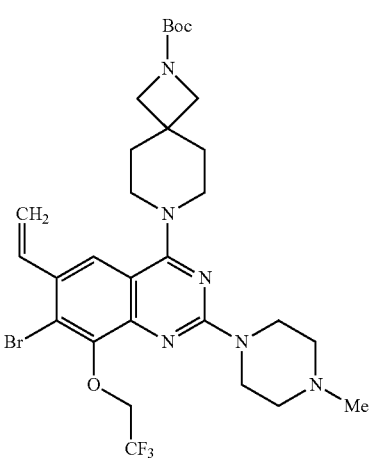 [SMILES: C=Cc1cc2c(N3CCC4(CC3)CN(C(=O)OC(C)(C)C)C4)nc(N3CCN(C)CC3)nc2c(OCC(F)(F)F)c1Br] | ESI+; 657.3 |

TABLE 71-continued
| PEx | PSyn | Str | Dat |
|---|---|---|---|
| 173 | 7 | 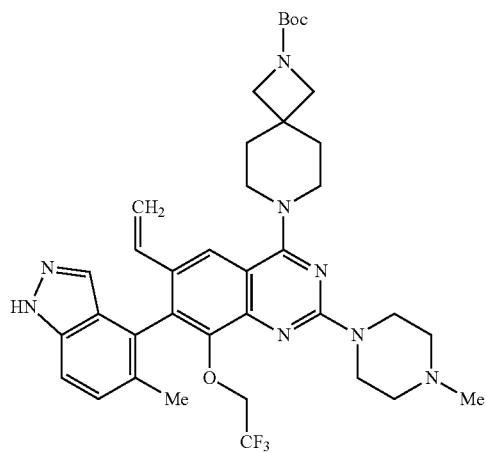 [SMILES: C=Cc1cc2c(N3CCC4(CC3)CN(C(=O)OC(C)(C)C)C4)nc(N3CCN(C)CC3)nc2c(OCC(F)(F)F)c1-c1c(C)ccc2[nH]ncc12] | ESI+; 707.5 |
| 174 | 4 | 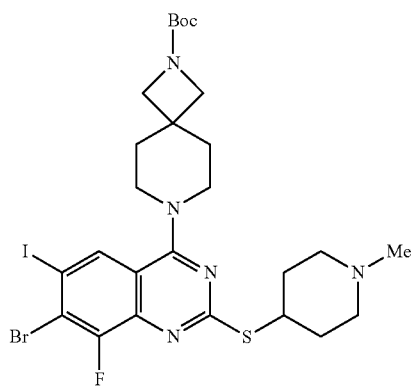 [SMILES: CN1CCC(Sc2nc(N3CCC4(CC3)CN(C(=O)OC(C)(C)C)C4)c3cc(I)c(Br)c(F)c3n2)CC1] | ESI+; 706.2 |

TABLE 72

| PEx | PSyn | Str | Dat |
|---|---|---|---|
| 175 | 175 | | ESI+; 688.3 |
| 176 | 4 | | ESI+; 708.2, 710.2 |
| | 39 | | ESI+; 790.2 |

TABLE 73

| PEx | PSyn | Str | Dat |
|---|---|---|---|
| 178 | 6 | (structure) | ESI+; 690.3 |
| 179 | 23 | (structure) | ESI+; 740.5 |
| 180 | 115 | (structure) | ESI+; 818.3, 820.2 |

TABLE 74

| PEx | PSyn | Str | Dat |
|---|---|---|---|
| 181 | 181 | (structure) | ESI+; 868.3, 870.3 |
| 182 | 6 | (structure) | ESI+; 768.5, 770.4 |
| 183 | 118 | (structure) | ESI+; 624.4 |

TABLE 75
| PEx | PSyn | Str | Dat |
|---|---|---|---|
| 184 | 144 | 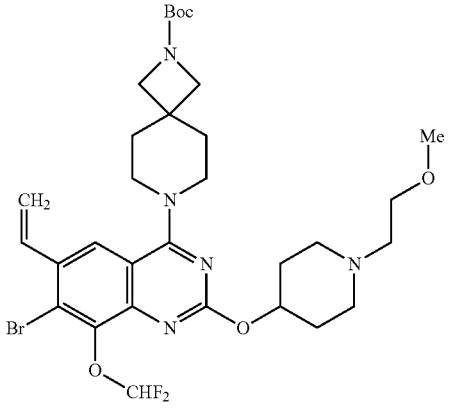 [SMILES: C=Cc1cc2c(N3CCC4(CC3)CN(C(=O)OC(C)(C)C)C4)nc(OC3CCN(CCOC)CC3)nc2c(OC(F)F)c1Br] | ESI+; 684.4 |
| 185 | 23 | 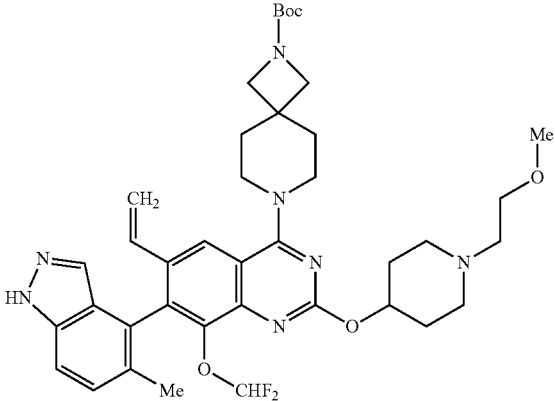 [SMILES: C=Cc1cc2c(N3CCC4(CC3)CN(C(=O)OC(C)(C)C)C4)nc(OC3CCN(CCOC)CC3)nc2c(OC(F)F)c1-c1c(C)ccc2[nH]ncc12] | ESI+; 734.6 |
| 186 | 4 | 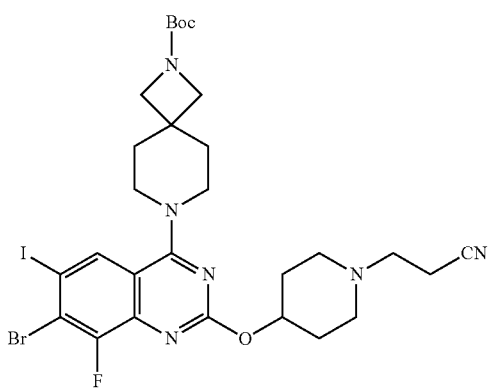 [SMILES: CC(C)(C)OC(=O)N1CC2(CCN(c3nc(OC4CCN(CCC#N)CC4)nc4c(F)c(Br)c(I)cc34)CC2)C1] | ESI+; 731.0 |

TABLE 76
| PEx | PSyn | Str | Dat |
|---|---|---|---|
| 187 | 8 | 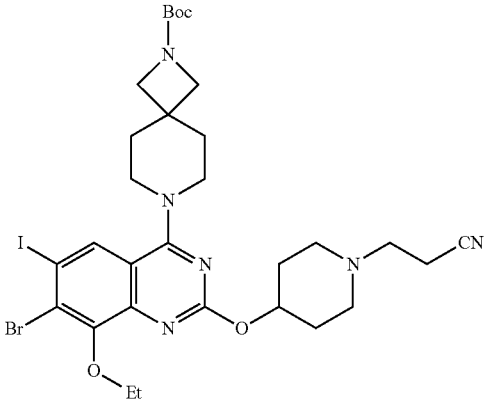 [SMILES: CCOc1c(Br)c(I)cc2c(N3CCC4(CC3)CN(C(=O)OC(C)(C)C)C4)nc(OC3CCN(CCC#N)CC3)nc12] | ESI+; 755.1 |
| 188 | 9 | 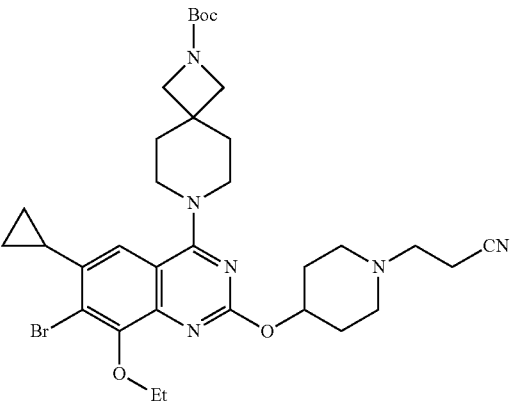 [SMILES: CCOc1c(Br)c(C2CC2)cc2c(N3CCC4(CC3)CN(C(=O)OC(C)(C)C)C4)nc(OC3CCN(CCC#N)CC3)nc12] | ESI+; 671.2 |
| 189 | 7 | 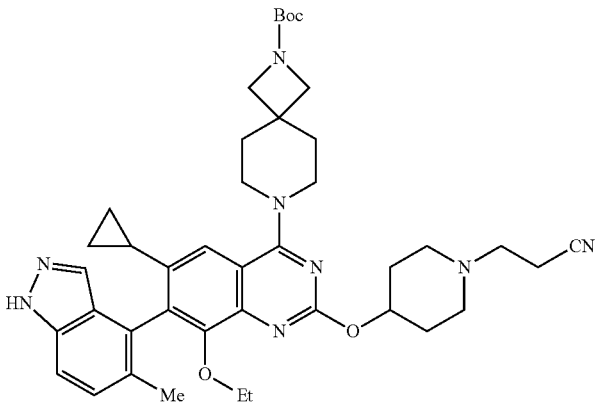 [SMILES: CCOc1c(-c2c(C)ccc3[nH]ncc23)c(C2CC2)cc2c(N3CCC4(CC3)CN(C(=O)OC(C)(C)C)C4)nc(OC3CCN(CCC#N)CC3)nc12] | ESI+; 721.4 |

TABLE 77
| PEx | PSyn | Str | Dat |
|---|---|---|---|
| 190 | 4 | 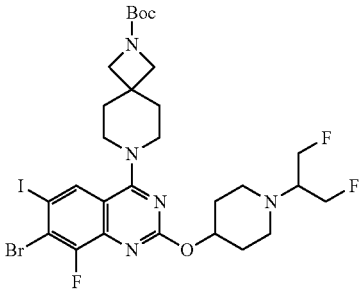 [SMILES: CC(C)(C)OC(=O)N1CC2(CCN(c3nc(OC4CCN(C(CF)CF)CC4)nc4c(F)c(Br)c(I)cc34)CC2)C1] | ESI+; 756.2 |
| 191 | 39 | 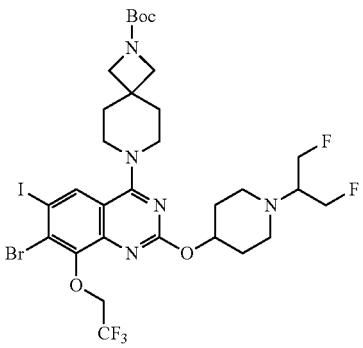 | ESI+; 836.3 |
| 192 | 6 | 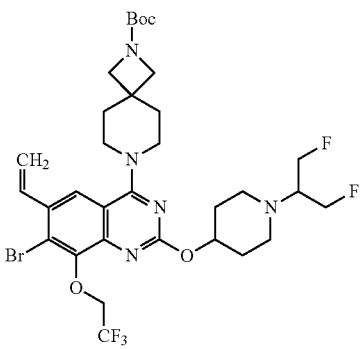 [SMILES: C=Cc1cc2c(N3CCC4(CC3)CN(C(=O)OC(C)(C)C)C4)nc(OC3CCN(C(CF)CF)CC3)nc2c(OCC(F)(F)F)c1Br] | ESI+; 736.3 |

TABLE 78
| PEx | PSyn | Str | Dat |
|---|---|---|---|
| 193 | 23 | | ESI+; 786.5 |
| 194 | 155 | 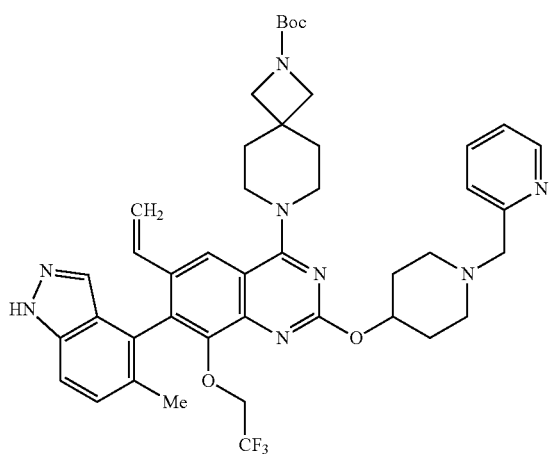 [SMILES: C=Cc1cc2c(N3CCC4(CC3)CN(C(=O)OC(C)(C)C)C4)nc(OC3CCN(Cc4ccccn4)CC3)nc2c(OCC(F)(F)F)c1-c1c(C)ccc2[nH]ncc12] | ESI+; 799.5 |
TABLE 79
| PEx | PSyn | Str | Dat |
|---|---|---|---|
| 195 | 5 | | ESI+; 810.3 |
TABLE 79-continued
| PEx | PSyn | Str | Dat |
|---|---|---|---|
| 196 | 6 | | ESI+; 710.5 |

TABLE 80
| PEx | PSyn | Str | Dat |
|---|---|---|---|
| 197 | 23 | 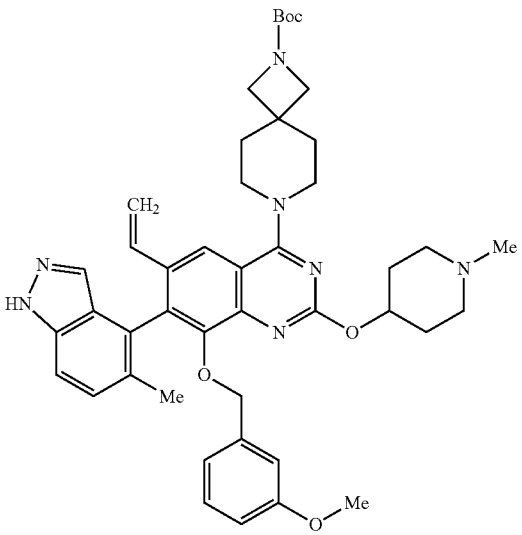 [SMILES: C=Cc1cc2c(N3CCC4(CC3)CN(C(=O)OC(C)(C)C)C4)nc(OC3CCN(C)CC3)nc2c(OCc2cccc(OC)c2)c1-c1c(C)ccc2[nH]ncc12] | ESI+; 760.7 |
| 198 | 5 | 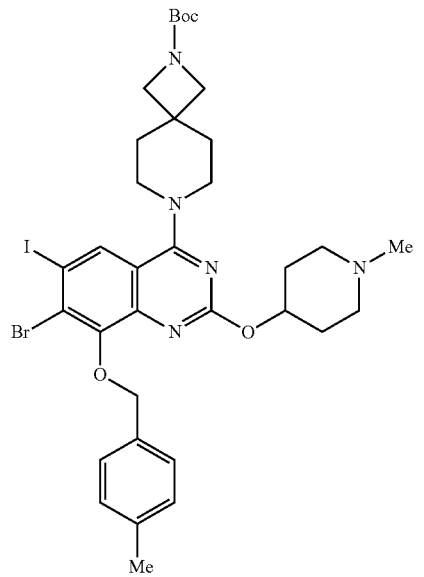 [SMILES: Cc1ccc(COc2c(Br)c(I)cc3c(N4CCC5(CC4)CN(C(=O)OC(C)(C)C)C5)nc(OC4CCN(C)CC4)nc23)cc1] | ESI+; 794.3 |

TABLE 81
| PEx | PSyn | Str | Dat |
|---|---|---|---|
| 199 | 6 | 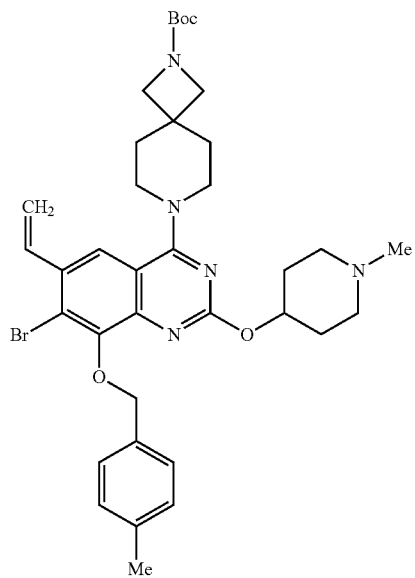 [SMILES: C=Cc1cc2c(N3CCC4(CC3)CN(C(=O)OC(C)(C)C)C4)nc(OC3CCN(C)CC3)nc2c(OCc2ccc(C)cc2)c1Br] | ESI+; 694.4 |
| 200 | 23 | 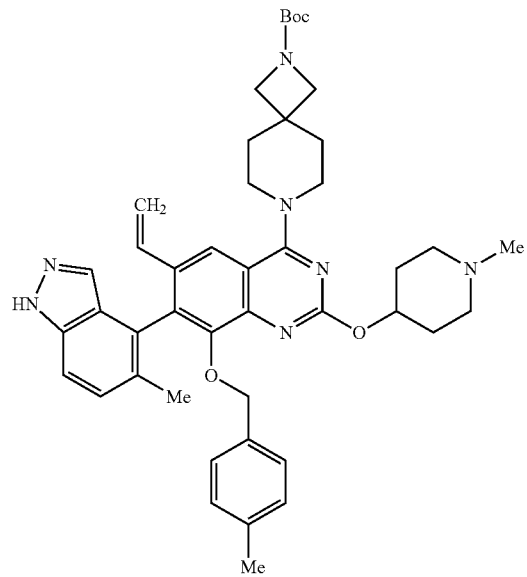 [SMILES: C=Cc1cc2c(N3CCC4(CC3)CN(C(=O)OC(C)(C)C)C4)nc(OC3CCN(C)CC3)nc2c(OCc2ccc(C)cc2)c1-c1c(C)ccc2[nH]ncc12] | ESI+; 744.7 |

TABLE 82
| PEx | PSyn | Str | Dat |
|---|---|---|---|
| 201 | 4 | 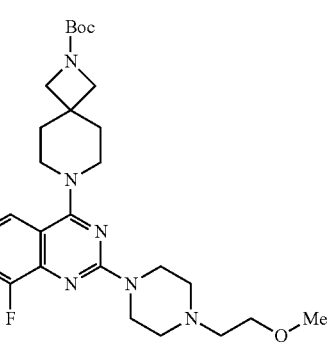 | ESI+; 721.3 |
| 202 | 39 | 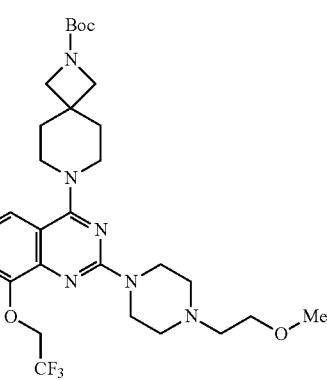 | ESI+; 801.3 |
| 203 | 6 | 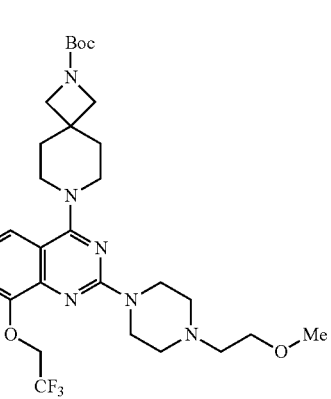 | ESI+; 699.4 |

TABLE 83
| PEx | PSyn | Str | Dat |
|---|---|---|---|
| 204 | 7 | 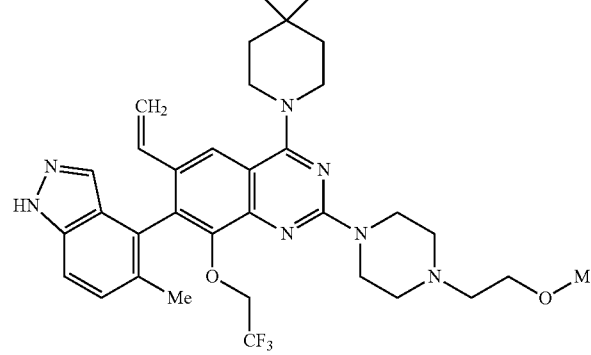 | ESI+; 751.5 |
| 205 | 4 | 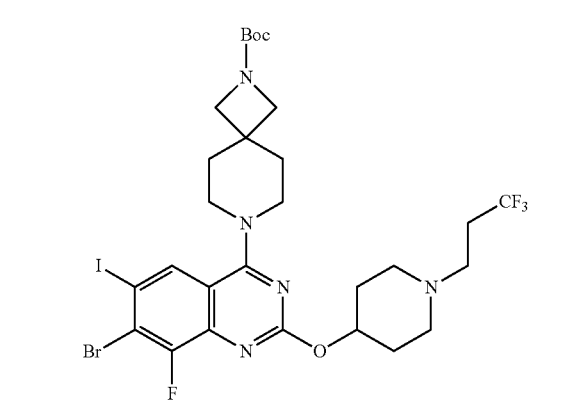 [SMILES: CC(C)(C)OC(=O)N1CC2(CCN(c3nc(OC4CCN(CCC(F)(F)F)CC4)nc4c(F)c(Br)c(I)cc34)CC2)C1] | ESI+; 772.2, 774.2 |
| 206 | 39 | 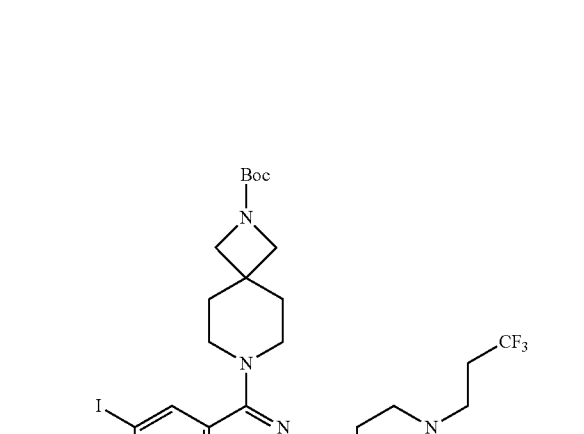 | ESI+; 854.4 |

TABLE 84
| PEx | PSyn | Str | Dat |
|---|---|---|---|
| 207 | 6 | 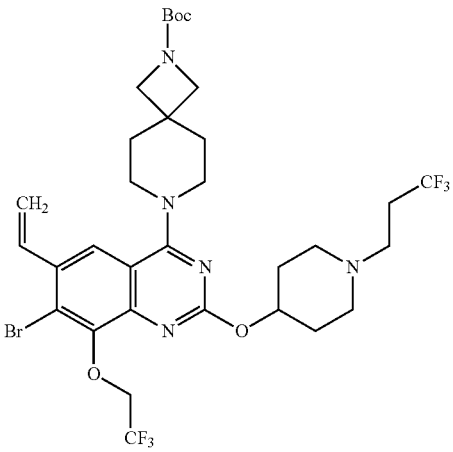 [SMILES: C=Cc1cc2c(N3CCC4(CC3)CN(C(=O)OC(C)(C)C)C4)nc(OC3CCN(CCC(F)(F)F)CC3)nc2c(OCC(F)(F)F)c1Br] | ESI+; 752.3, 754.3 |
| 208 | 23 | 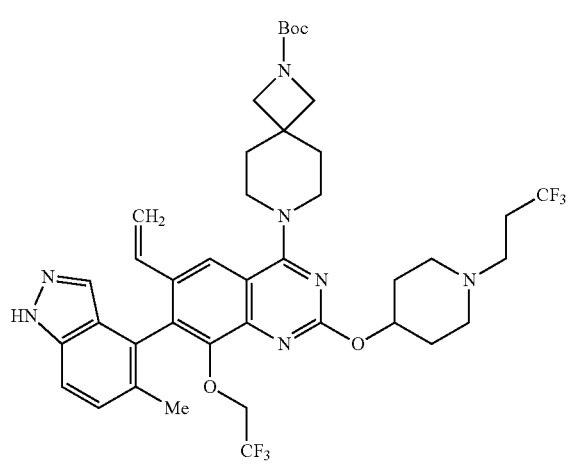 [SMILES: C=Cc1cc2c(N3CCC4(CC3)CN(C(=O)OC(C)(C)C)C4)nc(OC3CCN(CCC(F)(F)F)CC3)nc2c(OCC(F)(F)F)c1-c1c(C)ccc2[nH]ncc12] | ESI+; 804.5 |
TABLE 85
| PEx | PSyn | Str | Dat |
|---|---|---|---|
| 209 | 5 | 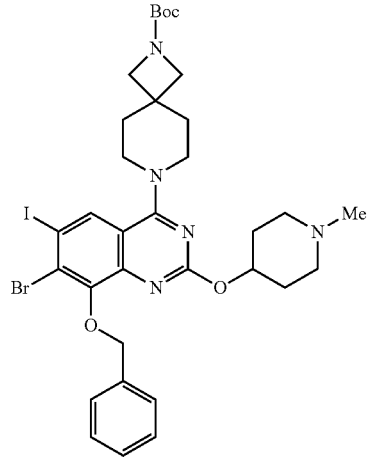 [SMILES: CN1CCC(Oc2nc(N3CCC4(CC3)CN(C(=O)OC(C)(C)C)C4)c3cc(I)c(Br)c(OCc4ccccc4)c3n2)CC1] | ESI+; 778.3 |
TABLE 85-continued
| PEx | PSyn | Str | Dat |
|---|---|---|---|
| 210 | 6 | 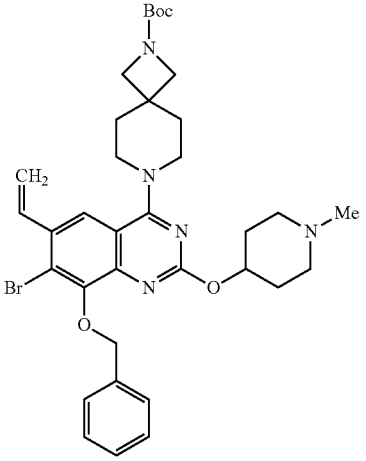 [SMILES: C=Cc1cc2c(N3CCC4(CC3)CN(C(=O)OC(C)(C)C)C4)nc(OC3CCN(C)CC3)nc2c(OCc2ccccc2)c1Br] | ESI+; 678.4, 680.3 |

TABLE 86
| PEx | PSyn | Str | Dat |
|---|---|---|---|
| 211 | 23 | 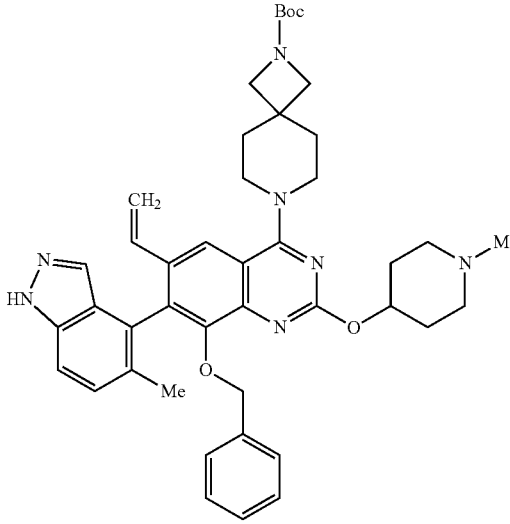 | ESI+; 730.7 |
| 212 | 23 | 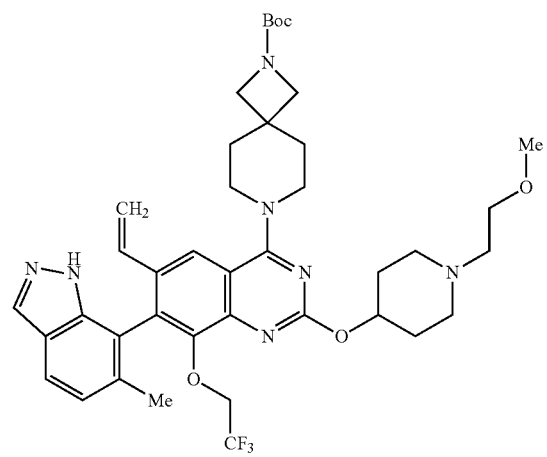 [SMILES: C=Cc1cc2c(N3CCC4(CC3)CN(C(=O)OC(C)(C)C)C4)nc(OC3CCN(CCOC)CC3)nc2c(OCC(F)(F)F)c1-c1c(C)ccc2cn[nH]c12] | ESI+; 766.6 |
TABLE 87
| PEx | PSyn | Str | Dat |
|---|---|---|---|
| 213 | 175 | 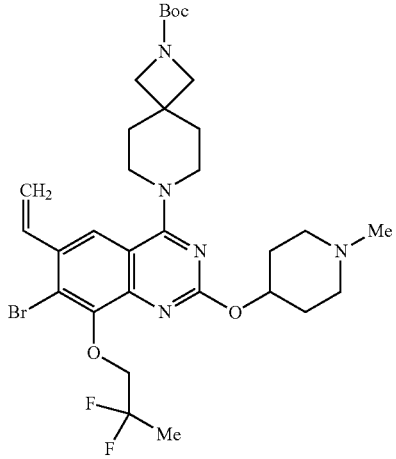 [SMILES: C=Cc1cc2c(N3CCC4(CC3)CN(C(=O)OC(C)(C)C)C4)nc(OC3CCN(C)CC3)nc2c(OCC(C)(F)F)c1Br] | ESI+; 668.3 |
| 214 | 7 | 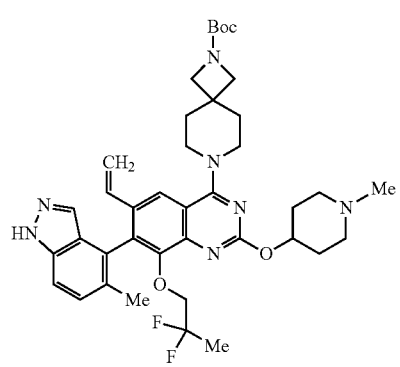 [SMILES: C=Cc1cc2c(N3CCC4(CC3)CN(C(=O)OC(C)(C)C)C4)nc(OC3CCN(C)CC3)nc2c(OCC(C)(F)F)c1-c1c(C)ccc2[nH]ncc12] | ESI+; [M + Na]+ 740.5 |

TABLE 88
| PEx | PSyn | Str | Dat |
|---|---|---|---|
| 215 | 4 | 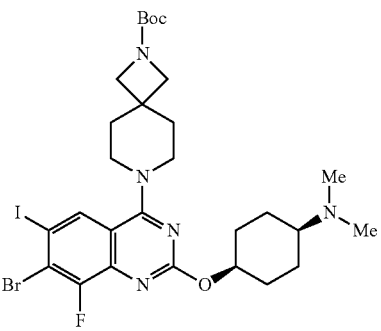 [SMILES: CN(C)[C@H]1CC[C@@H](Oc2nc(N3CCC4(CC3)CN(C(=O)OC(C)(C)C)C4)c3cc(I)c(Br)c(F)c3n2)CC1] | ESI+; 718.2, 720.2 |
| 216 | 39 | 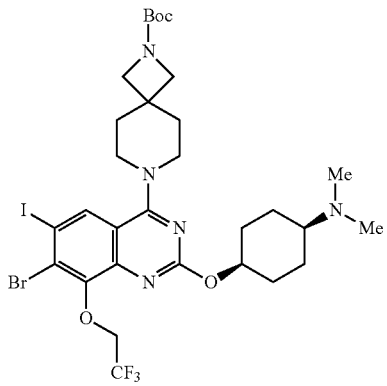 [SMILES: CN(C)[C@H]1CC[C@@H](Oc2nc(N3CCC4(CC3)CN(C(=O)OC(C)(C)C)C4)c3cc(I)c(Br)c(OCC(F)(F)F)c3n2)CC1] | ESI+; 800.2 |
| 217 | 6 | 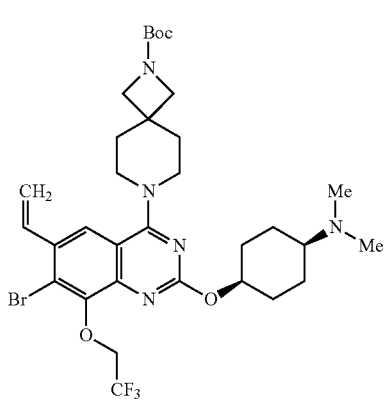 [SMILES: C=Cc1cc2c(N3CCC4(CC3)CN(C(=O)OC(C)(C)C)C4)nc(O[C@H]3CC[C@@H](N(C)C)CC3)nc2c(OCC(F)(F)F)c1Br] | ESI+; 700.5 |

TABLE 89
| PEx | PSyn | Str | Dat |
|---|---|---|---|
| 218 | 23 | 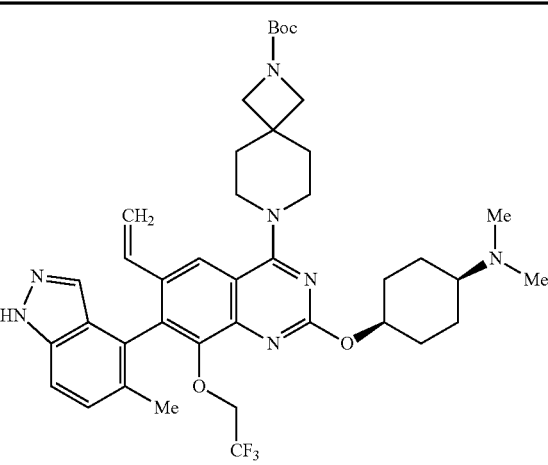 | ESI+; 750.6 |
| 219 | 4 | 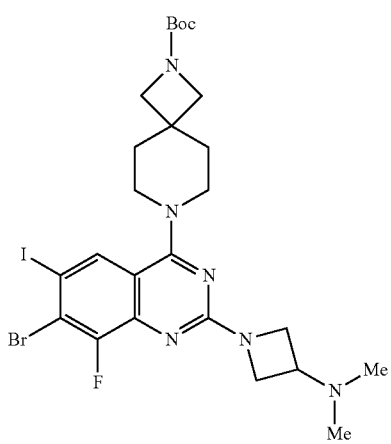 [SMILES: CN(C)C1CN(c2nc(N3CCC4(CC3)CN(C(=O)OC(C)(C)C)C4)c3cc(I)c(Br)c(F)c3n2)C1] | ESI+; 677.2 |
| 220 | 39 | 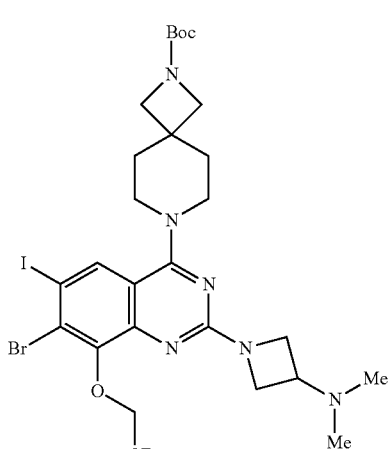 | ESI+; 757.3 |

TABLE 90
| PEx | PSyn | Str | Dat |
|---|---|---|---|
| 221 | 6 | 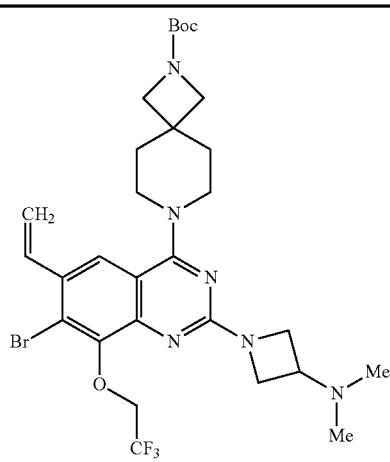 | ESI+; 657.3 |
| 222 | 7 | 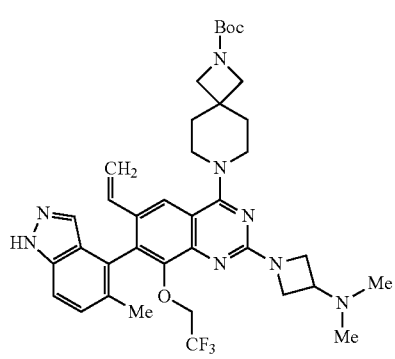 [SMILES: C=Cc1cc2c(N3CCC4(CC3)CN(C(=O)OC(C)(C)C)C4)nc(N3CC(N(C)C)C3)nc2c(OCC(F)(F)F)c1-c1c(C)ccc2[nH]ncc12] | ESI+; 707.6 |
TABLE 91
| PEx | PSyn | Str | Dat |
|---|---|---|---|
| 223 | 5 | 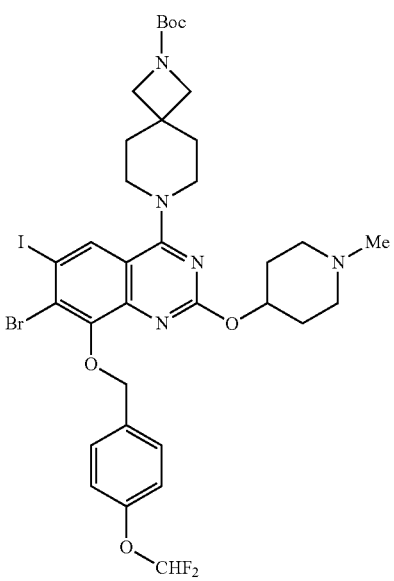 [SMILES: CN1CCC(Oc2nc(N3CCC4(CC3)CN(C(=O)OC(C)(C)C)C4)c3cc(I)c(Br)c(OCc4ccc(OC(F)F)cc4)c3n2)CC1] | ESI+; 846.2 |
| 224 | 6 | 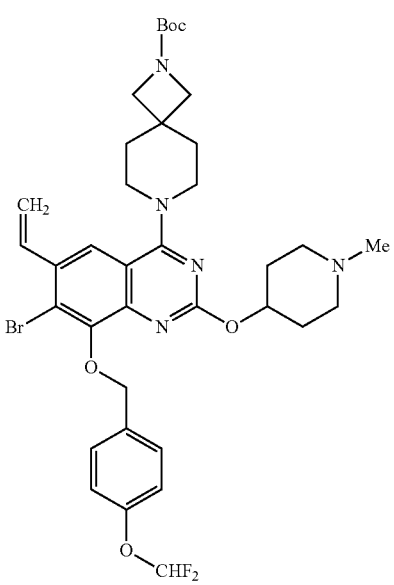 [SMILES: C=Cc1cc2c(N3CCC4(CC3)CN(C(=O)OC(C)(C)C)C4)nc(OC3CCN(C)CC3)nc2c(OCc2ccc(OC(F)F)cc2)c1Br] | ESI+; 746.5 |

TABLE 92
| PEx | PSyn | Str | Dat |
|---|---|---|---|
| 225 | 23 | 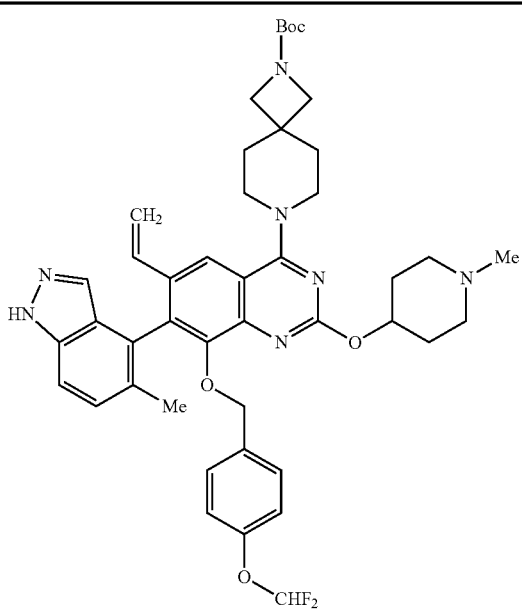 | ESI+; 796.6 |
| 226 | 144 | 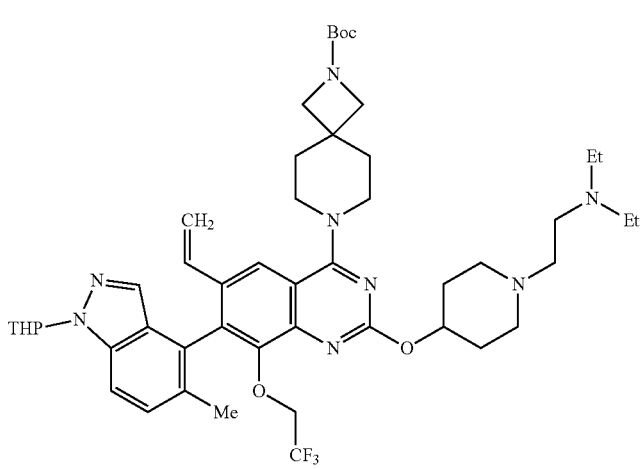 | ESI+; 891.7 |

TABLE 93

| PEx | PSyn | Str | Dat |
|---|---|---|---|
| 227 | 227 | (structure) | ESI+; 689.2, 691.2 |
| 228 | 39 | (structure) | ESI+; 769.3, 771.3 |
| 229 | 6 | (structure) | ESI+; 671.3 |

TABLE 94
| PEx | PSyn | Str | Dat |
|---|---|---|---|
| 230 | 23 | 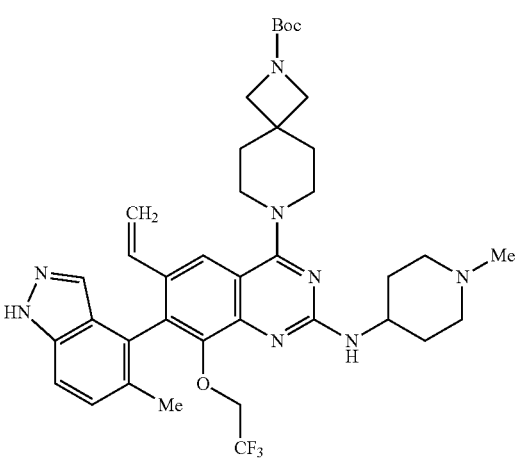 [SMILES: C=Cc1cc2c(N3CCC4(CC3)CN(C(=O)OC(C)(C)C)C4)nc(NC3CCN(C)CC3)nc2c(OCC(F)(F)F)c1-c1c(C)ccc2[nH]ncc12] | ESI+; 721.5 |
| 231 | 4 | 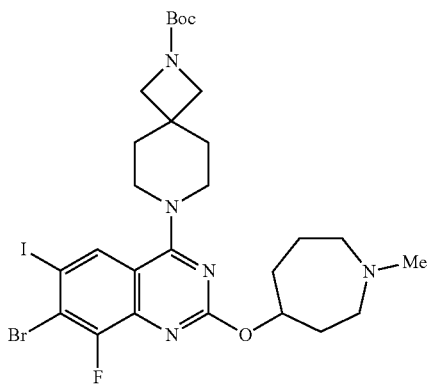 [SMILES: CN1CCCC(Oc2nc(N3CCC4(CC3)CN(C(=O)OC(C)(C)C)C4)c3cc(I)c(Br)c(F)c3n2)CC1] | ESI+; 704.2, 706.2 |
| 232 | 39 | 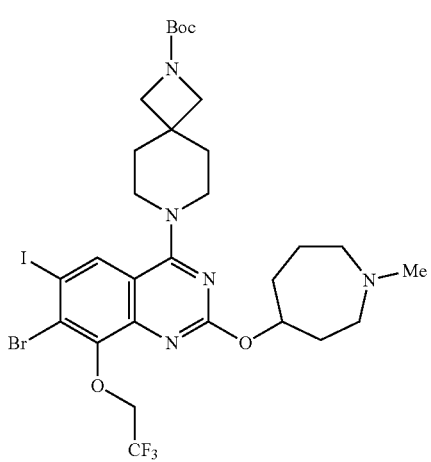 [SMILES: CN1CCCC(Oc2nc(N3CCC4(CC3)CN(C(=O)OC(C)(C)C)C4)c3cc(I)c(Br)c(OCC(F)(F)F)c3n2)CC1] | ESI+; 784.3 |

TABLE 95

| PEx | PSyn | Str | Dat |
|---|---|---|---|
| 233 | 6 | | ESI+; 684.5 |
| 234 | 23 | | ESI+; [M + Na]+ 758.5 |

TABLE 96

| PEx | PSyn | Str | Dat |
|---|---|---|---|
| 235 | 235 | | ESI+; 779.6 |

TABLE 96-continued

| PEx | PSyn | Str | Dat |
|---|---|---|---|
| 236 | 4 | (structure) | ESI+; 680.2 |
| 237 | 39 | (structure) | ESI+; 760.2 |

TABLE 97

| PEx | PSyn | Str | Dat |
|---|---|---|---|
| 238 | 6 | (structure) | ESI+; 660.3 |

TABLE 97-continued
| PEx | PSyn | Str | Dat |
|---|---|---|---|
| 239 | 23 | 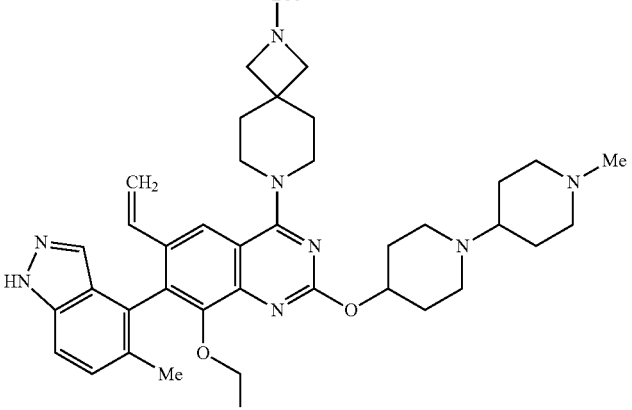 | ESI+; 710.5 |
TABLE 98
| PEx | PSyn | Str | Dat |
|---|---|---|---|
| 240 | 155 | 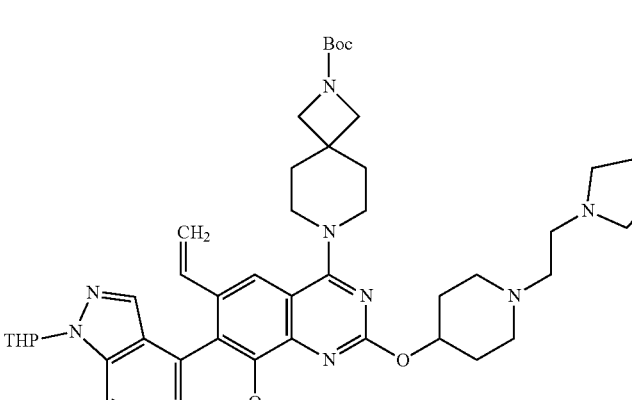 | ESI+; 805.5 |
| 241 | 141 |  | ESI+; 889.5 |

TABLE 99
| PEx | PSyn | Str | Dat |
|---|---|---|---|
| 242 | 5 | 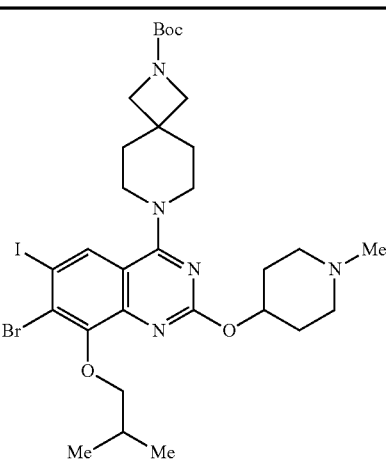 | ESI+; 746.3 |
TABLE 99-continued
| PEx | PSyn | Str | Dat |
|---|---|---|---|
| 243 | 6 | 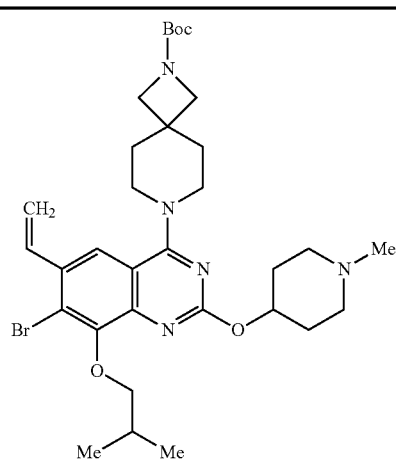 | ESI+; 646.4 |
TABLE 100
| PEx | PSyn | Str | Dat |
|---|---|---|---|
| 244 | 23 | 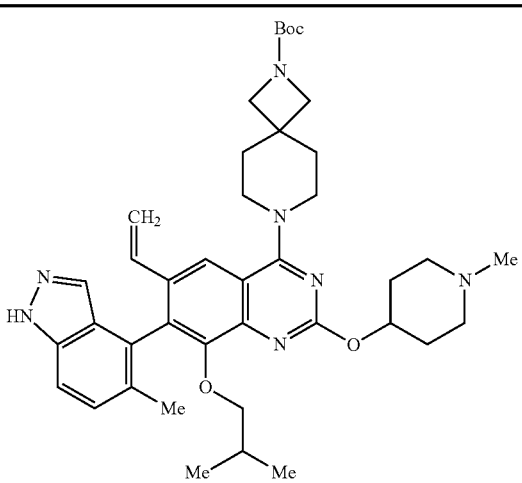 | ESI+; 696.6 |
| 245 | 4 | 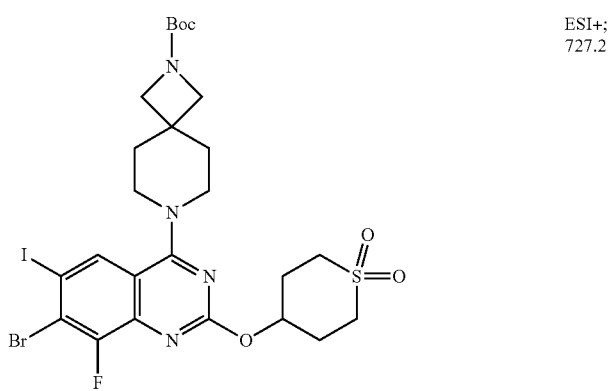 | ESI+; 727.2 |

TABLE 100-continued
| PEx | PSyn | Str | Dat |
|---|---|---|---|
| 246 | 39 | 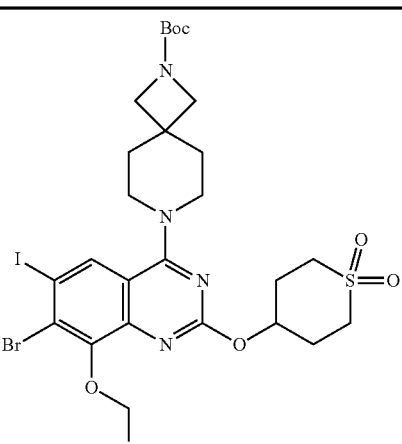 | ESI+; 805.2, 807.2 |
TABLE 101
| PEx | PSyn | Str | Det |
|---|---|---|---|
| 247 | 6 | 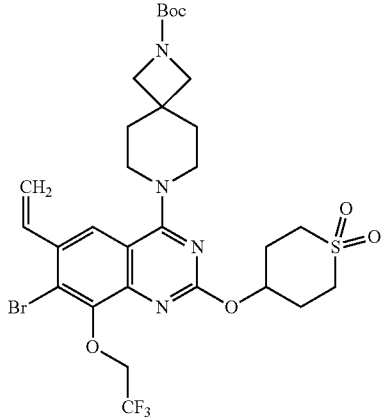 [SMILES: C=Cc1cc2c(N3CCC4(CC3)CN(C(=O)OC(C)(C)C)C4)nc(OC3CCS(=O)(=O)CC3)nc2c(OCC(F)(F)F)c1Br] | ESI+; 705.3, 707.3 |
| 248 | 23 | 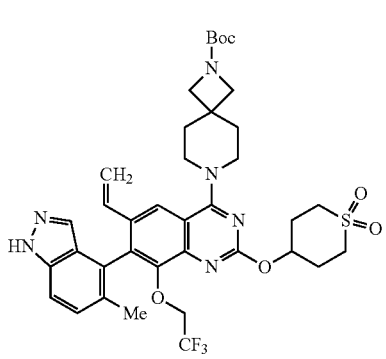 [SMILES: C=Cc1cc2c(N3CCC4(CC3)CN(C(=O)OC(C)(C)C)C4)nc(OC3CCS(=O)(=O)CC3)nc2c(OCC(F)(F)F)c1-c1c(C)ccc2[nH]ncc12] | ESI+; 757.5 |
TABLE 101-continued
| PEx | PSyn | Str | Det |
|---|---|---|---|
| 249 | 4 | 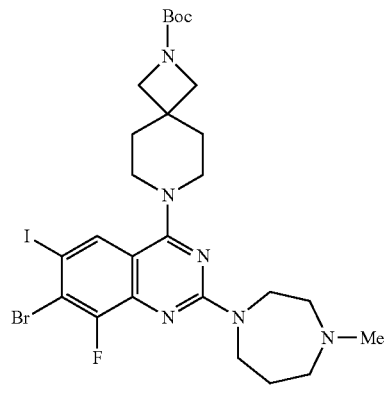 [SMILES: CN1CCCN(c2nc(N3CCC4(CC3)CN(C(=O)OC(C)(C)C)C4)c3cc(I)c(Br)c(F)c3n2)CC1] | ESI+; 691.2 |
TABLE 102
| PEx | PSyn | Str | Dat |
|---|---|---|---|
| 250 | 39 | | ESI+; 771.3 |

TABLE 102-continued
| PEx | PSyn | Str | Dat |
|---|---|---|---|
| 251 | 6 | 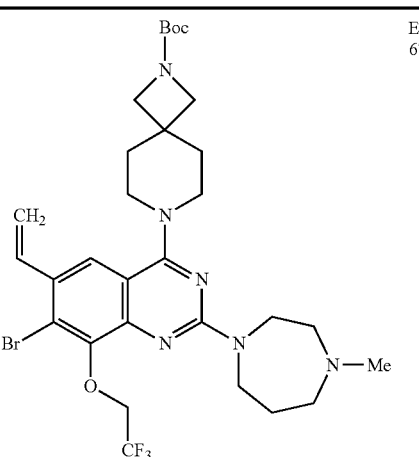 | ESI+; 671.4 |
TABLE 103
| PEx | PSyn | Str | Dat |
|---|---|---|---|
| 252 | 23 | 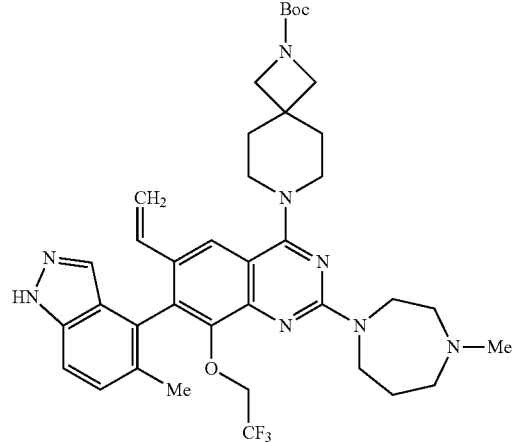 [SMILES: C=Cc1cc2c(N3CCC4(CC3)CN(C(=O)OC(C)(C)C)C4)nc(N3CCCN(C)CC3)nc2c(OCC(F)(F)F)c1-c1c(C)ccc2[nH]ncc12] | ESI+; 721.5 |
| 253 | 253 | 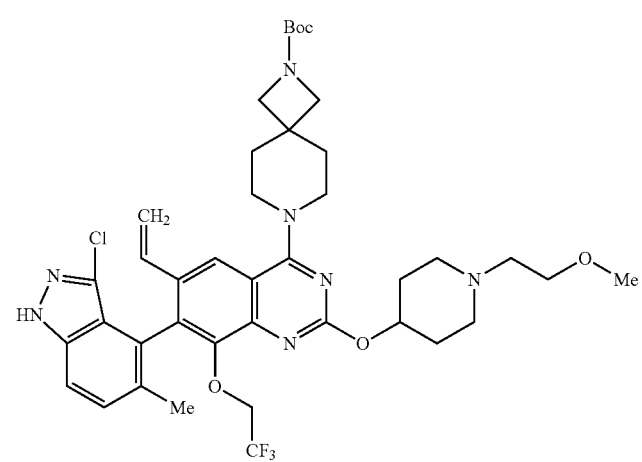 [SMILES: C=Cc1cc2c(N3CCC4(CC3)CN(C(=O)OC(C)(C)C)C4)nc(OC3CCN(CCOC)CC3)nc2c(OCC(F)(F)F)c1-c1c(C)ccc2[nH]nc(Cl)c12] | ESI+; 800.4, 802.5 |

TABLE 104

| PEx | PSyn | Str | Dat |
|---|---|---|---|
| 254 | 7 | (structure) | ESI+; 868.5 |
| 255 | 28 | (structure) | ESI+; 684.5 |

TABLE 105

| PEx | PSyn | Str | Dat |
|---|---|---|---|
| 256 | 39 | (structure) | ESI+; 864.4, 866.4 |
| 257 | 6 | (structure) | ESI+; 764.4, 766.3 |

TABLE 106
| PEx | PSyn | Str | Dat |
|---|---|---|---|
| 258 | 23 | 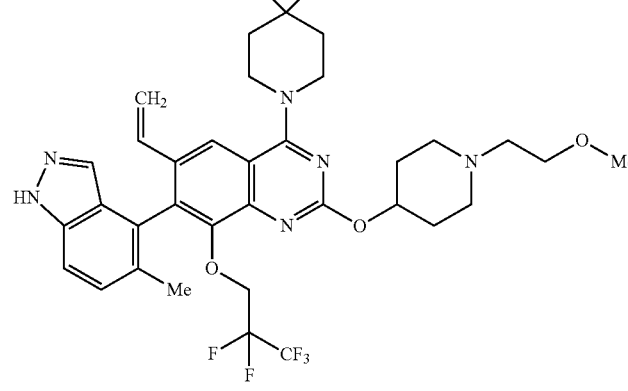 | ESI+; 816.5 |
| 259 | 4 | 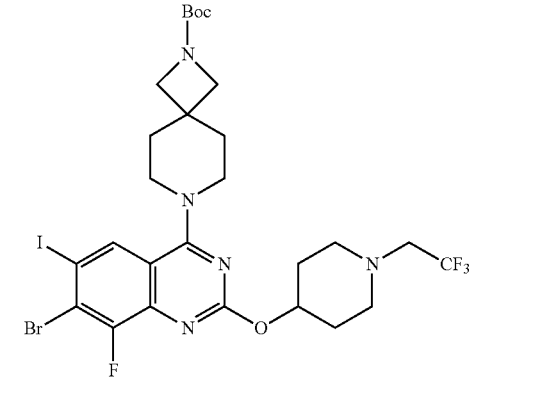 [SMILES: CC(C)(C)OC(=O)N1CC2(CCN(c3nc(OC4CCN(CC(F)(F)F)CC4)nc4c(F)c(Br)c(I)cc34)CC2)C1] | ESI+; 758.3, 760.3 |
| 260 | 39 | 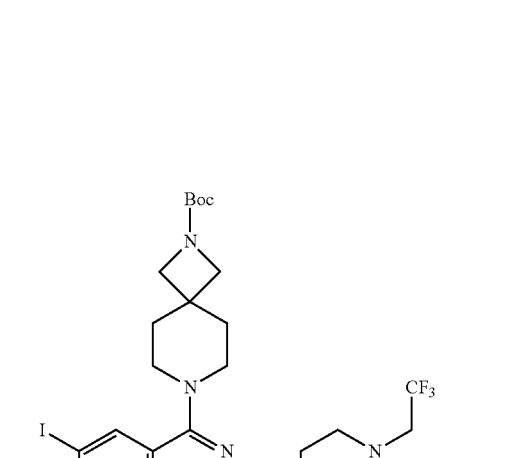 | ESI+; 838.2, 840.2 |

TABLE 107

| PEx | PSyn | Str | Dat |
|---|---|---|---|
| 261 | 6 | (structure) | ESI+; 740.3 |
| 262 | 23 | (structure) | ESI+; 790.6 |
| 263 | 4 | (structure) | ESI+; 784.0 |

TABLE 108

| PEx | PSyn | Str | Dat |
|---|---|---|---|
| 264 | 39 | (structure) | ESI+; 864.0 |
| 265 | 6 | (structure) | ESI+; 764.2 |

TABLE 109
| PEx | PSyn | Str | Dat |
|---|---|---|---|
| 266 | 23 | 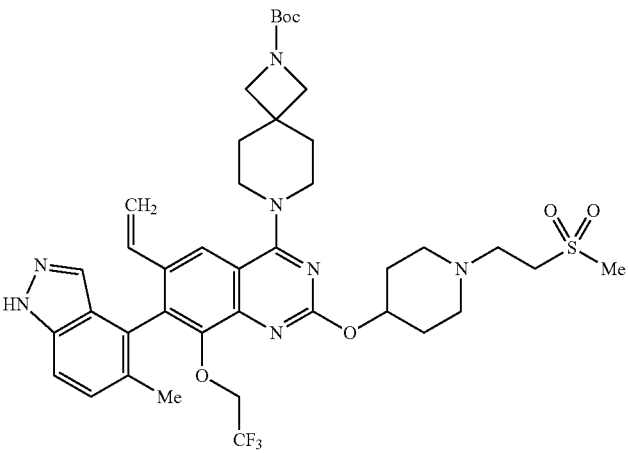 [SMILES: C=Cc1cc2c(N3CCC4(CC3)CN(C(=O)OC(C)(C)C)C4)nc(OC3CCN(CCS(C)(=O)=O)CC3)nc2c(OCC(F)(F)F)c1-c1c(C)ccc2[nH]ncc12] | ESI+; 814.3 |
| 267 | 23 | 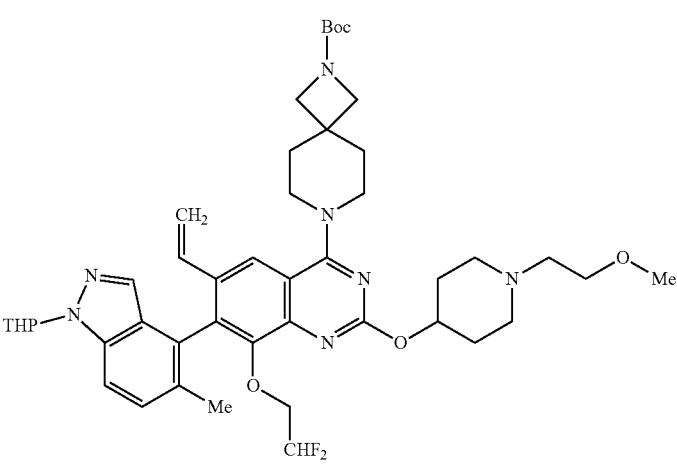 | ESI+; 846.6 |
TABLE 110
| PEx | PSyn | Str | Dat |
|---|---|---|---|
| 268 | 28 | 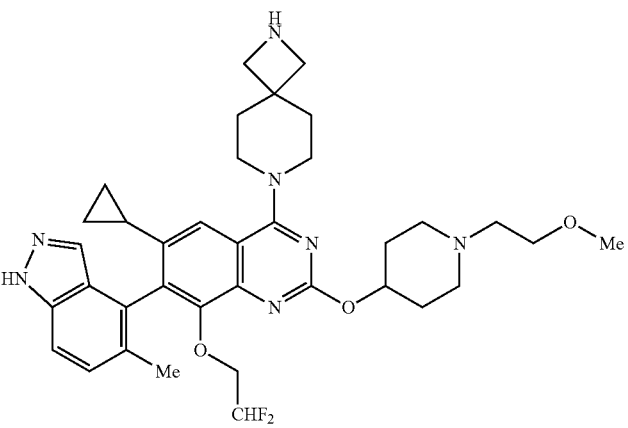 [SMILES: COCCN1CCC(Oc2nc(N3CCC4(CC3)CNC4)c3cc(C4CC4)c(-c4c(C)ccc5[nH]ncc45)c(OCC(F)F)c3n2)CC1] | ESI+; 662.5 |

TABLE 110-continued

| PEx | PSyn | Str | Dat |
|---|---|---|---|
| 269 | 144 | (structure) | ESI+; 918.5 |

TABLE 111

| PEx | PSyn | Str | Dat |
|---|---|---|---|
| 270 | 24 | (structure) | ESI+; 732.7 |
| 271 | 4 | (structure) | ESI+; 628.4, 630.4 |
| 272 | 8 | (structure) | ESI+; 654.4, 656.4 |

TABLE 112
| PEx | PSyn | Str | Dat |
|---|---|---|---|
| 273 | 7 | 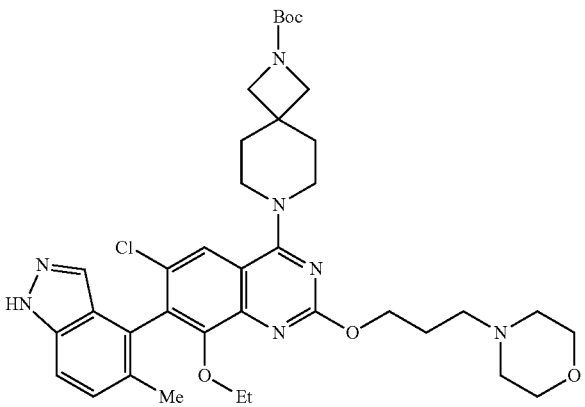 [SMILES: CCOc1c(-c2c(C)ccc3[nH]ncc23)c(Cl)cc2c(N3CCC4(CC3)CN(C(=O)OC(C)(C)C)C4)nc(OCCCN3CCOCC3)nc12] | ESI+; 706.5, 708.5 |
| 274 | 24 | 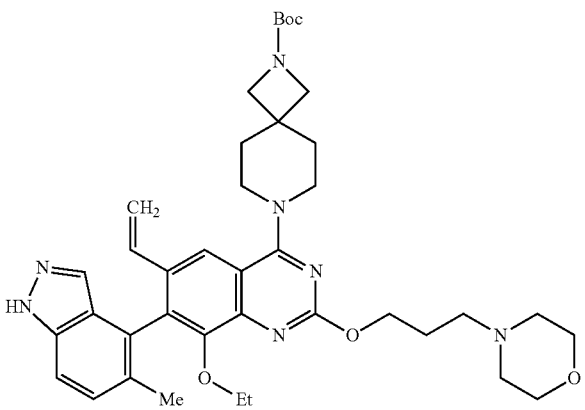 [SMILES: C=Cc1cc2c(N3CCC4(CC3)CN(C(=O)OC(C)(C)C)C4)nc(OCCCN3CCOCC3)nc2c(OCC)c1-c1c(C)ccc2[nH]ncc12] | ESI+; 698.7 |
| 275 | 235 | 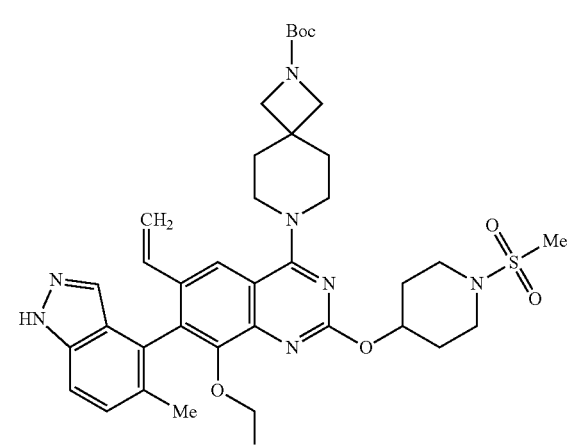 | ESI+; 786.5 |

TABLE 113
| PEx | PSyn | Str | Dat |
|---|---|---|---|
| 276 | 7 | 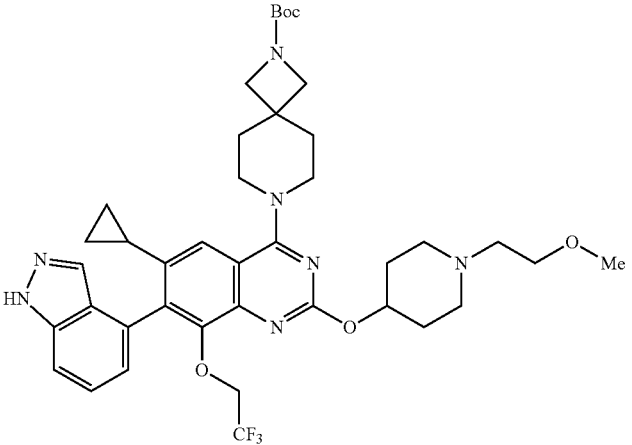 [SMILES: COCCN1CCC(Oc2nc(N3CCC4(CC3)CN(C(=O)OC(C)(C)C)C4)c3cc(C4CC4)c(-c4cccc5[nH]ncc45)c(OCC(F)(F)F)c3n2)CC1] | ESI+; 766.5 |
| 277 | 235 | 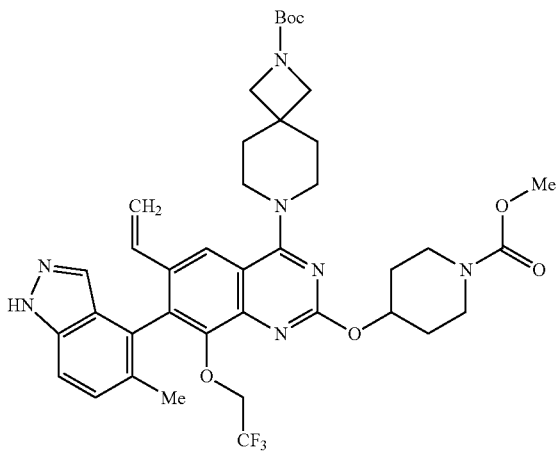 [SMILES: C=Cc1cc2c(N3CCC4(CC3)CN(C(=O)OC(C)(C)C)C4)nc(OC3CCN(C(=O)OC)CC3)nc2c(OCC(F)(F)F)c1-c1c(C)ccc2[nH]ncc12] | ESI+; 766.4 |
TABLE 114
| PEx | PSyn | Str | Dat |
|---|---|---|---|
| 278 | 4 | 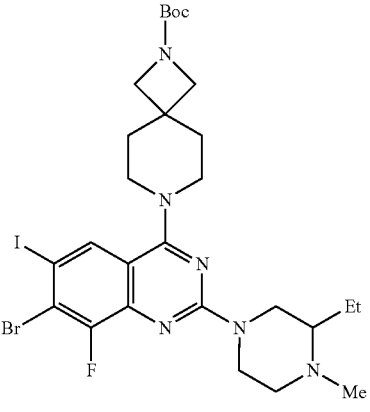 [SMILES: CCC1CN(c2nc(N3CCC4(CC3)CN(C(=O)OC(C)(C)C)C4)c3cc(I)c(Br)c(F)c3n2)CCN1C] | ESI+; 705.2 |
TABLE 114-continued
| PEx | PSyn | Str | Dat |
|---|---|---|---|
| 279 | 39 | 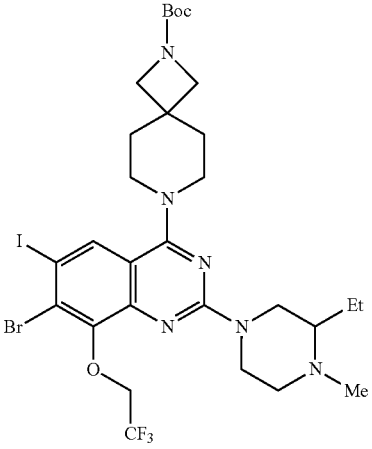 [SMILES: CCC1CN(c2nc(N3CCC4(CC3)CN(C(=O)OC(C)(C)C)C4)c3cc(I)c(Br)c(OCC(F)(F)F)c3n2)CCN1C] | ESI+; 783.3 |

TABLE 115

| PEx | PSyn | Str | Dat |
|---|---|---|---|
| 280 | 6 | (structure) | ESI+; 685.4 |
| 281 | 23 | (structure) | ESI+; 735.5 |

TABLE 116

| PEx | PSyn | Str | Dat |
|---|---|---|---|
| 282 | 235 | (structure) | ESI+; 750.5 |
| 283 | 283 | (structure) | ESI−; 608.2 |
| 284 | 284 | (structure) | ESI+; 818.3, 820.3 |

TABLE 117

| PEx | PSyn | Str | Dat |
|---|---|---|---|
| 285 | 39 | (structure) | ESI+; 898.3, 900.4 |
| 286 | 6 | (structure) | ESI+; 798.5, 800.5 |

TABLE 118
| PEx | PSyn | Str | Dat |
|---|---|---|---|
| 287 | 118 | 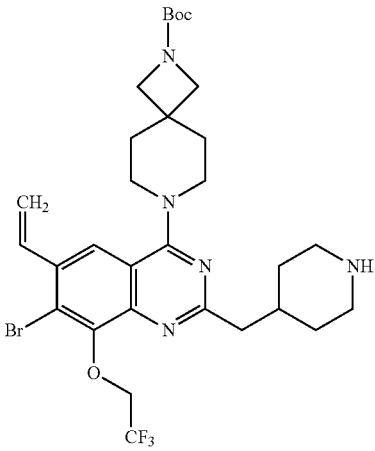 [SMILES: C=Cc1cc2c(N3CCC4(CC3)CN(C(=O)OC(C)(C)C)C4)nc(CC3CCNCC3)nc2c(OCC(F)(F)F)c1Br] | ESI+; 656.3 |
| 288 | 144 | 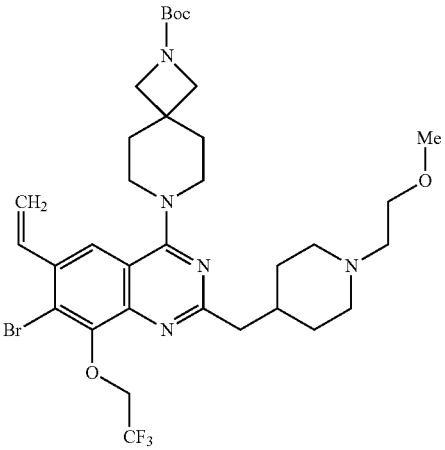 [SMILES: C=Cc1cc2c(N3CCC4(CC3)CN(C(=O)OC(C)(C)C)C4)nc(CC3CCN(CCOC)CC3)nc2c(OCC(F)(F)F)c1Br] | ESI+; 714.4 |
| 289 | 23 | 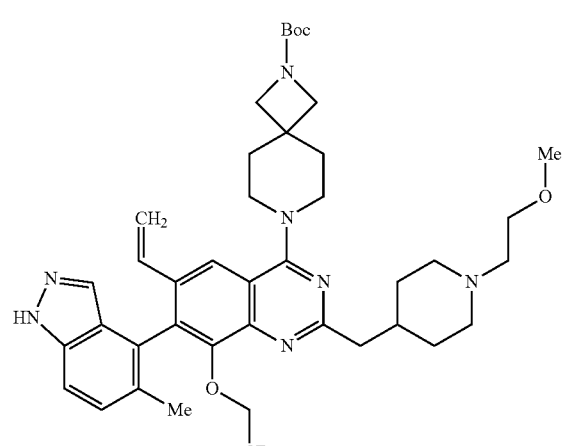 | ESI+; 764.5 |

TABLE 119
| Ex | Str |
|---|---|
| 1 | 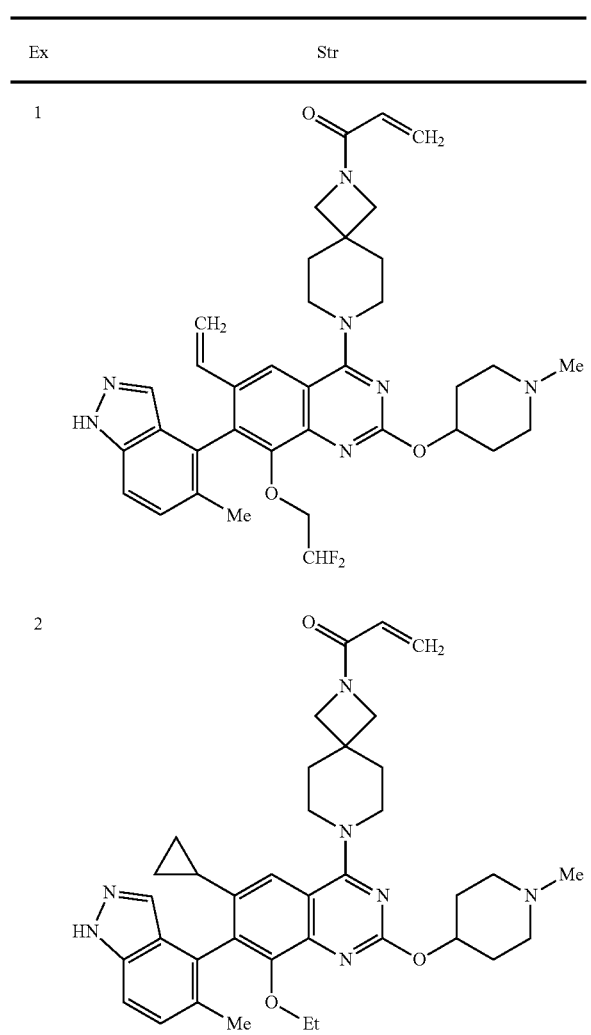 |
| 2 | |
TABLE 120
| Ex | Str |
|---|---|
| 3 | 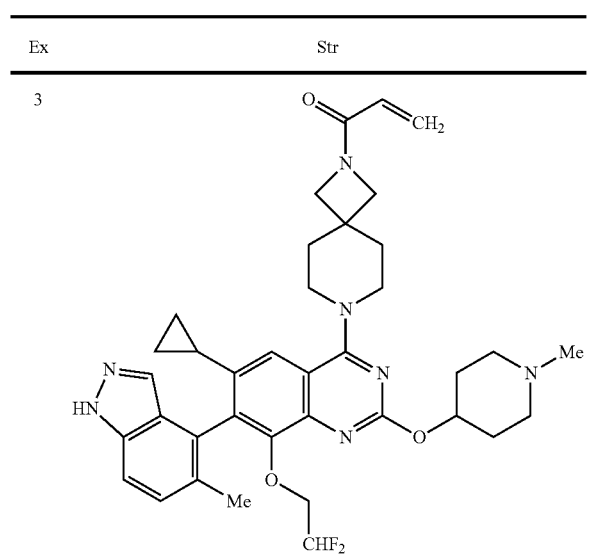 |
TABLE 120-continued
| Ex | Str |
|---|---|
| 4 | 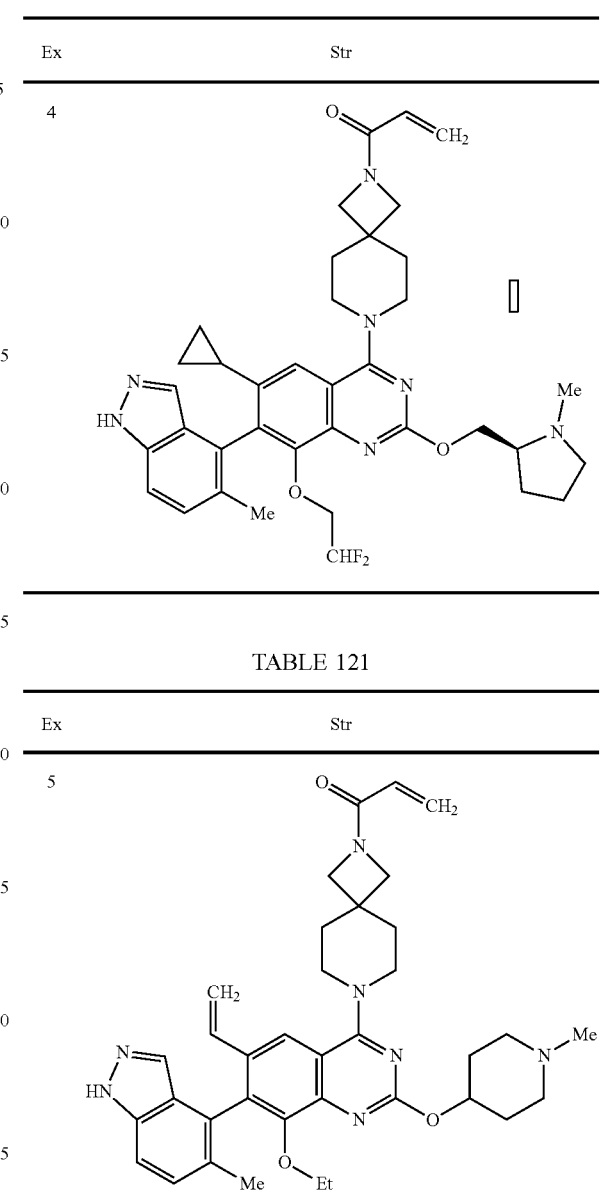 |
TABLE 121
| Ex | Str |
|---|---|
| 5 | |
| 6 | |

TABLE 121-continued

| Ex | Str |
|---|---|
| 7 | (structure) |

TABLE 122

| Ex | Str |
|---|---|
| 8 | (structure) |
| 9 | (structure) |

TABLE 123

| Ex | Str |
|---|---|
| 10 | (structure) |
| 11 | (structure) |

TABLE 124

| Ex | Str |
|---|---|
| 12 | (structure) |

TABLE 124-continued

| Ex | Str |
|---|---|
| 13 | (structure) |
| 14 | (structure) |

TABLE 125

| Ex | Str |
|---|---|
| 15 | (structure) |
| 16 | (structure) |
| 17 | (structure) |

TABLE 126

| Ex. | Str |
|---|---|
| 18 | (structure) |

TABLE 126-continued

| Ex. | Str |
|---|---|
| 19 | (structure) |

TABLE 127

| Ex. | Str |
|---|---|
| 20 | (structure) |
| 21 | (structure) |

TABLE 128

| Ex | Str |
|---|---|
| 22 | (structure) |
| 23 | (structure) |

TABLE 129

| Ex | Str |
|---|---|
| 24 | (structure) |

TABLE 129-continued
| Ex | Str |
|---|---|
| 25 | 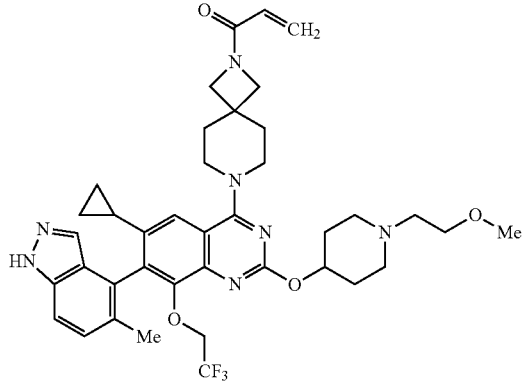 [SMILES: C=CC(=O)N1CC2(CCN(c3nc(OC4CCN(CCOC)CC4)nc4c(OCC(F)(F)F)c(-c5c(C)ccc6[nH]ncc56)c(C5CC5)cc34)CC2)C1] |
| 26 | 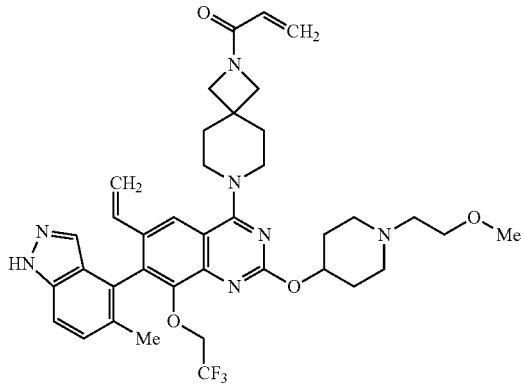 [SMILES: C=CC(=O)N1CC2(CCN(c3nc(OC4CCN(CCOC)CC4)nc4c(OCC(F)(F)F)c(-c5c(C)ccc6[nH]ncc56)c(C=C)cc34)CC2)C1] |
TABLE 130
| Ex | Str |
|---|---|
| 27 | 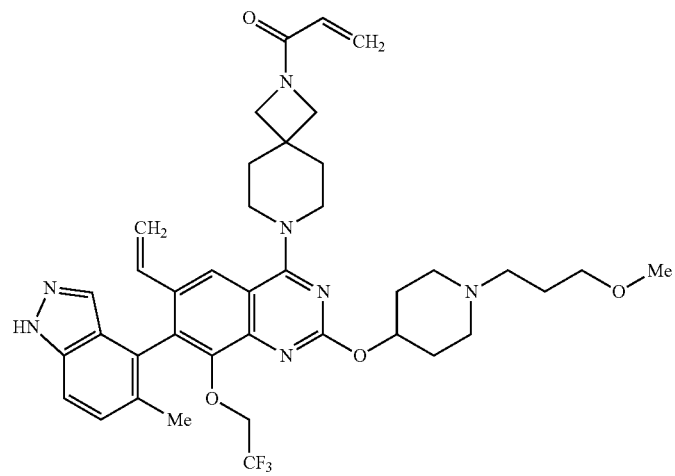 [SMILES: C=CC(=O)N1CC2(CCN(c3nc(OC4CCN(CCCOC)CC4)nc4c(OCC(F)(F)F)c(-c5c(C)ccc6[nH]ncc56)c(C=C)cc34)CC2)C1] |
| 28 | 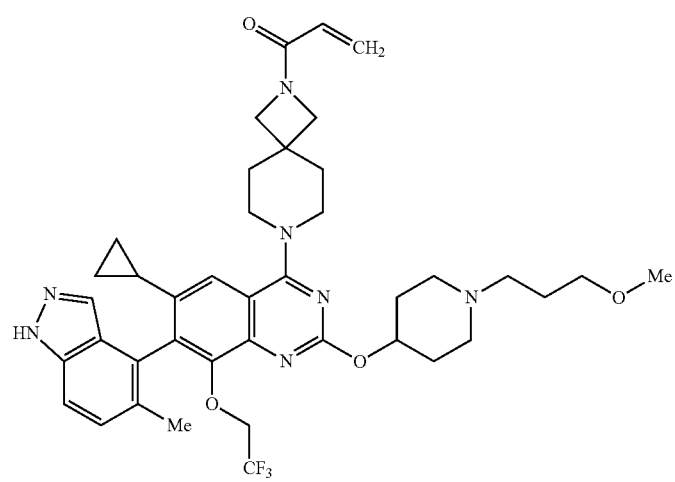 [SMILES: C=CC(=O)N1CC2(CCN(c3nc(OC4CCN(CCCOC)CC4)nc4c(OCC(F)(F)F)c(-c5c(C)ccc6[nH]ncc56)c(C5CC5)cc34)CC2)C1] |

TABLE 131
| Ex | Str |
|---|---|
| 29 | 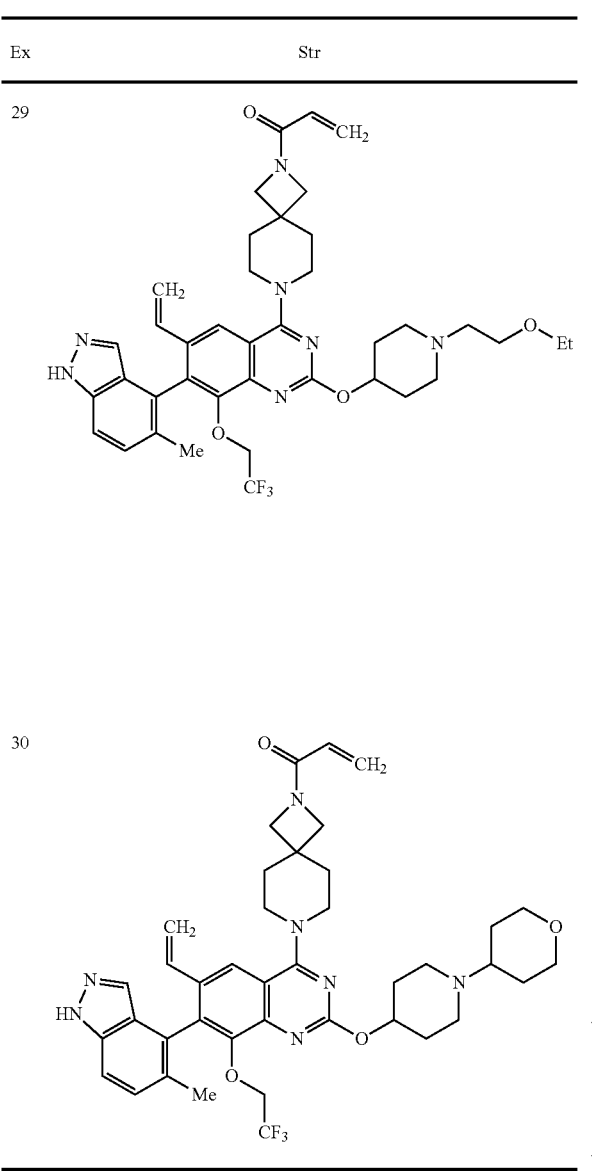 |
| 30 | |
TABLE 132
| Ex | Str |
|---|---|
| 31 | 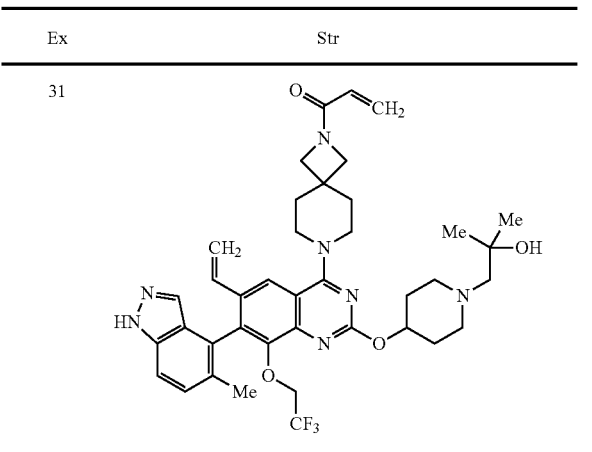 |
TABLE 132-continued
| Ex | Str |
|---|---|
| 32 | 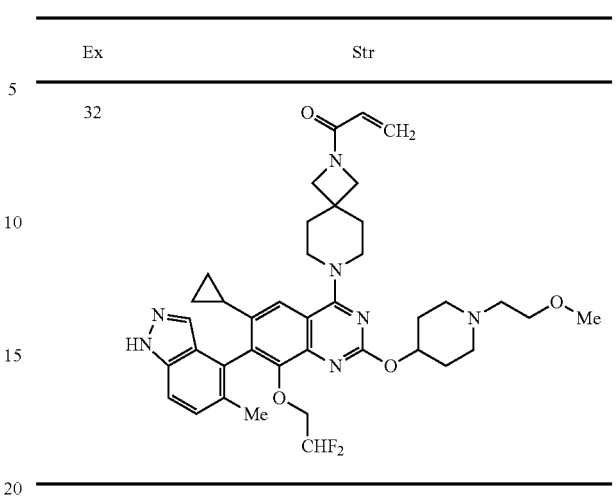 |
TABLE 133
| Ex | Str |
|---|---|
| 33 | 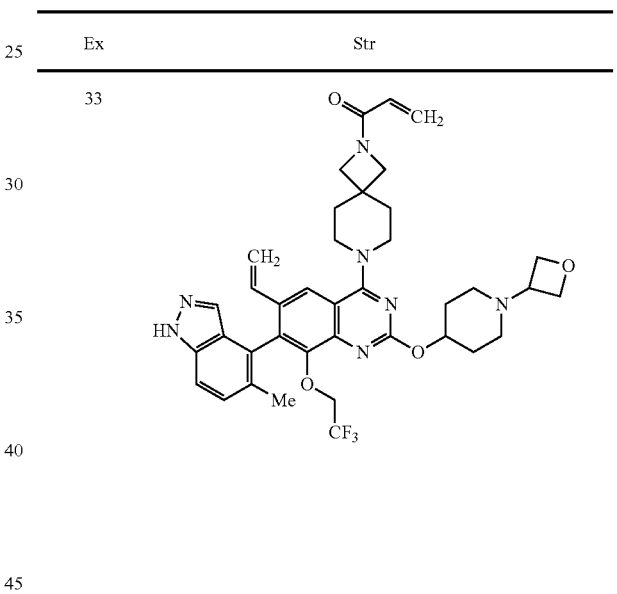 |
| 34 | 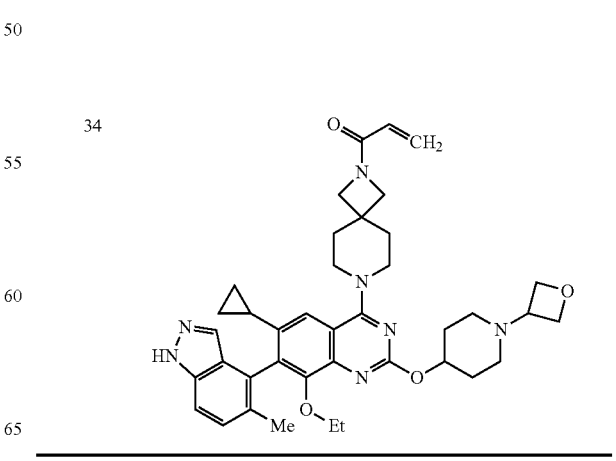 |

TABLE 134
| Ex | Str |
|---|---|
| 35 | 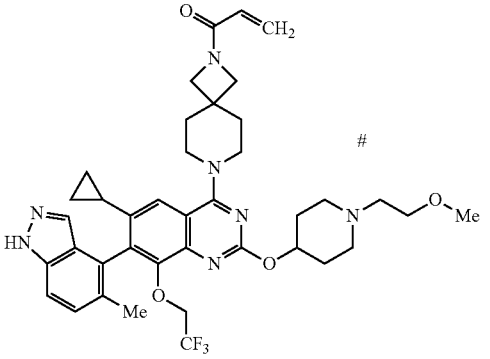 [SMILES: C=CC(=O)N1CC2(CCN(c3nc(OC4CCN(CCOC)CC4)nc4c(OCC(F)(F)F)c(-c5c(C)ccc6[nH]ncc56)c(C5CC5)cc34)CC2)C1] # |
| 36 | 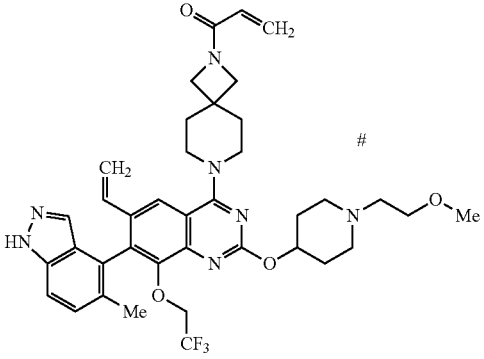 [SMILES: C=CC(=O)N1CC2(CCN(c3nc(OC4CCN(CCOC)CC4)nc4c(OCC(F)(F)F)c(-c5c(C)ccc6[nH]ncc56)c(C=C)cc34)CC2)C1] # |
TABLE 135
| Ex | Str |
|---|---|
| 37 | 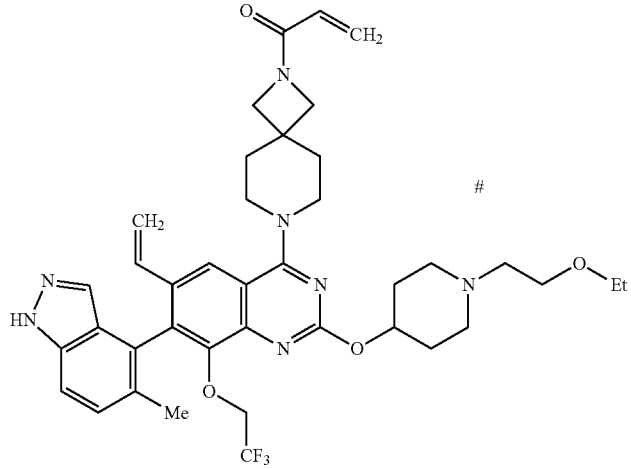 [SMILES: C=CC(=O)N1CC2(CCN(c3nc(OC4CCN(CCOCC)CC4)nc4c(OCC(F)(F)F)c(-c5c(C)ccc6[nH]ncc56)c(C=C)cc34)CC2)C1] # |
| 38 | 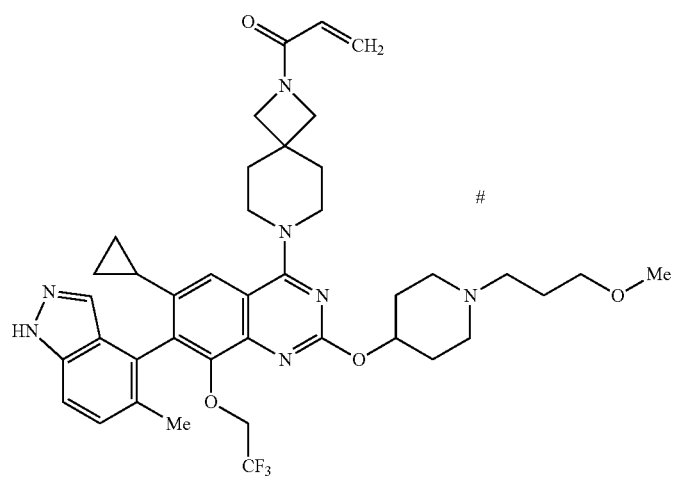 [SMILES: C=CC(=O)N1CC2(CCN(c3nc(OC4CCN(CCCOC)CC4)nc4c(OCC(F)(F)F)c(-c5c(C)ccc6[nH]ncc56)c(C5CC5)cc34)CC2)C1] # |

TABLE 136
| Ex | Str |
|---|---|
| 39 | 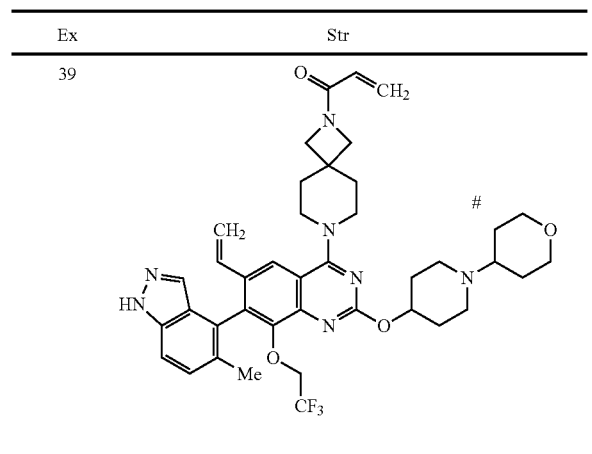 |
| 40 | 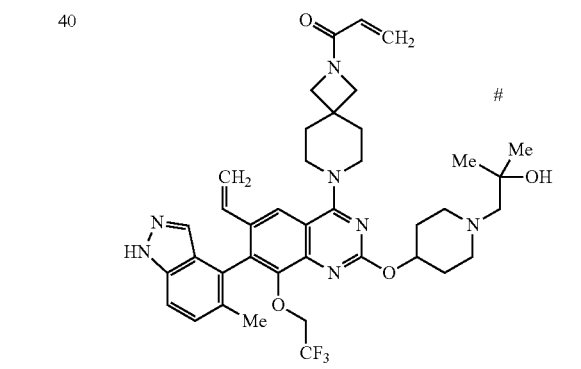 |
TABLE 137
| Ex | Str |
|---|---|
| 41 | 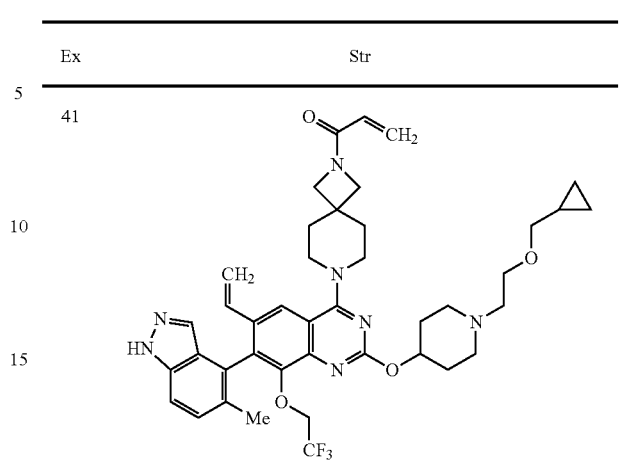 |
| 42 | 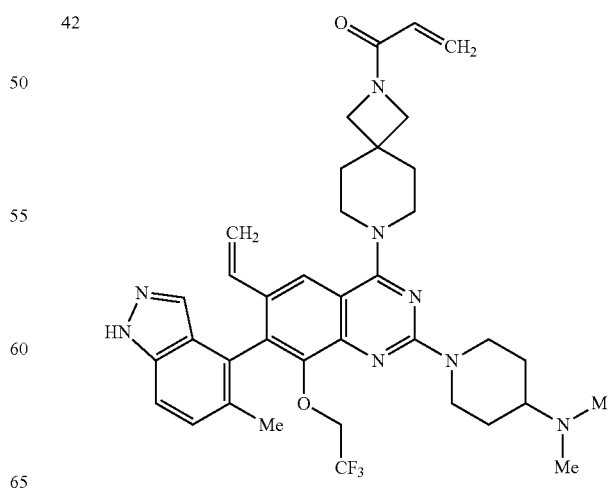 |

TABLE 138
| Ex | Str |
|---|---|
| 43 | 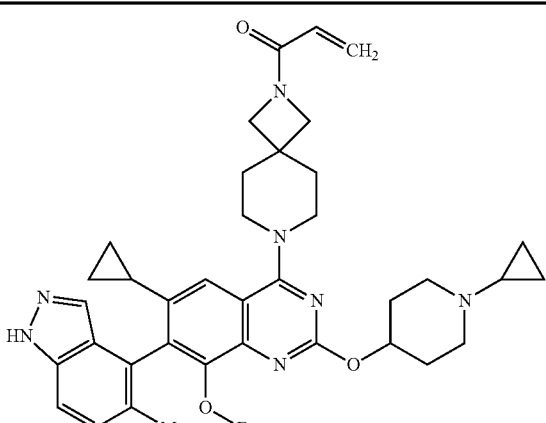 |
| 44 | 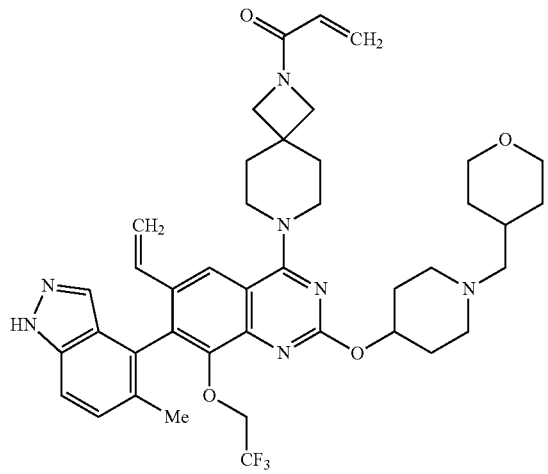 [SMILES: C=CC(=O)N1CC2(CCN(c3nc(OC4CCN(CC5CCOCC5)CC4)nc4c(OCC(F)(F)F)c(-c5c(C)ccc6[nH]ncc56)c(C=C)cc34)CC2)C1] |
| 45 | 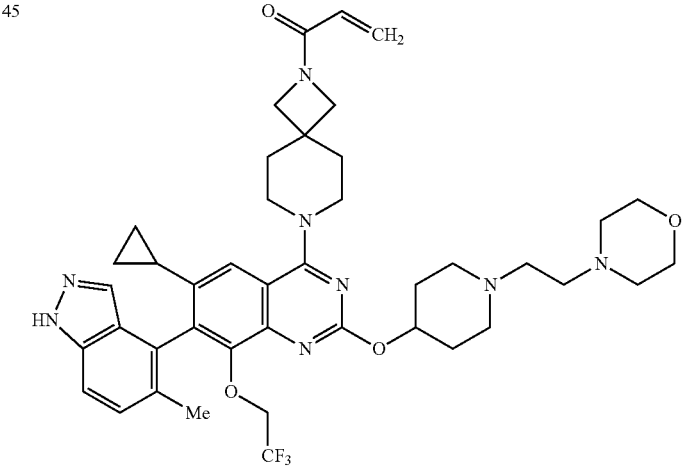 |

TABLE 139
| Ex | Str |
|---|---|
| 46 | 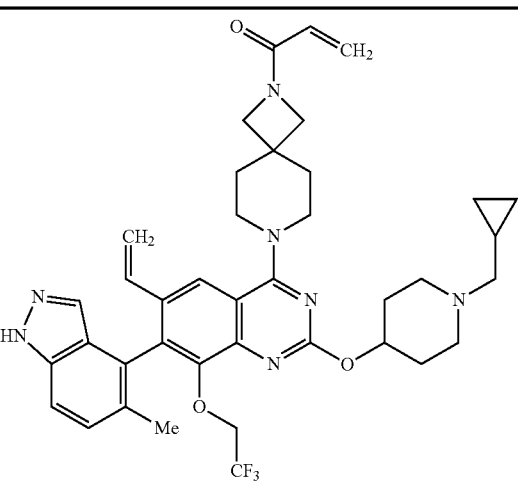 |
| 47 | 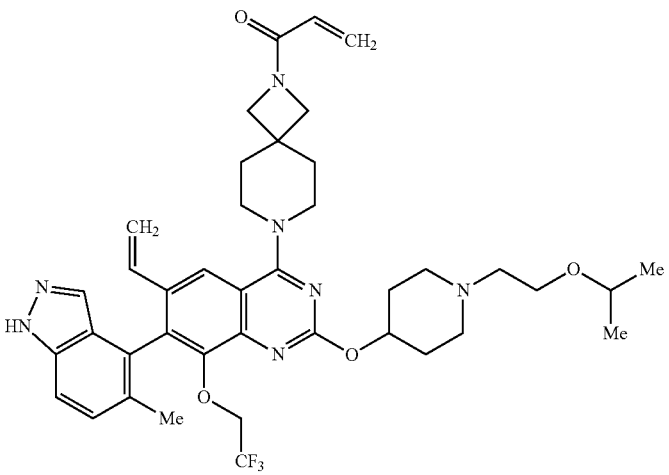 [SMILES: C=CC(=O)N1CC2(CCN(c3nc(OC4CCN(CCOC(C)C)CC4)nc4c(OCC(F)(F)F)c(-c5c(C)ccc6[nH]ncc56)c(C=C)cc34)CC2)C1] |
TABLE 140
| Ex | Str |
|---|---|
| 48 | 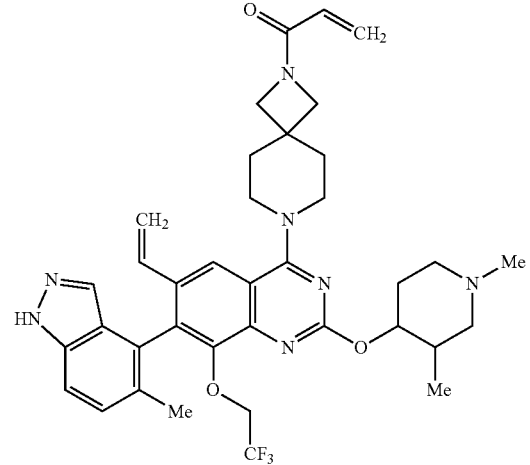 [SMILES: C=CC(=O)N1CC2(CCN(c3nc(OC4CCN(C)CC4C)nc4c(OCC(F)(F)F)c(-c5c(C)ccc6[nH]ncc56)c(C=C)cc34)CC2)C1] |
TABLE 140-continued
| Ex | Str |
|---|---|
| 49 | 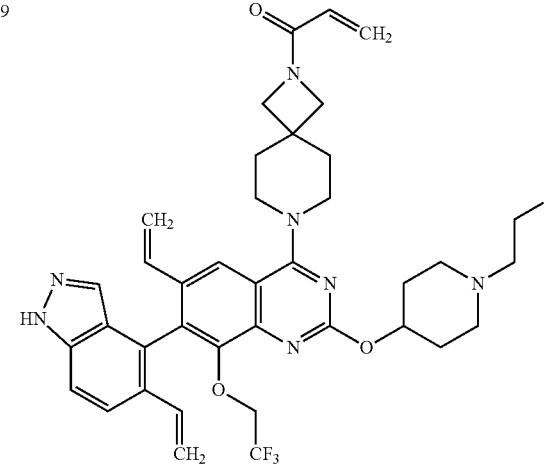 |

TABLE 141
| Ex | Str |
|---|---|
| 50 | 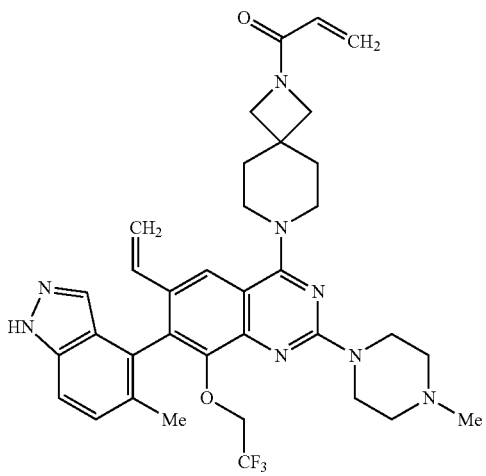 [SMILES: C=CC(=O)N1CC2(CCN(c3nc(N4CCN(C)CC4)nc4c(OCC(F)(F)F)c(-c5c(C)ccc6[nH]ncc56)c(C=C)cc34)CC2)C1] |
| 51 | 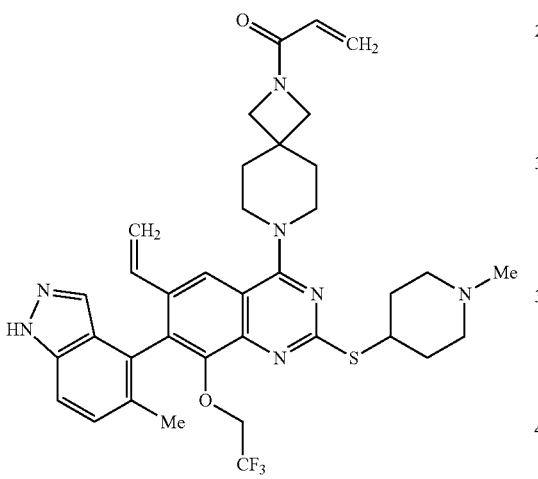 |
TABLE 142
| Ex | Str |
|---|---|
| 52 | 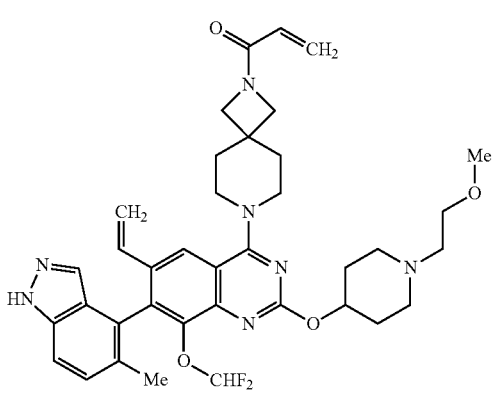 [SMILES: C=CC(=O)N1CC2(CCN(c3nc(OC4CCN(CCOC)CC4)nc4c(OC(F)F)c(-c5c(C)ccc6[nH]ncc56)c(C=C)cc34)CC2)C1] |
| 53 |  |
| 54 |  |

TABLE 143
| Ex | Str |
|---|---|
| 55 | 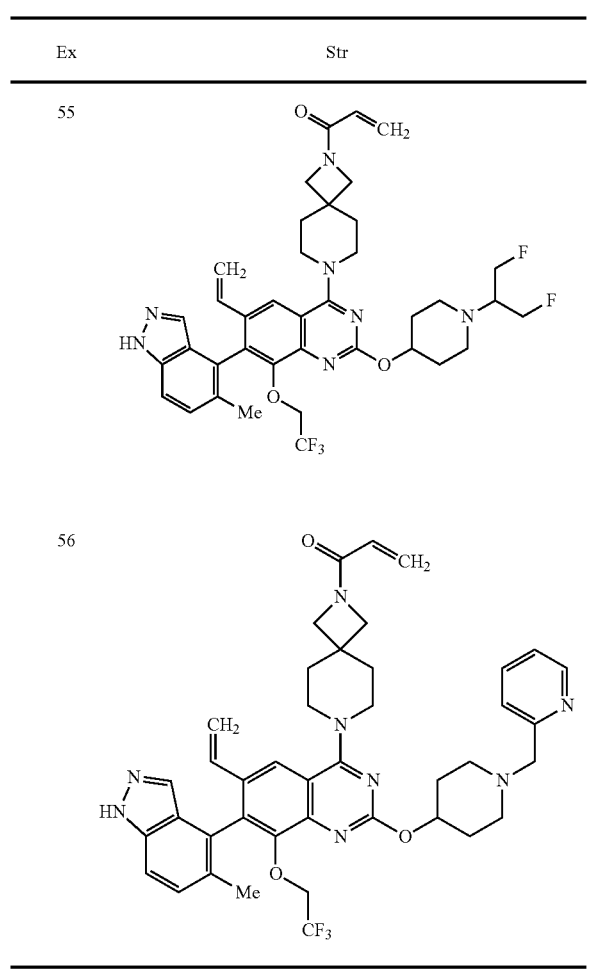 |
| 56 | |
TABLE 144
| Ex | Str |
|---|---|
| 57 | 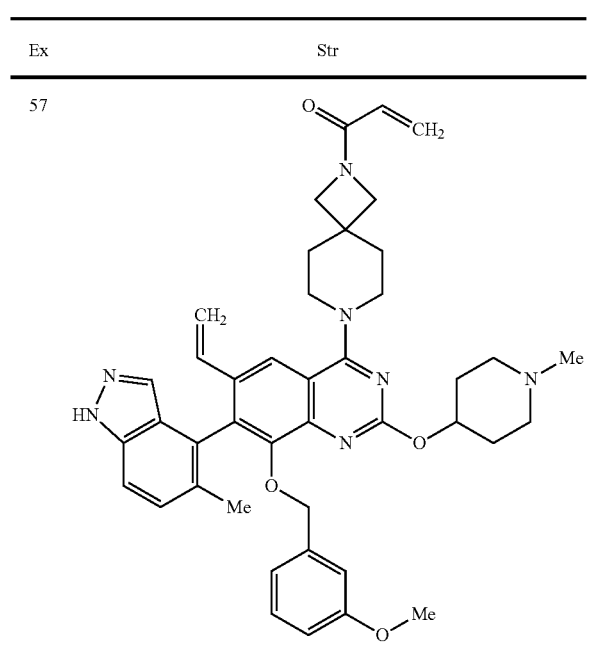 |
TABLE 144-continued
| Ex | Str |
|---|---|
| 58 | 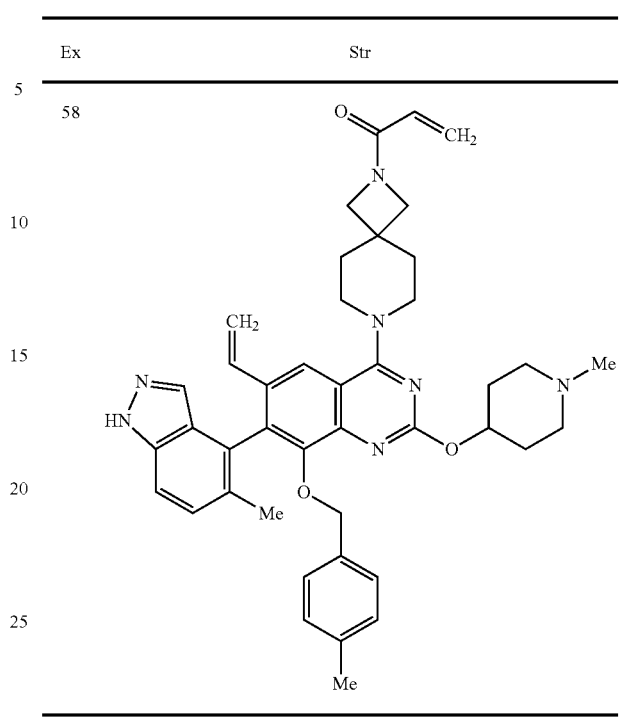 |
TABLE 145
| Ex | Str |
|---|---|
| 59 | 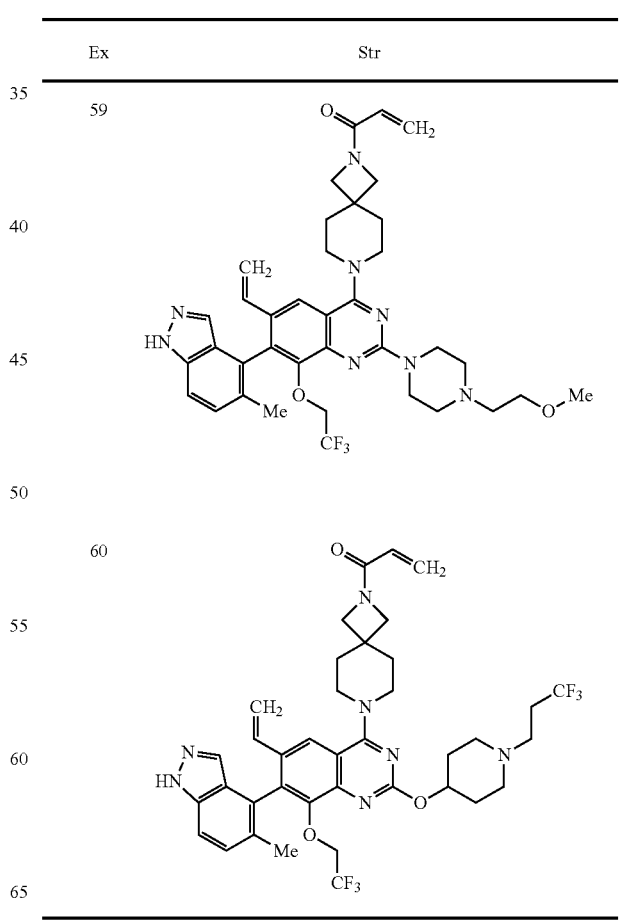 |
| 60 | |

TABLE 146
| Ex | Str |
|----|-----|
| 61 | 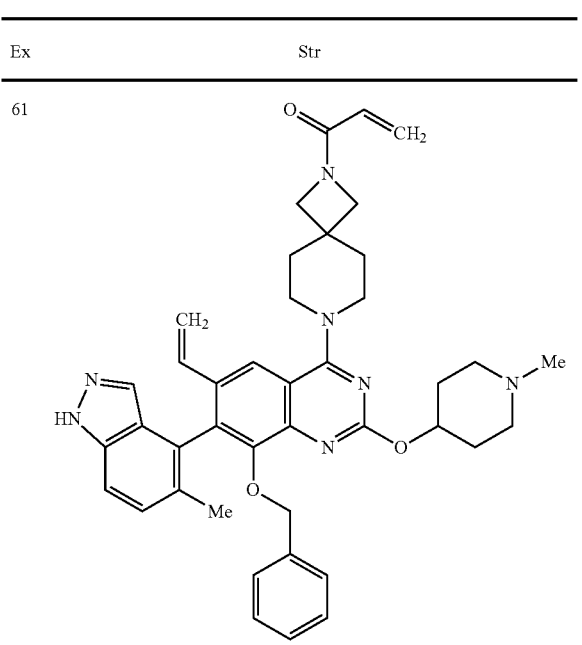 |
| 62 | 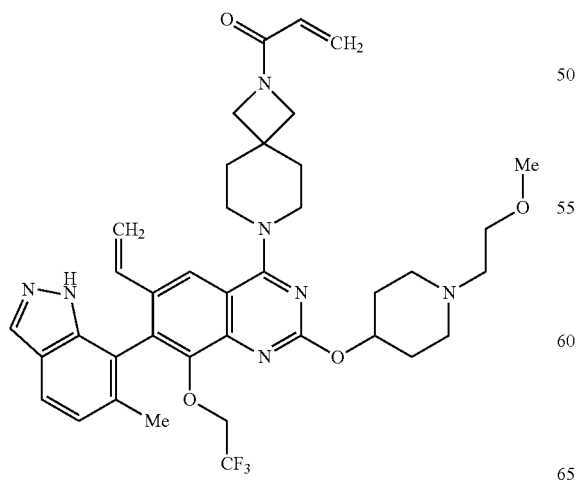 |
TABLE 147
| Ex | Str |
|----|-----|
| 63 | 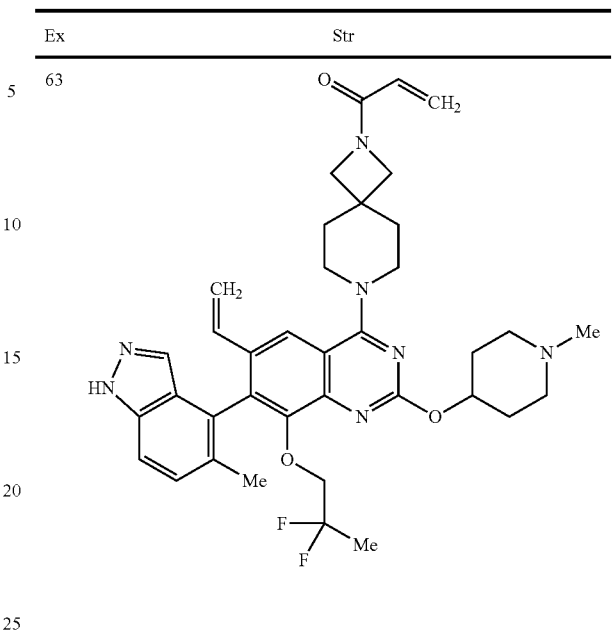 |
| 64 | 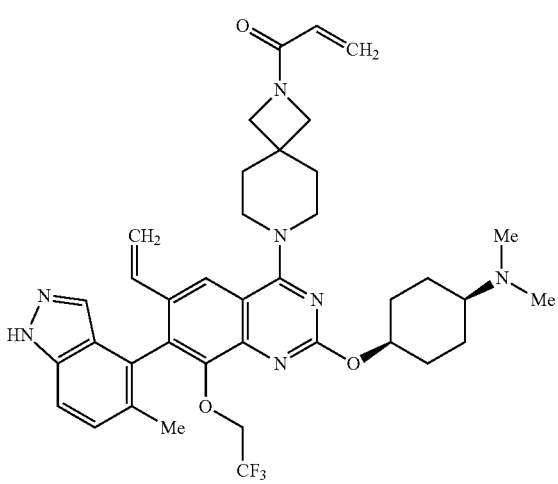 [SMILES: C=CC(=O)N1CC2(CCN(c3nc(O[C@H]4CC[C@@H](N(C)C)CC4)nc4c(OCC(F)(F)F)c(-c5c(C)ccc6[nH]ncc56)c(C=C)cc34)CC2)C1] |

TABLE 148
| Ex | Str |
|---|---|
| 65 | 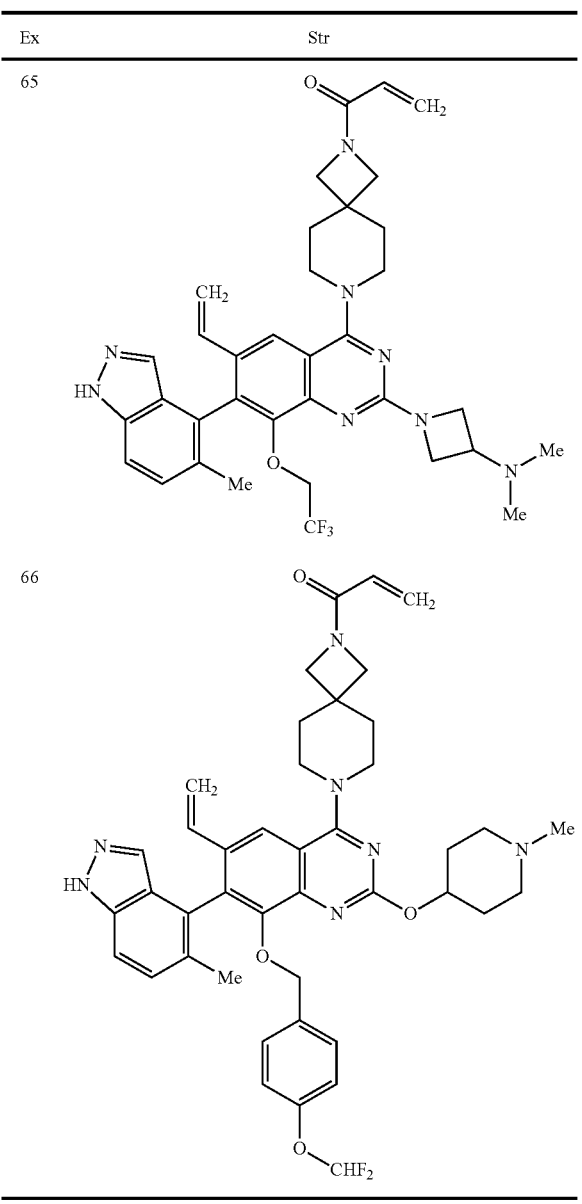 |
| 66 | |
TABLE 149
| Ex | Str |
|---|---|
| 67 | 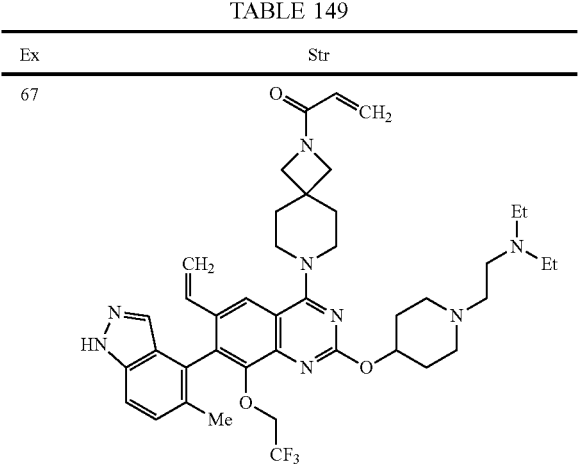 |
TABLE 149-continued
| Ex | Str |
|---|---|
| 68 | 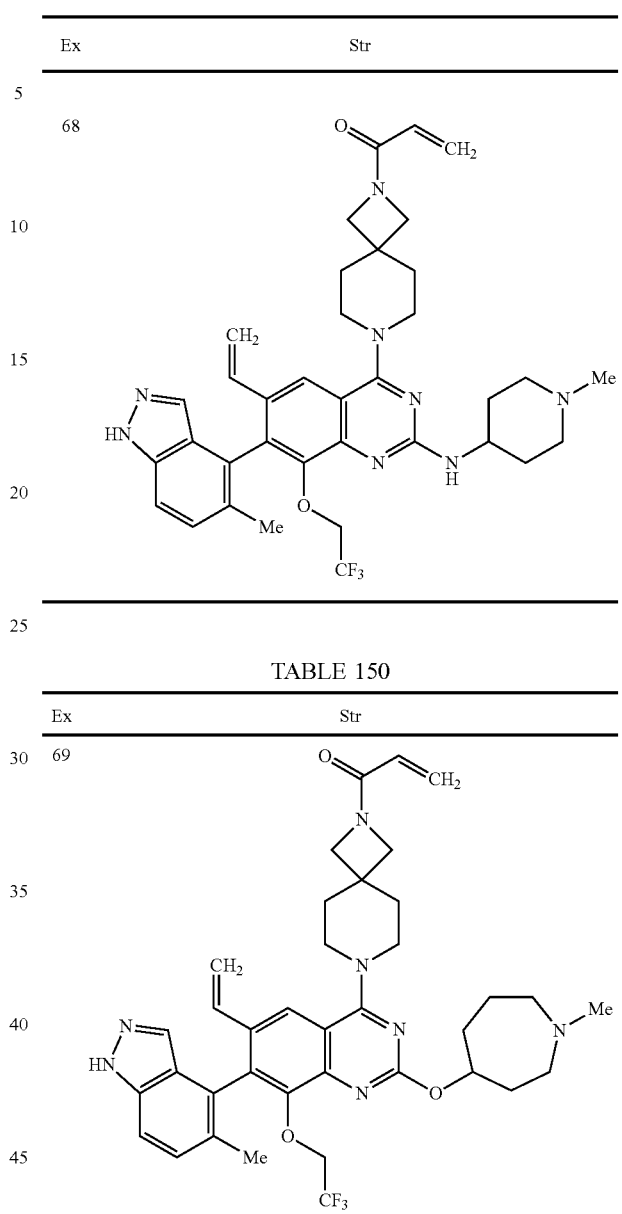 |
TABLE 150
| Ex | Str |
|---|---|
| 69 | 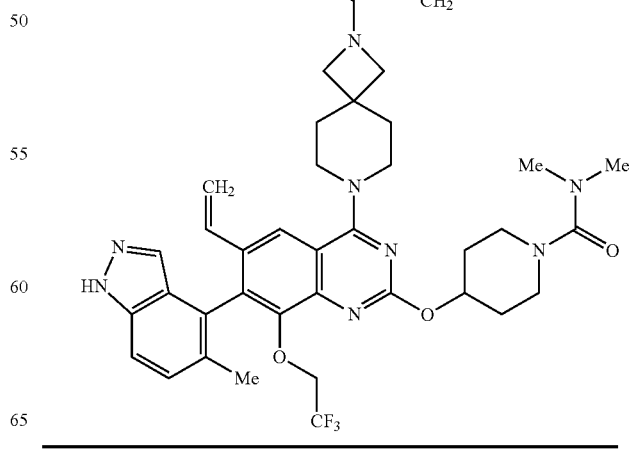 |
| 70 | |

TABLE 151
| Ex | Str |
|---|---|
| 71 | 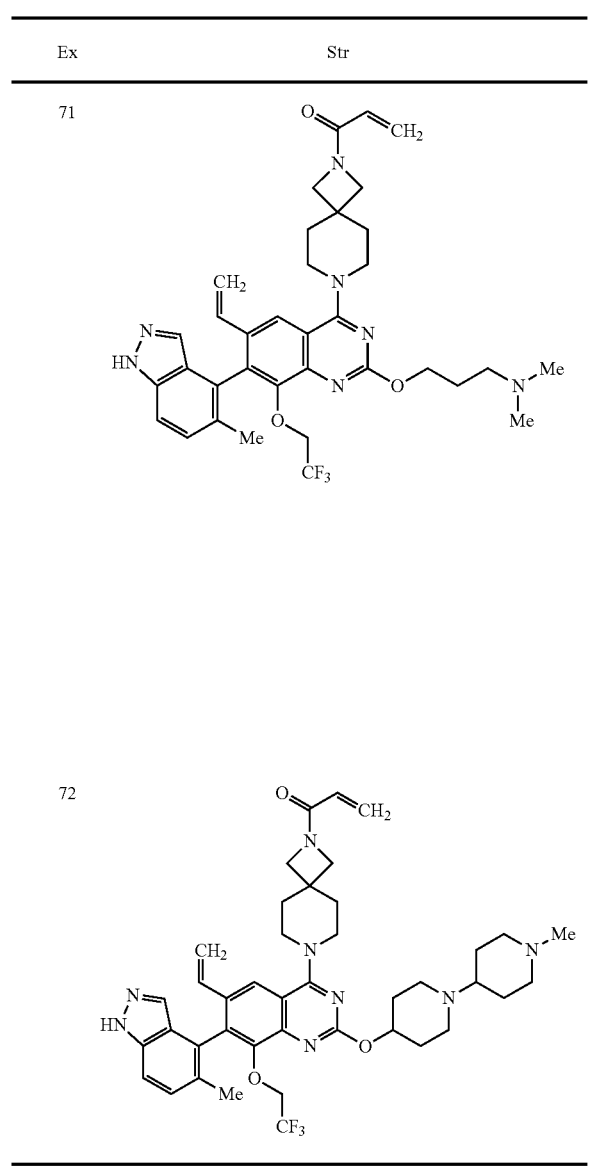 |
| 72 | |
TABLE 152
| Ex | Str |
|---|---|
| 73 | 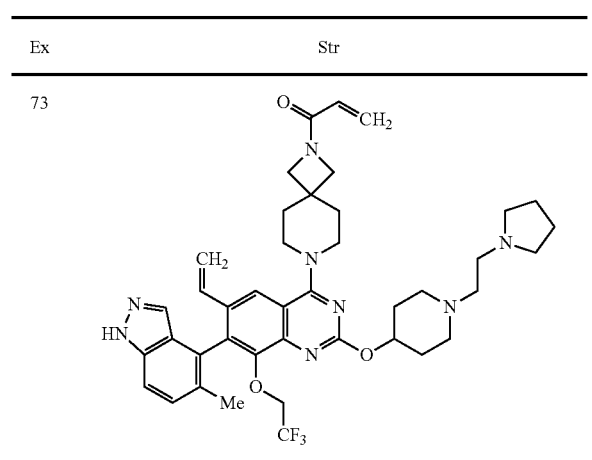 |
TABLE 152-continued
| Ex | Str |
|---|---|
| 74 | 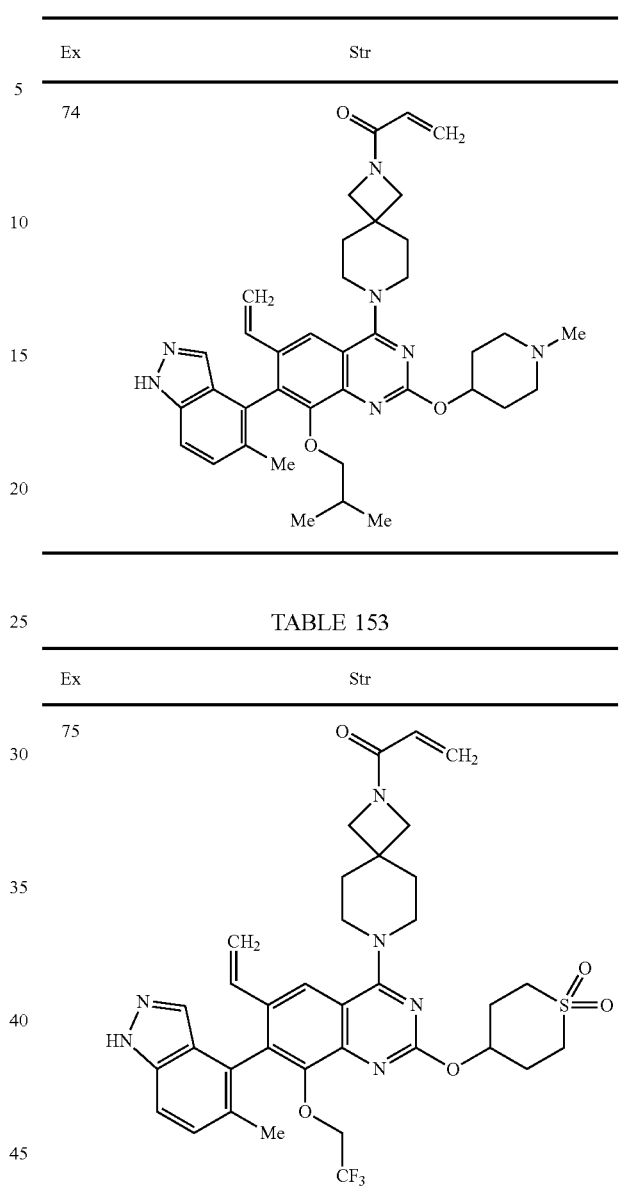 |
TABLE 153
| Ex | Str |
|---|---|
| 75 | |
| 76 | |

TABLE 154
| Ex | Str |
|---|---|
| 77 | 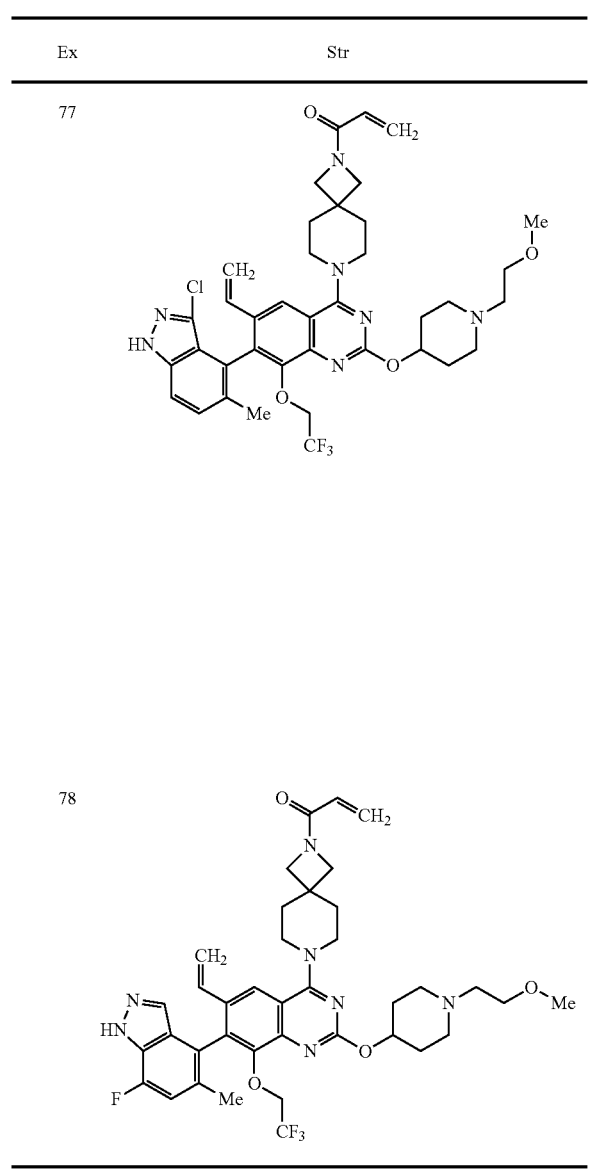 |
| 78 | |
TABLE 155
| Ex | Str |
|---|---|
| 79 | 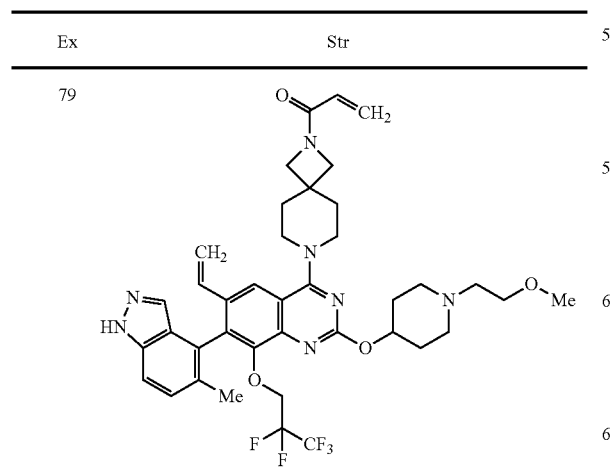 |
TABLE 155-continued
| Ex | Str |
|---|---|
| 80 | 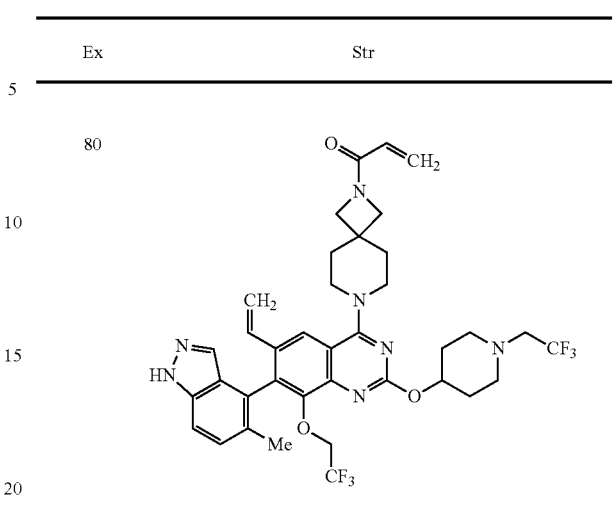 |
TABLE 156
| Ex | Str |
|---|---|
| 81 | 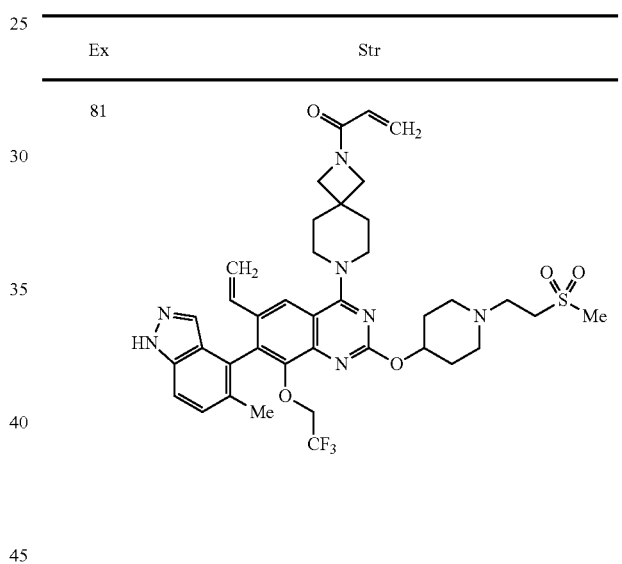 |
| 82 | 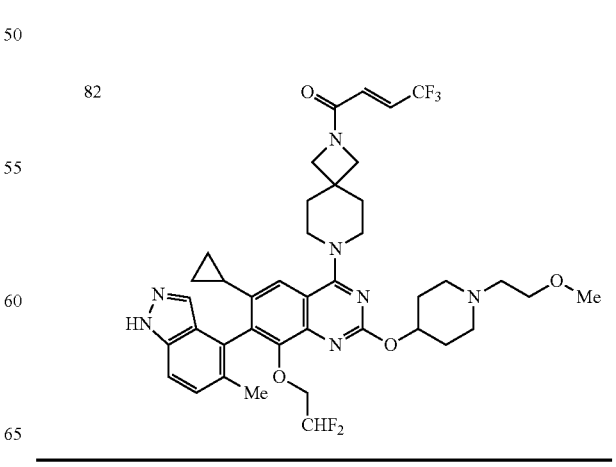 |

TABLE 157
| Ex | Str |
|----|-----|
| 83 | 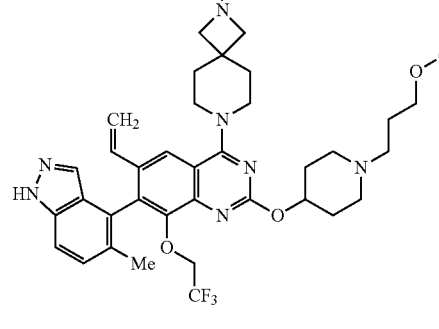 |
| 84 | |
| | TABLE 158 |
| Ex | Str |
| 85 | |
TABLE 158-continued
| Ex | Str |
|----|-----|
| 86 | 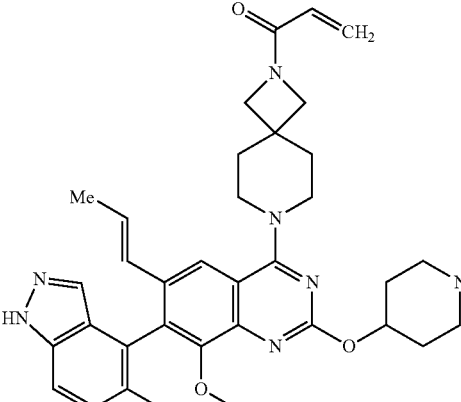 |
| 87 | |
TABLE 159
| Ex | Str |
|----|-----|
| 88 | |

TABLE 159-continued

| Ex | Str |
|---|---|
| 89 | 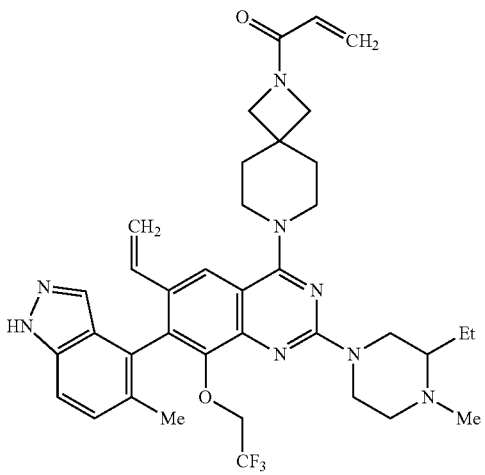 [SMILES: C=CC(=O)N1CC2(CCN(c3nc(N4CCN(C)C(CC)C4)nc4c(OCC(F)(F)F)c(-c5c(C)ccc6[nH]ncc56)c(C=C)cc34)CC2)C1] |

TABLE 160

| Ex | Str |
|---|---|
| 90 | |
| 91 | |

TABLE 161

| Ex | Syn | Dat |
|---|---|---|
| 1 | E1 | ESI+; 658.5<br>NMR (400 MHz): 1.63-1.80 (2H, m) 1.91-2.22 (8H, m) 2.04 (3H, s) 2.17 (3H, s) 2.59-2.79 (2H, m) 3.65-3.84 (4H, m) 3.75 (2H, s) 4.00-4.17 (1H, m) 4.04 (2H, s) 4.25-4.44 (1H, m) 4.92-5.11 (2H, m) 5.72 (1H, tt, J = 55.3, 4.0 Hz) 5.65-5.71 (2H, m) 5.99-6.18 (2H, m) 6.34 (1H, dd, J = 17.0, 10.4 Hz) 7.33 (1H, d, J = 8.6 Hz) 7.38-7.45 (1H, m) 7.50 (1H, d, J = 8.4 Hz) 7.96 (1H, s) 13.03 (1H, s) |
| 2 | E2 | ESI+; 636.6<br>NMR (500 MHz): 0.42-0.71 (4H, m) 0.83 (3H, t, J = 7.0 Hz) 1.23-1.36 (1H, m) 1.59-1.79 (2H, m) 1.90-1.98 (4H, m) 1.99-2.25 (4H, m) 2.11 (3H, s) 2.18 (3H, s) 2.65-2.77 (2H, m) 3.57-3.68 (4H, m) 3.75 (2H, s) 3.77-3.87 (1H, m) 3.98-4.12 (1H, m) 4.03 (2H, s) 4.92-5.03 (1H, m) 5.68 (1H, dd, J = 10.3, 2.3 Hz) 6.12 (1H, dd, J = 17.0, 2.3Hz) 6.34 (1H, dd, J = 17.0, 10.3 Hz) 7.14 (1H, s) 7.33 (1H, d, J = 8.6 Hz) 7.41-7.44 (1H, m) 7.46 (1H, d, J = 8.6 Hz) 12.96 (1H, s) |
| 3 | E3 | ESI+; 672.6<br>NMR (500 MHz): 0.46-0.73 (4H, m) 1.24-1.37 (1H, m) 1.62-1.80 (2H, m) 1.89-2.23 (8H, m) 2.11 (3H, s) 2.17 (3H, s) 2.60-2.76 (2H, m) 3.57-3.69 (4H, m) 3.75 (2H, s) 3.97-4.15 (1H, m) 4.03 (2H, s) 4.22-4.48 (1H, m) 4.87-5.03 (1H, m) 5.72 (1H, tt, J = 55.2, 3.8 Hz) 5.68 (1H, dd, J = 10.3, 2.3 Hz) 6.12 (1H, dd, J = 17.0, 2.3 Hz) 6.34 (1H, dd. J = 16.8, 10.3 Hz) 7.20 (1H, s) 7.34 (1H, d, J = 8.4 Hz) 7.43-7.52 (2H, m) 12.99 (1H, s) |

TABLE 162

| Ex | Syn | Dat |
|---|---|---|
| 4 | E4 | ESI+; 672.6<br>NMR (400 MHz): 0.46-0.76 (4H, m) 1.21-1.45 (1H, m) 1.57-3.01 (14H, m) 2.11 (3H, s) 3.58-3.83 (4H, m) 3.76 (2H, s) 3.95-4.19 (1H, m) 4.04 (2H, s) 4.21-4.65 (3H, m) 5,72 (1H, tt, J = 55.1, 3.7 Hz) 5.69 (1H, dd, J = 10.1, 2.2 Hz) 6.12 (1H, dd, J = 16.8, 2.2 Hz) 6.34 (1H, dd, J = 17.0, 10.1 Hz) 7.22 (1H, s) 7.35 (1H, d, J = 8.6 Hz) 7.44-7.48 (1H, m) 7.49 (1H, d, J = 8.6 Hz) 13.01 (1H, s) |
| 5 | E5<br>E5-2 | ESI+; 622.5<br>NMR (400 MHz): 0.83 (3H, t, J = 7.1 Hz) 1.62-1.83 (2H, m) 1.87-2.27 (8H, m) 2.04 (3H, s) 2.18 (3H, s) 2.62-2.78 (2H, m) 3.63-3.80 (4H, m) 3.76 (2H, s) 3.78-3.91 (1H, m) 3.98-4.16 (1H, m) 4.04 (2H, s) 4.93-5.08 (2H, m) 5.60-5.74 (2H, m) 6.00-6.17 (2H, m) 6.34 (1H, dd, J = 17.0, 10.4 Hz) 7.32 (1H, d, J = 8.6 Hz) 7.36-7.41 (1H, m) 7.49 (1H, d, J = 8.4 Hz) 7.90 (1H, s) 13.01 (1H, s) |
| 6 | E6 | ESI+; 662.5 |
| 7 | E7 | ESI+; 636.5 |
| 8 | E3 | ESI+; 654.6 |
| 9 | E1 | ESI+; 690.6 |
| 10 | E1 | ESI+; 672.6 |
| 11 | E1 | ESI+; 698.6 |
| 12 | E1 | ESI+; 650.6 |
| 13 | E1 | ESI+; 666.6 |
| 14 | E3 | ESI+; 658.6 |
| 15 | E1 | ESI+; 648.6 |
| 16 | E1 | ESI+; 622.6 |
| 17 | E1 | ESI+; 648.6 |
| 18 | E3 | ESI+; 650.5 |

TABLE 163

| Ex | Syn | Dat |
|---|---|---|
| 19 | E3 | ESI+; 676.5 |
| 20 | E3 | ESI+; 662.6 |
| 21 | E3 | ESI+; 656.5 |
| 22 | E6 | ESI+; 686.5 |
| 23 | E1 | ESI+; 636.5 |
| 24 | E24 | ESI+; 622.4<br>NMR (500 MHz): 0.83 (3H, t, J = 7.0 Hz) 1.64-1.79 (2H, m) 1.90-2.23 (8H, m) 2.04 (3H, s) 2.17 (3H, s) 2.65-2.75 (2H, m) 3.67-3.75 (4H, m) 3.76 (2H, s) 3.79-3.88 (1H, m) 4.00-4.13 (1H, m) 4.04 (2H, s) 4.94-5.07 (2H, m) 5.62-5.72 (2H, m) 6.06 (1H, dd, J = 17.5, 10.9 Hz) 6.12 (1H, dd, J = 17.0, 2.3 Hz) 6.35 (1H, dd, J = 17.1, 10.3 Hz) 7.32 (1H, d, J = 8.6 Hz) 7.35-7.41 (1H, m) 7.49 (1H, d, J = 8.6 Hz) 7.90 (1H, s) 13.01 (1H, s)<br>$[\alpha]_D^{20}$ + 39.6 (c 0.35, MeOH) |
| 25 | E25 | ESI+; 734.5 |
| 26 | E26 | ESI+; 720.5<br>NMR (500 MHz): 1.63-1.76 (2H, m) 1.91-2.11 (6H, m) 2.05 (3H, s) 2.12-2.22 (2H, m) 2.47 (2H, t, J = 5.8 Hz) 2.75-2.87 (2H, m) 3.22 (3H, s) 3.42 (2H, t, J = 5.8 Hz) 3.68-3.82 (4H, m) 3.76 (2H, s) 4.04 (2H, s) 4.42-4.54 (1H, m) 4.70-4.85 (1H, m) 4.92-5.03 (1H, m) 5.07 (1H, d, J = 11.8 Hz) 5.64-5.75 (2H, m) 6.02-6.18 (2H, m) 6.35 (1H, dd, J = 17.0, 10.3 Hz) 7.32 (1H, d, J = 8.7 Hz) 7.38-7.42 (1H, m) 7.49 (1H, d, J = 8.6 Hz) 7.98 (1H, s) 13.00 (1H, s) |
| 27 | E5-2 | ESI+; 734.5 |

TABLE 164

| Ex | Syn | Dat |
|---|---|---|
| 28 | E28 | ESI+; 748.5<br>NMR (400 MHz): 0.46-0.78 (4H, m) 1.24-1.41 (1H, m) 1.58-1.77 (4H, m) 1.87-2.16 (8H, m) 2.11 (3H, s) 2.25-2.36 (2H, m) 2.70-2.84 (2H, m) 3.21 (3H, s) 3.27-3.37 (2H, m) 3.59-3.72 (4H, m) 3.75 (2H, s) 4.03 (2H, s) 4.38-4.53 (1H, m) 4.69-4.84 (1H, m) 4.89-5.03 (1H, m) 5.68 (1H, dd, J = 10.1, 2.2 Hz) 6.12 (1H, dd, J = 17.1, 2.3 Hz) 6.34 (1H, dd, J = 17.0, 10.1 Hz) 7.22 (1H, s) 7.33 (1H, d, J = 8.6 Hz) 7.42-7.51 (2H, m) 12.96 (1H, s) |
| 29 | E5-2 | ESI+; 734.5 |
| 30 | E30 | ESI+; 746.6<br>NMR (500 MHz): 1.34-1.50 (2H, m) 1.59-1.76 (4H, m) 1.90-2.13 (6H, m) 2.05 (3H, s) 2.22-2.33 (2H, m) 2.38-2.50 (1H, m) 2.80-2.92 (2H, m) 3.20-3.33 (2H, m) 3.69-3.81 (4H, m) 3.76 (2H, s) 3.82-3.92 (2H, m) 4.04 (2H, s) 4.42-4.54 (1H, m) 4.72-4.84 (1H, m) 4.93-5.01 (1H, m) 5.06 (1H, d, J = 11.9 Hz) 5.65-5.74 (2H, m) 6.03-6.17 (2H, m) 6.35 (1H, dd, J = 17.0, 10.4 Hz) 7.32 (1H, d, J = 8.7 Hz) 7.37-7.43 (1H, m) 7.49 (1H, d, J = 8.9 Hz) 7.98 (1H, s) 12.74-13.27 (1H, m) |
| 31 | E31 | ESI+; 734.5 |
| 32 | E5-2 | ESI+; 716.6 |
| 33 | E5-2 | ESI+; 718.5 |
| 34 | E31 | ESI+; 678.5 |

TABLE 165

| Ex | Syn | Dat |
|---|---|---|
| 35 | E24 | ESI+; 734.5<br>$[\alpha]_D^{20}$ + 19.7 (c 0.35, MeOH) |
| 36 | E36 | ESI+; 720.5<br>NMR (400 MHz): 1.62-1.77 (2H, m) 1.91-2.09 (6H, m) 2.05 (3H, s) 2.11-2.23 (2H, m) 2.45-2.52 (2H, m) 2.75-2.89 (2H, m) 3.22 (3H, s) 3.42 (2H, t, J = 5.8 Hz) 3.69-3.81 (4H, m) 3.76 (2H, s) 4.04 (2H, s) 4.41-4.54 (1H, m) 4.71-4.84 (1H, m) 4.92-5.03 (1H, m) 5.06 (1H, d, J = 11.7 Hz) 5.64-5.76 (2H, m) 6.01-6.19 (2H, m) 6.34 (1H, dd, J = 17.0, 10.4 Hz) 7.32 (1H, d, J = 8.6 Hz) 7.37-7.43 (1H, m) 7.49 (1H, d, J = 8.6 Hz) 7.98 (1H, s) 12.94-13.06 (1H, m)<br>$[\alpha]_D^{20}$ + 33.2 (c 0.35, MeOH) |
| 37 | E24 | ESI+; 734.5<br>$[\alpha]_D^{20}$ + 34.2 (c 0.35, MeOH) |
| 38 | E38 | ESI+; 748.5<br>NMR (400 MHz): 0.48-0.74 (4H, m) 1.27-1.40 (1H, m) 1.58-1.75 (4H, m) 1.88-2.16 (8H, m) 2.11 (3H, s) 2.24-2.38 (2H, m) 2.71-2.83 (2H, m) 3.21 (3H, s) 3.27-3.36 (2H, m) 3.51-3.71 (4H, m) 3.75 (2H, s) 4.03 (2H, s) 4.35-4.55 (1H, m) 4.67-4.85 (1H, m) 4.88-5.06 (1H, m) 5.68 (1H, dd, J = 10.1, 2.2 Hz) 6.12 (1H, dd, J = 17.0. 2.2 Hz) 6.34 (1H, dd, J = 17.0, 10.1 Hz) 7.22 (1H, s) 7.33 (1H, d, J = 8.6 Hz) 7.42-7.52 (2H, m) 12.96 (1H, s)<br>$[\alpha]_D^{20}$ + 20.0 (c 0.35, MeOH) |

TABLE 166

| Ex | Syn | Dat |
|---|---|---|
| 39 | E39 | ESI+; 746.5<br>NMR (500 MHz): 1.35-1.49 (2H, m) 1.60-1.75 (4H, m) 1.91-2.12 (6H, m) 2.05 (3H, s) 2.23-2.34 (2H, m) 2.38-2.54 (1H, m) 2.80-2.92 (2H, m) 3.19-3.35 (2H, m) 3.69-3.81 (4H, m) 3.76 (2H, s) 3.82-3.91 (2H, m) 4.04 (2H, s) 4.42-4.53 (1H, m) 4.72-4.85 (1H, m) 4.92-5.02 (1H, m) 5.06 (1H, d, J = 11.8 Hz) 5.64-5.75 (2H, m) 6.02-6.17 (2H, m) 6.35 (1H, dd, J = 17.1, 10.3 Hz) 7.32 (1H, d, J = 8.7 Hz) 7.38-7.43 (1H, m) 7.49 (1H, d, J = 8.7 Hz) 7.98 (1H, s) 12.76-13.18 (1H, m)<br>$[\alpha]_D^{20}$ + 32.7 (c 0.35, MeOH) |
| 40 | E39 | ESI+; 734.5<br>$[\alpha]_D^{20}$ + 31.2 (c 0.35, MeOH) |
| 41 | E41 | ESI+; 760.5 |
| 42 | E5-2 | ESI+; 689.5 |
| 43 | E25 | ESI+; 662.5 |
| 44 | E5-2 | ESI+; 760.5 |
| 45 | E5-2 | ESI+; 789.5 |
| 46 | E5-2 | ESI+; 716.5 |
| 47 | E5-2 | ESI+; 748.5 |
| 48 | E5-2 | ESI+; 690.5 |
| 49 | E41 | ESI+; 732.5 |
| 50 | E5-2 | ESI+; 661.5 |
| 51 | E51 | ESI+; 692.4 |
| 52 | E5-2 | ESI+; 694.4 |
| 53 | E5-2 | ESI+; 688.5 |
| 54 | E25 | ESI+; 675.6 |
| 55 | E5-2 | ESI+; 740.5 |
| 56 | E5-2 | ESI+; 753.5 |
| 57 | E5-2 | ESI+; 714.5 |
| 58 | E5-2 | ESI+; 698.5 |

TABLE 167

| Ex | Syn | Dat |
|---|---|---|
| 59 | E5-2 | ESI+; 705.5 |
| 60 | E5-2 | ESI+; 758.4 |
| 61 | E5-2 | ESI+; 684.5 |
| 62 | E5-2 | ESI+; 720.5 |
| 63 | E5-2 | ESI+; 672.5 |
| 64 | E5-2 | ESI+; 704.5 |
| 65 | E5-2 | ESI+; 661.5 |
| 66 | E5-2 | ESI+; 750.5 |
| 67 | E41 | ESI+; 761.5 |
| 68 | E5-2 | ESI+; 675.5 |

TABLE 167-continued
| Ex | Syn | Dat |
|----|------|------|
| 69 | E5-2 | ESI+; 690.5 |
| 70 | E5-2 | ESI+; 733.5 |
| 71 | E5-2 | ESI+; 664.4 |
| 72 | E5-2 | ESI+; 759.5 |
| 73 | E41 | ESI+; 759.5 |
| 74 | E5-2 | ESI+; 650.4 |
| 75 | E5-2 | ESI+; 711.4 |
| 76 | E5-2 | ESI+; 675.5 |
| 77 | E5-2 | ESI+; 754.5 |
| 78 | E31 | ESI+; 738.5 |
| 79 | E5-2 | ESI+; 770.5 |
| 80 | E5-2 | ESI+; 744.5 |
| 81 | E5-2 | ESI+; 768.4 |
| 82 | E82 | ESI+; 784.5 |
| 83 | E41 | ESI+; 788.5 |
| 84 | E1 | ESI+; 686.6 |
| 85 | E1 | ESI+; 652.5 |
| 86 | E5-2 | ESI+; 740.4 |
| 87 | E5-2 | ESI+; 720.4 |
| 88 | E5-2 | ESI+; 720.5 |
| 89 | E5-2 | ESI+; 689.5 |
| 90 | E5-2 | ESI+; 704.5 |
| 91 | E5-2 | ESI+; 718.5 |
TABLE 168
| Reference example 1 | 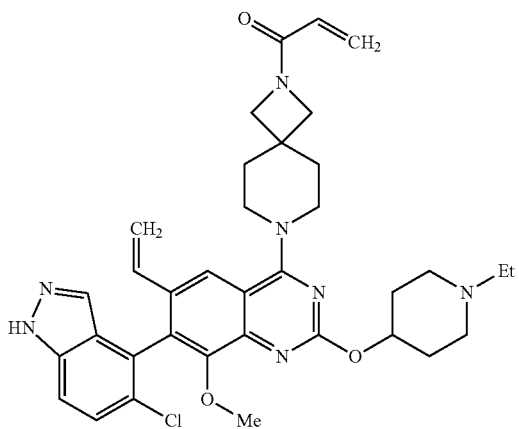 | Syn: E3<br>Dat: ESI+; 642.5 |
|---|---|---|
| Reference example 2 | 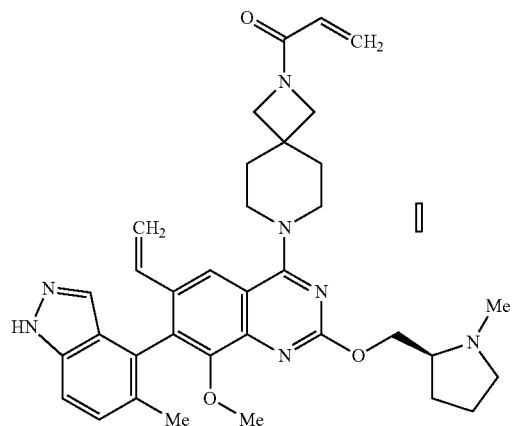 [SMILES: C=CC(=O)N1CC2(CCN(c3nc(OC[C@@H]4CCCN4C)nc4c(OC)c(-c5c(C)ccc6[nH]ncc56)c(C=C)cc34)CC2)C1] | Syn: E3<br>Dat: ESI+; 608.6 |

INDUSTRIAL APPLICABILITY

The compound of the present invention and a salt thereof are useful as a G12C mutation KRAS inhibitor, and may be used as a pharmaceutical composition, for example, an active ingredient of a pharmaceutical composition for treating lung cancer.

The invention claimed is:

1. A compound of Formula (I) or a salt thereof:

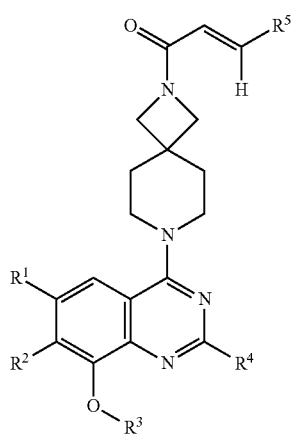

(I)

wherein:

$R^1$ is vinyl, (E)-1-propenyl or cyclopropyl, $R^2$ is Formula (II) or (III),

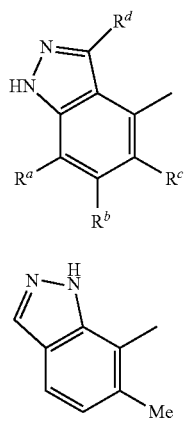

$R^3$ is $C_{3-4}$ alkyl, methyl or n-propyl each of which is substituted with two or more F's, ethyl or $C_{3-4}$ cycloalkyl each of which may be substituted with F, benzyl which may be substituted with $C_{1-3}$ alkyl, benzyl which may be substituted with —O—$C_{1-3}$ alkyl, or benzyl which may be substituted with —O—($C_{1-3}$ alkyl which is substituted with F), $R^4$ is —O—$C_{3-5}$ alkyl which may be substituted, —O—cycloalkyl which may be substituted, or Formula (IV), (V), (VI), or (VII),

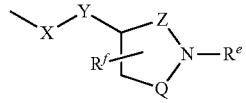
(IV)

(V)

(VI)

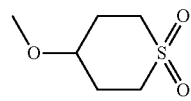
(VII)

$R^5$ is H or $CF_3$, $R^a$ is H or F, $R^b$ is H or F, $R^c$ is H, methyl, vinyl, or Cl, $R^d$ is H or Cl, $R^e$ is $CO_2Me$, $COMe$, $CON(Me)_2$, $SO_2Me$, $C_{3-4}$ cycloalkyl, a nonaromatic heterocyclic group having 4 to 6 ring members which may be substituted, or $C_{1-3}$ alkyl which may be substituted with a group selected from the Group G, the Group G is —O—$C_{1-3}$ alkyl, —O—($C_{1-3}$ alkyl which is substituted with F or $C_{3-4}$ cycloalkyl), $C_{3-4}$ cycloalkyl, —F, —CN, —$SO_2Me$, an aromatic heterocyclic group, a nonaromatic heterocyclic group having 4 to 6 ring members, —N($C_{1-3}$ alkyl)$_2$, and —C(Me)$_2$OH, $R^f$ is H, methyl, or F, $R^g$ is H, methyl, or ethyl, $R^h$ is $C_{1-3}$ alkyl which may be substituted with -OMe, X is O, NH, S, or methylene, Y is a bond or methylene, Z is a bond, methylene, or ethylene, Q is methylene or ethylene, n is an integer of 1 or 2, and m is an integer in a range of 1 to 3.

2. The compound or salt thereof according to claim 1, wherein $R^2$ is Formula (II).

3. The compound or salt thereof according to claim 2, wherein $R^4$ is Formula (IV).

4. The compound or salt thereof according to claim 3, wherein X is O.

5. The compound or salt thereof according to claim 4, wherein $R^5$ is H.

6. The compound or salt thereof according to claim 5, wherein $R^1$ is vinyl or cyclopropyl.

7. The compound or salt thereof according to claim 6, wherein $R^a$ is H, $R^b$ is H or F, $R^c$ is methyl or Cl, and $R^d$ is H.

8. The compound or salt thereof according to claim 7, wherein $R^3$ is $C_{3-4}$ alkyl, methyl or n-propyl each of which is substituted with two or more F's, or ethyl or $C_{3-4}$ cycloalkyl each of which may be substituted with F.

9. The compound or salt thereof according to claim 8, wherein $R^e$ is a nonaromatic heterocyclic group having 4 to 6 ring members which may be substituted, or $C_{1-3}$ alkyl which may be substituted with a group selected from the Group G.

10. The compound or salt thereof according to claim 9, wherein $R^e$ is oxetanyl, tetrahydropyranyl, or $C_{1-3}$ alkyl which may be substituted with a group selected from the group consisting of -OMe, -OEt, and —C(Me)$_2$OH.

11. A pharmaceutical composition, comprising:
the compound or salt thereof according to claim 1; and
a pharmaceutically acceptable excipient.

12. A method of treating lung cancer, comprising:
administering an effective dose of the compound or salt thereof according to claim 1 to a subject in need thereof.

13. The method according to claim 12, wherein said cancer is non-small cell lung cancer.

14. The method according to claim 13, wherein said non-small cell lung cancer is KRAS G12C mutation positive non-small cell lung cancer.

* * * * *